US012799517B2

(12) United States Patent
Ito et al.

(10) Patent No.: US 12,799,517 B2
(45) Date of Patent: Nov. 17, 2026

(54) METHOD FOR PRODUCING PEPTIDE HAVING PHYSIOLOGICAL ACTIVITY, AND PEPTIDE COMPRISING SHORT LINKER

(71) Applicant: AJINOMOTO CO., INC., Tokyo (JP)

(72) Inventors: Kenichiro Ito, Kawasaki (JP); Yoshihiko Matsuda, Kawasaki (JP); Naoko Yamada, Kawasaki (JP); Yoshimi Kikuchi, Kawasaki (JP); Atsushi Konishi, Kawasaki (JP); Michiya Kanzaki, Kawasaki (JP); Kazutoshi Takahashi, Kawasaki (JP); Hiroki Yamaguchi, Kawasaki (JP); Ayako Fujiwara, Kawasaki (JP); Kyohei Miyairi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1087 days.

(21) Appl. No.: 17/831,877

(22) Filed: Jun. 3, 2022

(65) Prior Publication Data

US 2022/0396819 A1 Dec. 15, 2022

Related U.S. Application Data

(63) Continuation of application No. PCT/JP2020/045327, filed on Dec. 4, 2020.

(30) Foreign Application Priority Data

Dec. 6, 2019 (JP) ................................ 2019-221040

(51) Int. Cl.

*C07K 7/64* (2006.01)
*C07K 5/04* (2006.01)
*C07K 7/04* (2006.01)
*C12P 21/02* (2006.01)

(52) U.S. Cl.

CPC .................................. *C12P 21/02* (2013.01)

(58) Field of Classification Search

CPC .............. C07K 7/02; C07K 5/12; C12P 21/02
See application file for complete search history.

(56) References Cited

U.S. PATENT DOCUMENTS

| | | | | |
|---|---|---|---|---|
| 5,986,047 | A | 11/1999 | Wrighton et al. | |
| 9,994,616 | B2 * | 6/2018 | Suga | A61P 1/16 |
| 2009/0005292 | A1 | 1/2009 | Holmes et al. | |
| 2009/0053242 | A1 | 2/2009 | Nichol et al. | |
| 2010/0256332 | A1 | 10/2010 | Wallrapp et al. | |
| 2010/0292130 | A1 | 11/2010 | Skerra et al. | |
| 2011/0071077 | A1 | 3/2011 | Nichol et al. | |
| 2012/0157660 | A1 | 6/2012 | Holmes et al. | |
| 2013/0072420 | A1 | 3/2013 | Skerra et al. | |
| 2013/0150291 | A1 | 6/2013 | Jowett et al. | |
| 2014/0050693 | A1 | 2/2014 | Skerra et al. | |
| 2014/0364362 | A1 | 12/2014 | Jowett et al. | |
| 2015/0147276 | A1 | 5/2015 | Ingber et al. | |
| 2016/0137698 | A1 | 5/2016 | Skerra et al. | |
| 2016/0237119 | A1 * | 8/2016 | Suga | A61P 9/04 |
| 2018/0354992 | A1 | 12/2018 | Skerra et al. | |
| 2019/0010192 | A1 * | 1/2019 | Binder | C12N 15/68 |
| 2019/0016822 | A1 | 1/2019 | Dumitru et al. | |
| 2020/0282071 | A1 | 9/2020 | Friedrich et al. | |
| 2020/0297854 | A1 | 9/2020 | Ingber et al. | |

FOREIGN PATENT DOCUMENTS

| | | | |
|---|---|---|---|
| JP | 2008-519858 | A | 6/2008 |
| JP | 2010-083808 | A | 4/2010 |
| JP | 2010-521980 | A | 7/2010 |
| JP | 2010-531139 | A | 9/2010 |
| JP | 2013-531480 | A | 8/2013 |
| JP | 2014-534265 | A | 12/2014 |
| JP | 2018-172415 | A | 11/2018 |
| JP | 2019-509054 | A | 4/2019 |
| WO | WO96/40750 | A1 | 12/1996 |
| WO | WO2007/087428 | A2 | 8/2007 |
| WO | WO2008/155134 | A1 | 12/2008 |
| WO | WO2011/144756 | A1 | 11/2011 |
| WO | WO2015/056713 | A1 | 4/2015 |
| WO | WO2018/234455 | A1 | 12/2018 |

OTHER PUBLICATIONS

Notice of Reasons for Refusal from Japanese Patent App. No. 2021-562760 (Sep. 26, 2024) with English language machine translation thereof.

Paul, F., Cell-specific targeting of interferon alpha activity [online], 2017, [Search date Sep. 17, 2024], Internet: <URL:https://theses.hal.science/tel-01511353> (English abstract).

Decision of Refusal for Japanese Patent App. No. 2021-562760 (Feb. 20, 2025) with English language translation thereof.

Guo, W., et al., "Efficient soluble expression of two copies of EMP1 connected in series in *Escherichia coli*, with enhanced EPO activity," Process Biochem. 2015;50:689-695.

Partial Supplementary European Search Report for European Patent App. No. 20897007.9 (May 16, 2024).

You, J., et al., "Protection of mice against enterotoxigenic *E. coli* by immunization with a polyvalent enterotoxin comprising a combination of LTB, STa, and STb," Appl. Microbiol. Biotechnol. 2011;89:1885-1893.

Toyama, K., et al., "Inhibition of EGFR Activation by Bivalent Ligands Based on a Cyclic Peptide Mimicking the Dimerization Arm Structure of EGFR," Chem. Pharm. Bull. 2018;66(11):1083-1089.

(Continued)

*Primary Examiner* — Maryam Monshipouri
(74) *Attorney, Agent, or Firm* — Cermak & McGowan LLP; Shelly Guest Cermak

(57) ABSTRACT

Provided are a method for producing a complicated peptide molecule, such as a dimeric peptide, in a simpler manner at lower cost compared with the conventional chemical synthesis methods; and a dimeric peptide which comprises a specific short linker and has a satisfactory activity; and others.

10 Claims, 80 Drawing Sheets

Specification includes a Sequence Listing.

(56) References Cited

OTHER PUBLICATIONS

Paul, F., "Ciblage de l'activite de l'interferon alpha: de la preuve de condept a l-activite biologique," Biologie Cellulaire, Universite Montpellier, 2016.

International Search Report and Written Opinion for PCT Patent App. No. PCT/JP2020/045327 (Feb. 9, 2021) with English translation of ISR.

Office Action issued in the Korean Patent App. No. 10-2022-7023127 on Feb. 13, 2026, with English language translation thereof.

Breibeck, J., et al., "The polypeptide biophysics of proline/alanine-rich sequences (PAS): Recombinant biopolymers with PEG-like properties," BIOPOLYMERS (2018):109:e23069, 12 pp.

* cited by examiner

FIG.11

| | | | | | | | | | | | |
|---|---|---|---|---|---|---|---|---|---|---|---|
| Pos ctrl | | | | | | | | | | | Pos ctrl |
| EGFR | ErbB2 | ErbB3 | ErbB4 | FGFR1 | FGFR2α | FGFR3 | FGFR4 | Ins R | IGF-IR | Axl | Dtk |
| Mer | Met | MSPR | PDGFRα | PDGFRβ | SCFR | Flt-3 | M-CSFR | c-Ret | POR1 | POR2 | Tie-1 |
| Tie-2 | TrkA | TrkB | TrkC | VEGFR1 | VEGFR2 | VEGFR3 | MuSK | EphA1 | EphA2 | EphA3 | EphA4 |
| EphA6 | EphA7 | EphB1 | EphB2 | EphB4 | EphB6 | ALK | DDR1 | DDR2 | EphA5 | EphA10 | |
| Pos ctrl | | EphB3 | RYK | | | | | | | | Neg ctrl |

1, Marker (XL-Ladder Broad, APRO science)
2, pPK4_CspBss-AET-aMD4dY-GS15
3, pPK4_CspBss-AET-aMD4dY-GS22
4, pPK4_CspBss-AET-aMD4dY-PAS8
5, pPK4_CspBss-AET-PAS-aMD4dY-PEG11
6, pPK4_CspBss-AET-aMD4dY-PAS49
7, pPK4_CspBss-AET-aMD4dY-PAS100
8, pPK4_CspBss-AET-aMD4dY-PAS200
9, pPK4 (empty vector)

AET-aMD4dY-GS15
Calc 5492.4
Obs 5492.6

AET-aMD4dY-PAS8
Calc 5193.4
Obs 5193.2

AET-aMD4dY-PAS22

Calc 6318.0

Obs 6318.2

AET-aMD4dY-PAS49

Calc 8497.1

Obs 8496.8

AET-aMD4dY-PAS100

Calc 12616.3

Obs 12616.5

AET-aMD4dY-PAS200

Calc 20712.7

Obs 20714.7

1, Marker (XL-Ladder Broad, APRO science)
2-5, pPK4_CspBss-AET-aMD4dY-PAS22-PAS200
6, pPK4 (empty vector)

AET-aMD4dY-PAS22-PAS200
Calc 22485.6
Obs 22484.0

AET-EPO-PAS8
Calc 5279.4
Obs 5279.1

AET-EPO-PAS22

Calc 6405.0
Obs 6404.5

AET-TPO1-PAS8
Calc 4092.2
Obs 4092.5

AET-TPO2-PAS8
Calc 4577.0
Obs 4576.7

TPO2-PAS8
Calc 4274.9
Obs 4275.5

FIG.45

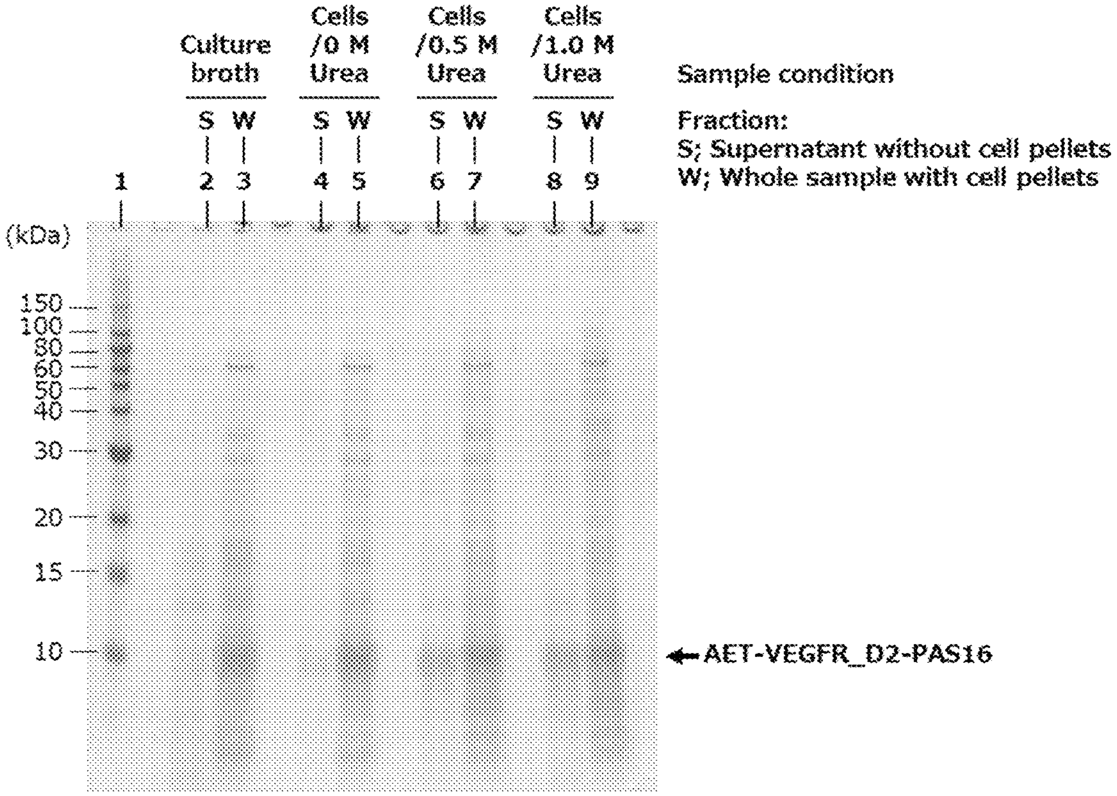

1, Marker (XL-Ladder Broad, APRO science)

2, pPK4_CspBss-VEGFR_D2-PAS16, culture supernatant
3, pPK4_CspBss-VEGFR_D2-PAS16, whole culture broth with cells 4, pPK4_CspBss-VEGFR_D2-PAS16, cell pallet, treated with 0 M Urea, supernatant
5, pPK4_CspBss-VEGFR_D2-PAS16, cell pallet, treated with 0 M Urea, whole sample with cells 6, pPK4_CspBss-VEGFR_D2-PAS16, cell pallet, treated with 0.5 M Urea, supernatant
7, pPK4_CspBss-VEGFR_D2-PAS16, cell pallet, treated with 0.5 M Urea, whole sample with cells 8, pPK4_CspBss-VEGFR_D2-PAS16, cell pallet, treated with 1.0 M Urea, supernatant
9, pPK4_CspBss-VEGFR_D2-PAS16, cell pallet, treated with 1.0 M Urea, whole sample with cells

AET-VEGFR_D2-PAS16
Calc 5768.5
Obs 5758.1

AET-EPO-GS8
Calc 5119.2
Obs 5119.0

AET-EPO-GS22
Calc 6007.6
Obs 6008.3

AET-EPO-PAS49
Calc 8584.2
Obs 8584.1

AET-EPO-PAS49-b
Calc 8700.9
Obs 8701.2

AET-EPO-PAS100
Calc 12703.4
Obs 12702.1

AET-EPO-PAS100-b
Calc 12941.9
Obs 12941.5

AET-EPO-PAS22-PAS200
Calc 22571.6
Obs 22575.7

AET-EPO-PAS22-PAS600
Calc 54907.9
Obs 54903.8

MAET-aMD4-PAS22 [M+H$^+$] = 6805.6

MAET-aMD4dY-PAS8: [M+H$^{+}$] = 5354.0

MAET-aMD4dY-PAS22 [M+H$^+$] = 6479.3

MAET-EPO-PAS100b: [M+H$^+$] = 13104 (N-formyl), 13076

MAET-VEGFR_D2-PAS16: [M+K$^+$] = 5955 (N-formyl), 5927

1, Marker (XL-Ladder Broad, APRO science)
2-5, pPK4_CspBss-AET-aMD4dY-PAS22-Trimer
6, pPK4_CspBss-AET-aMD4dY-PAS22
7, pPK4 (empty vector)

AET-aMD4dY-
PAS22-Trimer
Calc 10262.92
Obs 10261.64

AET-VEGFR_D2-GS16
Calc 5468.2
Obs 5468.7

AET-VEGFR_D2-PAS49b
Calc 8533.6
Obs 8534.2

AET-VEGFR_D2-PAS100
Calc 12536.1
Obs 12535.8

AET-VEGFR_D2-PAS100b
Calc 12774.6
Obs 12775.1

TPO2-GS8
Calc 4114.7
Obs 4115.3

TPO2-PAS49
Calc 7579.7
Obs 7580.1

TPO2-PAS49b
Calc 7697.4
Obs 7697.1

TPO2-PAS100
Calc 11698.9
Obs 11699.5

TPO2-PAS100b
Calc 11938.4
Obs 11938.3

METHOD FOR PRODUCING PEPTIDE HAVING PHYSIOLOGICAL ACTIVITY, AND PEPTIDE COMPRISING SHORT LINKER

This application is a Continuation of, and claims priority under 35 U.S.C. § 120 to, International Application No. PCT/JP2020/045327, filed Dec. 4, 2020, and claims priority therethrough under 35 U.S.C. § 119 to Japanese Patent Application No. 2019-221040, filed Dec. 6, 2019, the entireties of which are incorporated by reference herein. Also, the Sequence Listing filed electronically herewith is hereby incorporated by reference (File name: 2022-06-03T_US-641_Seq_List; File size: 175 KB; Date recorded: Jun. 3, 2022).

BACKGROUND

Technical Field

The present invention relates to a method for producing a peptide having physiological activity, a peptide comprising a short linker, and the like.

Background Art

In recent years, biopharmaceuticals such as antibody medicine, regenerative medicine, nucleic acid medicine, and the like have been studied and actually used as modality of medicines. In addition, medium molecules, especially peptides, are attracting attention as new modality of medicines. In particular, a number of peptides having a special shape (special peptides) such as cyclic peptides have been developed, and are expected to be applied to pharmaceuticals.

Under such circumstances, the development of dimer peptides and peptide complexes is expected to accelerate in the future. For example, regarding dimer peptides, APL-2 of Apellis Pharmaceuticals has been clinically studied as a therapeutic agent for age-related macular degeneration and the like and is expected to be put into practical use.

The dimer peptide generally has a structure in which two peptide chains are linked by a short linker, and the peptide complex generally has a structure in which a peptide chain and a drug are linked by a short linker. As such a short linker, a PEG linker is mainly used.

However, in the production of dimer peptides and peptide complexes, conventional chemical synthesis methods require chemical synthesis of peptide chains, addition of PEG linkers, and purification, and many production steps are required. In addition, if the peptide is a cyclic peptide, the peptide chain must be further cyclized. Therefore, in order to produce dimer peptides or peptide complexes by conventional chemical synthesis methods, it is necessary to go through complicated steps, which is very time-consuming. Moreover, in the conventional chemical synthesis methods, the synthesis of a dimer peptide obtained by binding a first peptide and a second peptide via a PEG linker yields a product in which the C-terminus of the first peptide binds to the linker and the C-terminus of the second peptide also binds to the linker, but cannot perform efficient synthesis of dimer peptides such that the C-terminus of the first peptide binds to the linker and the N-terminus of the second peptide binds to the linker.

In addition, the PEG linker mainly used is expensive, and it cannot be said that the conventional chemical synthesis methods are economically preferable.

Published Japanese Translation of PCT International Application No. 2013-531480 describes a drug conjugate comprising a biologically active protein and a random coil polypeptide containing an amino acid sequence composed of at least 50 proline and alanine amino acid residues. Patent Literature 1 states that the random coil polypeptide provides increased blood stability of the drug conjugate.

However, Published Japanese Translation of PCT International Application No. 2013-531480 does not specifically disclose the use of the random coil polypeptide in place of a short linker such as a PEG linker in a dimer peptide or peptide complex.

Further, in order to utilize a peptide molecule such as a dimer peptide as a pharmaceutical, it is desired not only to improve the stability of the peptide molecule such as a dimer peptide but also to maintain or improve the activity. As described above, the PEG linker is mainly used as a short linker for linking two peptide chains, and the use of the PEG linker poses a manufacturing problem, and from the viewpoint of the activity of peptide molecules such as dimer peptides, more useful short linkers are eagerly desired.

SUMMARY OF THE INVENTION

As described above, in the production of peptide molecules such as dimer peptides, the conventional chemical synthesis methods are not easy to operate and require high costs.

Therefore, an aspect of the present invention aims to provide a method for producing a peptide molecule such as a dimer peptide easily and inexpensively as compared with the conventional chemical synthesis methods.

As described above, as a short linker for linking two peptide chains, more useful short linkers are desired from the viewpoint of the activity of peptide molecules such as dimer peptides.

Therefore, an aspect of the present invention aims to provide a peptide molecule such as a dimer peptide having good activity containing a specific short linker.

The present invention may include, for example, the following aspects.

It is an aspect of the present invention to provide a peptide molecule comprising:

(I) a first physiologically active peptide portion;

(II) a linker portion composed of 49 or less amino acid residues; and (III) a second physiologically active peptide portion located on the opposite side of the linker portion from the first physiologically active peptide portion, wherein the first physiologically active peptide portion and the second physiologically active peptide portion may be the same as or different from each other, and at least 90% of an amino acid sequence of the linker portion is composed of amino acid residues selected from alanine (A), proline (P), and serine (S).

It is a further aspect of the present invention to provide the peptide molecule as described above, wherein the first physiologically active peptide portion constitutes a cyclic peptide and/or the second physiologically active peptide portion constitutes a cyclic peptide.

It is a further aspect of the present invention to provide the peptide molecule as described above, wherein the first physiologically active peptide portion constitutes a cyclic peptide having a cyclic structure formed by a disulfide bond and/or the second physiologically active peptide portion constitutes a cyclic peptide having a cyclic structure formed by a disulfide bond.

It is a further aspect of the present invention to provide the peptide molecule as described above, wherein the first physiologically active peptide portion and the second physiologically active peptide portion each constitute a cyclic peptide that binds to a c-Met protein, and may be the same as or different from each other.

It is a further aspect of the present invention to provide the peptide molecule according to as described above, wherein the cyclic peptide is a cyclic peptide having a cyclic structure formed by a disulfide bond, containing an amino acid sequence selected from the following (a) to (i):

(a) (SEQ ID NO: 1) CYRQFNRRTHEVWNLDC;

(b) (SEQ ID NO: 2) CRQFNRRTHEVWNLDC;

(c) (SEQ ID NO: 3) CYWYYAWDQTYKAFPC;

(d) (SEQ ID NO: 4) CWYYAWDQTYKAFPC;

(e) (SEQ ID NO: 5) CYISWNEFNSPNWRFITC;

(f) (SEQ ID NO: 6) CISWNEFNSPNWRFITC;

(g) a peptide in which one or two amino acid residues other than a cysteine residue are substituted, deleted, or added in any of the amino acid sequences (a) to (f), and which binds to a c-Met protein;

(h) a peptide which is composed of an amino acid sequence having 90% or more sequence identity with any of the amino acid sequences (a) to (f), but having cysteine residues at both ends, and which binds to a c-Met protein; and (i) a peptide in which at least one amino acid other than the cysteine residues at both ends in any of the amino acid sequences (a) to (h) is modified (the amino acid modification is phosphorylation, methylation, acetylation, adenylylation, ADP-ribosylation, or glycosylation).

It is a further aspect of the present invention to provide the peptide molecule as described above, wherein the first physiologically active peptide portion and the second physiologically active peptide portion each constitute a cyclic peptide that binds to an erythropoietin receptor, and may be the same as or different from each other.

It is a further aspect of the present invention to provide the peptide molecule as described above, wherein the cyclic peptide is a cyclic peptide having a cyclic structure formed by a disulfide bond, containing an amino acid sequence selected from the following (j) to (n):

(j) (SEQ ID NO: 65) GGLYACHMGPMTWVCQPLRG;

(k) (SEQ ID NO: 66) CISWNEFNSPNWRFITC;

(l) a peptide in which one or two amino acid residues other than a cysteine residue are substituted, deleted, or added in the amino acid sequence of (j) or (k), and which binds to an erythropoietin receptor;

(m) a peptide which is composed of an amino acid sequence having 90% or more sequence identity with either the amino acid sequence of (j) or (k), but having a cysteine residue at the same position in (j) or (k), and which binds to an erythropoietin receptor; and (n) a peptide in which at least one amino acid other than the cysteine residue in any of the amino acid sequences (j) to (m) is modified (the amino acid modification is phosphorylation, methylation, acetylation, adenylylation, ADP-ribosylation, or glycosylation).

It is a further aspect of the present invention to provide the peptide molecule as described above, wherein the first physiologically active peptide portion and the second physiologically active peptide portion are each composed of a physiologically active peptide that binds to a thrombopoietin receptor, and may be the same as or different from each other.

It is a further aspect of the present invention to provide the peptide molecule as described above, wherein the physiologically active peptide contains an amino acid sequence selected from the following (o) to (u):

(o) (SEQ ID NO: 67) IEGPTLRQWLAARA;

(p) (SEQ ID NO: 68) GGCADGPTLREWISFCGG;

(q) (SEQ ID NO: 69) GGCTLREWLHGGFCGG;

(r) (SEQ ID NO: 70) LAIEGPTLRQWLHGNGRDT;

(s) a peptide in which one or two amino acid residues other than a cysteine residue are substituted, deleted, or added in any of the amino acid sequences (o) to (r), and which binds to a thrombopoietin receptor;

(t) a peptide which is composed of an amino acid sequence having 90% or more sequence identity with any of the amino acid sequences (o) to (r), but having a cysteine residue at the same position in (p) or (q) when based on (p) or (q), and which binds to a thrombopoietin receptor; and (u) a peptide in which at least one amino acid other than the cysteine residue in any of the amino acid sequences (o) to (t) is modified (the amino acid modification is phosphorylation, methylation, acetylation, adenylylation, ADP-ribosylation, or glycosylation).

It is a further aspect of the present invention to provide the peptide molecule as described above, further comprising: a functional modification portion at a position not adjacent to the linker portion (II).

It is a further aspect of the present invention to provide the peptide molecule as described above, wherein the linker portion (II) is a first linker portion, and the peptide molecule further comprising:

a second linker portion on the opposite side of the second physiologically active peptide portion from the first linker portion; and a third physiologically active peptide portion located on the opposite side of the second linker portion from the second physiologically active peptide portion, wherein the third physiologically active peptide portion may be the same as or different from the first physiologically active peptide portion and/or second physiologically active peptide portion, and the second linker portion is composed of 49 or less amino acid residues, and at least 90% of the amino acid sequence thereof is composed of amino acid residues selected from alanine (A), proline (P), and serine (S), which may be the same as or different from the first linker portion.

It is a further aspect of the present invention to provide the peptide molecule as described above, wherein the linker portion (II) repeatedly contains two or more amino acid sequences selected from the group consisting of AP, AAP, AS, ASP, and ASS, and if a second linker portion is present, the second linker portion repeatedly contains two or more amino acid sequences selected from the group consisting of AP, AAP, AS, ASP, and ASS.

It is a further aspect of the present invention to provide a method for producing a peptide molecule, comprising the steps of: producing the peptide molecule by expressing a polynucleotide in a host cell containing the polynucleotide encoding the peptide molecule or by expressing a polynucleotide encoding the peptide molecule in a cell-free expression system, wherein the peptide molecule contains (I) a first physiologically active peptide portion, (II) a linker portion composed of an amino acid residue, and (III) a second physiologically active peptide portion and/or an additional amino acid sequence composed of at least one amino acid residue, located on the opposite side of the linker portion from the first physiologically active peptide portion, the first physiologically active peptide portion and the second physiologically active peptide portion each have a molecular weight of 10,000 or less and are composed of 50 or less amino acid residues, and may be the same as or different from each other, and the additional amino acid sequence has a molecular weight of 10,000 or less and is composed of 50 or less amino acid residues.

It is a further aspect of the present invention to provide the production method as described above, wherein the first physiologically active peptide portion constitutes a cyclic peptide and/or the second physiologically active peptide portion constitutes a cyclic peptide.

It is a further aspect of the present invention to provide a method for producing a peptide molecule, comprising the steps of: producing the peptide molecule by expressing a polynucleotide in a host cell containing the polynucleotide encoding the peptide molecule or by expressing a polynucleotide encoding the peptide molecule in a cell-free expression system, wherein the peptide molecule contains (I) a first physiologically active peptide portion constituting a cyclic peptide, (II) a linker portion composed of an amino acid residue, and (III) a second physiologically active peptide portion and/or an additional amino acid sequence composed of at least one amino acid residue, located on the opposite side of the linker portion from the first physiologically active peptide portion, the first physiologically active peptide portion and the second physiologically active peptide portion may be the same as or different from each other, and the additional amino acid sequence has a molecular weight of 10,000 or less and is composed of 50 or less amino acid residues.

It is a further aspect of the present invention to provide the production method as described above, wherein the peptide molecule contains the second physiologically active peptide portion, and the second physiologically active peptide portion constitutes a cyclic peptide.

It is a further aspect of the present invention to provide the production method as described above, wherein the linker portion has a molecular weight of 10,000 or less and is composed of 50 or less amino acid residues.

It is a further aspect of the present invention to provide the production method as described above, wherein the linker portion is a linker portion having a molecular weight of 10,000 or less and composed of 49 or less amino acid residues, and at least 90% of the amino acid sequence thereof is composed of amino acid residues selected from alanine (A), proline (P), and serine (S).

It is a further aspect of the present invention to provide the production method as described above, wherein the linker portion repeatedly contains two or more amino acid sequences selected from the group consisting of AP, AAP, AS, ASP, and ASS.

According to an embodiment as described herein, it is possible to produce a peptide molecule such as a dimer peptide easily and inexpensively as compared with the conventional chemical synthesis methods.

According to an embodiment as described herein, it is possible to efficiently synthesize a dimer peptide such that the C-terminus of the first peptide binds to a linker and the N-terminus of the second peptide binds to a linker.

According to an embodiment as described herein, it is possible to provide a dimer peptide having good activity.

BRIEF DESCRIPTION OF DRAWINGS

FIG. 11 is a diagram showing each array of Proteome Profiler Human Phospho-RTK Array Kit (R&D Systems).

FIG. 45 shows the results of SDS-polyacrylamide electrophoresis showing the secretory expression of the heterodimer peptide (VEGFR_D2-PAS) in *C. glutamicum*. Lane 1 is a marker (XL-Ladder Broad, APRO science), lanes 2 and 3 are for the culture supernatant and for the entire culture solution containing cells, respectively, when pPK4_CspBss-VEGFR_D2-PAS16 is used, lanes 4 and 5 are for the supernatant fraction and for the entire mixture containing cells, respectively, after adding Tris-HCl to the precipitate fraction containing cells when pPK4_CspBss-VEGFR_D2-PAS16 is used, lanes 6 and 7 are for the supernatant fraction and for the entire mixture containing cells, respectively, after adding the urea treatment solution (0.5 M urea) to the precipitate fraction containing cells when pPK4_CspBss-VEGFR_D2-PAS16 is used, and lanes 8 and 9 are for the supernatant fraction and for the entire mixture containing cells, respectively, after adding the urea treatment solution (1.0 M urea) to the precipitate fraction containing cells when pPK4_CspBss-VEGFR_D2-PAS16 is used.

DETAILED DESCRIPTION OF EXEMPLARY EMBODIMENTS

Figure 1:
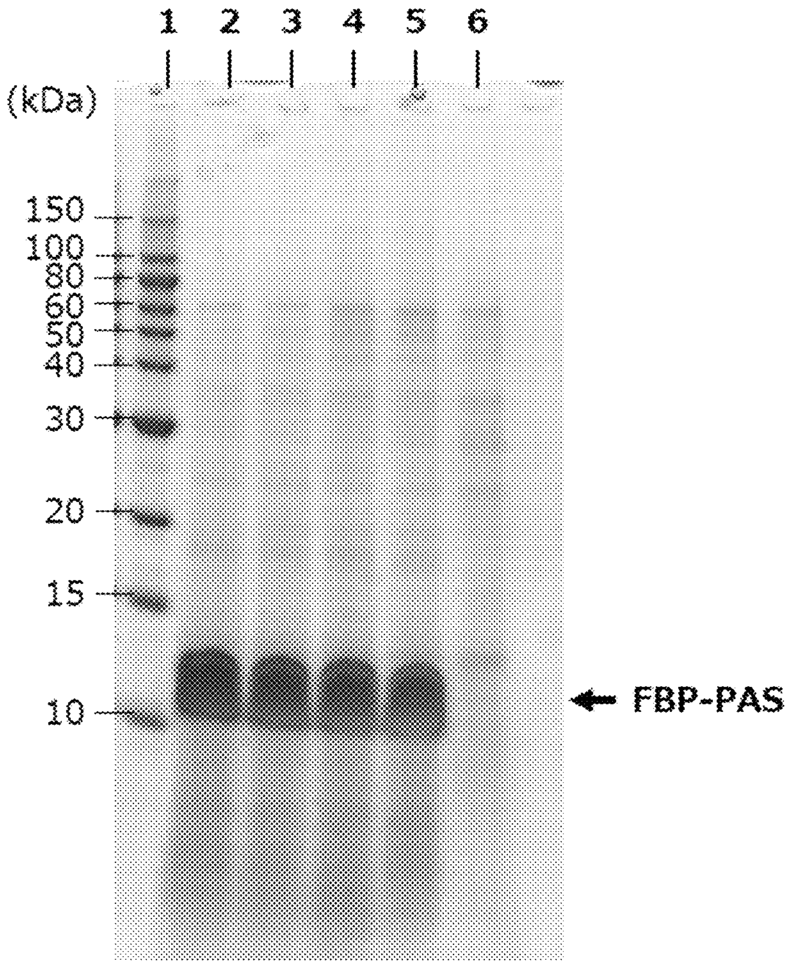
FIG. 1 shows the results of SDS-polyacrylamide electrophoresis showing the secretory expression of the dimer peptide (FBP-PAS) in *C. glutamicum*. Lane 1 is a marker (XL-Ladder Broad, APRO science), lanes 2 to 5 are ones using pPK10_TorAss-FBP-PAS, and lane 6 is one using pPK10 (empty vector).

An embodiment as described herein relates to a peptide molecule. Such a peptide molecule is a peptide molecule comprising:

(I) a first physiologically active peptide portion;

(II) a linker portion composed of 49 or less amino acid residues; and (III) a second physiologically active peptide portion located on the opposite side of the linker portion from the first physiologically active peptide portion, wherein the first physiologically active peptide portion and the second physiologically active peptide portion may be the same as or different from each other, and at least 90% of an amino acid sequence of the linker portion is composed of amino acid residues selected from alanine (A), proline (P), and serine (S).

In one embodiment as described herein, the peptide molecule may contain a first physiologically active peptide portion on the N-terminus side of the linker portion and a second physiologically active peptide portion on the C-terminus side of the linker portion, or may contain a first physiologically active peptide portion on the C-terminus side of the linker portion and a second physiologically active peptide portion on the N-terminus side of the linker portion. Further, in one embodiment as described herein, the peptide molecule may contain an arbitrary amino acid sequence as long as it does not inhibit the functions of the first physiologically active peptide and second physiologically active peptide on the N-terminus side and/or the C-terminus side of the first physiologically active peptide portion and/or second physiologically active peptide portion, or in the space with the linker portion. As such an arbitrary amino acid sequence, for example, a sequence useful for enhancing the expression or secretion of peptide molecules in a host cell, or a sequence for simply adjusting the length (such as 1, 2, 3, or 1 to 5 Gly) may be used.

In the peptide molecule, each amino acid may be an L-amino acid or a D-amino acid, and may be a natural type or an unnatural type. Further, in the peptide molecule, each amino acid includes an α-, β-, or γ-amino acid, and an α-amino acid is a particular example.

In one embodiment as described herein, the peptide molecule may be configured to have two or more linker portions, such as "first physiologically active peptide portion"-"linker portion"-"second physiologically active peptide portion"-"linker portion"–"arbitrary sequence" from the N-terminus side. Here, the arbitrary sequence may be a third physiologically active peptide portion (may be the same as or different from the first physiologically active peptide portion and/or second physiologically active peptide portion), or may be an additional amino acid sequence composed of at least one amino acid residue. Examples of the additional amino acid sequence include a sequence having a molecular weight of 10,000 or less and composed of 50 or less amino acid residues. Such additional amino acid sequences include enzyme identification sequences such as SortaseA identification signal and Butelase identification signal, tag sequences such as FLAG tag, PA tag, and histidine tag, reactive amino acids such as lysine, cysteine, glutamic acid, and aspartic acid, or sequences containing the reactive amino acids.

In one embodiment of the peptide molecule as described herein, the linker portion (II) is a first linker portion, and the peptide molecule further comprising:

a second linker portion on the opposite side of the second physiologically active peptide portion from the first linker portion; and a third physiologically active peptide portion located on the opposite side of the second linker portion from the second physiologically active peptide portion, wherein the third physiologically active peptide portion may be the same as or different from the first physiologically active peptide portion and/or second physiologically active peptide portion, and the second linker portion is composed of 49 or less amino acid residues, and at least 90% of the amino acid sequence thereof is composed of amino acid residues selected from alanine (A), proline (P), and serine (S), which may be the same as or different from the first linker portion.

As used in the present specification, the term "physiologically active peptide" means a peptide that can exhibit physiological activity in a living body such as a human or an animal. Here, the "physiological activity" is a property that acts on the physiological functions of a living body, and may include both a property that enhances physiological functions and a property that suppresses physiological functions.

In the present specification, the "physiologically active peptide" includes not only a peptide itself that can exhibit physiological activity in a living body such as a human or an animal, but also a peptide that exhibits physiological activity by modification in vivo (that is, a precursor substance), and the "physiologically active peptide" may be composed of a naturally occurring amino acid sequence or may be composed of an unnaturally occurring amino acid sequence. Examples of the "physiologically active peptide" include, but are not limited to, a target-binding peptide, a target-inhibiting peptide, a target-activating peptide, and an enzyme-recognizing peptide.

As used in the present specification, the term "target-binding peptide" means a physiologically active peptide that binds to a target (mainly a protein) such as a receptor, enzyme, ion channel, or transporter (including those that start exhibiting binding property to a target or physiological activity by modification in vivo). Examples of the target-binding peptide include, but are not limited to, an albumin-binding cyclic peptide and an organ delivery cyclic peptide.

As used in the present specification, the term "target-inhibiting peptide" means a physiologically active peptide that has an action of inhibiting the biological reactions caused by activation of a target (mainly a protein) such as a receptor, enzyme, ion channel, or transporter or the physiological functions in which the target is involved. The "target-inhibiting peptide" includes not only a physiologically active peptide that, by binding to a target itself, inhibits the biological reactions caused by activation of the target or the physiological functions in which the target is involved, but also a physiologically active peptide that inhibits the biological reactions caused by activation of the target or the physiological functions in which the target is involved based on binding to a factor that binds to the target to alter the properties or shape of that factor.

As used in the present specification, the term "target-activating peptide" means a physiologically active peptide that has an action of activating a target (mainly a protein) such as a receptor, enzyme, ion channel, or transporter to cause biological reactions or an action of enhancing the physiological functions in which the target is involved (including those that start exhibiting activating effects or enhancing effects by modification in vivo). The "target-activating peptide" includes not only a physiologically active peptide that, by binding to a target itself, activates the target to cause biological reactions or enhances the physiological functions in which the target is involved, but also a physiologically active peptide that activates the target to cause biological reactions or enhances the physiological functions in which the target is involved based on binding to a factor to alter the properties or shape of that factor and making the factor start binding to the target.

Targets in the "target-binding peptide", "target-inhibiting peptide", and "target-activating peptide" can include receptors that are activated by dimerization, such as proliferation factor receptors, growth factor receptors, and cytokine receptors.

As used in the present specification, the term "enzyme-recognizing peptide" means a physiologically active peptide that is recognized as a substrate by enzymes (including those that start being recognized as a substrate by enzymes or start exhibiting physiological activity by modification in vivo).

In one embodiment of the peptide molecule, the molecular weights of the first physiologically active peptide portion and second physiologically active peptide portion are not particularly limited, but may be, for example, 250 or more, 500 or more, 800 or more, or 1,000 or more, and may be 10,000 or less, 9,000 or less, 8,000 or less, 7,000 or less, 6,000 or less, 5,000 or less, or 4,000 or less.

In one embodiment of the peptide molecule, the lengths of the first physiologically active peptide portion and second physiologically active peptide portion are not particularly limited, but may be, for example, each independently one composed of 3 or more, 6 or more, 10 or more, or 12 or more amino acid residues, and may be one composed of 50 or less, 45 or less, 40 or less, 35 or less, 30 or less, 25 or less, or 20 or less amino acid residues.

In one embodiment of the peptide molecule, the first physiologically active peptide portion and/or second physiologically active peptide portion may be a straight chain or a branched chain, and may constitute a cyclic peptide. The cyclic peptide in the first physiologically active peptide portion and/or second physiologically active peptide portion is not particularly limited in what kind of binding mode it has a cyclic structure, and it can form a cyclic structure, for example, by a disulfide bond between two cysteine residues, by a thioether bond (bond between a thiol group and a haloalkyl group), or by a bond of 1,2,3-triazole (bond between an azido group and an alkyne group). Note that the disulfide bond may be formed spontaneously inside or outside cells by culturing the cells, or by an enzymatic reaction by the cells.

In one embodiment of the peptide molecule, the first physiologically active peptide portion may contain two cysteine residues, or at least two cysteine residues.

In one embodiment of the peptide molecule, the second physiologically active peptide portion may contain two cysteine residues, or at least two cysteine residues.

In one embodiment of the peptide molecule, the first physiologically active peptide portion constitutes a cyclic peptide.

In one embodiment of the peptide molecule, the second physiologically active peptide portion constitutes a cyclic peptide.

When the peptide molecule has a cyclic peptide in the first physiologically active peptide portion and/or second physiologically active peptide portion, examples of the cyclic peptide include, but are not particularly limited to, FGFR binding peptide, c-Met (HGFR) binding peptide, erythropoietin receptor binding peptide, thrombopoietin receptor binding peptide, albumin binding peptide, EGFR binding peptide, VEGFR binding peptide, PDGFR binding peptide, Axl binding peptide, PDGFR binding peptide, SCFR binding peptide, Flt-3 binding peptide, c-Ret binding peptide, ROR binding peptide, Tie binding peptide, NGFR binding peptide, Insulin receptor binding peptide, EphR binding peptide, Alk binding peptide, DDR binding peptide, TGFBR binding peptide, Activin receptor binding peptide, BMP receptor binding peptide, interleukin receptor binding peptide, T-cell receptor binding peptide, transferrin receptor binding peptide, lipoprotein receptor binding peptide, ubiquitin ligase binding peptide, antibody binding peptide, complement binding peptide, GPCR binding peptide, ion channel binding peptide, virus binding peptide, and the like.

In one embodiment of the peptide molecule, the first physiologically active peptide portion and the second physiologically active peptide portion each constitute a cyclic peptide that binds to a c-Met (also referred to simply as Met) protein and may be the same as or different from each other. The cyclic peptide that binds to the c-Met protein includes, but is not limited to, a cyclic peptide having a cyclic structure formed by a disulfide bond, containing or composed of an amino acid sequence selected from the following (a) to (i):

```
(a)
                                  (SEQ ID NO: 1)
CYRQFNRRTHEVWNLDC;

(b)
                                  (SEQ ID NO: 2)
CRQFNRRTHEVWNLDC;

(c)
                                  (SEQ ID NO: 3)
CYWYYAWDQTYKAFPC;

(d)
                                  (SEQ ID NO: 4)
CWYYAWDQTYKAFPC;

(e)
                                  (SEQ ID NO: 5)
CYISWNEFNSPNWRFITC;

(f)
                                  (SEQ ID NO: 6)
CISWNEFNSPNWRFITC;
```

(g) a peptide in which one or two amino acid residues other than a cysteine residue are substituted, deleted, or added in any of the amino acid sequences (a) to (f), and which binds to a c-Met protein;

(h) a peptide which is composed of an amino acid sequence having 90% or more sequence identity with any of the amino acid sequences (a) to (f), but having cysteine residues at both ends, and which binds to a c-Met protein. For example, the sequence identity may be 92% or higher, 95% or higher, or 98% or higher. Note that in the present specification, the amino acid sequence homology may be calculated by using a known analysis tool, and may be calculated, for example, by using the National Center for Biotechnology Information (NCBI) homology algorithm BLAST (Basic local alignment search tool). In addition, the default (initial setting) parameters in the analysis tool may be used to calculate the amino acid sequence homology.

(i) A peptide in which at least one amino acid other than the cysteine residues at both ends in any of the amino acid sequences (a) to (h) is modified. Here, the amino acid modification is phosphorylation, methylation, acetylation, adenylylation, ADP-ribosylation, or glycosylation.

Note that it is known Met is an HGF receptor, a tyrosine kinase type receptor, and a cyclic peptide that binds to such Met (HGFR) functions as a Met (HGFR) agonist by dimerization.

As used in the present specification, in the expression "substituted, deleted, or added", substitution means substitution with a known amino acid, including a conservative amino acid substitution. A "conservative amino acid substitution" is a substitution in which an amino acid residue is substituted with another amino acid residue having a side chain R group with similar chemical properties (for example, charge or hydrophobicity). Examples of the amino acid groups having side chains with similar chemical properties include glycine, alanine, valine, leucine, and isoleucine having aliphatic side chains, serine and threonine having aliphatic hydroxyl side chains, asparagine and glutamine having amide-containing side chains, phenylalanine, tyrosine, and tryptophan having aromatic side chains, lysine, arginine, and histidine having basic side chains, and aspartic acid and glutamic acid having acidic side chains. Each amino acid introduced by substitution may be an L-amino acid or a D-amino acid, and may be a natural type amino acid or an unnatural type amino acid, or an amino acid that constitutes a protein in humans and animals.

As used in the present specification, in the expression "substituted, deleted, or added", addition means that a known amino acid is added to the terminus of the amino acid sequence, or that a known amino acid is inserted between amino acid residues of the amino acid sequence. Each amino acid introduced by addition may be an L-amino acid or a D-amino acid, and may be a natural type amino acid or an unnatural type amino acid, or an amino acid that constitutes a protein in humans and animals.

In one embodiment of the peptide molecule, the first physiologically active peptide portion and the second physiologically active peptide portion each constitute a cyclic peptide that binds to an erythropoietin receptor and may be the same as or different from each other. The cyclic peptides that binds to an erythropoietin receptor includes, but is not limited to, a cyclic peptide having a cyclic structure formed by a disulfide bond, containing or composed of an amino acid sequence selected from the following (j) to (n):

```
(j)
                                   (SEQ ID NO: 65)
GGLYACHMGPMTWVCQPLRG;

(k)
                                   (SEQ ID NO: 66)
CISWNEFNSPNWRFITC;
```

(l) a peptide in which one or two amino acid residues other than a cysteine residue are substituted, deleted, or added in the amino acid sequence of (j) or (k), and which binds to an erythropoietin receptor;

(m) a peptide which is composed of an amino acid sequence having 90% or more sequence identity with either the amino acid sequence of (j) or (k), but having a cysteine residue at the same position in (j) or (k), and which binds to an erythropoietin receptor. For example, the sequence identity may be 92% or higher, 95% or higher, or 98% or higher.

(n) a peptide in which at least one amino acid other than the cysteine residue in any of the amino acid sequences (j) to (m) is modified. Here, the amino acid modification is phosphorylation, methylation, acetylation, adenylylation, ADP-ribosylation, or glycosylation.

In one embodiment of the peptide molecule, the first physiologically active peptide portion and the second physiologically active peptide portion are each composed of a physiologically active peptide that binds to a thrombopoietin receptor and may be the same as or different from each other. The physiologically active peptide that binds to a thrombopoietin receptor includes, but is not limited to, a peptide containing or composed of an amino acid sequence selected from the following (o) to (u):

```
(o)
                                   (SEQ ID NO: 67)
IEGPTLRQWLAARA;

(p)
                                   (SEQ ID NO: 68)
GGCADGPTLREWISFCGG;

(q)
                                   (SEQ ID NO: 69)
GGCTLREWLHGGFCGG;

(r)
                                   (SEQ ID NO: 70)
LAIEGPTLRQWLHGNGRDT;
```

(s) a peptide in which one or two amino acid residues other than a cysteine residue are substituted, deleted, or added in any of the amino acid sequences (o) to (r), and which binds to a thrombopoietin receptor;

(t) a peptide which is composed of an amino acid sequence having 90% or more sequence identity with any of the amino acid sequences (o) to (r), but having a cysteine residue at the same position in (p) or (q) when based on (p) or (q), and which binds to a thrombopoietin receptor. For example, the sequence identity may be 92% or higher, 95% or higher, or 98% or higher.

(u) a peptide in which at least one amino acid other than the cysteine residue in any of the amino acid sequences (o) to (t) is modified. Here, the amino acid modification is phosphorylation, methylation, acetylation, adenylylation, ADP-ribosylation, or glycosylation.

The peptides set forth in SEQ ID NO: 68 and SEQ ID NO: 69 are each a cyclic peptide having a cyclic structure formed by a disulfide bond.

In one embodiment of the peptide molecule, the first physiologically active peptide portion and the second physiologically active peptide portion each constitute a cyclic peptide that binds to a vascular endothelial growth factor receptor (VEGFR) and may be the same or different from each other. The cyclic peptide that binds to VEGFR includes, but is not limited to, a cyclic peptide having a cyclic structure formed by a disulfide bond, containing or composed of an amino acid sequence selected from the following (aa) to eff):

```
(aa)
                                  (SEQ ID NO: 71)
AGPTWCEDDWYYCWLFGT;

(bb)
                                  (SEQ ID NO: 72)
VCWEDSWGGEVCWLFGT;

(cc)
                                  (SEQ ID NO: 73)
VCWEDSWGGEVCFRYDP;
```

(dd) a peptide in which one or two amino acid residues other than a cysteine residue are substituted, deleted, or added in any of the amino acid sequences (aa) to (cc), and which binds to VEGFR.

(ee) a peptide which is composed of an amino acid sequence having 90% or more sequence identity with any of the amino acid sequences of (aa) to (cc), but having a cysteine residue at the same position in (aa) or (cc), and which binds to VEGFR. For example, the sequence identity may be 92% or higher, 95% or higher, or 98% or higher.

(f) a peptide in which at least one amino acid other than the cysteine residue in any of the amino acid sequences (aa) to (ee) is modified. Here, the amino acid modification is phosphorylation, methylation, acetylation, adenylylation, ADP-ribosylation, or glycosylation.

In one embodiment of the peptide molecule, the linker portion may have a molecular weight of 10,000 or less.

In one embodiment of the peptide molecule, for the linker portion, at least 90%, at least 95%, or 100% of the amino acid sequence thereof may be composed of amino acid residues selected from alanine (A), proline (P) and serine (S). The proline residues may constitute more than 4% and less than 40% in the amino acid sequence of the linker portion. For example, in the amino acid sequence of the linker portion, the proline residues may constitute more than about 4%, more than about 5%, more than about 6%, more than about 8%, more than about 10%, more than about 15%, or more than about 20%, and may constitute less than about 40% or less than about 35%. Further, the alanine residues and the serine residue may each independently constitute more than about 4%, more than about 10%, or more than about 20%, and may constitute less than about 50%.

As used in the present specification, the term "about X %" is not limited to the number X, but also includes values of additional 10% to 20% more residues, or 10% to 20% less residues. For example, the term "about 10%" also relates to 11% or 12% and 9% or 8%.

In the amino acid sequence of the linker portion, amino acid residues different from alanine, serine, and proline may be selected from, for example, the group consisting of Arg, Asn, Asp, Cys, Gln, Glu, Gly, His, Ile, Leu, Lys, Met, Phe, Thr, Trp, Tyr, and Val as well as ones obtained by modifying these amino acids and ones obtained by adding functional groups or protecting groups to these amino acids (such as chloroacetylated amino acids, homocysteine, mercapto norvaline, mercapto norleucine, 2-amino-7-mercaptoheptanoic acid, and 2-amino-8-mercaptooctanoic acid, as well as amino acids whose protecting groups have been deprotected after the SH groups of these amino acids have been protected once, propargylglycine, homopropargylglycine, 2-amino-6-heptynoic acid, 2-amino-7-octynoic acid, 2-amino-8-nonynoic acid, 4-pentynoylated and 5-hexynoylated amino acids, azidoalanine, 2-amino-4-azidobutanoic acid, azidoptonorvaline, azidonorleucine, 2-amino-7-azidoheptanoic acid, 2-amino-8-azidooctanoic acid, azidoacetylated and 3-azidopentanoylated amino acids, N-(4-aminomethyl-benzoyl)-phenylalanine (AMBF), 4-3-aminomethyltyrosine, 5-hydroxytryptophan (WOH), N-3-chloromethylbenzoyl-L-phenylalanine, N-3-chloromethylbenzoyl-L-tyrosine, N-3-chloromethylbenzoyl-L-tryptophane). Further, each amino acid may be an L-amino acid or a D-amino acid. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the peptide molecule, for the linker portion, at least 90%, at least 95%, or 100% of the amino acid sequence thereof may be composed of amino acid residues selected from alanine (A) and proline (P). In this case, proline residues may constitute more than 10% and less than 75% in the amino acid sequence of the linker portion. For example, in the amino acid sequence of the linker portion, the proline residues may constitute more than about 10%, more than about 12%, more than about 14%, more than about 18%, more than about 20%, more than about 22%, more than about 23%, more than about 24%, or more than about 25%, and may constitute less than about 75%, less than about 70%, less than about 65%, less than about 60%, less than about 55%, less than about 50%, less than about 48%, less than about 46%, less than about 44%, less than about 42%, less than about 41%, less than about 40%, less than about 39%, less than about 38%, less than about 37%, less than about 36%, or less than about 35%. Further, the alanine residues may constitute more than about 25%, more than about 30%, more than about 35%, more than about 40%, more than about 45%, more than about 50%, more than about 52%, more than about 54%, more than about 56%, more than about 58%, more than about 59%, more than about 60%, more than about 61%, more than about 62%, more than about 63%, more than about 64%, or more than about 65%, and may constitute less than about 90%, less than about 88%, less than about 86%, less than about 84%, less than about 82%, less than about 80%, less than about 79%, less than about 78%, less than about 77%, less than about 76%, or less than about 75%.

In the amino acid sequence of the linker portion, the amino acid residues different from alanine, serine and proline may be selected from the group consisting of Arg, Asn, Asp, Cys, Gln, Glu, Gly, His, Ile, Leu, Lys, Met, Phe, Thr, Trp, Tyr, and Val. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the peptide molecule, the linker portion contains multiple amino acid repeats, the amino acid repeats are composed of alanine (A), proline (P), and serine (S), and in the amino acid repeats, the number of consecutive identical amino acid residues may be 6 residues or less, 5 residues or less, 4 residues or less, or 3 residues or less.

In one embodiment of the peptide molecule, the linker portion contains multiple amino acid repeats, the amino acid repeats are composed of alanine (A) and proline (P), and in the amino acid repeats, the number of consecutive identical amino acid residues may be 6 residues or less, 5 residues or less, 4 residues or less, or 3 residues or less.

In one embodiment of the peptide molecule, the linker portion may repeatedly contain two or more amino acid sequences selected from the group consisting of AP, AAP, AS, ASP, and ASS.

In one embodiment of the peptide molecule, the linker portion may be composed of, for example, 5 or more, 6 or more, 7 or more, or 8 or more amino acid residues.

In one embodiment of the peptide molecule, specific examples of the linker portion include, but are not limited to, those containing any of the following amino acid sequences and those consisting of any of the following amino acid sequences: AAPAAPAP (SEQ ID NO: 74), AAPAAPAPAAPAAPAP (SEQ ID NO: 75), AAPAAPAPAAPAAPAPAAPAAPAPAAPAAPAPAAPAAPAPAAPAAPAPA (SEQ ID NO: 76), SAPSPSSAPASASAPASPASASASASPASSPASASSASPAASSASPASS (SEQ ID NO: 77), AAPAAPAPAAPAAPAPAAPA (SEQ ID NO: 7), AAPAAPAPAAPAAPAPAAPAAP (SEQ ID NO: 8), AAPAAPAPAAPAAP (SEQ ID NO: 9), AAPAAAPAPAAPAAPAPAAP (SEQ ID NO 10), AAAPAAAPAAAPAAAPAAAP (SEQ ID NO 11), AAPAAPAAPAAPAAPAAPAAP (SEQ ID NO 12), APAAAPAPAAAPAPAAAPAPAAAP (SEQ ID NO 13), AAAPAAPAAPPAAAAPAAPAAPPA (SEQ ID NO 14), and APAPAPAPAPAPAPAPAPAP (SEQ ID NO 15), ASPAAPAPASPAAPAPSAPA (SEQ ID NO 16), AAPASPAPAAPSAPAPAAPS (SEQ ID NO 17), APSSPSPSAPSSPSPASPSS (SEQ ID NO 18), SAPSSPSPSAPSSPSPASPS (SEQ ID NO 19), SSPSAPSPSSPASPSPSSPA (SEQ ID NO 20), AASPAAPSAPPAAASPAAPSAPPA (SEQ ID NO 21), and ASAAAPAAASAAASAPSAAA (SEQ ID NO 22), as well as circular permutation mutant sequences thereof.

Taking AAPAAPAPAAPAAPAPAAPA (SEQ ID NO: 7) as an example, a circular permutation mutant sequence may be easily prepared, for example, by removing the first alanine of the above sequence and adding another alanine to the terminus of the above sequence. Such a circular permutation mutant sequence for SEQ ID NO: 7 is APAAPAPAAPAAPAPAAPAA (SEQ ID NO: 23). Furthermore, non-limited examples of the circular permutation mutant sequence with circularly permutated amino acid residues for SEQ ID NO: 7 include the following.

(SEQ ID NO: 24)
PAAPAPAAPAAPAPAAPAAA, (SEQ ID NO: 25)
AAPAPAAPAAPAPAAPAAAP, (SEQ ID NO: 26)
APAPAAPAAPAPAAPAAAPA, (SEQ ID NO: 27)
PAPAAPAAPAPAAPAAAPAA, (SEQ ID NO: 28)
APAAPAAPAPAAPAAAPAAP, (SEQ ID NO: 29)
PAAPAAPAPAAPAAAPAAPA,

-continued (SEQ ID NO: 30)
AAPAAPAPAAPAAAPAAPAP, (SEQ ID NO: 31)
APAAPAPAAPAAAPAAPAPA,
and (SEQ ID NO: 32)
PAAPAPAAPAAAPAAPAPAA.

In one embodiment of the peptide molecule, the peptide molecule may further contain a functional modification portion at a position not adjacent to the linker portion.

As used in the present specification, the term "functional modification portion" means a portion in a peptide molecule that imparts some function to the peptide molecule in addition to the functions of the physiologically active peptide, and can be composed of an amino acid sequence. Examples of the functional modification portion include, but are not limited to, a stabilizing sequence, a water-solubility improving sequence, an enzyme identification sequence, a tag sequence, a target binding sequence, and the like.

Specific examples of the stabilizing sequence or water-solubility improving sequence include, but are not limited to, a random coil polypeptide containing an amino acid sequence composed of at least 50 proline and alanine amino acid residues as described in Published Japanese Translation of PCT International Application No. 2013-531480 (cited herein by reference to the content of that document as constituting part of the present specification), a random coil polypeptide containing an amino acid sequence composed of proline, alanine, and serine amino acid residues as described in Published Japanese Translation of PCT International Application No. 2010-531139 (cited herein by reference to the content of that document as constituting part of the present specification), and the like.

Specific examples of the enzyme identification sequence include, but are not limited to, SortaseA identification signal, Butelase identification signal, Transglutaminase identification signal, and the like.

Specific examples of the tag sequence include, but are not limited to, FLAG tags, PA tags, histidine tags, and the like.

Specific examples of the target binding sequence include, but are not limited to, small molecule antibodies such as VHH and scFv.

In one embodiment of the peptide molecule, the functional modification portion may be composed of, for example, 3 or more, 6 or more, 10 or more, or 12 or more amino acid residues, and may be composed of 1000 or less, 500 or less, 300 or less, or 150 or less amino acid residues.

An embodiment as described herein relates to a method for producing a peptide molecule. The peptide molecule produced by the production method may contain (I) a first physiologically active peptide portion, (II) a linker portion composed of an amino acid residue, and (III) a second physiologically active peptide portion or an additional amino acid sequence composed of at least one amino acid residue, located on the opposite side of the linker portion from the first physiologically active peptide portion.

In one embodiment of the production method, the peptide molecule may have, but is not limited to, a structure "first physiologically active peptide portion"–"linker portion"-"second physiologically active peptide portion" from the N-terminus side or a structure "first physiologically active peptide portion"-"linker portion"-"additional amino acid sequence" from the N-terminus side, for example. In addition, the peptide molecule may be configured to have two or more linker portions, such as "first physiologically active peptide portion"-"linker portion"-"second physiologically active peptide portion"-"linker portion"-"arbitrary sequence" from the N-terminus side (so as to link three or more additional amino acid sequences in tandem, composed of the first physiologically active peptide portion as well as the second physiologically active peptide portion and/or at least one amino acid residue, via two or more linker portions). Here, the arbitrary sequence may be a physiologically active peptide portion (may be the same as the first physiologically active peptide portion and/or second physiologically active peptide portion), or may be an additional amino acid sequence composed of at least one amino acid residue.

A specific example of such a produced peptide molecule may be the above-mentioned peptide molecule comprising:

(I) a first physiologically active peptide portion;

(II) a linker portion composed of 49 or less amino acid residues; and (III) a second physiologically active peptide portion located on the opposite side of the linker portion from the first physiologically active peptide portion, wherein the first physiologically active peptide portion and the second physiologically active peptide portion may be the same as or different from each other, and at least 90% of an amino acid sequence of the linker portion is composed of amino acid residues selected from alanine (A), proline (P), and serine (S).

In the peptide molecule produced by the production method, the first physiologically active peptide portion and second physiologically active peptide portion each may have a molecular weight of 10,000 or less and may be composed of 50 or less amino acid residues, and may be the same as or different from each other. Examples of the first physiologically active peptide portion and/or second physiologically active peptide portion include, but are not limited to, FGFR binding peptide, c-Met (HGFR) binding peptide, erythropoietin receptor binding peptide, thrombopoietin receptor binding peptide, albumin binding peptide, EGFR binding peptide, VEGFR binding peptide, PDGFR binding peptide, Axl binding peptide, PDGFR binding peptide, SCFR binding peptide, Flt-3 binding peptide, c-Ret binding peptide, ROR binding peptide, Tie binding peptide, NGFR binding peptide, Insulin receptor binding peptide, EphR binding peptide, Alk binding peptide, DDR binding peptide, TGFBR binding peptide, Activin receptor binding peptide, BMP receptor binding peptide, interleukin receptor binding peptide, T-cell receptor binding peptide, transferrin receptor binding peptide, lipoprotein receptor binding peptide, ubiquitin ligase binding peptide, antibody binding peptide, complement binding peptide, GPCR binding peptide, ion channel binding peptide, virus binding peptide, and the like.

In one embodiment of the production method, the molecular weights of the first physiologically active peptide portion and second physiologically active peptide portion may be, for example, 9,000 or less, 8,000 or less, 7,000 or less, 6,000 or less, 5,000 or less, or 4,000 or less, and 250 or more, 500 or more, 800 or more, or 1,000 or more.

In one embodiment of the production method, the lengths of the first physiologically active peptide portion and second physiologically active peptide portion may be, for example, each independently composed of 45 or less, 40 or less, 35 or less, 30 or less, 25 or less, or 20 or less amino acid residues, and may be composed of 3 or more, 6 or more, 10 or more, or 12 or more amino acid residues.

In one embodiment of the production method, the first physiologically active peptide portion and/or second physiologically active peptide portion may be a straight chain or a branched chain, and may constitute a cyclic peptide. The cyclic peptide in the first physiologically active peptide portion and/or second physiologically active peptide portion is not particularly limited in what kind of binding mode it has a cyclic structure, and it can form a cyclic structure, for example, by a disulfide bond between two cysteine residues, by a thioether bond (bond between a thiol group and a haloalkyl group), or by a bond of 1,2,3-triazole (bond between an azido group and an alkyne group). Note that the disulfide bond may be formed spontaneously inside or outside cells by culturing the cells, or by an enzymatic reaction by the cells.

In one embodiment of the production method, the first physiologically active peptide portion may contain two cysteine residues, or at least two cysteine residues.

In one embodiment of the production method, the second physiologically active peptide portion may contain two cysteine residues, or at least two cysteine residues.

It is considered that various cyclic peptides exist, but what kind of cyclic peptide is constituted in the first physiologically active peptide portion and/or second physiologically active peptide portion is not particularly limited.

In one embodiment of the production method, when the peptide molecule is a dimer peptide, there may be one having higher physiological activity than a monomer peptide. For example, if the peptide molecule produced by the production method is one obtained by binding two FGFR-binding cyclic peptides via a linker portion, it may have higher FGFR inhibitory activity than the case of one FGFR-binding cyclic peptide.

Specific examples of the cyclic peptide include cyclic peptides that bind to c-Met (also referred to simply as Met), but the cyclic peptide is not limited to this in the peptide molecule obtained by the production method.

cyclic peptide having a cyclic structure formed by a disulfide bond, containing or composed of an amino acid sequence selected from the following (a) to (i):

(a)
(SEQ ID NO: 1)
CYRQFNRRTHEVWNLDC;

(b)
(SEQ ID NO: 2)
CRQFNRRTHEVWNLDC;

(c)
(SEQ ID NO: 3)
CYWYYAWDQTYKAFPC;

(d)
(SEQ ID NO: 4)
CWYYAWDQTYKAFPC;

(e)
(SEQ ID NO: 5)
CYISWNEFNSPNWRFITC;

(f)
(SEQ ID NO: 6)
CISWNEFNSPNWRFITC;

(g) a peptide in which one or two amino acid residues other than a cysteine residue are substituted, deleted, or added in any of the amino acid sequences (a) to (f), and which binds to a c-Met protein;

(h) a peptide which is composed of an amino acid sequence having 90% or more sequence identity with any of the amino acid sequences (a) to (f), but having cysteine residues at both ends, and which binds to a c-Met protein. For example, the sequence identity may be 92% or higher, 95% or higher, or 98% or higher. In the present specification, the amino acid sequence homology may be calculated by using a known analysis tool, and may be calculated, for example, by using the National Center for Biotechnology Information (NCBI) homology algorithm BLAST (Basic local alignment search tool). In addition, the default (initial setting) parameters in the analysis tool may be used to calculate the amino acid sequence homology.

(i) A peptide in which at least one amino acid other than the cysteine residues at both ends in any of the amino acid sequences (a) to (h) is modified. Here, the amino acid modification is phosphorylation, methylation, acetylation, adenylylation, ADP-ribosylation, or glycosylation.

Note that it is known Met is an HGF receptor, a tyrosine kinase type receptor, and a cyclic peptide that binds to such Met (HGFR) functions as a Met (HGFR) agonist by dimerization.

In one embodiment of the production method, the first physiologically active peptide portion and/or second physiologically active peptide portion of the peptide molecule produced may constitute a cyclic peptide that binds to an erythropoietin receptor. If both the first physiologically active peptide portion and the second physiologically active peptide portion constitute a cyclic peptide that binds to an erythropoietin receptor, the cyclic peptides may be the same as or different from each other. The cyclic peptide that binds to an erythropoietin receptor includes, but is not limited to, a cyclic peptide having a cyclic structure formed by a disulfide bond, containing or composed of an amino acid sequence selected from the following (j) to (n).

```
(j)
                                (SEQ ID NO: 65)
GGLYACHMGPMTWVCQPLRG;

(k)
                                (SEQ ID NO: 66)
CISWNEFNSPNWRFITC;
```

(l) a peptide in which one or two amino acid residues other than a cysteine residue are substituted, deleted, or added in the amino acid sequence of (j) or (k), and which binds to an erythropoietin receptor;

(m) a peptide which is composed of an amino acid sequence having 90% or more sequence identity with either the amino acid sequence of (j) or (k), but having a cysteine residue at the same position in (j) or (k), and which binds to an erythropoietin receptor. For example, the sequence identity may be 92% or higher, 95% or higher, or 98% or higher.

(n) A peptide in which at least one amino acid other than the cysteine residue in any of the amino acid sequences (j) to (m) is modified. Here, the amino acid modification is phosphorylation, methylation, acetylation, adenylylation, ADP-ribosylation, or glycosylation.

In one embodiment of the production method, the first physiologically active peptide portion and/or second physiologically active peptide portion of the peptide molecule produced may be composed of a physiologically active peptide that binds to a thrombopoietin receptor. If both the first physiologically active peptide portion and the second physiologically active peptide portion are composed of a physiologically active peptide that binds to a thrombopoietin receptor, the physiologically active peptides may be the same as or different from each other. The physiologically active peptide that binds to a thrombopoietin receptor includes, but is not limited to, a peptide containing or composed of an amino acid sequence selected from the following (o) to (u).

```
(o)
                                (SEQ ID NO: 67)
IEGPTLRQWLAARA;

(p)
                                (SEQ ID NO: 68)
GGCADGPTLREWISFCGG;

(q)
                                (SEQ ID NO: 69)
GGCTLREWLHGGFCGG;

(r)
                                (SEQ ID NO: 70)
LAIEGPTLRQWLHGNGRDT;
```

(s) a peptide in which one or two amino acid residues other than a cysteine residue are substituted, deleted, or added in any of the amino acid sequences (o) to (r), and which binds to a thrombopoietin receptor;

(t) a peptide which is composed of an amino acid sequence having 90% or more sequence identity with any of the amino acid sequences (o) to (r), but having a cysteine residue at the same position in (p) or (q) when based on (p) or (q), and which binds to a thrombopoietin receptor. For example, the sequence identity may be 92% or higher, 95% or higher, or 98% or higher.

(u) A peptide in which at least one amino acid other than the cysteine residue in any of the amino acid sequences (o) to (t) is modified. Here, the amino acid modification is phosphorylation, methylation, acetylation, adenylylation, ADP-ribosylation, or glycosylation.

The peptides set forth in SEQ ID NO: 68 and SEQ ID NO: 69 are each a cyclic peptide having a cyclic structure formed by a disulfide bond.

In one embodiment of the production method, the first physiologically active peptide portion and/or second physiologically active peptide portion of the peptide molecule produced may constitute a cyclic peptide that binds to a vascular endothelial growth factor receptor (VEGFR). If both the first physiologically active peptide portion and the second physiologically active peptide portion constitute a cyclic peptide that binds to VEGFR, the cyclic peptides may be the same as or different from each other. The cyclic peptide that binds to VEGFR includes, but is not limited to, a cyclic peptide having a cyclic structure formed by a disulfide bond, containing or composed of an amino acid sequence selected from the following (aa) to (ff).

```
(aa)
                                (SEQ ID NO: 71)
AGPTWCEDDWYYCWLFGT;

(bb)
                                (SEQ ID NO: 72)
VCWEDSWGGEVCWLFGT;

(cc)
                                (SEQ ID NO: 73)
VCWEDSWGGEVCFRYDP;
```

(dd) a peptide in which one or two amino acid residues other than a cysteine residue are substituted, deleted, or added in any of the amino acid sequences (aa) to (cc), and which binds to VEGFR;

(ee) a peptide which is composed of an amino acid sequence having 90% or more sequence identity with any of the amino acid sequences of (aa) to (cc), but having a cysteine residue at the same position in (aa) or (cc), and which binds to VEGFR. For example, the sequence identity may be 92% or higher, 95% or higher, or 98% or higher.

(f) A peptide in which at least one amino acid other than the cysteine residue in any of the amino acid sequences (aa) to (ee) is modified. Here, the amino acid modification is phosphorylation, methylation, acetylation, adenylylation, ADP-ribosylation, or glycosylation.

In one embodiment of the production method, the linker portion has a molecular weight of 10,000 or less and may be composed of 50 or less amino acid residues.

Further, in one embodiment of the production method, the linker portion may be a linker portion having a molecular weight of 10,000 or less and composed of 50 or less or 49 or less amino acid residues, and at least 90%, at least 95%, or at least 100% of the amino acid sequence is composed of amino acid residues selected from alanine (A), proline (P), and serine (S). In this case, the proline residues may constitute more than 4% and less than 40% in the amino acid sequence of the linker portion. For example, in the amino acid sequence of the linker portion, the proline residues may constitute more than about 4%, more than about 5%, more than about 6%, more than about 8%, more than about 10%, more than about 15%, or more than about 20%, and may constitute less than about 40% or less than about 35%. Further, the alanine residues and the serine residue may each independently constitute more than about 4%, more than about 10%, or more than about 20%, and may constitute less than about 50%.

As used in the present specification, the term "about X %" is not limited to a concise number of percentages, but also includes values of additional 10% to 20% more residues, or 10% to 20% less residues. For example, the term "about 10%" also relates to 110% or 12% and 9% or 8%.

In the amino acid sequence of the linker portion, amino acid residues different from alanine, serine, and proline may be selected from the group consisting of Arg, Asn, Asp, Cys, Gln, Glu, Gly, His, Ile, Leu, Lys, Met, Phe, Thr, Trp, Tyr, and Val. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the production method, the linker portion may be a linker portion having a molecular weight of 10,000 or less and composed of 50 or less or 49 or less amino acid residues, and at least 90%, at least 95%, or at least 100% of the amino acid sequence is composed of amino acid residues selected from alanine (A) and proline (P). In this case, proline residues may constitute more than 10% and less than 75% in the amino acid sequence of the linker portion. For example, in the amino acid sequence of the linker portion, the proline residues may constitute more than about 10%, more than about 12%, more than about 14%, more than about 18%, more than about 20%, more than about 22%, more than about 23%, more than about 24%, or more than about 25%, and may constitute less than about 75%, less than about 70%, less than about 65%, less than about 60%, less than about 55%, less than about 50%, less than about 48%, less than about 46%, less than about 44%, less than about 42%, less than about 41%, less than about 40%, less than about 39%, less than about 38%, less than about 37%, less than about 36%, or less than about 35%. Further, the alanine residues may constitute more than about 25%, more than about 30%, more than about 35%, more than about 40%, more than about 45%, more than about 50%, more than about 52%, more than about 54%, more than about 56%, more than about 58%, more than about 59%, more than about 60%, more than about 61%, more than about 62%, more than about 63%, more than about 64%, or more than about 65%, and may constitute less than about 90%, less than about 88%, less than about 86%, less than about 84%, less than about 82%, less than about 80%, less than about 79%, less than about 78%, less than about 77%, less than about 76%, or less than about 75%.

In the amino acid sequence of the linker portion, the amino acid residues different from alanine, serine and proline may be selected from the group consisting of Arg, Asn, Asp, Cys, Gln, Glu, Gly, His, Ile, Leu, Lys, Met, Phe, Thr, Trp, Tyr, and Val. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the production method, the linker portion contains multiple amino acid repeats, the amino acid repeats are composed of alanine (A), proline (P), and serine (S), and in the amino acid repeats, the number of consecutive identical amino acid residues may be 6 residues or less, 5 residues or less, 4 residues or less, or 3 residues or less.

In one embodiment of the production method, the linker portion contains multiple amino acid repeats, the amino acid repeats are composed of alanine (A) and proline (P), and in the amino acid repeats, the number of consecutive identical amino acid residues may be 6 residues or less, 5 residues or less, 4 residues or less, or 3 residues or less.

In one embodiment of the production method, the linker portion may repeatedly contain two or more amino acid sequences selected from the group consisting of AP, AAP, AS, ASP, and ASS.

In one embodiment of the production method, the linker portion may contain a sequence composed of glycine (G) and serine (S). In this case, the linker portion may repeatedly contain an amino acid sequence selected from the group consisting of GGGGS, GGGS, GGS, and GS.

In one embodiment of the production method, the linker portion may repeatedly contain glycine or may be composed solely of glycine.

In one embodiment of the production method, the linker portion may repeatedly contain the amino acid sequence represented by EAAAK.

In one embodiment of the production method, the amino acid sequence of the linker portion can be, but is not limited to, one composed of A, P, and S, one composed of A and P, or one composed of a repetition of the sequence represented by GGGGS.

In one embodiment of the production method, the length of the linker portion may be composed of 50 or less amino acid residues, and for example, the linker portion may be composed of 49 or less, 40 or less, 35 or less, 30 or less, or 25 or less amino acid residues.

In one embodiment of the production method, the linker portion may be composed of 1 or more amino acid residues, and for example, the linker portion may be composed of 4 or more, 8 or more, 12 or more, or 16 or more amino acid residues.

In one embodiment of the production method, specific examples of the linker portion include, but are not limited to, those containing any of the following amino acid sequences and those consisting of any of the following amino acid sequences: AAPAAPAP (SEQ ID NO: 74), AAPAAPAPAAPAAPAP (SEQ ID NO: 75), AAPAAPAPAAPAAPAPAAPAAPAPAAPAAPAPAAPAAPAPAAPAAPAPA (SEQ ID NO: 76), SAPSPSSAPASASAPASPASASASASPASSPASASSASPAASSASPASS (SEQ ID NO: 77), AAPAAPPAAPAAPAAPAAPAPAAPAAPAPAAPAAPAPAAPAAPAPAAPAAPAPAAPAAP APAAPAAPAPAAPAAPAPAAPAAPAPAAPAAPAPAAPA (SEQ ID NO: 78), SAPSPSSAPASASAPASPASASASASPASSPASASSASPAASSASPASSSASPSAPAAPSASA APSASPASSSPAPASAPSPAAAASSPSPAPSSASSAA (SEQ ID NO: 79), AAPAAPAPAAPAAPAPAAPAAPAPAAPAAPAPAAPAAPAPAAPAAPAPAAPAAPAPAAPAAP APAAPAAPAPAAPAAPAPAAPAAPAPAAPAAPAPAAPAAPAPAAPAAPAPAAPAAPAPAAPA APAPAAPAAPAPAAPAAPAPAAPAAPAPAAPAAPAPAAPAAPAPAAPAAPAPAAPAAPAPAA PAAPAPAAPAAPAP (SEQ ID NO: 80), AAPAAPAPAAPAAPAPAAPA (SEQ ID NO: 7), AAPAAPAPAAPAAPAPAAPAAP (SEQ ID NO: 8), AAPAAPAPAAPAAP (SEQ ID NO: 9), AAPAAAPAPAAPAAPAPAAP (SEQ ID NO 10), AAAPAAAPAAAPAAAPAAAP (SEQ ID NO 11), AAPAAPAAPAAPAAPAAPAAP (SEQ ID NO 12), APAAAPAPAAAPAPAAAPAPAAAP (SEQ ID NO 13), AAAPAAPAAPPAAAAPAAPAAPPA (SEQ ID NO 14), and APAPAPAPAPAPAPAPAPAP (SEQ ID NO 15), ASPAAPAPASPAAPAPSAPA (SEQ ID NO 16), AAPASPAPAAPSAPAPAAPS (SEQ ID NO 17), APSSPSPSAPSSPSPASPSS (SEQ ID NO 18), SAPSSPSPSAPSSPSPASPS (SEQ ID NO 19), SSPSAPSPSSPASPSPSSPA (SEQ ID NO 20), AASPAAPSAPPAAASPAAPSAPPA (SEQ ID NO 21), and ASAAAPAAASAAASAPSAAA (SEQ ID NO 22), as well as circular permutation mutant sequences thereof.

Taking AAPAAPAPAAPAAPAPAAPA (SEQ ID NO: 7) as an example, a circular permutation mutant sequence may be easily prepared, for example, by removing the first alanine of the above sequence and adding another alanine to the terminus of the above sequence. Such a circular permutation mutant sequence for SEQ ID NO: 7 is APAAPAPAAPAAPAPAAPAA (SEQ ID NO: 23). Furthermore, non-limited examples of the circular permutation mutant sequence with circularly permutated amino acid residues for SEQ ID NO: 7 include the following.

```
                              (SEQ ID NO: 24)
PAAPAPAAPAAPAPAAPAAA,

                              (SEQ ID NO: 25)
AAPAPAAPAAPAPAAPAAAP,

                              (SEQ ID NO: 26)
APAPAAPAAPAPAAPAAAPA,

                              (SEQ ID NO: 27)
PAPAAPAAPAPAAPAAAPAA,

                              (SEQ ID NO: 28)
APAAPAAPAPAAPAAAPAAP,

                              (SEQ ID NO: 29)
PAAPAAPAPAAPAAAPAAPA,

                              (SEQ ID NO: 30)
AAPAAPAPAAPAAAPAAPAP,
```

-continued

```
                              (SEQ ID NO: 31)
APAAPAPAAPAAAPAAPAPA,
and

                              (SEQ ID NO: 32)
PAAPAPAAPAAAPAAPAPAA.
```

In one embodiment of the production method, the peptide molecule produced by the production method may contain an additional amino acid sequence composed of at least one amino acid residue on the opposite side of the linker portion from the first physiologically active peptide portion. This additional amino acid sequence has a molecular weight of 10,000 or less and is composed of 50 or less amino acid residues. Such additional amino acid sequences include enzyme identification sequences such as SortaseA identification signal and Butelase identification signal, tag sequences such as FLAG tag, PA tag, and histidine tag, reactive amino acids such as lysine, cysteine, glutamic acid, and aspartic acid, or sequences containing the reactive amino acids.

If the peptide molecule produced by the production method contains an additional amino acid sequence composed of at least one amino acid residue on the opposite side of the linker portion from the first physiologically active peptide portion, and the additional amino acid sequence is a sequence composed of a reactive amino acid or containing a reactive amino acid, the peptide molecule may be used as a conjugate reagent for preparing a physiologically active peptide-drug conjugate or the like.

The peptide molecule produced by the production method may contain a second physiologically active peptide portion and an additional amino acid sequence composed of at least one amino acid residue, on the opposite side of the linker portion from the first physiologically active peptide portion.

The peptide molecule produced by the production method may contain a first physiologically active peptide portion on the N-terminus side of the linker portion and a second physiologically active peptide portion and/or an additional amino acid sequence on the C-terminus side of the linker portion. Further, the peptide molecule produced by the production method may contain a first physiologically active peptide portion on the C-terminus side of the linker portion and a second physiologically active peptide portion and/or an additional amino acid sequence on the N-terminus side of the linker portion. Moreover, the peptide molecule produced by the production method may contain an arbitrary amino acid sequence as long as it does not inhibit the functions of the first physiologically active peptide and second physiologically active peptide on the N-terminus side and/or the C-terminus side of the first physiologically active peptide portion and/or second physiologically active peptide portion, or in the space with the linker portion. As such an arbitrary amino acid sequence, for example, a sequence useful for enhancing the expression or secretion of peptide molecules in a host cell may be used.

In one embodiment of the production method, the peptide molecule produced may further contain a functional modification portion at a position not adjacent to the linker portion. The functional modification portion is as described above.

The production method can include the step of producing the peptide molecule by expressing a polynucleotide in a host cell containing the polynucleotide encoding the peptide molecule or by expressing a polynucleotide encoding the peptide molecule in a cell-free expression system. Host cells containing polynucleotides encoding the peptide molecule may be prepared by known techniques. For example, a host cell containing a polynucleotide encoding the peptide molecule may be prepared by, e.g., introducing a recombinant vector containing the polynucleotide into the host cell.

In one embodiment of the production method, examples of host cells include, but are not limited to, prokaryotic cells (bacteria) such as genus *Escherichia* (such as *Escherichia coli*) and genus *Corynebacterium* (such as *Corynebacterium glutamicum*), fungal cells (fungi) such as yeast, plant cells, insect cells, and animal cells. As for the bacteria of the genus *Corynebacterium* as host cells, the ones described in WO2016/171224 can be used.

In one embodiment of the production method, expression of the polynucleotide in a host cell may be transient or stable. The conditions for culturing the host cells may be appropriately selected by those skilled in the art based on common general technical knowledge according to the type of host cells used. For example, the temperature, humidity, carbon dioxide concentration, and other conditions of the culture environment may be such that polynucleotide expression is possible in the host cells, and the culture medium used is not limited to ones suitable for each host cell and may be selected from conventionally known ones.

In one embodiment of the production method, the synthesis of the peptide molecule in the cell-free expression system may be carried out using a cell extract or using a commercially available cell-free expression reagent, and may be carried out based on a technique known to those skilled in the art. The components contained in the cell-free expression system include nucleic acids encoding the desired polypeptide as a template (DNA or mRNA), proteins required for transcription, translation, energy regeneration, and post-translational modification (such as RNA polymerase, ribosome, aminoacyl-tRNA synthetase, translation initiation factor, translation elongation factor, translation termination factor, ribosome recycling factor, nucleoside diphosphate kinase, adenosine kinase, creatine kinase, prolyl isomerase, disulfide-binding isomerase, and chaperone), tRNA, aminoacyl tRNA, natural amino acids, unnatural amino acids, NTP, buffer, and the like.

Examples of commercially available cell-free expression reagents include PUREfrex 2.0 (GeneFrontier Corporation) and PURExpress In Vitro Protein Synthesis Kit (New England BioLabs).

In producing a peptide molecule, the production method may include the steps of introducing into a host cell a polynucleotide encoding a peptide molecule or a recombinant vector containing the polynucleotide, and expressing the polynucleotide in the host cell to generate a peptide molecule. The introduction means in the introduction step may be appropriately selected by those skilled in the art based on common general technical knowledge according to the type of host cells used. The vector usable may be one capable of functionally inserting a polynucleotide encoding a peptide molecule and carrying the fragments into the host cells to result in replication and/or expression of heterologous nucleic acid fragments in the host cells, and examples thereof include plasmids, phages, cosmids, and viruses. The vector can be appropriately selected by those skilled in the art according to the type of host cells used.

In one embodiment of the production method, a polynucleotide encoding the peptide molecule may be appropriately synthesized by those skilled in the art using a conventional polynucleotide synthesis technique based on the amino acid sequence of that peptide molecule. Examples of the polynucleotide encoding the peptide molecule include one encoding a peptide molecule having a structure "first physiologically active peptide portion"-"linker portion"-"second physiologically active peptide portion" or "first physiologically active peptide portion"-"linker portion"-"additional amino acid sequence". Peptide molecules may be easily and inexpensively produced from such polynucleotides.

In one embodiment of the production method, the polynucleotide encoding the peptide molecule may appropriately contain a promoter sequence or a signal sequence on the N-terminus side thereof. In addition, the polynucleotide may contain a restriction enzyme recognition sequence on the N-terminus side and/or the C-terminus side. Such promoter sequences, signal sequences, and restriction enzyme recognition sequences may be appropriately selected by those skilled in the art according to the type of host cells or vectors used.

In one embodiment of the production method, the produced peptide molecule may be appropriately isolated from host cells, and may be purified and/or recovered based on the common general technical knowledge of those skilled in the art.

In one embodiment of the production method, the produced peptide molecule may be appropriately isolated after being secreted from host cells, and may be purified and/or recovered based on the common general technical knowledge of those skilled in the art.

In one embodiment of the production method, a desired peptide molecule such as a dimer peptide may be expressed from a single polynucleotide chain, and a desired peptide molecule such as a dimer peptide may be produced easily and inexpensively as compared with conventional chemical synthesis methods.

In one embodiment of the production method, if the first physiologically active peptide portion and/or second physiologically active peptide portion constitutes a cyclic peptide, a straight chain peptide molecule is generated from a single polynucleotide chain, and it is possible to construct a cyclic peptide from the straight chain peptide molecule in the host cells or after secretion from the host cells. Therefore, regarding the synthesis of a peptide molecule containing a cyclic peptide, the conventional chemical synthesis methods require a large number of steps resulting in complexity, but according to the production method, a peptide molecule containing a cyclic peptide may be produced easily and inexpensively. Regarding the composition of the cyclic peptide, a cyclic structure may be formed by a disulfide bond between two cysteine residues, but is not limited thereto.

An embodiment as described herein relates to a polynucleotide for encoding a peptide molecule. The peptide molecule produced by the expression of this polynucleotide may contain (I) a first physiologically active peptide portion, (II) a linker portion composed of an amino acid residue, and (III) a second physiologically active peptide portion and/or an additional amino acid sequence composed of at least one amino acid residue, located on the opposite side of the linker portion from the first physiologically active peptide portion. Here, the first physiologically active peptide portion and second physiologically active peptide portion may be the same as or different from each other. Such polynucleotides may be appropriately synthesized by those skilled in the art using conventional polynucleotide synthesis techniques based on the amino acid sequence of the peptide molecule produced.

One embodiment of the polynucleotide may be the same as that described in relation to the production method as described herein.

In one embodiment of the polynucleotide, the polynucleotide may be for use in the production method as described above.

In one embodiment of the polynucleotide, the first physiologically active peptide portion, the linker portion composed of amino acid residues, the second physiologically active peptide portion, and the additional amino acid sequence composed of at least one amino acid residue in the peptide molecule produced by the expression of the polynucleotide may be the same as those described in relation to the production method as described above.

An embodiment as described herein relates not only to the above-mentioned peptide molecules but also to the following peptide molecules. This peptide molecule may contain (I) a first physiologically active peptide portion, (II) a linker portion composed of an amino acid residue, and (III) a second physiologically active peptide portion located on the opposite side of the linker portion from the first physiologically active peptide portion.

In one embodiment of the peptide molecule, it may contain a first physiologically active peptide portion on the N-terminus side of the linker portion and a second physiologically active peptide portion on the C-terminus side of the linker portion, or may contain a first physiologically active peptide portion on the C-terminus side of the linker portion and a second physiologically active peptide portion on the N-terminus side of the linker portion. Further, in one embodiment, the peptide molecule may contain an arbitrary amino acid sequence as long as it does not inhibit the functions of the first physiologically active peptide and second physiologically active peptide on the N-terminus side and/or the C-terminus side of the first physiologically active peptide portion and/or second physiologically active peptide portion, or in the space with the linker portion. As such an arbitrary amino acid sequence, for example, a sequence useful for enhancing the expression or secretion of peptide molecules in a host cell may be used.

In one embodiment of the peptide molecule, the first physiologically active peptide portion and second physiologically active peptide portion each constitute a cyclic peptide that binds to a c-Met protein, and may be the same as or different from each other. Such cyclic peptide that binds to a c-Met (also referred to simply as Met) protein includes a cyclic peptide having a cyclic structure formed by a disulfide bond, containing an amino acid sequence selected from the following (a) to (i).

```
(a)
                                    (SEQ ID NO: 1)
CYRQFNRRTHEVWNLDC;

(b)
                                    (SEQ ID NO: 2)
CRQFNRRTHEVWNLDC;

(c)
                                    (SEQ ID NO: 3)
CYWYYAWDQTYKAFPC;

(d)
                                    (SEQ ID NO: 4)
CWYYAWDQTYKAFPC;

(e)
                                    (SEQ ID NO: 5)
CYISWNEFNSPNWRFITC;

(f)
                                    (SEQ ID NO: 6)
CISWNEFNSPNWRFITC;
```

(g) a peptide in which one or two amino acid residues other than a cysteine residue are substituted, deleted, or added in any of the amino acid sequences (a) to (f), and which binds to a c-Met protein;

(h) a peptide which is composed of an amino acid sequence having 90% or more sequence identity with any of the amino acid sequences (a) to (f), but having cysteine residues at both ends, and which binds to a c-Met protein. For example, the sequence identity may be 92% or higher, 95% or higher, or 98% or higher. In the present specification, the amino acid sequence homology may be calculated by using a known analysis tool, and may be calculated, for example, by using the National Center for Biotechnology Information (NCBI) homology algorithm BLAST (Basic local alignment search tool). In addition, the default (initial setting) parameters in the analysis tool may be used to calculate the amino acid sequence homology.

A peptide in which at least one amino acid other than the cysteine residues at both ends in any of the amino acid sequences (a) to (h) is modified. Here, the amino acid modification is phosphorylation, methylation, acetylation, adenylylation, ADP-ribosylation, or glycosylation.

Note that it is known a cyclic peptide that binds to such Met (HGFR) functions as a Met (HGFR) agonist by dimerization.

In one embodiment of the peptide molecule, the linker portion has a molecular weight of 10,000 or less and may be composed of 50 or less amino acid residues.

Further, in one embodiment of the peptide molecule, the linker portion may be a linker portion having a molecular weight of 10,000 or less and composed of 50 or less or 49 or less amino acid residues, and at least 90%, at least 95%, or at least 100% of the amino acid sequence is composed of amino acid residues selected from alanine (A), proline (P), and serine (S). In this case, the proline residues may constitute more than 4% and less than 40% in the amino acid sequence of the linker portion. For example, in the amino acid sequence of the linker portion, the proline residues may constitute more than about 4%, more than about 5%, more than about 6%, more than about 8%, more than about 10%, more than about 15%, or more than about 20%, and may constitute less than about 40% or less than about 35%. Further, the alanine residues and the serine residue may each independently constitute more than about 4%, more than about 10%, or more than about 20%, and may constitute less than about 50%.

In the amino acid sequence of the linker portion, amino acid residues different from alanine, serine, and proline may be selected from the group consisting of Arg, Asn, Asp, Cys, Gln, Glu, Gly, His, Ile, Leu, Lys, Met, Phe, Thr, Trp, Tyr, and Val. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the peptide molecule, the linker portion may be a linker portion having a molecular weight of 10,000 or less and composed of 50 or less or 49 or less amino acid residues, and at least 90%, at least 95%, or at least 100% of the amino acid sequence is composed of amino acid residues selected from alanine (A) and proline (P). In this case, proline residues may constitute more than 10% and less than 75% in the amino acid sequence of the linker portion. For example, in the amino acid sequence of the linker portion, the proline residues may constitute more than about 10%, more than about 12%, more than about 14%, more than about 18%, more than about 20%, more than about 22%, more than about 23%, more than about 24%, or more than about 25%, and may constitute less than about 75%, less than about 70%, less than about 65%, less than about 60%, less than about 55%, less than about 50%, less than about 48%, less than about 46%, less than about 44%, less than about 42%, less than about 41%, less than about 40%, less than about 39%, less than about 38%, less than about 37%, less than about 36%, or less than about 35%. Further, the alanine residues may constitute more than about 25%, more than about 30%, more than about 35%, more than about 40%, more than about 45%, more than about 50%, more than about 52%, more than about 54%, more than about 56%, more than about 58%, more than about 59%, more than about 60%, more than about 61%, more than about 62%, more than about 63%, more than about 64%, or more than about 65%, and may constitute less than about 90%, less than about 88%, less than about 86%, less than about 84%, less than about 82%, less than about 80%, less than about 79%, less than about 78%, less than about 77%, less than about 76%, or less than about 75%.

In the amino acid sequence of the linker portion, the amino acid residues different from alanine, serine and proline may be selected from the group consisting of Arg, Asn, Asp, Cys, Gln, Glu, Gly, His, Ile, Leu, Lys, Met, Phe, Thr, Trp, Tyr, and Val. Such amino acid residues different from alanine, serine, and proline include ones without a hydrophobic side chain such as Val, Ile, Leu, Met, Phe, Tyr, or Trp, and/or ones without a charged side chain such as Lys, Arg, Asp, or Glu.

In one embodiment of the peptide molecule, the linker portion contains multiple amino acid repeats, the amino acid repeats are composed of alanine (A), proline (P), and serine (S), and in the amino acid repeats, the number of consecutive identical amino acid residues may be 6 residues or less, 5 residues or less, 4 residues or less, or 3 residues or less.

In one embodiment of the peptide molecule, the linker portion contains multiple amino acid repeats, the amino acid repeats are composed of alanine (A) and proline (P), and in the amino acid repeats, the number of consecutive identical amino acid residues may be 6 residues or less, 5 residues or less, 4 residues or less, or 3 residues or less.

In one embodiment of the peptide molecule, the linker portion may repeatedly contain two or more amino acid sequences selected from the group consisting of AP, AAP, AS, ASP, and ASS.

In one embodiment of the peptide molecule, the linker portion may contain a sequence composed of glycine (G) and serine (S). In this case, the linker portion may repeatedly contain an amino acid sequence selected from the group consisting of GGGGS, GGGS, GGS, and GS.

In one embodiment of the peptide molecule, the linker portion may repeatedly contain glycine or may be composed solely of glycine.

In one embodiment of the peptide molecule, the linker portion may repeatedly contain the amino acid sequence represented by EAAAK.

In one embodiment of the peptide molecule, the amino acid sequence of the linker portion can be, but is not limited to, one composed of A, P, and S, one composed of A and P, or one composed of a repetition of the sequence represented by GGGGS.

In one embodiment of the peptide molecule, the length of the linker portion may be composed of 50 or less amino acid residues, and for example, the linker portion may be composed of 49 or less, 40 or less, 35 or less, 30 or less, or 25 or less amino acid residues.

In one embodiment of the peptide molecule, the linker portion may be composed of 1 or more amino acid residues, and for example, the linker portion may be composed of 4 or more, 8 or more, 12 or more, or 16 or more amino acid residues.

In one embodiment of the peptide molecule, specific examples of the linker portion include, but are not limited to, those containing any of the following amino acid sequences and those consisting of any of the following amino acid sequences: AAPAAPAP (SEQ ID NO: 74), AAPAAPAPAAPAAPAP (SEQ ID NO: 75), AAPAAPAPAAPAAPAPAAPAAPAPAAPAAPAPAAPAAPAPAAPAAPAPA (SEQ ID NO: 76), SAPSPSSAPASASAPASPASASASASPASSPASASSASPAASSASPASS (SEQ ID NO: 77), AAPAAPPAAPAAPAAPAAPAPAAPAAPAPAAPAAPAPAAPAAPAPAAPAAPAPAAPAAP APAAPAAPAPAAPAAPAPAAPAAPAPAAPAAPAPAAPA (SEQ ID NO: 78), SAPSPSSAPASASAPASPASASASASPASSPASASSASPAASSASPASSSASPSAPAAPSASA APSASPASSSPAPASAPSPAAAASSPSPAPSSASSAA (SEQ ID NO: 79), AAPAAPAPAAPAAPAPAAPAAPAPAAPAAPAPAAPAAPAPAAPAAPAPAAPAAPAPAAPAAP APAAPAAPAPAAPAAPAPAAPAAPAPAAPAAPAPAAPAAPAPAAPAAPAPAAPAAPAPAAPA APAPAAPAAPAPAAPAAPAPAAPAAPAPAAPAAPAPAAPAAPAPAAPAAPAPAAPAAPAPAA PAAPAPAAPAAPAP (SEQ ID NO: 80), AAPAAPAPAAPAAPAPAAPA (SEQ ID NO: 7), AAPAAPAPAAPAAPAPAAPAAP (SEQ ID NO: 8), AAPAAPAPAAPAAP (SEQ ID NO: 9), AAPAAAPAPAAPAAPAPAAP (SEQ ID NO 10), AAAPAAAPAAAPAAAPAAAP (SEQ ID NO 11), AAPAAPAAPAAPAAPAAPAAP (SEQ ID NO 12), APAAAPAPAAAPAPAAAPAPAAAP (SEQ ID NO 13), AAAPAAPAAPPAAAAPAAPAAPPA (SEQ ID NO 14), and APAPAPAPAPAPAPAPAPAP (SEQ ID NO 15), ASPAAPAPASPAAPAPSAPA (SEQ ID NO 16), AAPASPAPAAPSAPAPAAPS (SEQ ID NO 17), APSSPSPSAPSSPSPASPSS (SEQ ID NO 18), SAPSSPSPSAPSSPSPASPS (SEQ ID NO 19), SSPSAPSPSSPASPSPSSPA (SEQ ID NO 20), AASPAAPSAPPAAASPAAPSAPPA (SEQ ID NO 21), and ASAAAPAAASAAASAPSAAA (SEQ ID NO 22), as well as circular permutation mutant sequences thereof.

Taking AAPAAPAPAAPAAPAPAAPA (SEQ ID NO: 7) as an example, a circular permutation mutant sequence may be easily prepared, for example, by removing the first alanine of the above sequence and adding another alanine to the terminus of the above sequence. Such a circular permutation mutant sequence for SEQ ID NO: 7 is APAAPAPAAPAAPAPAAPAA (SEQ ID NO: 23). Furthermore, nonlimited examples of the circular permutation mutant sequence with circularly permutated amino acid residues for SEQ ID NO: 7 include the following.

```
                                    (SEQ ID NO: 24)
PAAPAPAAPAAPAPAAPAAA,

                                    (SEQ ID NO: 25)
AAPAPAAPAAPAPAAPAAAP,

                                    (SEQ ID NO: 26)
APAPAAPAAPAPAAPAAAPA,

                                    (SEQ ID NO: 27)
PAPAAPAAPAPAAPAAAPAA,
```

-continued (SEQ ID NO: 28)
APAAPAAPAPAAPAAAPAAP, (SEQ ID NO: 29)
PAAPAAPAPAAPAAAPAAPA, (SEQ ID NO: 30)
AAPAAPAPAAPAAAPAAPAP, (SEQ ID NO: 31)
APAAPAPAAPAAAPAAPAPA,
and (SEQ ID NO: 32)
PAAPAPAAPAAAPAAPAPAA.

EXAMPLES

Hereinafter, the present invention will be described in more detail by way of examples, but the present invention is not limited thereto.

Note that the HGF used in the examples are all recombinant human HGF (rhHGF, R&D Systems), and the recombinant human HGF is simply referred to as HGF in the present specification and the drawings.

Reference Example 1: Construction of a Shortened Vector (pPK10) of the tatABC Gene Amplification Vector pPK6

The pPK6 vector described in WO2016/171224 is a vector for amplifying the tatABC gene encoding the Tat secretion system. By removing unnecessary sequences from pPK6, a shortened vector was constructed as follows.

First, pPK6 was used as a template to amplify the 5'-side of the removed region with the primers set forth in SEQ ID NO: 33 and SEQ ID NO: 34, and the 3'-side with the primers set forth in SEQ ID NO: 35 and SEQ ID NO: 36. The two amplified DNA fragments were introduced into the SalI-SalI site of pPK6 by an infusion reaction to obtain a plasmid with 548 bases removed from pPK6. This plasmid was named pPK6b.

Next, pPK6b was used as a template to amplify the 5'-side of the removed region with the primers set forth in SEQ ID NO: 37 and SEQ ID NO: 38, and the 3'-side with the primers set forth in SEQ ID NO: 39 and SEQ ID NO: 40. The two amplified DNA fragments were introduced into the ClaI-SpeI site of pPK6b by an infusion reaction to construct plasmids with 310 bases further removed from pPK6b. For the infusion reaction, In-Fusion (registered trademark) HD Cloning Kit (Takara Bio) was used, and the reaction conditions were according to the protocol recommended by the manufacturer.

In this way, an unnecessary sequence of 858 bases was removed from the pPK6 vector to construct a shortened plasmid. This vector was named pPK10.

TABLE 1

| Primer Sequence Number | Base Sequence |
|---|---|
| SEQ ID NO: 33 | tcagaggaatgtcgactgctcgcaaccggcccgt |
| SEQ ID NO: 34 | cctacattcagcgcaggttcccctagagcacgt |
| SEQ ID NO: 35 | tgcgctgaatgtagggaag |
| SEQ ID NO: 36 | atcgctgcaggtcgactctagaggatccccggaa |
| SEQ ID NO: 37 | cttcccatacaatcgatagattgtcgcacctgattg |
| SEQ ID NO: 38 | cctcaggctggtgttgggcgagctcgaattcgt |
| SEQ ID NO: 39 | aacaccagcctgaggcaa |
| SEQ ID NO: 40 | gatcttcgggactagttactttcaaatgctcagcatg |

Example 1: Design of FBP-PAS Dimer Peptide and its Secretory Expression in *C. glutamicum*

(1-1) Outline of FBP-PAS Dimer Peptide Design

A peptide molecule with two FGFR1 binding cyclic peptides (FBPs) bound with a PAS linker is expressed as one polypeptide in *C. glutamicum*. Therefore, the peptide sequence was designed to be "first FBP"-"PAS linker"-"second FBP (same sequence as the above first FBP)". That is, the C-terminus of the first FBP and the N-terminus of the PAS linker are linked to the N-terminus of the second FBP and the C-terminus of the PAS linker by an amide bond, and may be expressed in *C. glutamicum* as a single polypeptide chain.

(1-2) Preparation of FBP-PAS Dimer Peptide

The prepared FBP-PAS dimer peptide is as follows.

(a) FBP-PAS
(SEQ ID NO: 41)
RPGCGPRKPRTPKKCGSHGAAPAAPAPAAPAAPAPAAPAGRPGCGPRKP

RTPKKCGSH (1-3) Expression of FBP-PAS Dimer Peptide

Corynex (registered trademark) was used to examine the expression of FBP-PAS dimer peptide. Hereinafter, examples of expression examinations using Corynex (registered trademark) will be described.

(1-4) Construction of Secretory Expression Plasmid of FBP-PAS Dimer Peptide Using TorA Signal Sequence As the FBP-PAS dimer peptide, the amino acid sequence of the above (a) FBP-PAS (which may be hereinafter referred to as "FBP-PAS") was designed, and the base sequence encoding this protein was designed in consideration of the codon usage frequency of *C. glutamicum*. Furthermore, the following expression cassette was designed to enable secretion expression by *C. glutamicum*.

FBP-PAS was secretory-expressed as a fusion protein of FBP-PAS and a signal peptide 39 amino acid residue of TorA derived from *E. coli* (hereinafter referred to as "TorAss-FBP-PAS"). The base sequence and amino acid sequence encoding the designed TorAss-FBP-PAS are set forth in SEQ ID NOs: 42 and 43, respectively.

Base sequence encoding TorAss-FBP-PAS
(SEQ ID NO: 42)
atgaacaataacgatctctttcaggcatcacgtcggcgttttctggc acaactcggcggcttaaccgtcgccgggatgctggggccgtcattgt -continued

```
taacgccgcgacgtgcgactgcgcgtcctggttgtggtcctcgcaag

ccccgcacccctaagaaatgtggttctcacggcgccgctcctgccgc

acccgcacccgctgctccagcagccccagccccagctgcaccagcag

gtcgcccaggctgtggtccccgcaaaccccgcacccctaagaaatgt

ggctctcactaa
```

Amino acid sequence of TorAss-FBP-PAS (SEQ ID NO: 43)

```
MNNNDLFQASRRRFLAQLGGLTVAGMLGPSLLTPRRATARPGCGPRK

PRTPKKCGSHGAAPAAPAPAAPAAPAPAAPAGRPGCGPRKPRTPKKC

GSH
```

The promoter of the cspB gene derived from the *C. glutamicum* ATCC 13869 strain was linked upstream of the base sequence set forth in TorAss-FBP-PAS, and furthermore, an expression cassette of TorAss-FBP-PAS having a KpnI site on the 5'-side and an ApaI site on the 3'-side was designed and totally synthesized. The totally synthesized DNA fragment (TorAss-FBP-PAS expression cassette) was inserted into the KpnI-ApaI site of pPK10 described in Reference Example 1 to construct pPK10_TorAss-FBP-PAS, a secretory expression plasmid for the FBP-PAS dimer peptide using the TorA signal sequence. As a result of determining the base sequence of the inserted fragment, it was confirmed that the TorAss-FBP-PAS expression cassette as designed had been constructed. Base sequences were determined using BigDye (registered trademark) Terminator v3.1 Cycle Sequencing Kit (Applied Biosystems) and 3130 Genetic Analyzer (Applied Biosystems).

(1-5) Secretory Expression of FBP-PAS Dimer Peptide in *C. glutamicum*

The pPK10_TorAss-FBP-PAS constructed above was used to transform the *C. glutamicum* YDK0107 strain described in WO2016/171224 to obtain the YDK0107/pPK10_TorAss-FBP-PAS strain.

The obtained transformants were cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be FBP-PAS was detected in the culture supernatant of the YDK0107/pPK10_TorAss-FBP-PAS strain (FIG. 1, lanes 2 to 5).

(1-6) Purification of FBP-PAS Dimer Peptide

The culture supernatant containing FBP-PAS obtained above was purified by dialysis in PBS (Mg—/Ca—) buffer for 2 days using a dialysis membrane (MWCO=3.5 kDa, Spectrum).

Example 2: Confirmation of Molecular Weight and Disulfide Cyclic Structure of FBP-PAS Dimer Peptide Disulfide bonds were reduced by adding 5 mM Tris(2-carboxyethyl)phosphine Hydrochloride (TCEP-HCl) to the FBP-PAS dimer peptide solution and incubating at room temperature for 48 hours. The FBP-PAS dimer peptides treated with FBP-PAS and TCEP-HCl were each mixed with α-Cyano-4-hydroxycinnamic Acid (CHCA), and the molecular weight was measured with MALDI-TOF-MS (Shimadzu, AXIMA-TOF 2).

Figure 2:
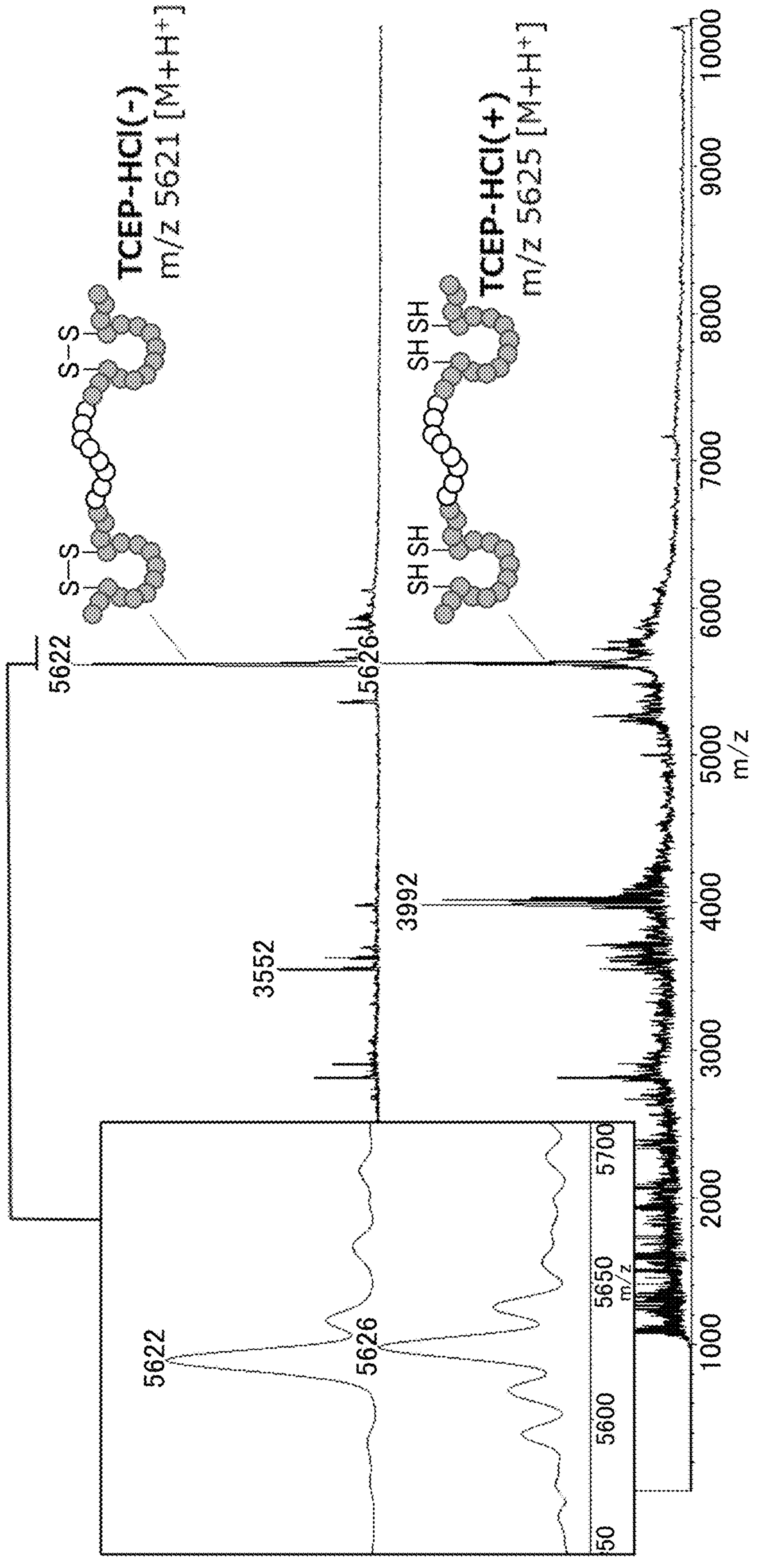
FIG. 2 shows measurement results for the dimer peptide (FBP-PAS) by MALDI-TOF-MS. The schematic molecular diagrams in the figure show the FBP-PAS dimer peptide, the central part (without color) represents PAS, and both side parts (colored) represent FBP.

As shown in FIG. 2, a value close to the molecular weight (m/z 5621) of the FBP-PAS dimer peptide forming two disulfide bonds in the molecule was obtained before reduction with TCEP-HCl. In addition, after reduction with TCEP-HCl, a value close to the molecular weight (m/z 5625) with all disulfide bonds reduced was obtained.

From these results, it was confirmed that the FBP-PAS dimer peptide expressed by Corynex (registered trademark) had a peptide sequence as designed and had a structure containing two disulfide bonds in the molecule.

Example 3: Evaluation of FGFR Inhibitory Activity of FBP-PAS Dimer Peptide

The inhibitory activity of the FBP monomer peptide chemically synthesized with the FBP-PAS dimer peptide on FGFR was evaluated by luciferase assay. To 25 μL of Opti-MEM medium (Thermo Fisher Scientific), 0.6 μL of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

FBP-PAS dimer peptide or FBP monomer peptide at 10 μM was added to the evaluation basal medium containing 0 to 10 ng/mL bFGF, and 100 μL thereof was added to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the FGFR-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 3:
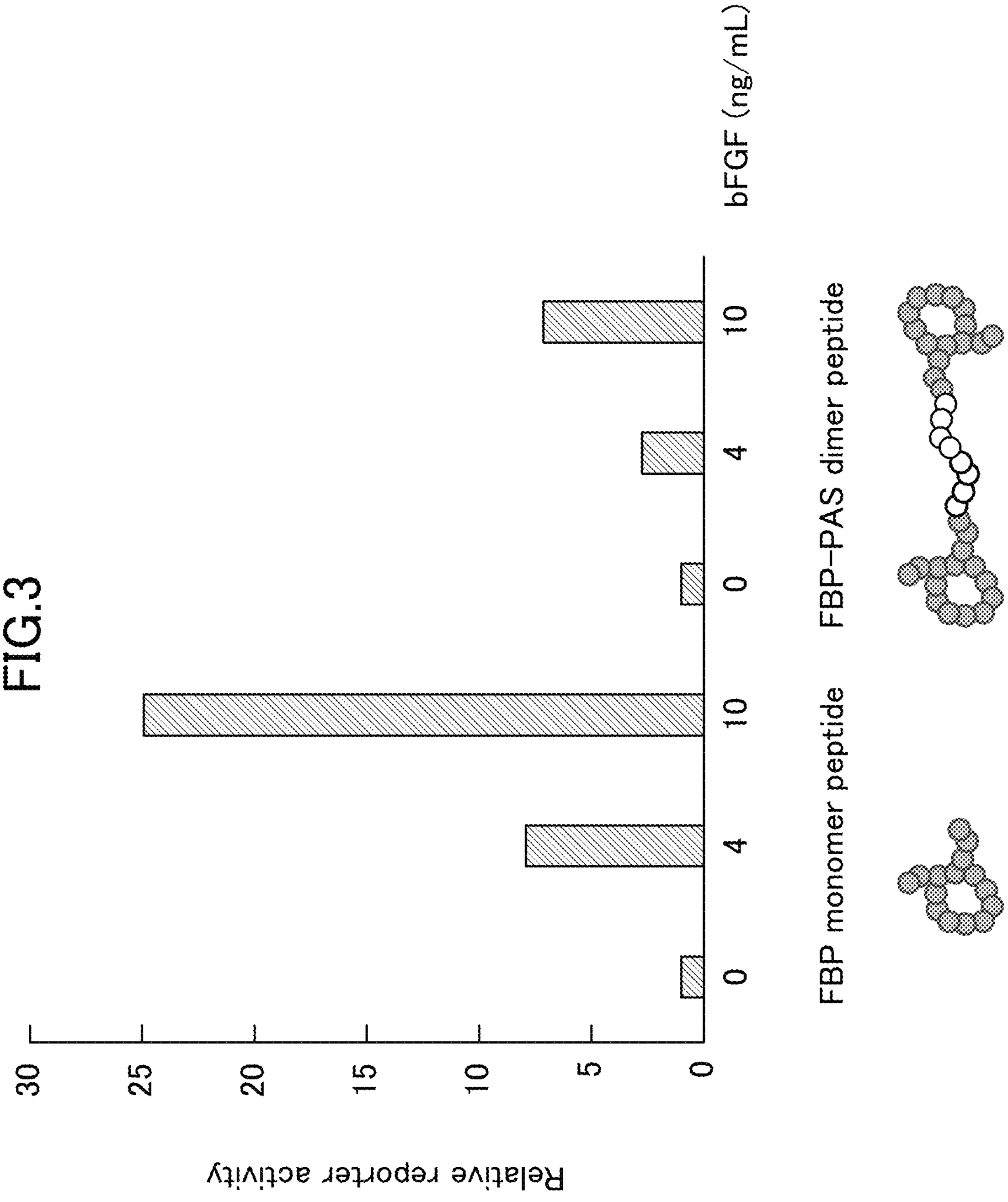
FIG. 3 is a graph showing the activity evaluation of a monomer peptide (FBP) and a dimer peptide (FBP-PAS). The vertical axis represents relative receptor activity and the horizontal axis represents bFGF concentration. In the molecular schematic diagrams in the figure, the uncolored part represents PAS and the colored part represents FBP.

As shown in FIG. 3, it was revealed that the FBP-PAS dimer peptide strongly inhibited the FGFR signal by the same amount of bFGF as compared with the FBP monomer peptide. From these results, it was clarified that the FBP- PAS dimer peptide inhibited FGFR and had a higher inhibitory activity than the FBP monomer peptide.

Example 4: Design of HGF-PAS Dimer Peptide and its Secretory Expression in *C. glutamicum*

(4-1) Outline of HGF-PAS Dimer Peptide Design

It is impossible to express peptide dimer molecules of Met-linked cyclic peptide aMD4 reported in K. Ito, et al. Nat. Commun. 6, 6373, 2015, dimerized by a PEG linker, as a single polypeptide chain in *C. glutamicum* for the following reasons.

(1) aMD4 is cyclized by an intramolecular thioether bond formed by the reaction of the chloroacetyl groups added to the N-terminus amino groups with the sulfhydryl groups of the cysteine-side chains in the sequence, but the thioether bond cannot express in *C. glutamicum.*

(2) Dimerization is achieved by binding the C-terminuses of the cyclic peptides to each other using a Bis-Maleimide-PEG linker, and cannot be expressed in *C. glutamicum.*

Therefore, the molecule was converted as follows to design an expressible form. Regarding (1) above, the thioether bond was converted into a disulfide bond by two cysteine-side chain sulfhydryl groups. The conversion to a disulfide bond lengthened the cyclized site by 2 atoms, but by deleting the residue next to cysteine on the N-terminus side (tyrosine in the case of aMD4), the cyclized site was designed to be shortened by one atom. The above (2) was addressed by using a PAS sequence instead of the PEG linker and further designing the peptide sequence to be "first disulfide conversion aMD4"-"PAS linker"-"second disulfide conversion aMD4" so that it could be expressed as a single polypeptide chain. That is, the C-terminus of the first disulfide conversion aMD4 and the N-terminus of the PAS linker, and the N-terminus of the second disulfide conversion aMD4 and the C-terminus of the PAS linker are bound by an amide bond, and can be expressed as a single polypeptide chain.

(4-2) Preparation of HGF-PAS Dimer Peptides

The prepared HGF-PAS dimer peptides are as follows.

```
(b) PAS-aMD4-PEG11
                                        (SEQ ID NO: 44)
CYRQFNRRTHEVWNLDCGAAPAAPAPAAPAAPAPAAPAAPGCYRQFNR

RTHEVWNLDC

(c) PAS-aMD4dY-PEG11
                                        (SEQ ID NO: 45)
CRQFNRRTHEVWNLDCGAAPAAPAPAAPAAPAPAAPAAPGCRQFNRRT

HEVWNLDC

(d) PAS-aMD4-PEG3
                                        (SEQ ID NO: 46)
CYRQFNRRTHEVWNLDCGAAPAAPAPAAPAAPGCYRQFNRRTHEVWNL

DC

(e)AET-PAS-aMD4-PEG11
                                        (SEQ ID NO: 47)
AETCYRQFNRRTHEVWNLDCGAAPAAPAPAAPAAPAPAAPAAPGCYRQ

FNRRTHEVWNLDC

(f) AET-PAS-aMD4dY-PEG11
                                        (SEQ ID NO: 48)
AETCRQFNRRTHEVWNLDCGAAPAAPAPAAPAAPAPAAPAAPGCRQFN

RRTHEVWNLDC
```

-continued

```
(g) AET-PAS-aMD4-PEG3
                                        (SEQ ID NO: 49)
ETCYRQFNRRTHEVWNLDCGAAPAAPAPAAPAAPGCYRQFNRRTHEV

WNLDC
```

(4-3) Expression of HGF-PAS Dimer Peptides

The expression of these HGF-PAS dimer peptides was examined using Corynex (registered trademark). Hereinafter, examples of expression examinations using Corynex (registered trademark) will be described.

(4-4) Construction of Each Secretory Expression Plasmid of PAS-aMD4-PEG11, PAS-aMD4dY-PEG11, and PAS-aMD4-PEG3 Using TorA Signal Sequence.

As the HGF-PAS dimer peptide, three types of amino acid sequences of the above (b) PAS-aMD4-PEG11 (which may be hereinafter referred to as "PAS-aMD4-PEG11"), (c) PAS-aMD4dY-PEG11 (which may be hereinafter referred to as "PAS-aMD4dY-PEG11"), and (d) PAS-aMD4-PEG3 (which may be hereinafter referred to as "PAS-aMD4-PEG3") were designed, and the base sequences encoding these proteins were designed in consideration of the codon usage frequency of *C. glutamicum*. Furthermore, the following expression cassettes were designed to enable secretory expression by *C. glutamicum.*

PAS-aMD4-PEG11 was secretory-expressed as a fusion protein of PAS-aMD4-PEG11 and a signal peptide 39 amino acid residue of TorA derived from *E. coli* (hereinafter referred to as "TorAss-PAS-aMD4-PEG11"). The base sequence and amino acid sequence encoding the designed TorAss-PAS-aMD4-PEG11 are set forth in SEQ ID NOs: 50 and 51, respectively.

```
Base sequence encoding TorAss-PAS-aMD4-PEG11
                                        (SEQ ID NO: 50)
atgaacaataacgatctctttcaggcatcacgtcggcgttttctggc

acaactcggcggcttaaccgtcgccgggatgctggggccgtcattgt

taacgccgcgacgtgcgactgcgtgttaccgtcaattcaaccgtcgc

acccacgaagtttggaacctggactgtggcgcagcacccgcagcccc

agcccccgcagcacctgcagccccagcaccagctgcaccagccgctc

caggctgctaccgtcagttcaaccgccgcacccacgaagtttggaat

ttggattgctaa

Amino acid sequence of TorAss-PAS-aMD4-PEG11
                                        (SEQ ID NO: 51)
MNNNDLFQASRRRFLAQLGGLTVAGMLGPSLLTPRRATACYRQFNRR

THEVWNLDCGAAPAAPAPAAPAAPAPAAPAAPGCYRQFNRRTHEVWN

LDC
```

PAS-aMD4dY-PEG11 was secretory-expressed as a fusion protein of PAS-aMD4dY-PEG11 and a signal peptide 39 amino acid residue of TorA derived from *E. coli* (hereinafter referred to as "TorAss-PAS-aMD4dY-PEG11"). The base sequence and amino acid sequence encoding the designed TorAss-PAS-aMD4dY-PEG11 are set forth in SEQ ID NOs: 52 and 53, respectively.

```
Base sequence encoding TorAss-PAS-aMD4dY-PEG11
                                        (SEQ ID NO: 52)
atgaacaataacgatctctttcaggcatcacgtcggcgttttctggc
```

-continued

```
acaactcggcggcttaaccgtcgccgggatgctggggccgtcattgt

taacgccgcgacgtgcgactgcgtgccgtcagttcaaccgtcgcacc

cacgaagtttggaatctggactgtggcgcagcccccgcagcacccgc

tcccgcagcacccgcagctccagcaccagcagccccagcagcaccag

gctgccgccagttcaaccgtcgcacccacgaagtttggaatttggat

tgttag
```

```
Amino acid sequence of TorAss-PAS-aMD4dY-PEG11
                                        (SEQ ID NO: 53)
MNNNDLFQASRRRFLAQLGGLTVAGMLGPSLLTPRRATACRQFNRRT

HEVWNLDCGAAPAAPAPAAPAAPAPAAPAAPGCRQFNRRTHEVWNLD

C
```

PAS-aMD4-PEG3 was secretory-expressed as a fusion protein of PAS-aMD4-PEG3 and a signal peptide 39 amino acid residue of TorA derived from *E. coli* (hereinafter referred to as “TorAss-PAS-aMD4-PEG3”). The base sequence and amino acid sequence encoding the designed TorAss-PAS-aMD4-PEG3 are set forth in SEQ ID NOs: 54 and 55, respectively.

```
Base sequence encoding TorAss-PAS-aMD4-PEG3
                                        (SEQ ID NO: 54)
atgaacaataacgatctctttcaggcatcacgtcggcgttttctggc

acaactcggcggcttaaccgtcgccgggatgctggggccgtcattgt

taacgccgcgacgtgcgactgcgtgttaccgtcagttcaaccgccgt

acccacgaagtctggaacctggattgtggtgccgcccccgccgctcc

cgctcccgccgctccggcagcccctggctgctaccgtcagtttaacc

gtcgcacccacgaagtctggaacctggattgctaa
```

```
Amino acid sequence of TorAss-PAS-aMD4-PEG3
                                        (SEQ ID NO: 55)
MNNNDLFQASRRRFLAQLGGLTVAGMLGPSLLTPRRATACYRQFNRR

THEVWNLDCGAAPAAPAPAAPAAPGCYRQFNRRTHEVWNLDC
```

The promoter of the cspB gene derived from the *C. glutamicum* ATCC 13869 strain was linked upstream of the base sequences set forth in TorAss-PAS-aMD4-PEG11, TorAss-PAS-aMD4dY-PEG11, and TorAss-PAS-aMD4-PEG3, and furthermore, an expression cassette of each HGF-PAS dimer peptide having a KpnI site on the 5'-side and an ApaI site on the 3'-side was designed and totally synthesized. The totally synthesized DNA fragment (HGF-PAS dimer peptide expression cassette) was inserted into the KpnI-ApaI site of pPK10 described in Reference Example 1 to construct pPK10_TorAss-PAS-aMD4-PEG11, pPK10_TorAss-PAS-aMD4dY-PEG11, and pPK10_TorAss-PAS-aMD4-PEG3, a secretory expression plasmid for each HGF-PAS dimer peptide using the TorA signal sequence. As a result of determining the base sequence of the inserted fragment, it was confirmed that each HGF-PAS dimer peptide expression cassette as designed had been constructed. Base sequences were determined using BigDye (registered trademark) Terminator v3.1 Cycle Sequencing Kit (Applied Biosystems) and 3130 Genetic Analyzer (Applied Biosystems).

(4-5) Secretory Expression of Each HGF-PAS Dimer Peptide in *C. glutamicum*

The pPK10_TorAss-PAS-aMD4-PEG11, pPK10_TorAss-PAS-aMD4dY-PEG11, and pPK10_TorAss-PAS-aMD4-PEG3 constructed above were used to transform the *C. glutamicum* YDK0107 strain described in WO2016/171224 to obtain the YDK0107/pPK10_TorAss-PAS-aMD4-PEG11 strain, YDK0107/pPK10_TorAss-PAS-aMD4dY-PEG11 strain, and YDK0107/pPK10_TorAss-PAS-aMD4-PEG3 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 4:
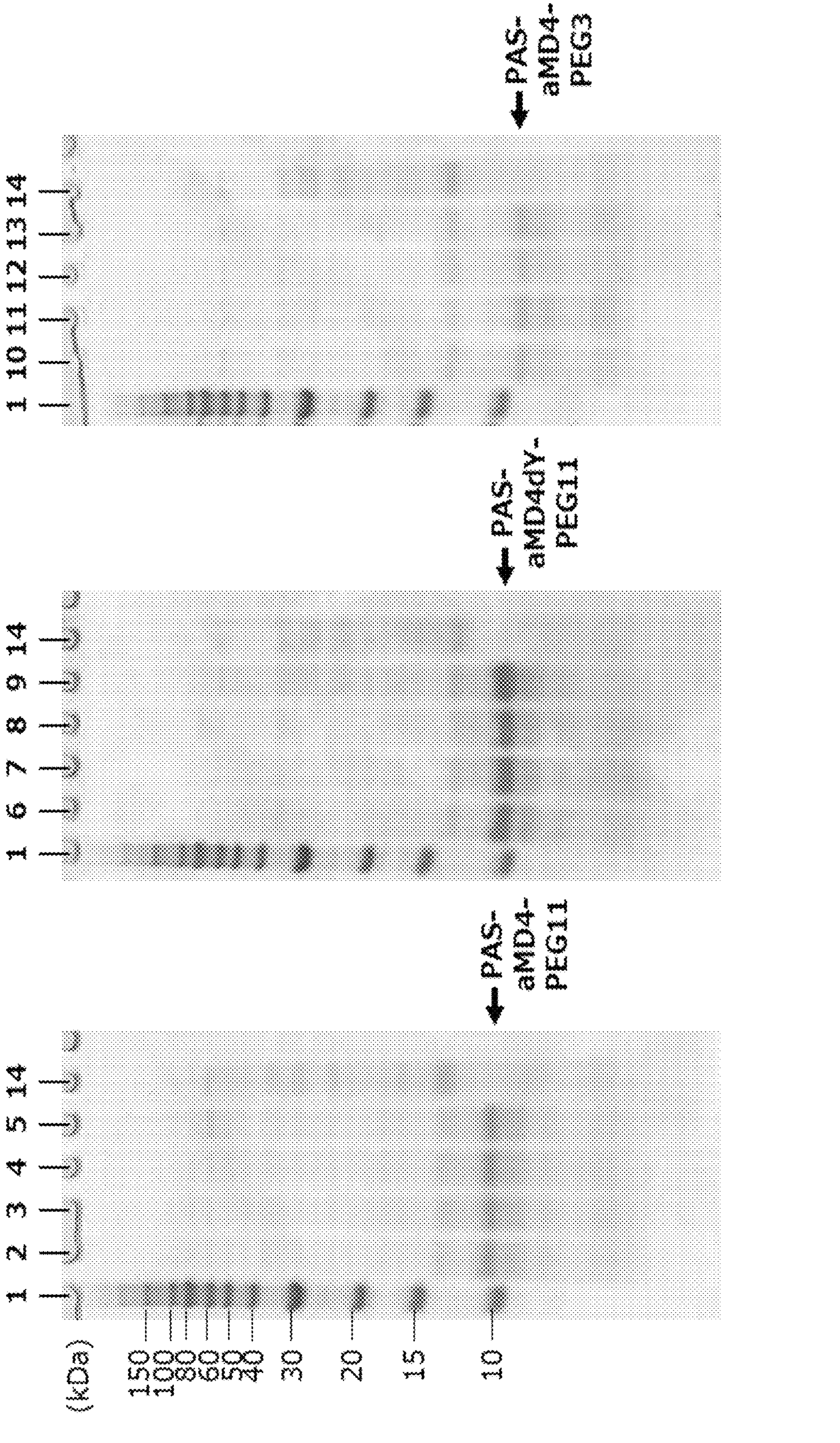
FIG. 4 shows the results of SDS-polyacrylamide electrophoresis showing the secretory expression of the dimer peptide (HGF-PAS) in *C. glutamicum*. Lane 1 is a marker (XL-Ladder Broad, APRO science), lanes 2 to 5 are ones using pPK10_TorAss-PAS-aMD4-PEG11, lanes 6 to 9 are ones using pPK10_TorAss-PAS-aMD4dY-PEG11, lanes 10 to 13 are ones using pPK10_TorAss-PAS-aMD4-PEG3, and lane 14 uses pPK10 (empty vector).

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be PAS-aMD4-PEG11 was detected in the culture supernatant of the YDK0107/pPK10_TorAss-PAS-aMD4-PEG11 strain (FIG. 4, lanes 2 to 5), a protein band presumed to be PAS-aMD4dY-PEG11 was detected in the culture supernatant of the YDK0107/pPK10_TorAss-PAS-aMD4dY-PEG11 strain (FIG. 4, lanes 6 to 9), and a protein band presumed to be PAS-aMD4-PEG3 was detected in the culture supernatant of the YDK0107/pPK10_TorAss-PAS-aMD4-PEG3 strain (FIG. 4, lanes 10 to 13).

(4-6) Construction of Each Secretory Expression Plasmid of AET-PAS-aMD4-PEG11, AET-PAS-aMD4dY-PEG11, and AET-PAS-aMD4-PEG3 Using CspB Signal Sequence As the HGF-PAS dimer peptide, three types of amino acid sequences of the above (e) AET-PAS-aMD4-PEG11 (which may be hereinafter referred to as “AET-PAS-aMD4-PEG11”), (f) AET-PAS-aMD4dY-PEG11 (which may be hereinafter referred to as “AET-PAS-aMD4dY-PEG11”), and (g) AET-PAS-aMD4-PEG3 (which may be hereinafter referred to as “AET-PAS-aMD4-PEG3”) were designed, and the base sequences encoding these proteins were designed in consideration of the codon usage frequency of *C. glutamicum*. Furthermore, the following expression cassettes were designed to enable secretory expression by *C. glutamicum*.

AET-PAS-aMD4-PEG11 was secretory-expressed as a fusion protein of AET-PAS-aMD4-PEG11 and a signal peptide 30 amino acid residue of CspB derived from *C. glutamicum* ATCC 13869 strain (hereinafter referred to as “CspBss-AET-PAS-aMD4-PEG11”). The base sequence and amino acid sequence encoding the designed CspBss-AET-PAS-aMD4-PEG11 are set forth in SEQ ID NOs: 56 and 57, respectively.

```
Base sequence encoding CspBss-AET-PAS-aMD4-
PEG11
                                        (SEQ ID NO: 56)
atgtttaacaaccgtatccgcactgcagctctcgctggtgcaatcgc

aatctccaccgcagcttccggcgtagctatcccagcattcgctgcag

agacctgttaccgtcaattcaaccgtcgcacccacgaagtttggaac

ctggactgtggcgcagcacccgcagccccagcccccgcagcacctgc

agccccagcaccagctgcaccagccgctccaggctgctaccgtcagt
```

-continued tcaaccgccgcacccacgaagtttggaatttggattgctaa

Amino acid sequence of CspBss-AET-PAS-aMD4-PEG11

(SEQ ID NO: 57)

MFNNRIRTAALAGAIAISTAASGVAIPAFAAETCYRQFNRRTHEVWN

LDCGAAPAAPAPAAPAAPAPAAPAAPGCYRQFNRRTHEVWNLDC

AET-PAS-aMD4dY-PEG11 was secretory-expressed as a fusion protein of AET-PAS-aMD4dY-PEG11 and a signal peptide 30 amino acid residue of CspB derived from *C. glutamicum* ATCC 13869 strain (hereinafter referred to as "CspBss-AET-PAS-aMD4dY-PEG11"). The base sequence and amino acid sequence encoding the designed CspBss-AET-PAS-aMD4dY-PEG11 are set forth in SEQ ID NOs: 58 and 59, respectively.

Base sequence encoding CspBss-AET-PAS-aMD4dY-PEG11

(SEQ ID NO: 58)

atgtttaacaaccgtatccgcactgcagctctcgctggtgcaatcgc aatctccaccgcagcttccggcgtagctatcccagcattcgctgcag agacctgccgtcagttcaaccgtcgcacccacgaagtttggaatctg gactgtggcgcagcccccgcagcacccgctcccgcagcacccgcagc tccagcaccagcagccccagcagcaccaggctgccgccagttcaacc gtcgcacccacgaagtttggaatttggattgttag Amino acid sequence of CspBss-AET-PAS-aMD4dY-PEG11

(SEQ ID NO: 59)

MFNNRIRTAALAGAIAISTAASGVAIPAFAAETCRQFNRRTHEVWNL

DCGAAPAAPAPAAPAAPAPAAPAAPGCRQFNRRTHEVWNLDC

AET-PAS-aMD4-PEG3 was secretory-expressed as a fusion protein of AET-PAS-aMD4-PEG3 and a signal peptide 30 amino acid residue of CspB derived from *C. glutamicum* ATCC 13869 strain (hereinafter referred to as "CspBss-AET-PAS-aMD4-PEG3"). The base sequence and amino acid sequence encoding the designed CspBss-AET-PAS-aMD4-PEG3 are set forth in SEQ ID NOs: 60 and 61, respectively.

Base sequence encoding CspBss-AET-PAS-aMD4-PEG3

(SEQ ID NO: 60)

atgtttaacaaccgtatccgcactgcagctctcgctggtgcaatcgc aatctccaccgcagcttccggcgtagctatcccagcattcgctgcag agacctgttaccgtcagttcaaccgccgtacccacgaagtctggaac ctggattgtggtgccgcccccgccgctcccgctcccgccgctccggc agcccctggctgctaccgtcagtttaaccgtcgcacccacgaagtct ggaacctggattgctaa Amino acid sequence of CspBss-AET-PAS-aMD4-PEG3

(SEQ ID NO: 61)

MFNNRIRTAALAGAIAISTAASGVAIPAFAAETCYRQFNRRTHEVWN

LDCGAAPAAPAPAAPAAPGCYRQFNRRTHEVWNLDC

The promoter of the cspB gene derived from the *C. glutamicum* ATCC 13869 strain was linked upstream of the base sequences set forth in AET-PAS-aMD4-PEG11, AET-PAS-aMD4dY-PEG11, and AET-PAS-aMD4-PEG3, and furthermore, an expression cassette of each HGF-PAS dimer peptide having a KpnI site on the 5'-side and a BamHI site on the 3'-side was designed and totally synthesized. The totally synthesized DNA fragment (HGF-PAS dimer peptide expression cassette) was inserted into the KpnI-BamHI site of pPK4 described in Japanese Patent Application Publication No. Hei 9-322774 to construct pPK4_CspBss-AET-PAS-aMD4-PEG11, pPK4_CspBss-AET-PAS-aMD4dY-PEG11, and pPK4_CspBss-AET-PAS-aMD4-PEG3, a secretory expression plasmid for each HGF-PAS dimer peptide using the CspB signal sequence. As a result of determining the base sequence of the inserted fragment, it was confirmed that each HGF-PAS dimer peptide expression cassette as designed had been constructed. Base sequences were determined using BigDye (registered trademark) Terminator v3.1 Cycle Sequencing Kit (Applied Biosystems) and 3130 Genetic Analyzer (Applied Biosystems).

(4-7) Secretory Expression of Each HGF-PAS Dimer Peptide in *C. glutamicum*

The pPK4_CspBss-AET-PAS-aMD4-PEG11, pPK4_CspBss-AET-PAS-aMD4dY-PEG11, and pPK4_CspBss-AET-PAS-aMD4-PEG3 constructed above were used to transform the *C. glutamicum* YDK010:phoS (W302C) strain described in WO2016/171224 to obtain the YDK010:phoS(W302C)/pPK4_CspBss-AET-PAS-aMD4-PEG11 strain, YDK010:phoS(W302C)/pPK4_CspBss-AET-PAS-aMD4dY-PEG11 strain, and YDK010:phoS (W302C)/pPK4_CspBss-AET-PAS-aMD4-PEG3 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 5:
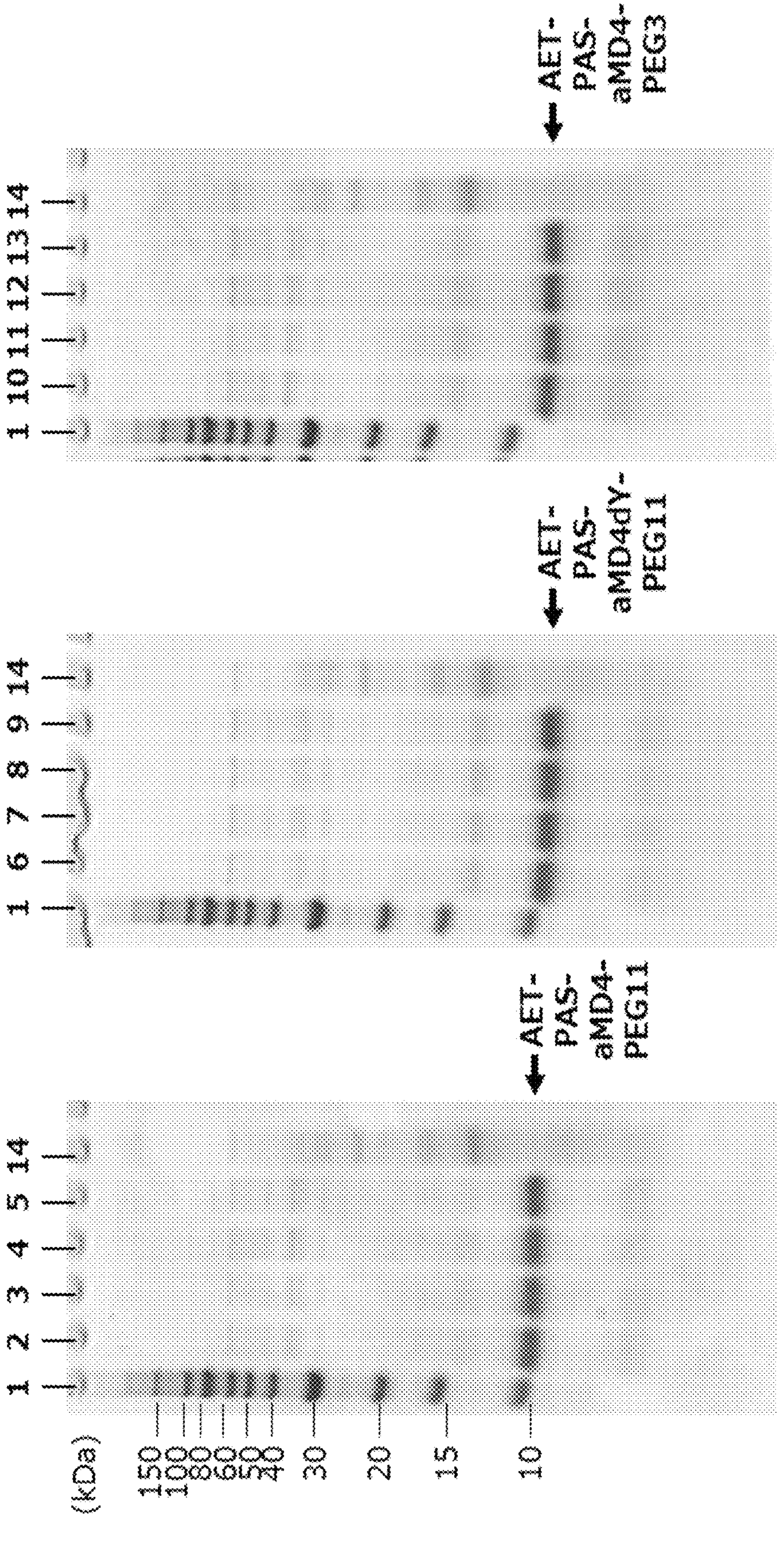
FIG. 5 shows the results of SDS-polyacrylamide electrophoresis showing the secretory expression of the dimer peptide (HGF-PAS) in *C. glutamicum*. Lane 1 is a marker (XL-Ladder Broad, APRO science), lanes 2 to 5 are ones using pPK4_CspBss-AET-PAS-aMD4-PEG11, lanes 6 to 9 are ones using pPK4_CspBss-AET-PAS-aMD4dY-PEG11, lanes 10 to 13 are ones using pPK4_CspBss-AET-PAS-aMD4-PEG3, and lane 14 uses pPK4 (empty vector).

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-PAS-aMD4-PEG11 was detected in the culture supernatant of the YDK010:phoS (W302C)/pPK4_CspBss-AET-PAS-aMD4-PEG11 strain (FIG. 5, lanes 2 to 5), a protein band presumed to be AET-PAS-aMD4dY-PEG11 was detected in the culture supernatant of the YDK010:phoS(W302C)/pPK4_CspBss-AET-PAS-aMD4dY-PEG11 strain (FIG. 5, lanes 6 to 9), and a protein band presumed to be AET-PAS-aMD4-PEG3 was detected in the culture supernatant of the YDK010:phoS (W302C)/pPK4_CspBss-AET-PAS-aMD4-PEG3 strain (FIG. 5, lanes 10 to 13).

(4-8) Purification of HGF-PAS Dimer Peptide

The HGF-PAS dimer peptides obtained above were purified using AKTA explorer (GE Healthcare) and Superdex 75 10/300 GL columns (GE Healthcare). The culture supernatant in an amount of 1 mL was injected into the AKTA explorer, and PBS (10 mM phosphate buffer, 140 mM NaCl, pH 7.4) was allowed to flow under the condition of a flow rate of 0.5 mL/min to fractionate the protein, thereby obtaining the desired HGF-PAS dimer peptide fraction.

Example 5: Molecular Weight Analysis of HGF-PAS Dimer Peptide

AET-PAS-aMD4dY-PEG11, AET-PAS-aMD4-PEG11, and AET-PAS-aMD4-PEG3 were each mixed with α-Cyano-4-hydroxycinnamic Acid (CHCA), and MALDI-TOF-MS (Shimadzu, AXIMA-TOF 2) was used to measure the molecular weights.

Figure 6:
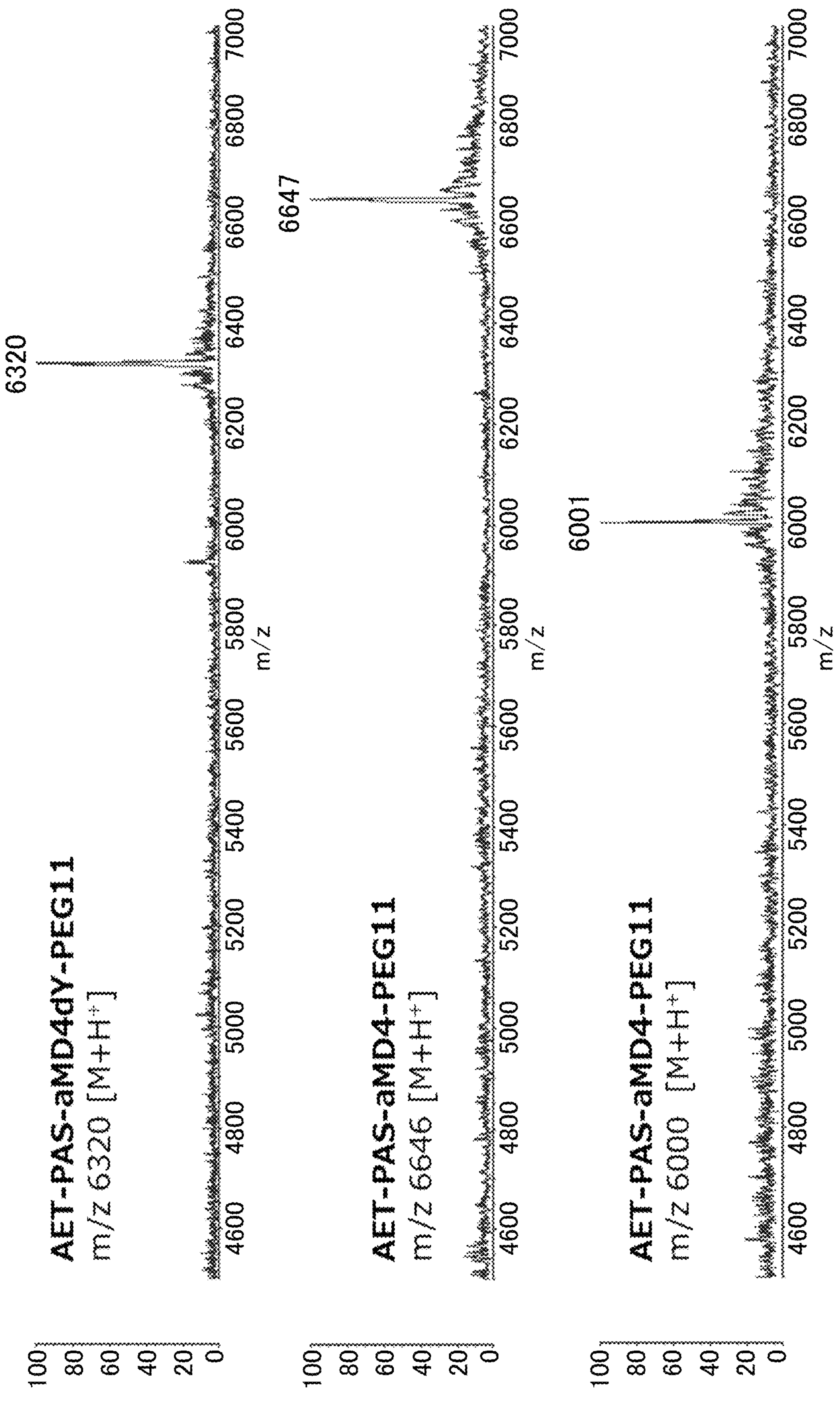
FIG. 6 shows measurement results for the dimer peptide (HGF-PAS) by MALDI-TOF-MS.

As shown in FIG. 6, a value substantially the same as the theoretical molecular weight value of each oxidized dimer peptide forming two disulfide bonds in the molecule (AET-PAS-aMD4dY-PEG11: m/z 6320, AET-PAS-aMD4-PEG11: m/z 6646, AET-PAS-aMD4-PEG3: m/z 6000) was obtained. It was confirmed that peptides having the correct amino acid sequence containing two disulfide bonds could be expressed.

Example 6: Activity Evaluation of HGF-PAS Dimer Peptide

The Met activation ability of the HGF-PAS dimer peptide was evaluated by luciferase assay. To 25 μL of Opti-MEM medium (Thermo Fisher Scientific), 0.6 μL of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 200 ng/mL HGF was added, or 0 to 800 ng/mL AET-PAS-aMD4dY-PEG11, AET-PAS-aMD4-PEG11, or AET-PAS-aMD4-PEG3 was added, or a culture supernatant containing PAS-aMD4dY-PEG11, PAS-aMD4-PEG11, or PAS-aMD4-PEG3 was added so as to be diluted 10-fold with respect to the medium, and the evaluation basal medium was added in an amount of 100 μL to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 7:
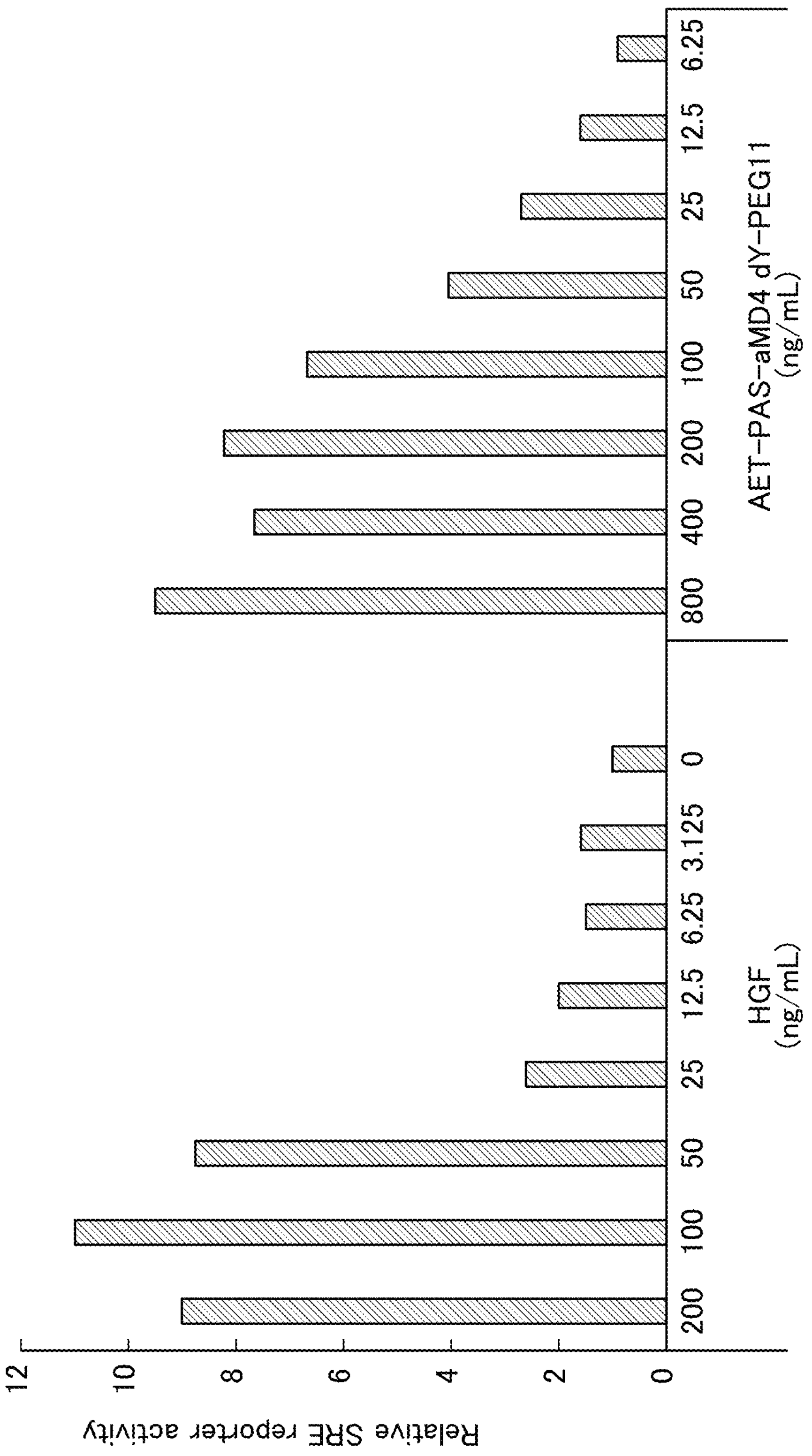
FIG. 7 is a graph showing the activity evaluation of HGF and dimer peptide (HGF-PAS). The vertical axis represents relative receptor activity and the horizontal axis represents concentration.
Figure 8:
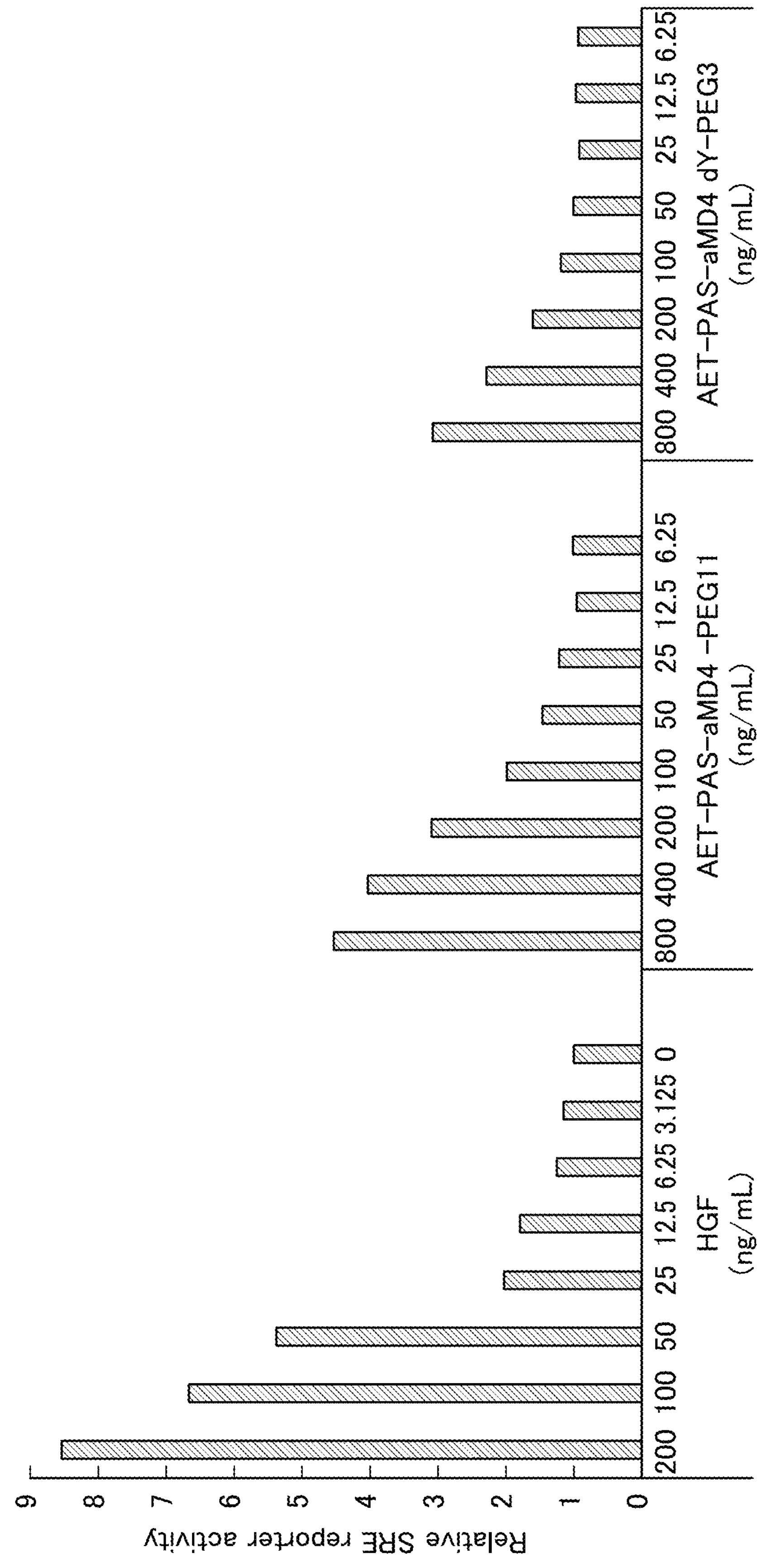
FIG. 8 is a graph showing the activity evaluation of HGF and dimer peptide (HGF-PAS). The vertical axis represents relative receptor activity and the horizontal axis represents concentration.
Figure 9:
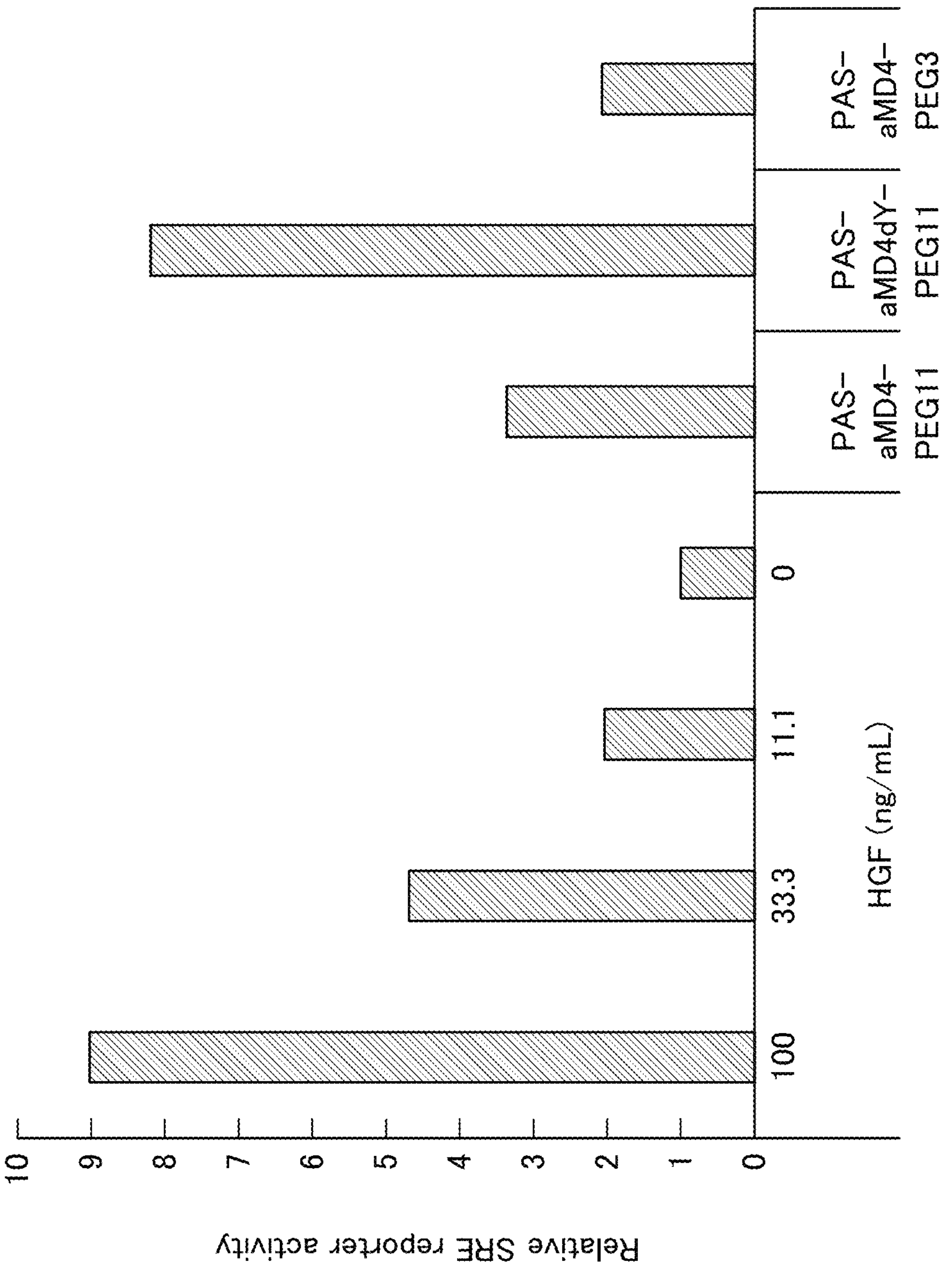
FIG. 9 is a graph showing the activity evaluation of HGF and dimer peptide (HGF-PAS). The vertical axis represents relative receptor activity, and the horizontal axis represents concentration for HGF and, for the dimer peptide (HGF-PAS), the used culture supernatant containing a 10-fold diluted dimer peptide (HGF-PAS) with respect to the medium used for the activity evaluation.

As shown in FIGS. 7 to 9, it was clarified that all HGF-PAS dimer peptides had a signal activation ability. In particular, AET-PAS-aMD4dY-PEG11 and PAS-aMD4dY-PEG11 were found to have maximum activity comparable to 100 ng/mL HGF.

Example 7: Specificity Evaluation of HGF-PAS Dimer Peptide

The receptor tyrosine kinase (RTK) specificity of the HGF-PAS dimer peptide was evaluated using Proteome Profiler Human Phospho-RTK Array Kit (R&D Systems).

HEK293E cells confluent in a 10 cm cell culture dish were starved by culturing for 24 hours in D-MEM medium containing 0.5% FBS (Thermo Fisher Scientific) and penicillin-streptomycin (Nacalai Tesque). The starved HEK293E cells were stimulated with 200 ng/mL AET-PAS-aMD4dY-PEG11 for 10 minutes. As a positive control, 100 ng/mL HGF was similarly stimulated for 10 minutes. As a negative control, PBS was added and stimulated for 10 minutes (Mock group). After removing the medium and washing the cells once with PBS, the cells were lysed by adding 1 mL of Lysis buffer 17 containing a Protease inhibitor cocktail (Nacalai Tesque). The lysate solution was centrifuged at 14,000 G for 5 minutes to obtain the supernatant as a lysate.

Figure 10:
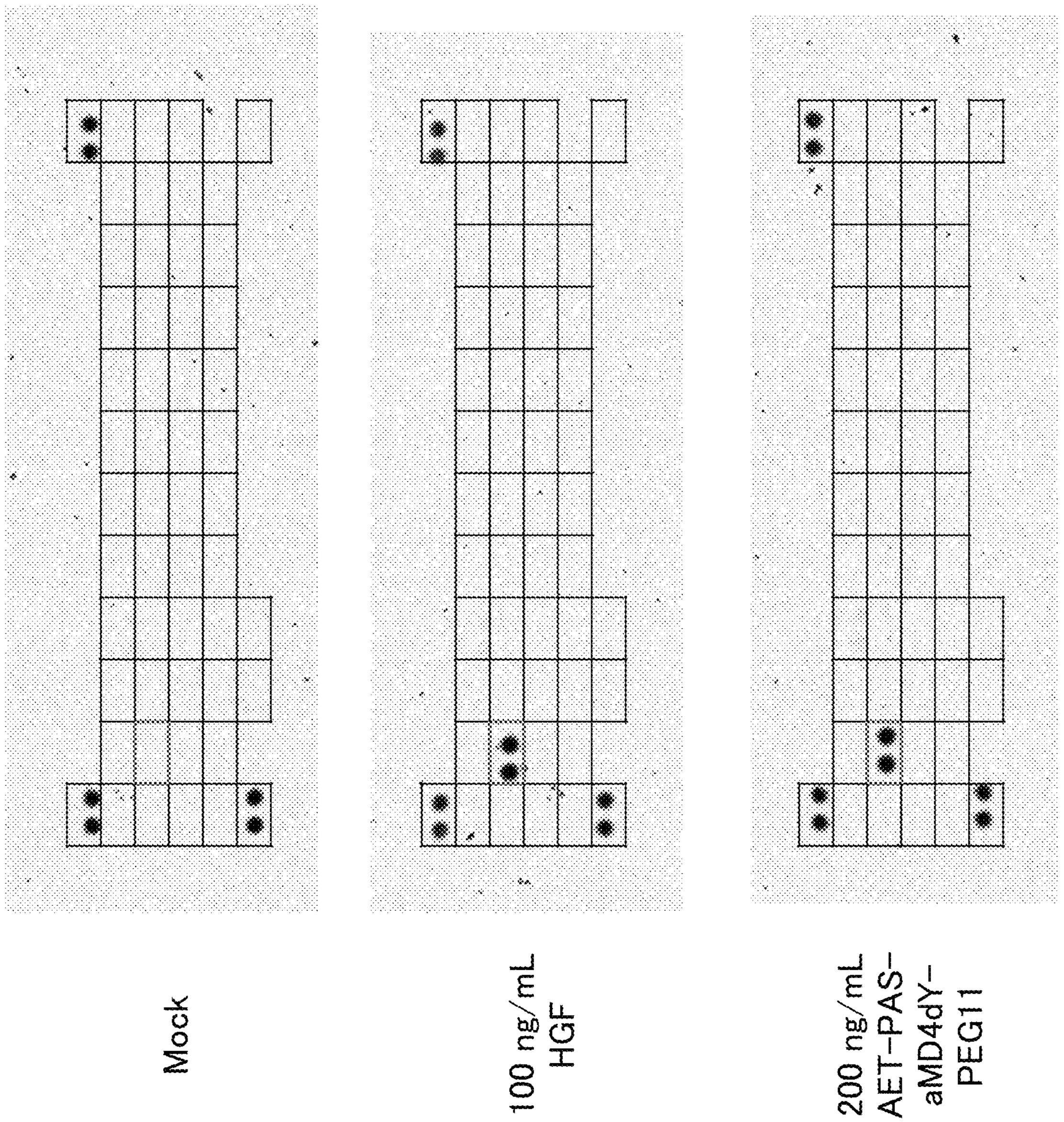
FIG. 10 is a diagram evaluating the receptor tyrosine kinase (RTK) specificity of the dimer peptide (HGF-PAS) using Proteome Profiler Human Phospho-RTK Array Kit (R&D Systems). The dimer peptide (HGF-PAS) has been confirmed to exhibit Met (HGF receptor) specificity.

The lysate was analyzed using Proteome Profiler Human Phospho-RTK Array Kit. Molecular Imager ChemiDoc XRS System (Bio-Rad) was used to detect chemiluminescence. As shown in FIG. 10, it was confirmed that all RTK of the cells stimulated with PBS (Mock group) were in a dephosphorylated state. It was also confirmed that when stimulated with HGF, the HGF receptor Met was specifically phosphorylated. When stimulated with AET-PAS-aMD4dY-PEG11, Met was specifically phosphorylated as in the case of HGF. From this result, it was clarified that AET-PAS-aMD4dY-PEG11 performed Met-specific activation. Note that FIG. 11 shows each array of Proteome Profiler Human Phospho-RTK Array Kit (R&D Systems).

Example 8: Evaluation of Cell Proliferation Promoting Activity of HGF-PAS Dimer Peptide HGF has been reported to promote cell proliferation by activating Met (K. Ito, et al. Nat. Commun. 6, 6373, 2015). Therefore, HuCCT1 cell culture was used to evaluate whether the HGF-PAS dimer peptide had the same activity of promoting cell proliferation as HGF.

RPMI 1640 medium (Nacalai Tesque) containing 5% FBS was added to a 24-well cell culture plate, and HuCCT1 cells were seeded at 5,000 cell/well. HGF at 35 ng/mL or AET-PAS-aMD4dY-PEG11 at 40 ng/mL was added, and the cells were cultured at 37 °C and 5% $CO_2$ for 5 days. The cells were detached with 0.25% Trypsin/EDTA (Thermo Fisher Scientific) and the number of cells was quantified with Countess Automated Cell Counter (Thermo Fisher Scientific) (N=3).

Figure 12:
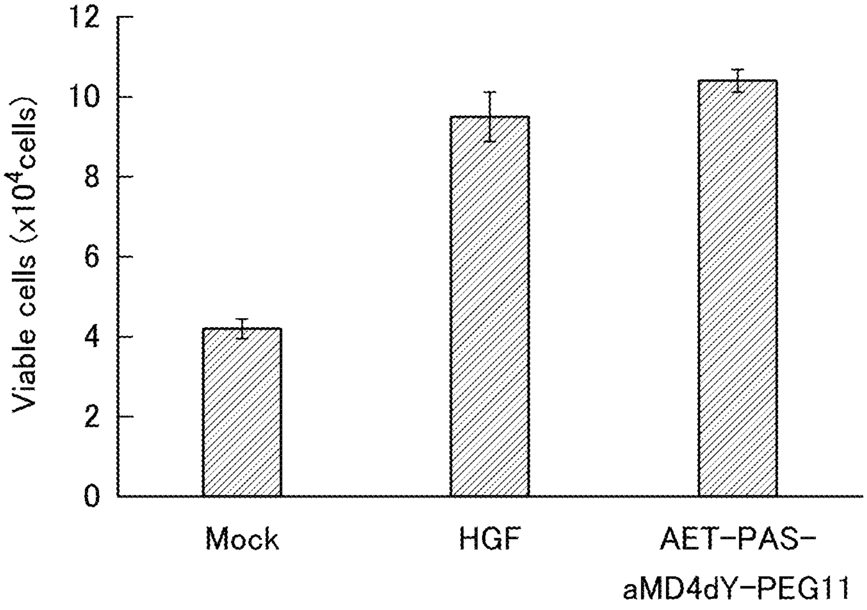
FIG. 12 is a graph showing the evaluation of cell proliferation promoting activity of HGF and dimer peptide (HGF-PAS). The vertical axis represents the number of viable cells.

As shown in FIG. 12, all the cells cultured with the addition of HGF or AET-PAS-aMD4dY-PEG11 showed a proliferation ability about 2.5 times higher than that of the non-added group (Mock). From this, it was clarified that AET-PAS-aMD4dY-PEG11 promoted cell proliferation as in the case of HGF.

Example 9: Evaluation of Migration Activity of HGF-PAS Dimer Peptide

HGF has been reported to promote cell migration ability by activating Met (K. Ito, et al. Nat. Commun. 6, 6373, 2015). Therefore, HuCCT1 cell culture was used to evaluate whether the HGF-PAS dimer peptide had the same activity of promoting cell migration as HGF.

Figure 13:
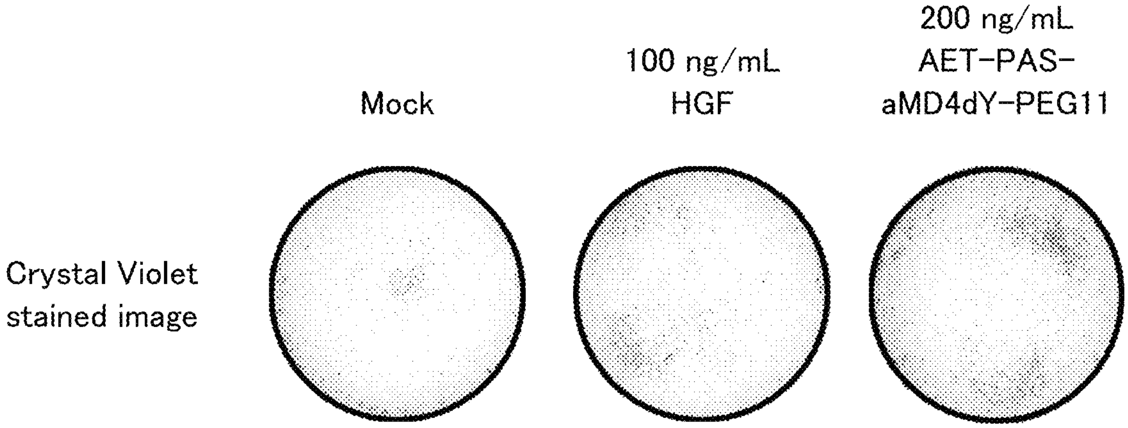
FIG. 13 is a micrograph in the evaluation of cell migration activity of HGF and dimer peptide (HGF-PAS).

To Transwell inserts for 24-well (pore size 3.0 m, Corning), 20,000 HuCCT1 cells suspended in low serum medium (RPMI 1640 medium with 0.5% FBS) were added. A low serum medium containing 100 ng/mL HGF or 200 ng/mL AET-PAS-aMD4dY-PEG11 was added to the lower layer. After culturing for 24 hours under the conditions of 37 °C and 5% $CO_2$, the Transwell inserts were washed 3 times with PBS and cell-fixed and stained with methanol containing 0.5% Crystal Violet (Nacalai Tesque) for 10 minutes. Immobilized and stained Transwell inserts were washed with distilled water. The cells inside the inserts were removed with a scraper. The cells migrated to the outside of the inserts and stained were photographed in the bright field observation mode of a BZ-X microscope (Keyence). FIG. 13 shows a bright field image of the lower part of the Transwell inserts stained with Crystal Violet and a quantitative value of migration ability.

Figure 14:
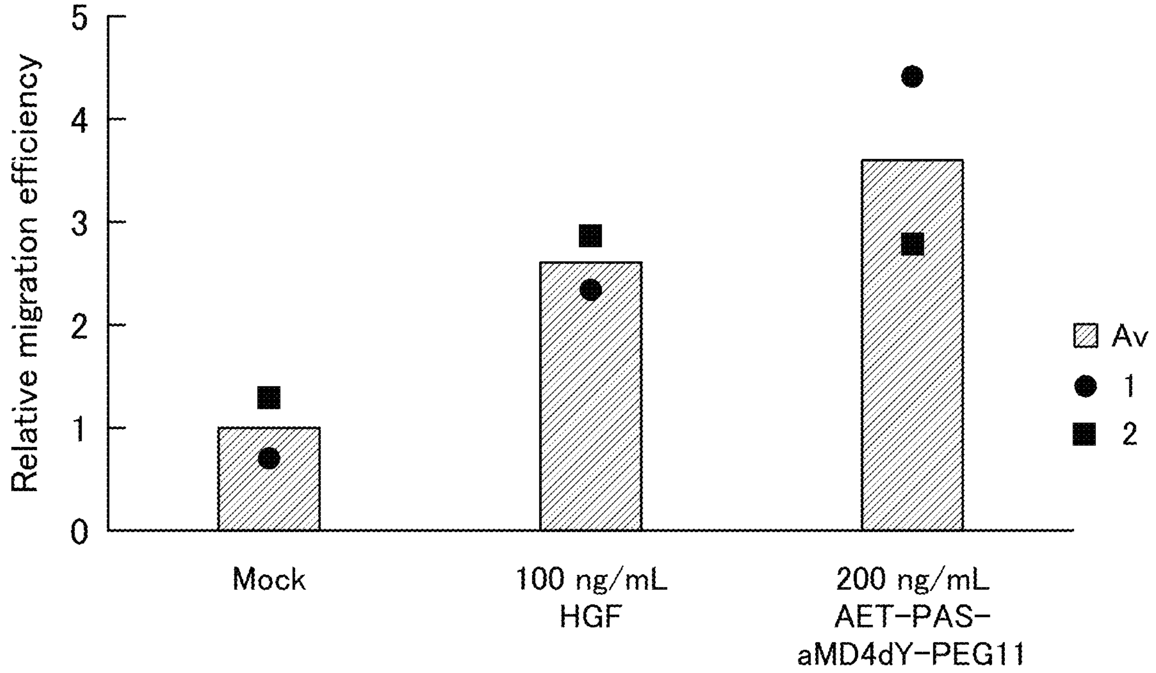
FIG. 14 is a graph showing the evaluation of cell migration activity of HGF and dimer peptide (HGF-PAS). The vertical axis represents the relative movement efficiency.

The migration ability was calculated as (area of stained region)/(insert area) and as a relative value (Relative migration efficiency) to the value of the non-added group (Mock) (N=2). FIG. 14 shows the results.

When HGF or AET-PAS-aMD4dY-PEG11 was added and cultured, the proportion of the cells migrating to the lower part of the Transwell inserts increased, and therefore it was clarified that AET-PAS-aMD4dY-PEG11 promoted cell migration as in the case of HGF.

Example 10: Evaluation of Wound Healing Effect of HGF-PAS Dimer Peptide

HGF has been reported to promote cell wound healing ability by activating Met (K. Ito, et al. Nat. Commun. 6, 6373, 2015). Therefore, HuCCT1 cell culture was used to evaluate whether the HGF-PAS dimer peptide would promote wound healing as HGF.

To 96-well cell culture plates, 50,000 HuCCT1 cells suspended in RPMI 1640 medium with 10% FBS were added per well and incubated overnight under the conditions of 37 °C and 5% $CO_2$. Cells in the center of the culture wells were scraped using a 1000 μL Thermo Scientific ART chip (Thermo Fisher Scientific) and washed with low serum medium (RPMI 1640 medium with 0.5% FBS). Low serum medium containing 33 ng/mL HGF or 100 ng/mL AET-PAS-aMD4dY-PEG11 was added, and the cells were cultured under the conditions of 37 °C and 5% $CO_2$. BioStudio-T (Nikon Corporation) was used for cell observation, and cells were automatically photographed every hour. The rate of wound healing (μm/h) was calculated as ((wound width 1 hour after wound creation)−(wound width 7 hours after wound creation))/6 (N=4).

Figure 15:
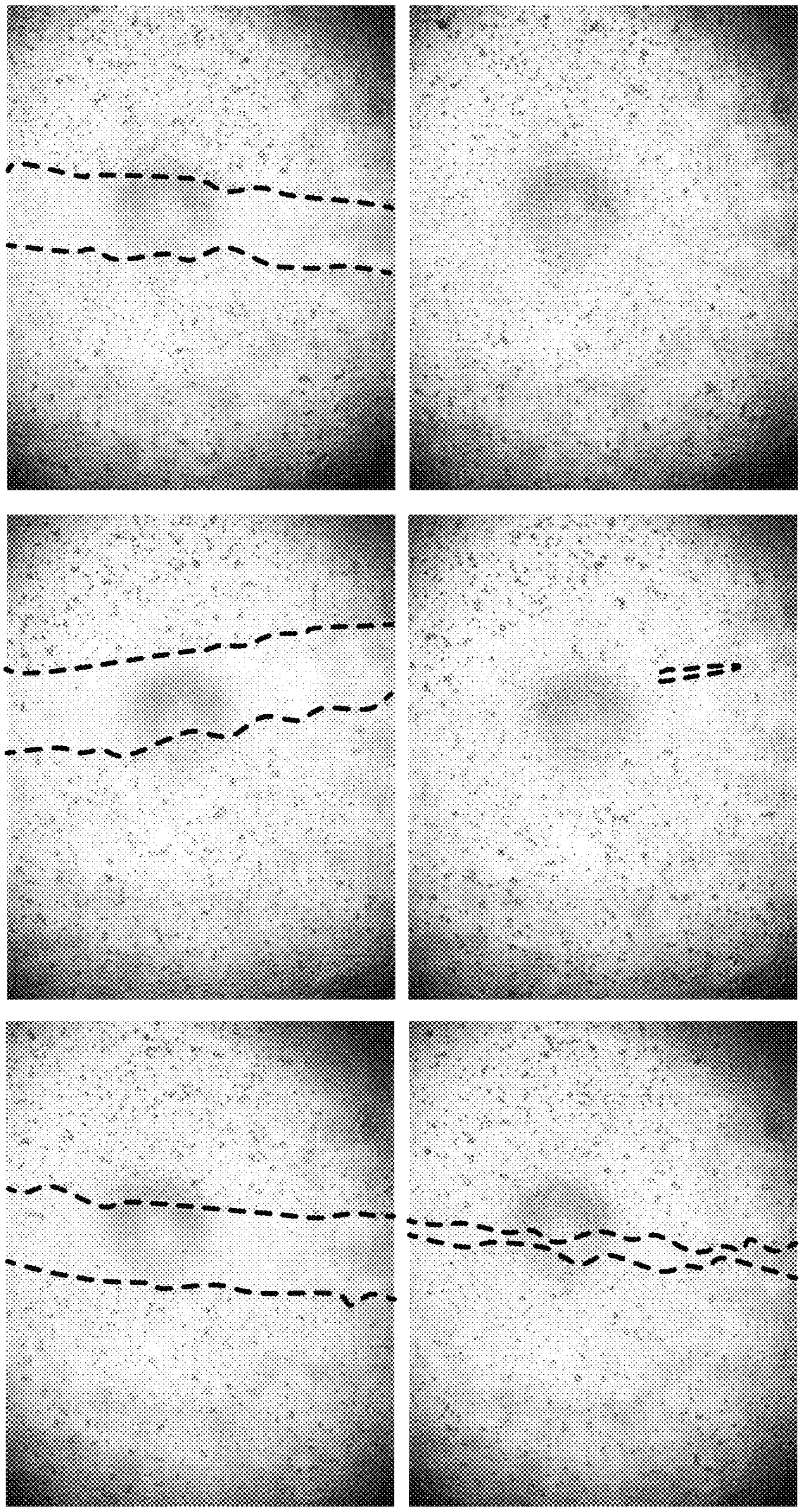
FIG. 15 is a photographic diagram taken with a cell observation device in the evaluation of the wound healing effect of HGF and dimer peptide (HGF-PAS).
Figure 16:
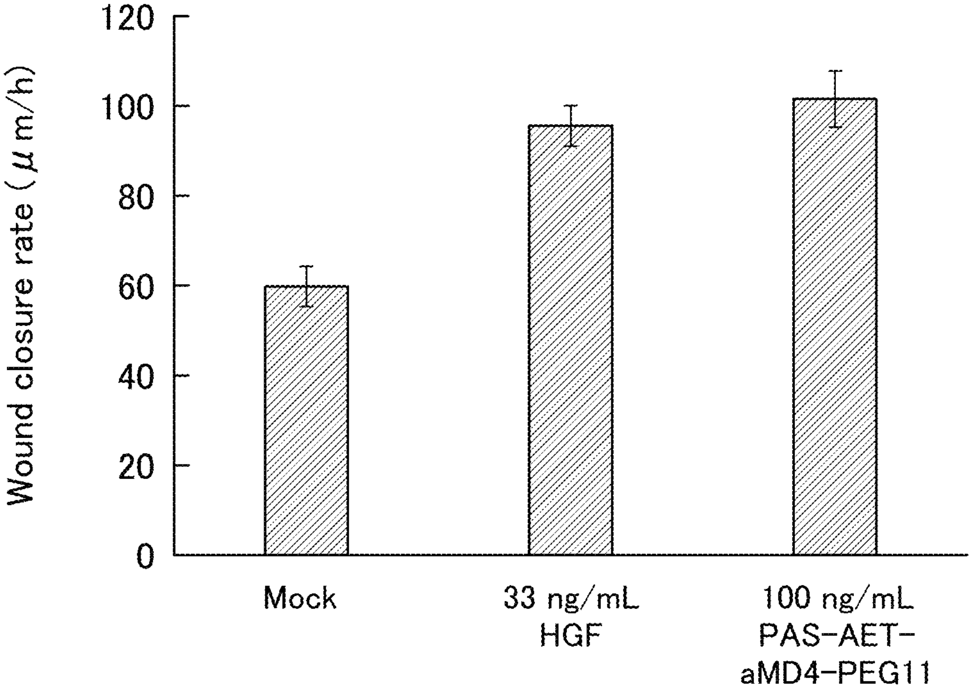
FIG. 16 is a graph showing the evaluation of the wound healing effect of HGF and dimer peptide (HGF-PAS). The vertical axis represents the wound healing rate.

FIG. 15 shows phase difference images of cells 1 hour and 9 hours after wound creation, and FIG. 16 shows the rate of wound healing. Cells supplemented with HGF or AET-PAS-aMD4dY-PEG11 improved in the rate of wound healing by about 1.6 times, and therefore it was clarified that AET-PAS-aMD4dY-PEG11 improve the wound healing ability of cells as well as HGF.

Example 11: Evaluation of Tubular Structure Forming Effect of HGF-PAS Dimer Peptide It is known that HGF is allowed to act on HUVEC cells and HuCCT1 cells contained in collagen gel to form a tubular structure (K. Ito, et al. Nat. Commun. 6, 6373, 2015). It has also been reported that a Met full agonist having a function similar to that of HGF can form a tubular structure in the above cells, whereas a partial agonist having only a partial function cannot promote the formation of a tubular structure (W. Miao, et al. Int. J. Mol. Sci. 19, 3141, 2018). Therefore, it was decided to confirm whether the HGF-PAS dimer peptide was a full agonist or a partial agonist by using a tubular structure formation experiment using HuCCT1 cells.

To 8 equivalents of CellMatrix type IA (Nitta Gelatin), 1 equivalent of 10-fold concentrated D-MEM/F12 (Thermo Fisher Scientific) and 1 equivalent of reconstitution buffer (22 g/L sodium bicarbonate, 47.7 g/L HEPES, 0.05N sodium hydroxide aqueous solution) were mixed in order on ice. HuCCT1 cells were added at 25,000 cells per mL of the mixture and mixed on ice. To a 48-well cell culture plate, 400 μL of the above mixture was added, and the mixture was allowed to stand for 4 hours under the conditions of 37 °C and 5% $CO_2$ for gelation. Onto the formed intracellular encapsulated collagen gel, 500 μL of RPMI 1640 medium containing 10% FBS was added. The cell-stimulating group was cultured by adding 35 ng/mL HGF or 40 ng/mL AET-PAS-aMD4dY-PEG11. The whole medium was replaced at a frequency not exceeding 3 days. On day 7 of culture, the morphology of the cells in the collagen gel was observed with an inverted microscope.

Figure 17:
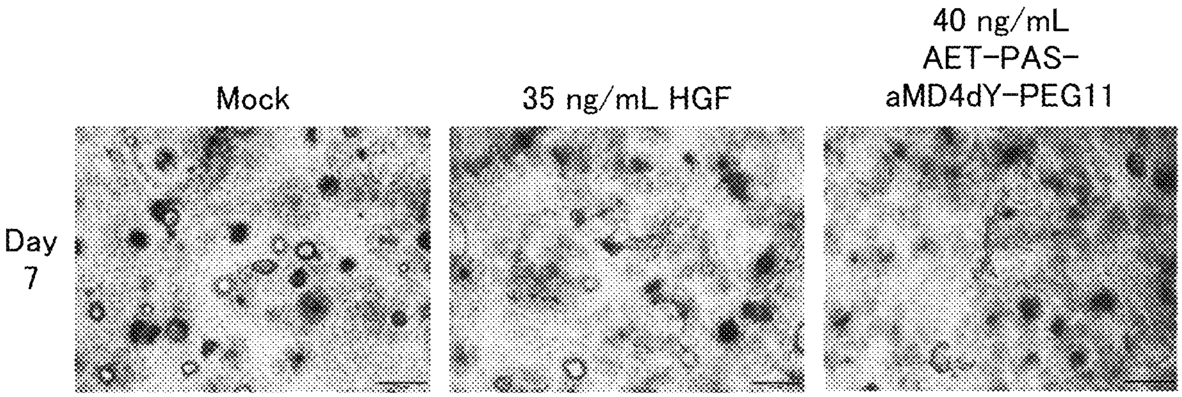
FIG. 17 is a micrograph in the evaluation of the tubular structure forming effect of HGF and dimer peptide (HGF-PAS). The scale bar represents 500 m.

FIG. 17 shows the morphology of HuCCT1 cells on day 7 of culture (scale bar: 500 m). The cells supplemented with HGF or AET-PAS-aMD4dY-PEG11 formed a tubular structure of about 500 to 1000 m, whereas the cells not supplemented showed a spherical morphology. From these results, it was clarified that AET-PAS-aMD4dY-PEG11 could promote the tubular structure formation of HuCCT1 cells as in the case of rhHGF and was a full agonist for Met.

Example 12: Design of HGF-PAS Heterodimer Peptide and its Secretory Expression in *C. glutamicum*

(12-1) Outline of HGF-PAS Heterodimer Peptide Design

The Met-linked cyclic peptides aMD4 and aMD5 reported in K. Ito, et al. Nat. Commun. 6, 6373, 2015 were expressed as heterodimeric molecules. In the dimer peptide synthesis method in K. Ito, et al. Nat. Commun. 6, 6373, 2015, it is difficult to selectively synthesize a dimer peptide having "aMD4"-"linker"-"aMD5". That is, when two types of peptides are bound via a PEG molecule, four types of dimer peptides of "aMD4"-"linker"-"aMD4", "aMD4"-"linker"-"aMD5", "aMD5"-"linker"-"aMD4", and "aMD5"-"linker"-"aMD5" are produced. Therefore, in this example, the following design enables the heterodimer peptide dimerized by the PAS linker to be expressed in *C. glutamicum* as one polypeptide chain.

(1) aMD4 and aMD5 are cyclized by an intramolecular thioether bond formed by the reaction of the chloroacetyl groups added to the N-terminus amino groups with the sulfhydryl groups of the cysteine-side chains in the sequence, and therefore cyclized by a disulfide bond due to the sulfhydryl groups of the two cysteine side chains.

(2) Dimerization is achieved by binding the C-terminuses of the cyclic peptides to each other using a Bis-Maleimide-PEG linker, and cannot be expressed in *C. glutamicum*, so that the C-terminus of aMD4 and the N-terminus of aMD5 are bound with a PAS linker peptide.

With the above design, the "aMD4"-"PAS linker"-"aMD5" peptide is selectively expressed.

(12-2) Preparation of HGF-PAS Heterodimer Peptide

The prepared HGF-PAS heterodimer peptide is as follows.

```
(h) AET-PAS-aMD4_aMD5-PEG11
                                        (SEQ ID NO: 62)
AETCYRQFNRRTHEVWNLDCGAAPAAPAPAAPAAPAPAAPAAPGCYW

YYAWDQTYKAFPC
```

(12-3) Expression of HGF-PAS Heterodimer Peptide

Corynex (registered trademark) was used to examine the expression of HGF-PAS heterodimer peptide. Hereinafter, examples of expression examinations using Corynex (registered trademark) will be described.

(12-4) Construction of Secretory Expression Plasmid of AET-PAS-aMD4_aMD5-PEG11 Using CspB Signal Sequence As the HGF-PAS heterodimer peptide, the amino acid sequence of the above (h) AET-PAS-aMD4_aMD5-PEG11 (which may be hereinafter referred to as "AET-PAS-aMD4_aMD5-PEG11") was designed, and the base sequence encoding this protein was designed in consideration of the codon usage frequency of *C. glutamicum*. Furthermore, the following expression cassette was designed to enable secretion expression by *C. glutamicum.*

AET-PAS-aMD4_aMD5-PEG11 was secretory-expressed as a fusion protein of AET-PAS-aMD4_aMD5-PEG11 and a signal peptide 30 amino acid residue of CspB derived from *C. glutamicum* ATCC 13869 strain (hereinafter referred to as "CspBss-AET-PAS-aMD4_aMD5-PEG11"). The base sequence and amino acid sequence encoding the designed CspBss-AET-PAS-aMD4_aMD5-PEG11 are set forth in SEQ ID NOs: 63 and 64, respectively.

```
Base sequence encoding CspBss-AET-PAS-
aMD4_aMD5-PEG11
                                    (SEQ ID NO: 63)
atgtttaacaaccgtatccgcactgcagctctcgctggtgcaatcgc

aatctccaccgcagcttccggcgtagctatcccagcattcgctgcag

agacctgttaccgtcagttcaaccgtcgcacccacgaagtttggaac

ctggattgtggcgcagcccccgcagcccccgcacccgcagcccctgc

agccccagccccagctgcaccagcagcacctggctgttactggtatt

atgcgtgggatcagacctacaaagcgtttccgtgttag

Amino acid sequence of CspBss-AET-PAS-
aMD4_aMD5-PEG11
                                    (SEQ ID NO: 64)
MFNNRIRTAALAGAIAISTAASGVAIPAFAAETCYRQFNRRTHEVWN

LDCGAAPAAPAPAAPAAPAPAAPAAPGCYWYYAWDQTYKAFPC
```

The promoter of the cspB gene derived from the *C. glutamicum* ATCC 13869 strain was linked upstream of the base sequence set forth in AET-PAS-aMD4_aMD5-PEG11, and furthermore, an expression cassette of HGF-PAS heterodimer peptide having a KpnI site on the 5'-side and an BamHI site on the 3'-side was designed and totally synthesized. The totally synthesized DNA fragment (HGF-PAS heterodimer peptide expression cassette) was inserted into the KpnI-BamHI site of pPK4 described in Japanese Patent Application Publication No. Hei 9-322774 to construct pPK4_CspBss-AET-PAS-aMD4_aMD5-PEG1, a secretory expression plasmid for the HGF-PAS heterodimer peptide using the CspB signal sequence. As a result of determining the base sequence of the inserted fragment, it was confirmed that the HGF-PAS heterodimer peptide expression cassette as designed had been constructed. Base sequences were determined using BigDye (registered trademark) Terminator v3.1 Cycle Sequencing Kit (Applied Biosystems) and 3130 Genetic Analyzer (Applied Biosystems).

(12-5) Secretory Expression of HGF-PAS Heterodimer Peptide in *C. glutamicum*

The pPK4_CspBss-AET-PAS-aMD4_aMD5-PEG11 constructed above was used to transform the *C. glutamicum* YDK010:phoS(W302C) strain described in WO2016/171224 to obtain the YDK010:phoS(W302C)/pPK4_CspBss-AET-PAS-aMD4_aMD5-PEG11 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 18:
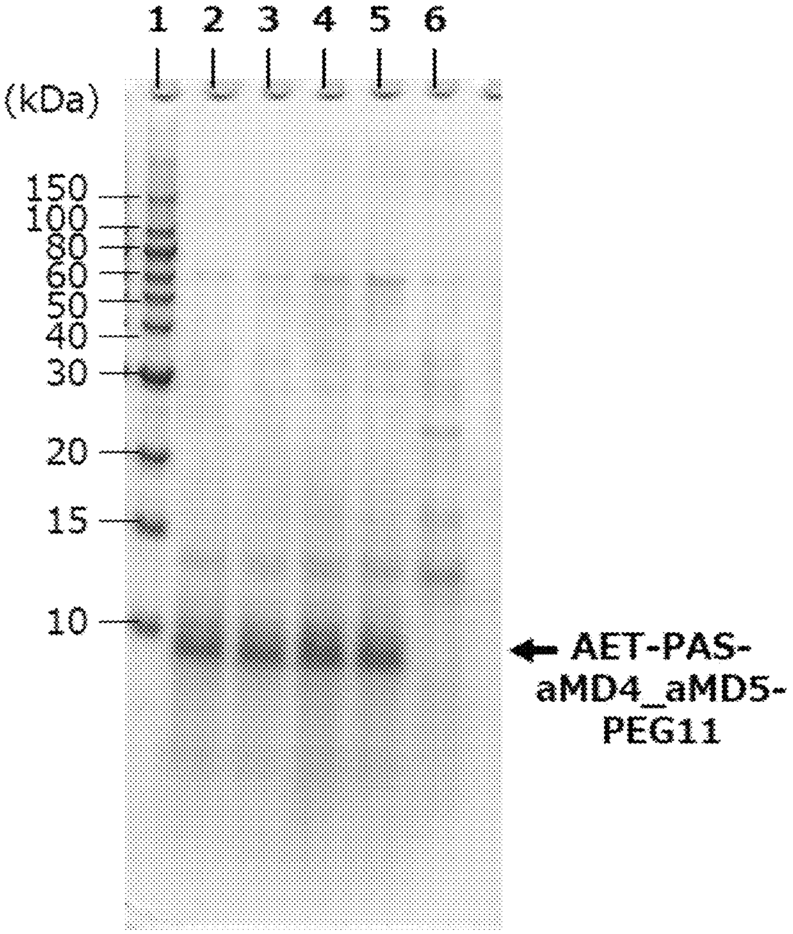
FIG. 18 shows the results of SDS-polyacrylamide electrophoresis showing the secretory expression of the heterodimer peptide (HGF-PAS) in *C. glutamicum*. Lane 1 is a marker (XL-Ladder Broad, APRO science), lanes 2 to 5 are ones using pPK4_CspBss-AET-PAS-aMD4_aMD5-PEG11, and lane 6 is one using pPK4 (empty vector).

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-PAS-aMD4_aMD5-PEG11 was detected in the culture supernatant of the YDK010:phoS(W302C)/pPK4_CspBss-AET-PAS-aMD4_aMD5-PEG11 strain (FIG. 18, lanes 2 to 5).

Example 13: Molecular Weight Analysis of HGF-PAS Heterodimer Peptide

AET-PAS-aMD4_aMD5-PEG11 peptide expression supernatant was mixed with α-Cyano-4-hydroxycinnamic Acid (CHCA), and MALDI-TOF-MS (Shimadzu, AXIMA-TOF 2) was used to measure the molecular weight.

Figure 19:
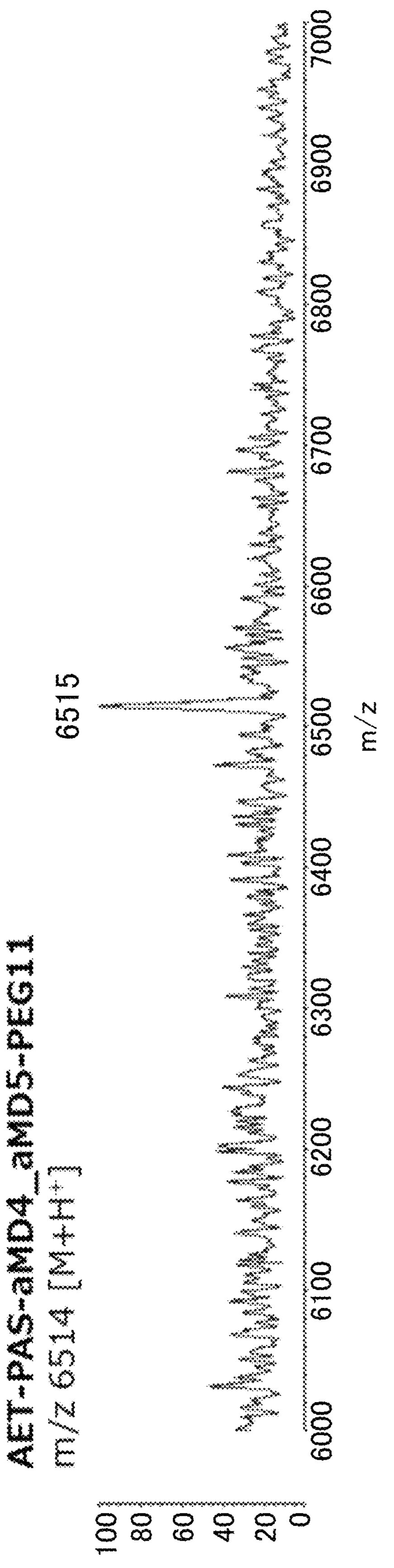
FIG. 19 shows measurement results for the heterodimer peptide (HGF-PAS) by MALDI-TOF-MS.

As shown in FIG. 19, a value substantially the same as the theoretical molecular weight value of the oxidized HGF-PAS heterodimer peptide forming two disulfide bonds in the molecule (AET-PAS-aMD4_aMD5-PEG11: m/z 6514) was obtained. It was confirmed that peptides having the correct amino acid sequence containing two disulfide bonds could be expressed.

Example 14: Design of HGF-PAS Dimer Peptide Linker Variant and its Secretory Expression in *C. glutamicum*

(14-1) Outline of HGF-PAS Dimer Peptide Linker Variant Design

AET-PAS-aMD4dY-PEG11 with HGF-like activity has a structure in which a PAS linker composed of 22 amino acids is linked between the first aMD4dY cyclic peptide (set forth in SEQ ID NO: 2) and the second aMD4dY cyclic peptide. By changing the length of this PAS linker, it is expected that the HGF-like activity will change. Therefore, a linker variant was designed in which the PAS linker portion was changed to a PAS repeat sequence from 8 amino acids to 200 amino acids.

In addition to the PAS linker, a GS linker, which is a repeating sequence of glycine and serin, is also known as a flexible linker. Therefore, the peptide sequence was designed to be a linker variant in which aMD4dY was bound to the N-terminus and C-terminus of the GS linker composed of a repeating sequence of 4 glycine residues and 1 serine residue (GGGGS), that is, a "first aMD4dY cyclic peptide"-"GS linker"-"second aMD4dY cyclic peptide".

(14-2) Preparation of HGF-PAS Dimer Peptide Linker Variants

The prepared HGF-PAS dimer peptide linker variants are as follows.

(i) AET-aMD4dY-PAS8
(SEQ ID NO: 81)
AETCRQFNRRTHEVWNLDCGAAPAAPAPGCRQFNRRTHEVWNLDC (j) AET-aMD4dY-PAS49
(SEQ ID NO: 82)
AETCRQFNRRTHEVWNLDCGAAPAAPAPAAPAAPAPAAPAAPAPAAP

AAPAPAAPAAPAPAAPAAPAPAGCRQFNRRTHEVWNLDC (k) AET-aMD4dY-PAS100
(SEQ ID NO: 83)
AETCRQFNRRTHEVWNLDCGAAPAAPAPAAPAAPAPAAPAAPAPAAP

AAPAPAAPAAPAPAAPAAPAPAAPAAPAPAAPAAPAPAAPAAPAPAA

PAAPAPAAPAAPAPAAPAAPAPAAPAGCRQFNRRTHEVWNLDC (l) AET-aMD4dY-PAS200
(SEQ ID NO: 84)
AETCRQFNRRTHEVWNLDCGAAPAAPAPAAPAAPAPAAPAAPAPAAP

AAPAPAAPAAPAPAAPAAPAPAAPAAPAPAAPAAPAPAAPAAPAPAA

PAAPAPAAPAAPAPAAPAAPAPAAPAAPAPAAPAAPAPAAPAAPAPA

APAAPAPAAPAAPAPAAPAAPAPAAPAAPAPAAPAAPAPAAPAAPAP

AAPAAPAPAAPAAPAPAAPAAPAPAAPAAPAPGCRQFNRRTHEVWNL

DC (m) AET-aMD4dY-GS15
(SEQ ID NO: 85)
AETCRQFNRRTHEVWNLDCGGGGGSGGGGSGGGGSGCRQFNRRTHEV

WNLDC (n) AET-aMD4dY-GS22
(SEQ ID NO: 86)
AETCRQFNRRTHEVWNLDCGGGGGSGGGGSGGGGSGGGGSGGGCRQ

FNRRTHEVWNLDC (14-3) Expression of HGF-PAS Dimer Peptide Linker Variants

The expression of these HGF-PAS dimer peptide linker variants was examined using Corynex (registered trademark). Hereinafter, examples of expression examinations using Corynex (registered trademark) will be described.

(14-4) Construction of Each Secretory Expression Plasmid of AET-aMD4dY-PAS8, AET-aMD4dY-PAS49, AET-aMD4dY-PAS100, AET-aMD4dY-PAS200, AET-aMD4dY-GS15, and AET-aMD4dY-GS22 Using CspB Signal Sequence As the HGF-PAS dimer peptide linker variant, six types of amino acid sequences of the above (i) AET-aMD4dY-PAS8 (which may be hereinafter referred to as "AET-aMD4dY-PAS8"), (j) AET-aMD4dY-PAS49 (which may be hereinafter referred to as "AET-aMD4dY-PAS49"), (k) AET-aMD4dY-PAS100 (which may be hereinafter referred to as "AET-aMD4dY-PAS100"), (1) AET-aMD4dY-PAS200 (which may be hereinafter referred to as "AET-aMD4dY-PAS200"), (m) AET-aMD4dY-GS15 (which may be hereinafter referred to as "AET-aMD4dY-GS15"), and (n) AET-aMD4dY-GS22 (which may be hereinafter referred to as "AET-aMD4dY-GS22") were designed, and base sequences encoding these proteins were designed in consideration of the codon usage frequency of *C. glutamicum*. Furthermore, the following expression cassettes were designed to enable secretory expression by *C. glutamicum*.

AET-aMD4dY-PAS8 was secretory-expressed as a fusion protein of AET-aMD4dY-PAS8 and a signal peptide 30 amino acid residue of CspB derived from *C. glutamicum* ATCC 13869 strain (hereinafter referred to as "CspBss-AET-aMD4dY-PAS8"). The base sequence and amino acid sequence encoding the designed CspBss-AET-aMD4dY-PAS8 are set forth in SEQ ID NOs: 87 and 88, respectively.

Base sequence encoding CspBss-AET-aMD4dY-PAS8
(SEQ ID NO: 87)
atgtttaacaaccgtatccgcactgcagctctcgctggtgcaatcgc aatctccaccgcagcttccggcgtagctatcccagcattcgctgcag agacctgccgccagttcaaccgccgcacccacgaagtgtggaacctg gattgcggcgctgcaccagccgctccagcaccaggctgccgccagtt caaccgccgcacccacgaagtgtggaacctggattgctaa Amino acid sequence of CspBss-AET-aMD4dY-PAS8
(SEQ ID NO: 88)
FNNRIRTAALAGAIAISTAASGVAIPAFAAETCRQFNRRTHEVWNLD

CGAAPAAPAPGCRQFNRRTHEVWNLDC

AET-aMD4dY-PAS49 was secretory-expressed as a fusion protein of AET-aMD4dY-PAS49 and a signal peptide 30 amino acid residue of CspB derived from *C. glutamicum* ATCC 13869 strain (hereinafter referred to as "CspBss-AET-aMD4dY-PAS49"). The base sequence and amino acid sequence encoding the designed CspBss-AET-aMD4dY-PAS49 are set forth in SEQ ID NOs: 89 and 90, respectively.

Base sequence encoding CspBss-AET-aMD4dY-PAS49
(SEQ ID NO: 89)
atgtttaacaaccgtatccgcactgcagctctcgctggtgcaatcgc aatctccaccgcagcttccggcgtagctatcccagcattcgctgcag agacctgtcgtcagttcaaccgtcgcacccacgaagtttggaatttg gactgtggcgcagcaccagcggcaccagcaccagcagccccagcggc accagccccagctgcaccagccgctccagcaccagcagcacccgcag cccccgctcccgcagcccccgccgcaccagcacccgcagcaccagca gcacccgctccagcaggttgtcgccaattcaaccgccgcacccacga agtgtggaacctggattgctaa Amino acid sequence of CspBss-AET-aMD4dY-PAS49
(SEQ ID NO: 90)
MFNNRIRTAALAGAIAISTAASGVAIPAFAAETCRQFNRRTHEVWNL

DCGAAPAAPAPAAPAAPAPAAPAAPAPAAPAAPAPAAPAAPAPAAPA

APAPAGCRQFNRRTHEVWNLDC

AET-aMD4dY-PAS100 was secretory-expressed as a fusion protein of AET-aMD4dY-PAS100 and a signal peptide 30 amino acid residue of CspB derived from *C. glutamicum* ATCC 13869 strain (hereinafter referred to as "CspBss-AET-aMD4dY-PAS100"). The base sequence and amino acid sequence encoding the designed CspBss-AET-aMD4dY-PAS100 are set forth in SEQ ID NOs: 91 and 92, respectively.

Base sequence encoding CspBss-AET-aMD4dY-PAS100
(SEQ ID NO: 91)
atgtttaacaaccgtatccgcactgcagctctcgctggtgcaatcgc aatctccaccgcagcttccggcgtagctatcccagcattcgctgcag agacctgtcgtcagttcaaccgtcgcacccacgaagtttggaatttg -continued gactgtggcgcagcaccagcggcaccagcaccagcagccccagcggc accagccccagctgcaccagccgctccagcaccagcagccccagcag cccccgctccagcagcacccgcagcaccagctcccgcagccccagca gccccagccccagcagcaccagcagccccagctccagcagccccagc tgcaccagctccagccgcaccagcagctccagccccagccgctcccg ccgccccagcccccgccgcaccagccgcccctgctcccgccgcccca gccgctcccgctccagccgctcctgccggttgccgccagttcaaccg ccgcacccacgaagtgtggaacctggattgctaa Amino acid sequence of CspBss-AET-aMD4dY-PAS100
(SEQ ID NO: 92)
MFNNRIRTAALAGAIAISTAASGVAIPAFAAETCRQFNRRTHEVWNL

DCGAAPAAPAPAAPAAPAPAAPAAPAPAAPAAPAPAAPAAPAPAAPA

APAPAAPAAPAPAAPAAPAPAAPAAPAPAAPAAPAPAAPAAPAPAAP

AAPAPAAPAGCRQFNRRTHEVWNLDC

AET-aMD4dY-PAS200 was secretory-expressed as a fusion protein of AET-aMD4dY-PAS200 and a signal peptide 30 amino acid residue of CspB derived from *C. glutamicum* ATCC 13869 strain (hereinafter referred to as "CspBss-AET-aMD4dY-PAS200"). The base sequence and amino acid sequence encoding the designed CspBss-AET-aMD4dY-PAS200 are set forth in SEQ ID NOs: 93 and 93, respectively.

Base sequence encoding CspBss-AET-aMD4dY-PAS200
(SEQ ID NO: 93)
atgtttaacaaccgtatccgcactgcagctctcgctggtgcaatcgc aatctccaccgcagcttccggcgtagctatcccagcattcgctgcag agacctgtcgtcagttcaaccgtcgcacccacgaagtttggaatttg gactgtggcgcagcaccagcggcaccagcaccagcagccccagcggc accagccccagctgcaccagccgctccagcaccagccgcccccgccg cccccgcccctgctgctcctgctgctcccgctcccgctgctcccgct gcccctgctcctgctgctcccgctgcgccagccccagcagcaccagc tgccccagcaccagctgcaccagccgcaccagctccagcagccccag ctgctccagcaccagcagcaccagcagcaccagctccagcggcacca gcagcaccagcacctgcggcaccagcggctccagccccagcagcacc agcagcgccagcaccagcagctccagcagcaccagcaccagcagcac cagcggcaccagccccagctgcaccagccgctccagcaccagctgcc ccagcagctccagccccagccgcacctgccgcacctgcccctgccgc tcctgctgcccccgctcctgccgctcctgctgcccctgcccctgctg ctcctgctgctccagctccagccgcaccagccgctccagcaccagct gcaccagcagctccagccccagctgccccagcagctccagcccctgg ttgccgccaatttaatcgccgcacccacgaggtctggaatcttgact gctaa Amino acid sequence of CspBss-AET-aMD4dY-PAS200
(SEQ ID NO: 94)
MFNNRIRTAALAGAIAISTAASGVAIPAFAAETCRQFNRRTHEVWNL -continued

DCGAAPAAPAPAAPAAPAPAAPAAPAPAAPAAPAPAAPAAPAPAAPA

APAPAAPAAPAPAAPAAPAPAAPAAPAPAAPAAPAPAAPAAPAPAAP

AAPAPAAPAAPAPAAPAAPAPAAPAAPAPAAPAAPAPAAPAAPAPAA

PAAPAPAAPAAPAPAAPAAPAPAAPAAPAPAAPAAPAPAAPAAPAPA

APAAPAPAAPAAPAPGCRQFNRRTHEVWNLDC

AET-aMD4dY-GS15 was secretory-expressed as a fusion protein of AET-aMD4dY-GS15 and a signal peptide 30 amino acid residue of CspB derived from *C. glutamicum* ATCC 13869 strain (hereinafter referred to as "CspBss-AET-aMD4dY-GS15"). The base sequence and amino acid sequence encoding the designed CspBss-AET-aMD4dY-GS15 are set forth in SEQ ID NOs: 95 and 96, respectively.

Base sequence encoding CspBss-AET-
aMD4dY-GS15
(SEQ ID NO: 95)
atgtttaacaaccgtatccgcactgcagctctcgctggtgcaatcgcaat ctccaccgcagcttccggcgtagctatcccagcattcgctgcagagacct gccgccagttcaaccgccgcacccacgaagtgtggaacctggattgcggc ggcggcggcggctccggcggcggcggctccggcggcggcggctccggctg ccgccagttcaaccgccgcacccacgaagtgtggaacctggattgctaa Amino acid sequence of CspBss-AET-
aMD4dY-GS15
(SEQ ID NO: 96)
MFNNRIRTAALAGAIAISTAASGVAIPAFAAETCRQFNRRTHEVWNLDCG

GGGGSGGGGSGGGGSGCRQFNRRTHEVWNLDC

AET-aMD4dY-GS22 was secretory-expressed as a fusion protein of AET-aMD4dY-GS22 and a signal peptide 30 amino acid residue of CspB derived from *C. glutamicum* ATCC 13869 strain (hereinafter referred to as "CspBss-AET-aMD4dY-GS22"). The base sequence and amino acid sequence encoding the designed CspBss-AET-aMD4dY-GS22 are set forth in SEQ ID NOs: 97 and 98, respectively.

Base sequence encoding CspBss-AET-
aMD4dY-GS22
(SEQ ID NO: 97)
atgtttaacaaccgtatccgcactgcagctctcgctggtgcaatcgcaat ctccaccgcagcttccggcgtagctatcccagcattcgctgcagagacct gccgccagttcaaccgccgcacccacgaagtgtggaacctggattgcggc ggcggcggcggctccggcggcggcggttctggcggtggcggttctggcgg cggcggttctggcggcggttgtcgtcagttcaatcgtcgcacccacgaag tctggaatctcgactgctaa Amino acid sequence of CspBss-AET-
aMD4dY-GS22
(SEQ ID NO: 98)
MFNNRIRTAALAGAIAISTAASGVAIPAFAAETCRQFNRRTHEVWNLDCG

GGGGSGGGGSGGGGSGGGGSGGGCRQFNRRTHEVWNLDC

The promoter of the cspB gene derived from the *C. glutamicum* ATCC 13869 strain was linked upstream of the base sequences set forth in CspBss-AET-aMD4dY-PAS8, CspBss-AET-aMD4dY-PAS49, CspBss-AET-aMD4dY-PAS100, CspBss-AET-aMD4dY-PAS200, CspBss-AET-aMD4dY-GS15, and CspBss-AET-aMD4dY-GS22, and furthermore, an expression cassette of each HGF-PAS dimer peptide linker variant having a KpnI site on the 5'-side and an BamHI site on the 3'-side was designed and totally synthesized. The totally synthesized DNA fragment (HGF-PAS dimer peptide linker variant expression cassette) was inserted into the KpnI-BamHI site of pPK4 described in Japanese Patent Application Publication No. Hei 9-322774 to construct pPK4_CspBss-AET-aMD4dY-PAS8, pPK4_CspBss-AET-aMD4dY-PAS49, pPK4_CspBss-AET-aMD4dY-PAS100, pPK4_CspBss-AET-aMD4dY-PAS200, pPK4_CspBss-AET-aMD4dY-GS15, and pPK4_CspBss-AET-aMD4dY-GS22, a secretory expression plasmid for each HGF-PAS dimer peptide linker variant using the CspB signal sequence. As a result of determining the base sequence of the inserted fragment, it was confirmed that each HGF-PAS dimer peptide linker variant expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

In addition, pPK4_CspBss-AET-PAS-aMD4dY-PEG11 was constructed in the same manner as above, and its construction was confirmed. AET-PAS-aMD4dY-PEG11 is from Example 4 and has a PAS linker composed of 22 amino acids.

(14-5) Secretory Expression of Each HGF-PAS Dimer Peptide in *C. glutamicum*

The pPK4_CspBss-AET-aMD4dY-PAS8, pPK4_CspBss-AET-aMD4dY-PAS49, pPK4_CspBss-AET-aMD4dY-PAS100, pPK4_CspBss-AET-aMD4dY-PAS200, pPK4_CspBss-AET-aMD4dY-GS15, and pPK4_CspBss-AET-aMD4dY-GS22 constructed above were used to transform the *C. glutamicum* YDK010:phoS(W302C) strain described in WO2016/171224 to obtain the YDK010:phoS (W302C)/pPK4_CspBss-AET-aMD4dY-PAS8 strain, YDK010:phoS(W302C)/pPK4_CspBss-AET-aMD4dY-PAS49 strain, YDK010:phoS(W302C)/pPK4_CspBss-AET-aMD4dY-PAS100 strain, YDK010:phoS(W302C)/pPK4_CspBss-AET-aMD4dY-PAS200 strain, YDK010:phoS(W302C)/pPK4_CspBss-AET-aMD4dY-GS15 strain, and YDK010:phoS(W302C)/pPK4_CspBss-AET-aMD4dY-GS22 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-aMD4dY-PAS8 was detected in the culture supernatant of the YDK010:phoS (W302C)/pPK4_CspBss-AET-aMD4dY-PAS8 strain (FIG. 20, lane 4), a protein band presumed to be AET-aMD4dY-PAS49 was detected in the culture supernatant of the YDK010:phoS(W302C)/pPK4_CspBss-AET-aMD4dY-PAS49 strain (FIG. 20, lane 6), a protein band presumed to be AET-aMD4dY-PAS100 was detected in the culture supernatant of the YDK010:phoS(W302C)/pPK4_CspBss-AET-aMD4dY-PAS100 strain (FIG. 20, lane 7), a protein band presumed to be AET-aMD4dY-PAS200 was detected in the culture supernatant of the YDK010:phoS(W302C)/pPK4_CspBss-AET-aMD4dY-PAS200 strain (FIG. 20, lane 8), a protein band presumed to be AET-aMD4dY-GS15 was detected in the culture supernatant of the YDK010:phoS (W302C)/pPK4_CspBss-AET-aMD4dY-GS15 strain (FIG. 20, lane 2), and a protein band presumed to be AET-aMD4dY-GS22 was detected in the culture supernatant of the YDK010:phoS(W302C)/pPK4_CspBss-AET-aMD4dY-GS22 strain (FIG. 20, lane 3).

Figure 20:
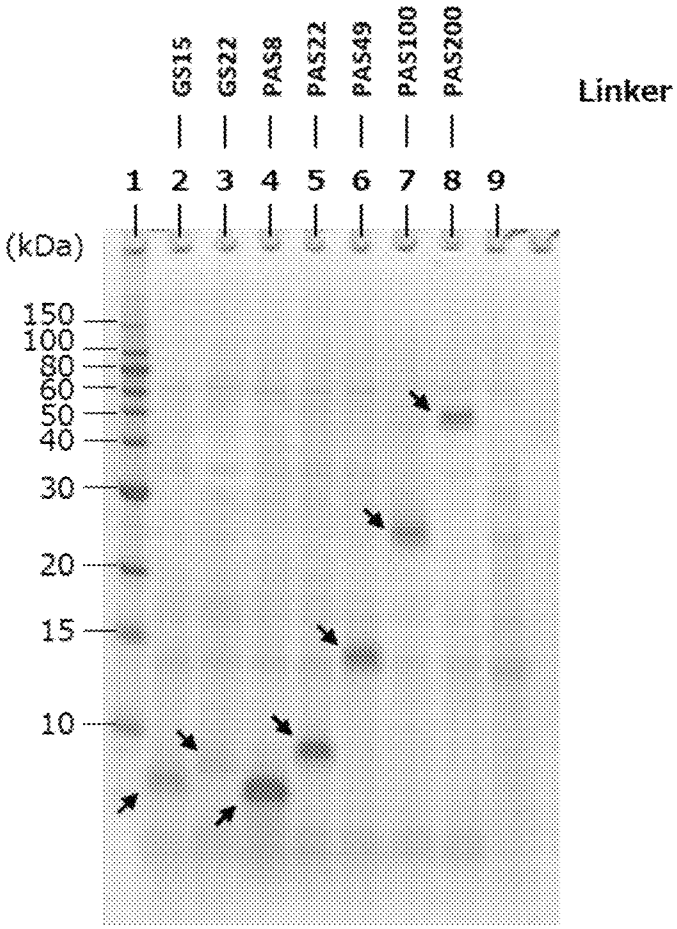
FIG. 20 shows the results of SDS-polyacrylamide electrophoresis showing the secretory expression of the dimer peptides (HGF-PAS and HGF-GS) in *C. glutamicum*. Lane 1 is a marker (XL-Ladder Broad, APRO science), lane 2 is one using pPK4_CspBss-AET-aMD4dY-GS15, lane 3 is one using pPK4_CspBss-AET-aMD4dY-GS22, lane 4 is one using pPK4_CspBss-AET-aMD4dY-PAS8, lane 5 is one using pPK4_CspBss-AET-PAS-aMD4dY-PEG11, lane 6 is one using pPK4_CspBss-AET-aMD4dY-PAS49, lane 7 is one using pPK4_CspBss-AET-aMD4dY-PAS100, lane 8 is one using pPK4_CspBss-AET-aMD4dY-PAS200, and lane 9 is one using pPK4 (empty vector).
Figure 21:
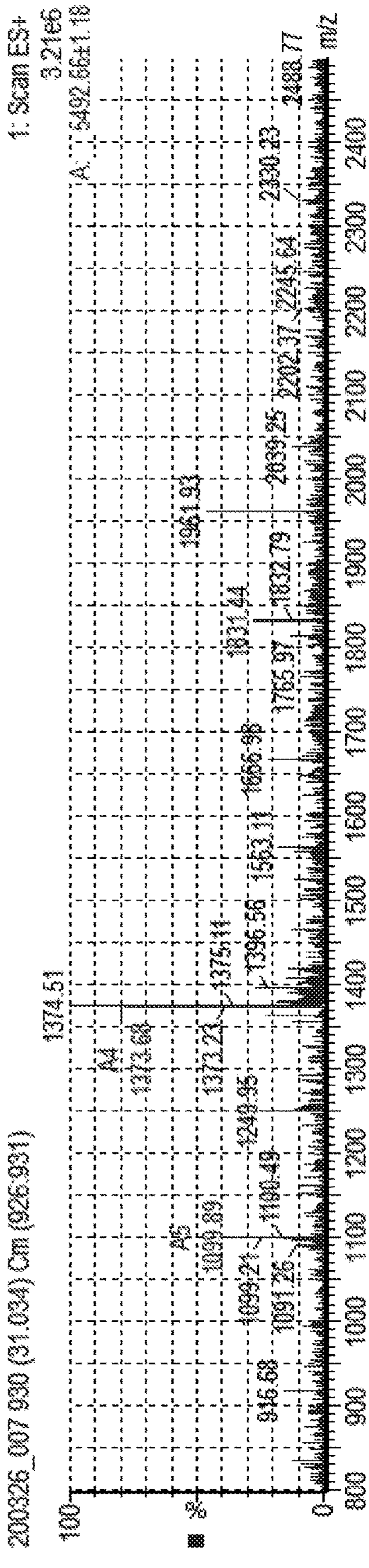
FIG. 21 shows measurement results for the dimer peptide (HGF-GS) by LC-MS. Calc represents the theoretical value and Obs represents the observed value.
Figure 22:
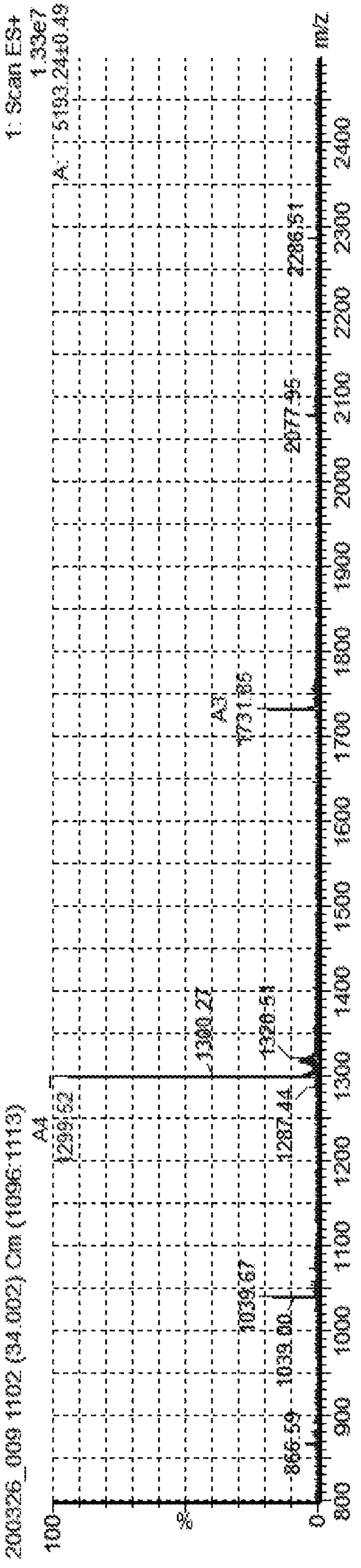
FIG. 22 shows measurement results for the dimer peptide (HGF-PAS) by LC-MS. Calc represents the theoretical value and Obs represents the observed value.
Figure 23:
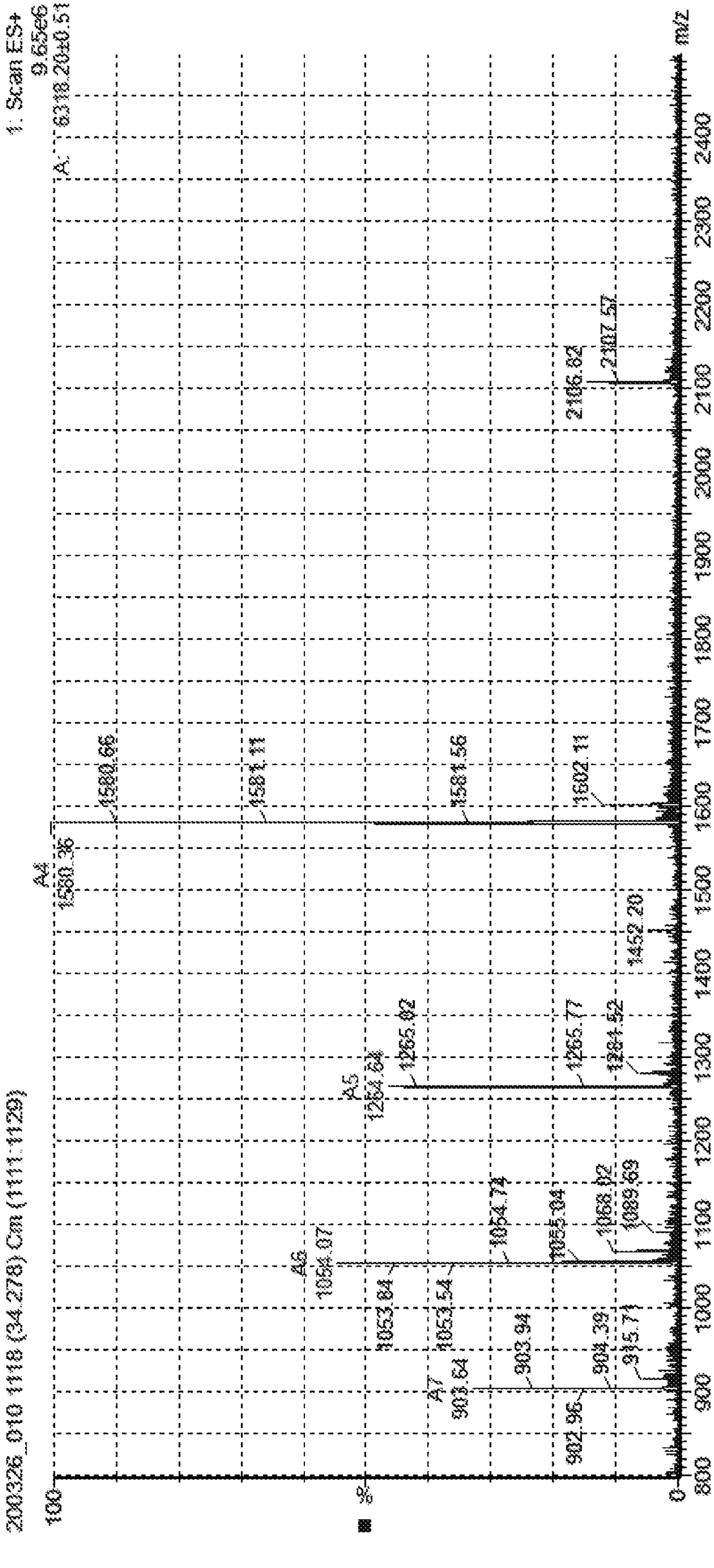
FIG. 23 shows measurement results for the dimer peptide (HGF-PAS) by LC-MS. Calc represents the theoretical value and Obs represents the observed value.
Figure 24:
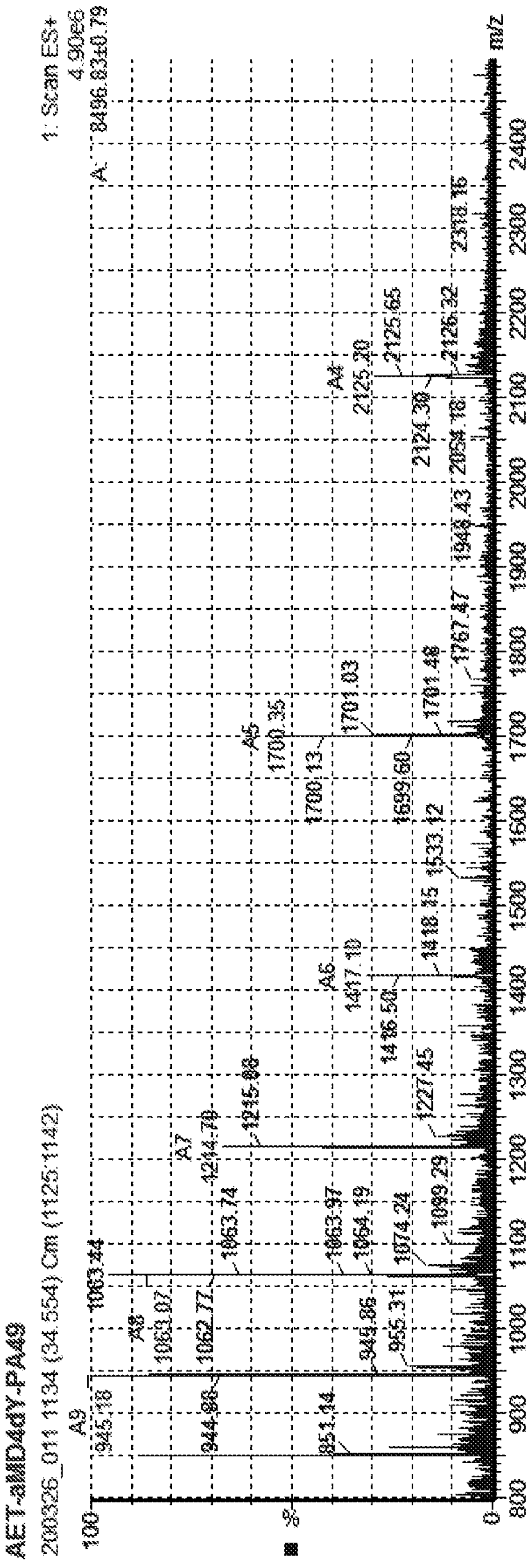
FIG. 24 shows measurement results for the dimer peptide (HGF-PAS) by LC-MS. Calc represents the theoretical value and Obs represents the observed value.
Figure 25:
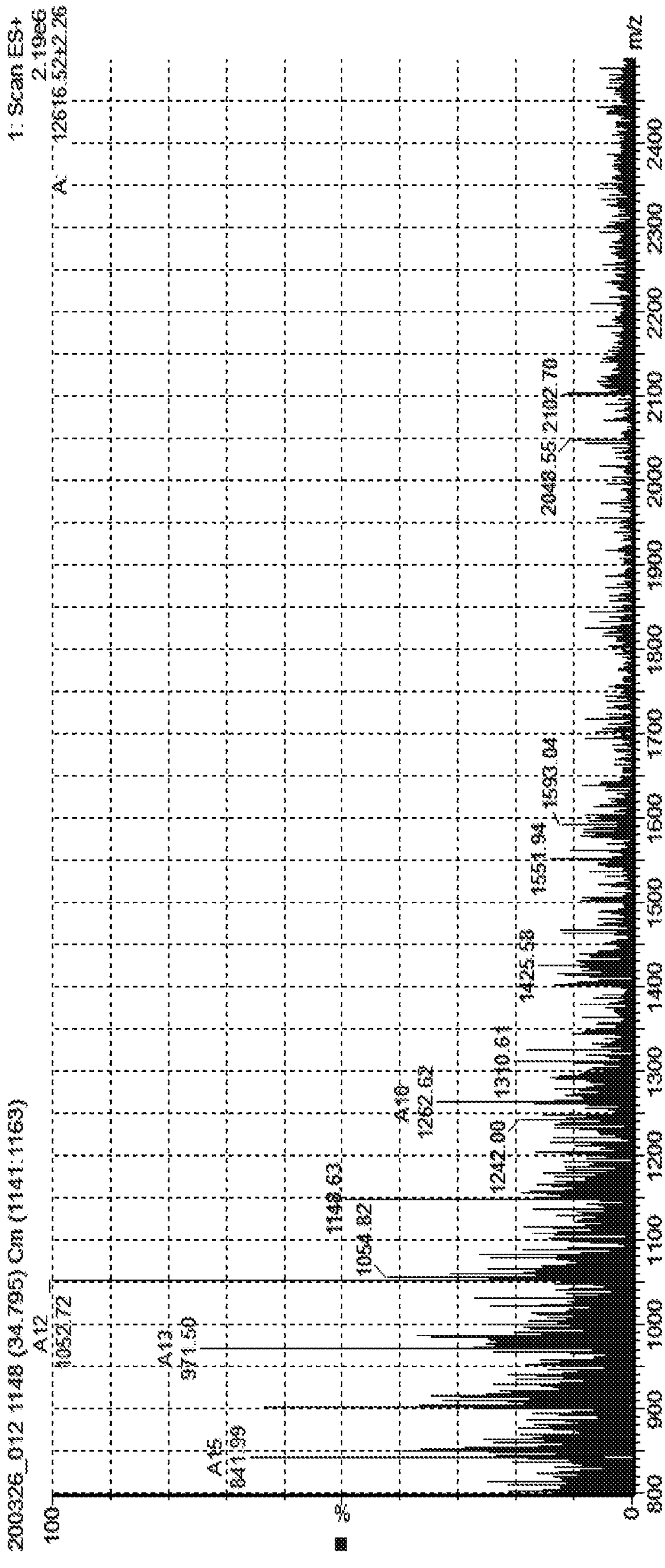
FIG. 25 shows measurement results for the dimer peptide (HGF-PAS) by LC-MS. Calc represents the theoretical value and Obs represents the observed value.
Figure 26:
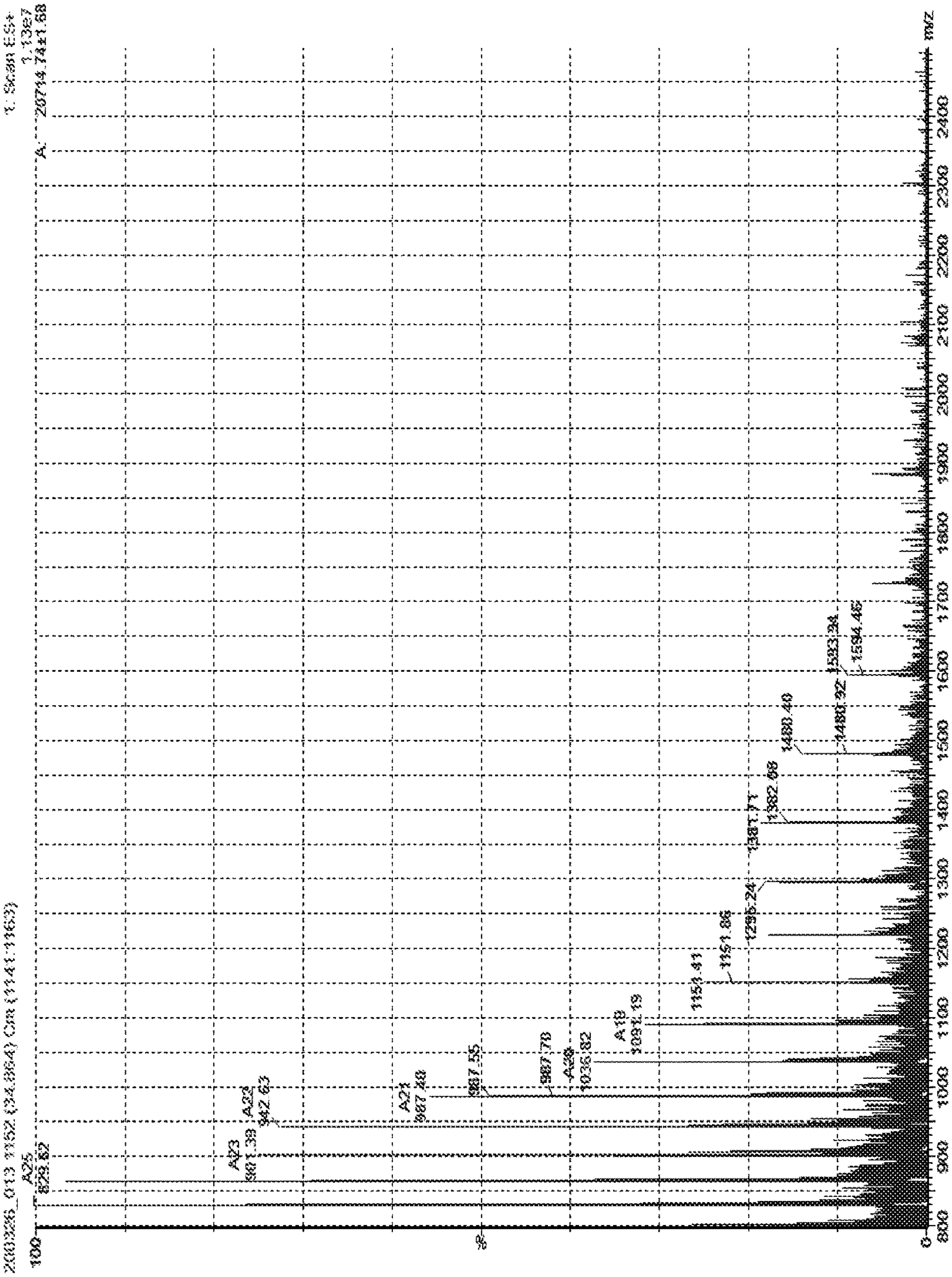
FIG. 26 shows measurement results for the dimer peptide (HGF-PAS) by LC-MS. Calc represents the theoretical value and Obs represents the observed value.

In addition, the YDK010:phoS(W302C)/pPK4_CspBss-AET-PAS-aMD4dY-PEG11 strain obtained by the same method as above was cultured in the same manner as above, and a protein band presumed to be AET-PAS-aMD4dY-PEG11 (hereinafter also referred to as "AET-aMD4dY-PAS22") was detected in the culture supernatant (FIG. 20, lane 5).

When comparing 22 residues with the same linker length, AET-aMD4dY-PAS22 (FIG. 20, lane 5: the same molecule as AET-PAS-aMD4dY-PEG11) showed higher secretion than AET-aMD4dY-GS22 (FIG. 20, lane 3), that is, the use of the PAS linker showed than that of the GS linker.

Example 15: Molecular Weight Analysis of HGF-PAS Dimer Peptide

The cell filtrate of each HGF-PAS dimer peptide after culturing in Example 14 was subjected to molecular weight measurement using LC-MS (Waters, ACQUITY UPLC H-Class/SQD2). The analysis conditions are shown in Table 2.

TABLE 2

| LC set up | | | |
|---|---|---|---|
| System | ACQUITYUPLC H-Class/SQD2 | | |
| Column | TMC-Triart C8 50 × 2.0 mmI.D. 1.9 um, 12 nm(TO12SP9-0502PT) | | |
| Solvent A | 0.1% TFA | | |
| B | 0.1% TFA, 80% Acetonitrile | | |
| Flow rate | 1.0 mL/min | | |
| Column temp. | 40 °C | | |
| Detection | 220 nm | | |
| Sample Vol. | 10 uL | | |
| Gradient program | Time (min) | % A | % B |
| | 0 | 100 | 0 |
| | 50 | 50 | 50 |
| | 53 | 0 | 100 |
| | 53.1 | 100 | 0 |

TABLE 2-continued

| | | | |
|---|---|---|---|
| | 56 | 100 | 0 |
| | 56.1 | 0 | 100 |
| | 59 | 0 | 100 |
| | 59.1 | 100 | 0 |
| | 65 | 100 | 0 |

| MS spectrometer set up | |
|---|---|
| Ion mode | ESI positive |
| Range | 800-2500 m/z |
| Scan time | 0.4 amu/sec |
| Capillary Voltage | 2.0 kV |
| Cone voltage | 10 V, 20 V, 40 V |
| Desolvation temp | 500 °C |
| Desolvation Gas Flow | 1000 L/hr |
| Cone Gas Flow | 50 L/hr |
| Software | Deconvolution is performed using "MassLynx" |

As shown in FIGS. 21 to 26, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 16: Activity Evaluation of HGF-PAS Dimer Peptide Linker Variant

The Met activation ability of the HGF-PAS dimer peptide linker variant was evaluated by luciferase assay. To 25 μL of Opti-MEM medium (Thermo Fisher Scientific), 0.6 L of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 100 ng/mL HGF was added, or a culture supernatant containing AET-aMD4dY-PAS8, AET-aMD4dY-PAS22 (the same molecule as AET-PAS-aMD4dY-PEG11), AET-aMD4dY-PAS49, AET-aMD4dY-PAS100, AET-aMD4dY-PAS200, AET-aMD4dY-GS15, or AET-aMD4dY-GS22 was added to the medium so as to be diluted at a predetermined ratio, and the evaluation basal medium was added in an amount of 100 μL to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 27:
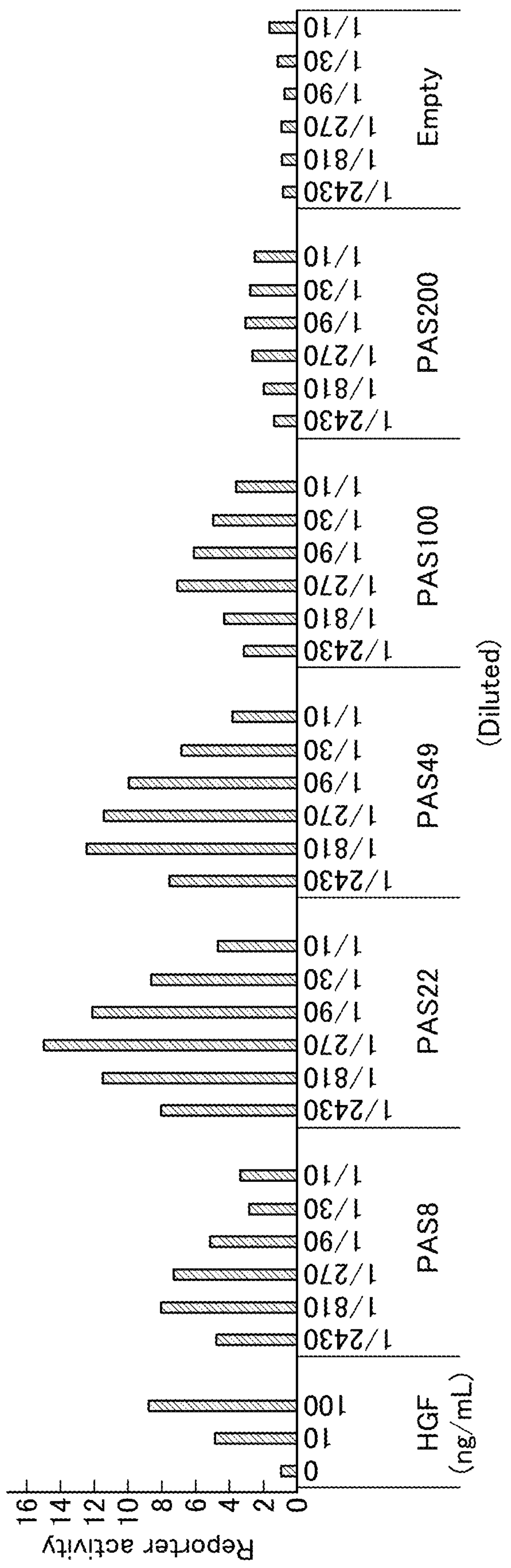
FIG. 27 is a graph showing the activity evaluation of HGF and dimer peptide (HGF-PAS). The vertical axis represents relative receptor activity, and the horizontal axis represents the concentration for HGF and, for dimer peptide (HGF-PAS), the dilution rate of the culture supernatant containing dimer peptide (HGF-PAS) with respect to the medium used for the activity evaluation. PAS8, PAS22, PAS49, PAS100, and PAS200 on the horizontal axis each represent AET-aMD4dY-PAS8, AET-aMD4dY-PAS22 (same as AET-PAS-aMD4dY-PEG11), AET-aMD4dY-PAS49, AET-aMD4dY-PAS100, and AET-aMD4dY-PAS200, respectively. Empty is the result of using an empty vector, and represents the dilution rate with respect to the medium used for the activity evaluation as in the case of using a culture supernatant containing the dimer peptide.
Figure 28:
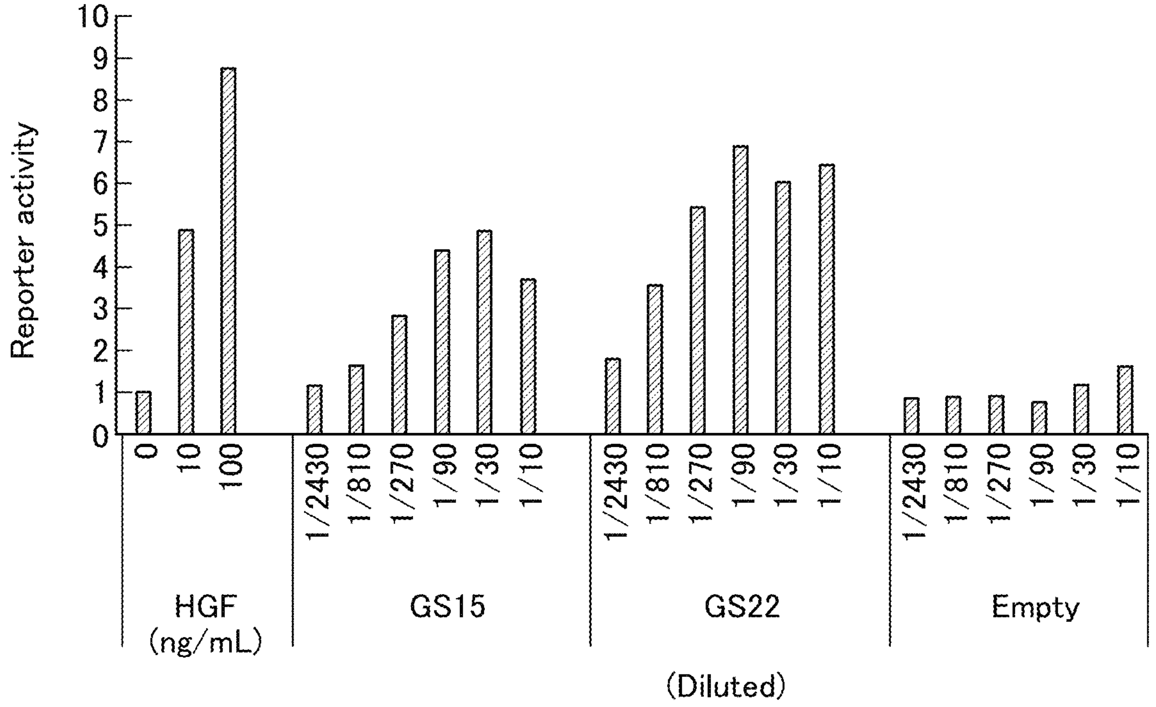
FIG. 28 is a graph showing the activity evaluation of HGF and dimer peptide (HGF-GS). The vertical axis represents relative receptor activity, and the horizontal axis represents the concentration for HGF and, for dimer peptide (HGF-GS), the dilution rate of the culture supernatant containing dimer peptide (HGF-PAS) with respect to the medium used for the activity evaluation. GS15 and GS22 on the horizontal axis represent AET-aMD4dY-GS15 and AET-aMD4dY-GS22, respectively. Empty is the result of using an empty vector, and represents the dilution rate with respect to the medium used for the activity evaluation as in the case of using a culture supernatant containing the dimer peptide.

As shown in FIG. 27, it was clarified that all HGF-PAS dimer peptides having different PAS linker lengths activated HGF signals. It was clarified that the highest efficiency was exhibited when the length of the PAS linker was 22 amino acids, and the maximum activity (EC50) was halved when the length exceeded 100 amino acids as shown in Table 3 below. In addition, as shown in FIG. 28, activity was also obtained by dimerization with 15 amino acid and 22 amino acid GS linkers, and their maximum activity (EC50) was less than half that of the PAS linker, as shown in Table 3 below. Thus, it was clarified that a dimer peptide having high activity could be produced by using a PAS linker.

TABLE 3

| Peptide | $E_{max}$ (%) |
|---|---|
| AET-aMD4dY-PAS22 | 100.0 |
| AET-aMD4dY-PAS8 | 56.4 |
| AET-aMD4dY-PAS49 | 82.8 |
| AET-aMD4dY-PAS100 | 47.2 |
| AET-aMD4dY-PAS200 | 20.4 |
| AET-aMD4dY-GS15 | 45.8 |
| AET-aMD4dY-GS22 | 32.3 |

Example 17: Design of Stabilized HGF-PAS Dimer Peptide and its Secretory Expression in *C. glutamicum*

(17-1) Outline of Design

The HGF-PAS peptide with enhanced stability was designed as follows. As a method for enhancing the stability of peptides and proteins, a method for adding a long-chain PAS sequence has been reported (Published Japanese Translation of PCT International Application No. 2013-531480 and Published Japanese Translation of PCT International Application No. 2010-531139). As an HGF-PAS peptide with enhanced stability, a peptide was designed in which a PAS sequence composed of 200 amino acids (PAS200) was bound to the C-terminus of AET-aMD4dY-PAS22 (the same molecule as AET-PAS-aMD4dY-PEG11). That is, the peptide sequence was designed to be "first aMD4dY cyclic peptide"-"PAS linker"-"second aMD4dY cyclic peptide"-"long-chain PAS sequence (PAS200)".

(17-2) Preparation of Stabilized HGF-PAS Dimer Peptide

The prepared stabilized HGF-PAS dimer peptide is as follows.

```
(o) AET-aMD4dY-PAS22-PAS200
                                        (SEQ ID NO: 99)
AETCRQFNRRTHEVWNLDCGAAPAAPAPAAPAAPAPAAPAAPGCRQFNRR

THEVWNLDCAAPAAPAPAAPAAPAPAAPAAPAPAAPAAPAPAAPAAPAPA

APAAPAPAAPAAPAPAAPAAPAPAAPAAPAPAAPAAPAPAAPAAPAPAAP

AAPAPAAPAAPAPAAPAAPAPAAPAAPAPAAPAAPAPAAPAAPAPAAPAA

PAPAAPAAPAPAAPAAPAPAAPAAPAPAAPAAPAPAAPAAPAPAAPAAPA

PAAPAAPAP
```

(17-3) Expression of Stabilized HGF-PAS Dimer Peptide

Corynex (registered trademark) was used to examine the expression of stabilized HGF-PAS dimer peptide. Hereinafter, examples of expression examinations using Corynex (registered trademark) will be described.

(17-4) Construction of Secretory Expression Plasmid of AET-aMD4dY-PAS22-PAS200 Using CspB Signal Sequence As the stabilized HGF-PAS dimer peptide, the amino acid sequence of the above (a) AET-aMD4dY-PAS22-PAS200 (which may be hereinafter referred to as "AET-aMD4dY-PAS22-PAS200") was designed, and the base sequence encoding this protein was designed in consideration of the codon usage frequency of *C. glutamicum*. Furthermore, the following expression cassette was designed to enable secretion expression by *C. glutamicum*.

AET-aMD4dY-PAS22-PAS200 was secretory-expressed as a fusion protein of AET-aMD4dY-PAS22-PAS200 and a signal peptide 30 amino acid residue of CspB derived from *C. glutamicum* ATCC 13869 strain (hereinafter referred to as "CspBss-AET-aMD4dY-PAS22-PAS200"). The base sequence and amino acid sequence encoding the designed CspBss-AET-aMD4dY-PAS22-PAS200 are set forth in SEQ ID NOs: 100 and 101, respectively.

```
Base sequence encoding CspBss-AET-aMD4dY-
PAS22-PAS200
                                       (SEQ ID NO: 100)
atgtttaacaaccgtatccgcactgcagctctcgctggtgcaatcgcaat

ctccaccgcagcttccggcgtagctatcccagcattcgctgcagagacct

gccgtcagttcaaccgccgtacccacgaagtttggaatctcgactgtggt

gccgcccctgccgctcctgcccctgccgccccagccgctccagcaccagc

cgctccagcagccccaggctgccgccagttcaaccgccgcacccacgaag

tgtggaacctggattgcgcagctccagcagcccctgcccccgccgcccca

gccgcccctgcccccgccgcccccgccgcacccgcccctgccgcccccgc

cgcccccgcccctgctgctcctgctgctcccgctcccgctgctcccgctg

cccctgctcctgctgctcccgctgcgccagccccagcagcaccagctgcc

ccagcaccagctgcaccagccgcaccagctccagcagccccagctgctcc

agcaccagcagcaccagcagcaccagctccagcggcaccagcagcaccag

cacctgcggcaccagcggctccagccccagcagcaccagcagcgccagca

ccagcagctccagcagcaccagcaccagcagcaccagcggcaccagcccc

agctgcaccagccgctccagcaccagctgccccagcagctccagccccag
```

-continued

```
ctgcccctgctgcccccgctcctgccgctcccgctgcccctgcccctgct

gctcctgctgctcccgctcctgccgctcccgctgcgccagctccagcagc

cccagctgcaccagccccagccgcaccagccgccccagcccccgcagcac

ccgcagcaccagccccataa

Amino acid sequence of CspBss-AET-aMD4dY-
PAS22-PAS200
                                       (SEQ ID NO: 101)
MFNNRIRTAALAGAIAISTAASGVAIPAFAAETCRQFNRRTHEVWNLDCG

AAPAAPAPAAPAAPAPAAPAAPGCRQFNRRTHEVWNLDCAAPAAPAPAAP

AAPAPAAPAAPAPAAPAAPAPAAPAAPAPAAPAAPAPAAPAAPAPAAPAA

PAPAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPAPA

APAAPAPAAPAAPAPAAPAAPAPAAPAAPAPAAPAAPAP
```

The promoter of the cspB gene derived from the *C. glutamicum* ATCC 13869 strain was linked upstream of the base sequence set forth in CspBss-AET-aMD4dY-PAS22-PAS200, and furthermore, an expression cassette of stabilized HGF-PAS dimer peptide having a KpnI site on the 5'-side and an BamHI site on the 3'-side was designed and totally synthesized. The totally synthesized DNA fragment (stabilized HGF-PAS dimer peptide expression cassette) was inserted into the KpnI-BamHI site of pPK4 described in Japanese Patent Application Publication No. Hei 9-322774 to construct pPK4_CspBss-AET-aMD4dY-PAS22-PAS200, a secretory expression plasmid for the stabilized HGF-PAS dimer peptide using the CspB signal sequence. As a result of determining the base sequence of the inserted fragment, it was confirmed that the stabilized HGF-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(17-5) Secretory Expression of Stabilized HGF-PAS Dimer Peptide in *C. glutamicum*

The pPK4_CspBss-AET-aMD4dY-PAS22-PAS200 constructed above was used to transform the *C. glutamicum* YDK010:phoS(W302C) strain described in WO2016/171224 to obtain the YDK010:phoS(W302C)/pPK4_CspBss-AET-aMD4dY-PAS22-PAS200 strain.

The obtained transformants were cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 29:
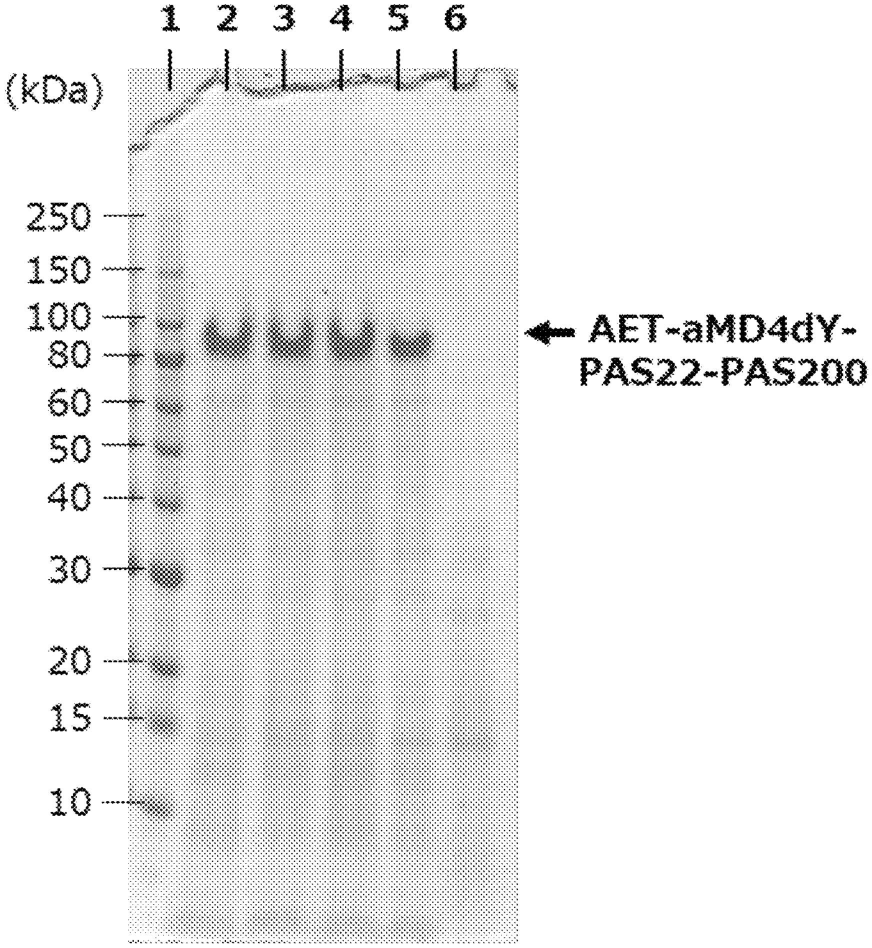
FIG. 29 shows the results of SDS-polyacrylamide electrophoresis showing the secretory expression of the dimer peptide (HGF-PAS) in *C. glutamicum*. Lane 1 is a marker (XL-Ladder Broad, APRO science), lanes 2 to 5 are ones using pPK4_CspBss-AET-aMD4dY-PAS22-PAS200, and lane 6 is one using pPK4 (empty vector).

After completion of the culture, 6.5 µL of the culture supernatant obtained by centrifuging each culture solution was subjected to reduced SDS-PAGE using NuPAGE (registered trademark) 4 to 12% Bis-Tirs Gel (Thermo Fisher Scientific), and then stained with Quick-CBB (Wako). As a result, a protein band presumed to be AET-aMD4dY-PAS22-PAS200 was detected in the culture supernatant of the YDK010:phoS(W302C)/pPK4_CspBss-AET-aMD4dY-PAS22-PAS200 strain (FIG. 29, lanes 2 to 5).

Example 18: Molecular Weight Analysis of Stabilized HGF-PAS Dimer Peptide

Figure 30:
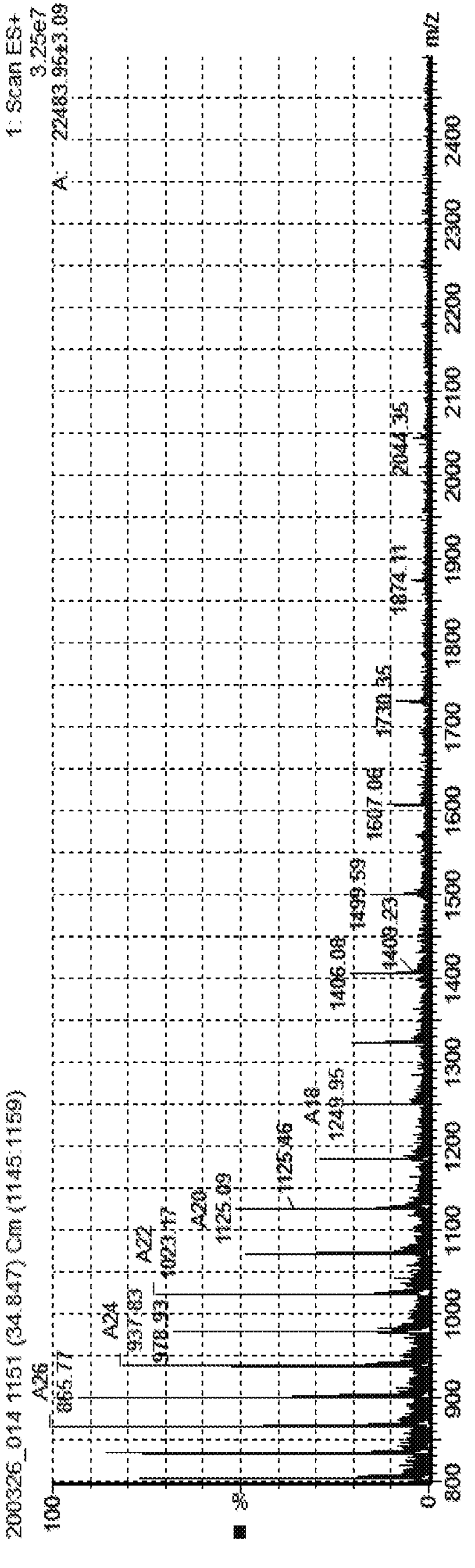
FIG. 30 shows measurement results for the dimer peptide (HGF-PAS) by LC-MS. Calc represents the theoretical value and Obs represents the measured value.

The cell filtrate of the stabilized HGF-PAS dimer peptide after culturing in Example 17 was subjected to molecular weight measurement using LC-MS (Waters, ACQUITY UPLC H-Class/SQD2). The analysis conditions are shown in Table 2. As shown in FIG. 30, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 19: Activity Evaluation of Stabilized HGF-PAS Dimer Peptide

The Met activation ability of the stabilized HGF-PAS dimer peptide was evaluated by luciferase assay. To 25 μL of Opti-MEM medium (Thermo Fisher Scientific), 0.6 L of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 100 ng/mL HGF was added, or a culture supernatant containing AET-aMD4dY-PAS22-PAS200 was added to the medium so as to be diluted at a predetermined ratio, and the evaluation basal medium was added in an amount of 100 μL to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 31:
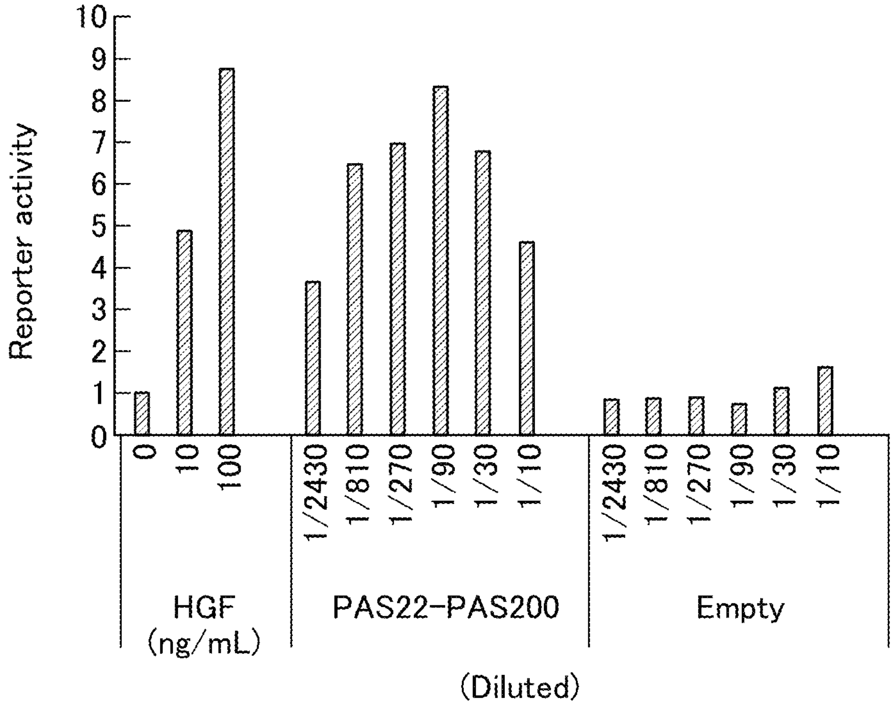
FIG. 31 is a graph showing the activity evaluation of HGF and dimer peptide (HGF-PAS). The vertical axis represents relative receptor activity, and the horizontal axis represents the concentration for HGF and, for dimer peptide (HGF-PAS), the dilution rate of the culture supernatant containing dimer peptide (HGF-PAS) with respect to the medium used for the activity evaluation. PAS22-PAS200 on the horizontal axis represents AET-aMD4dY-PAS22-PAS200. Empty is the result of using an empty vector, and represents the dilution rate with respect to the medium used for the activity evaluation as in the case of using a culture supernatant containing the dimer peptide.

As shown in FIG. 31, it was clarified that the stabilized HGF-PAS dimer peptide had a signal activation ability and the maximum activity was about the same as that of 100 ng/mL HGF.

Example 20: Design of EPO-PAS Dimer Peptide and its Secretory Expression in *C. glutamicum*

(20-1) Outline of Design

Peginesatide has been reported as an erythropoietin mimetic peptide. Pedinesatide has a structure in which a lysine is added to the C-terminus of an erythropoietin receptor-binding peptide and ε-amino groups are bound to each other with a dicarboxylic acid linker linked by a long-chain PEG. However, expression of Peginesatide in *C. glutamicum* as a single polypeptide chain cannot be performed for the following reasons.

(1) Peginesatide contains unnatural amino acids, and peptides containing unnatural amino acids cannot be expressed in *C. glutamicum*.
(2) Peptides containing a dicarboxylic acid linker cannot be expressed in *C. glutamicum*.
(3) Dimerization is achieved by binding the C-terminuses of two cyclic peptide molecules with the ε-amino group of lysine, but a structure with C-terminuses bound to each other and a structure with the ε-amino group of lysine and another amino acid forming an amide bond cannot be expressed in *C. glutamicum*.

Therefore, the molecule was converted as follows to design an expressible form. The above (1) can be expressed by using an erythropoietin receptor-binding cyclic peptide (U.S. Pat. No. 5,773,569A) that does not contain an unnatural amino acid. The above (2) can be expressed by using a peptidic linker. Regarding (3) above, the N-terminus of one cyclic peptide and the C-terminus of the other peptide were bound to each other using a PAS sequence instead of the C-terminuses of the cyclic peptides. That is, the obstacles were dealt with by designing the peptide sequence to be "first erythropoietin receptor-binding cyclic peptide"-"PAS linker"-"second erythropoietin receptor-binding cyclic peptide". That is, the C-terminus of the first erythropoietin receptor-binding cyclic peptide and the N-terminus of the PAS linker are linked by an amide bond to the N-terminus of the second erythropoietin receptor-binding cyclic peptide and the C-terminus of the PAS linker, respectively, and the peptide chain can be expressed as a single polypeptide chain.

(20-2) Preparation of EPO-PAS Dimer Peptides

The prepared EPO-PAS dimer peptides are as follows.

```
(p) EPO-PAS8
                                        (SEQ ID NO: 102)
GGLYACHMGPMTWVCQPLRGAAPAAPAPGGLYACHMGPMTWVCQPLRG

(q) EPO-PAS22
                                        (SEQ ID NO: 103)
GGLYACHMGPMTWVCQPLRGAAPAAPAPAAPAAPAPAAPAAPGGLYACHM

GPMTWVCQPLRG

(r) AET-EPO-PAS8
                                        (SEQ ID NO: 104)
AETGGLYACHMGPMTWVCQPLRGAAPAAPAPGGLYACHMGPMTWVCQPLR

G

(s) AET-EPO-PAS22
                                        (SEQ ID NO: 105)
AETGGLYACHMGPMTWVCQPLRGAAPAAPAPAAPAAPAPAAPAAPGGLYA

CHMGPMTWVCQPLRG
```

(20-3) Expression of EPO-PAS Dimer Peptides

The expression of these EPO-PAS dimer peptides was examined using Corynex (registered trademark). Hereinafter, examples of expression examinations using Corynex (registered trademark) will be described.

(20-4) Construction of EPO-PAS8 and EPO-PAS22 Secretory Expression Plasmids Using CspA Signal Sequence As the EPO-PAS dimer peptide, two types of amino acid sequences of the above (p) EPO-PAS8 (which may be hereinafter referred to as "EPO-PAS8") and (q) EPO-PAS22 (which may be hereinafter referred to as "EPO-PAS22") were designed, and the base sequences encoding these proteins were designed in consideration of the codon usage frequency of *C. glutamicum*. Furthermore, the following expression cassettes were designed to enable secretory expression by *C. glutamicum.*

EPO-PAS8 was secretory-expressed as a fusion protein of EPO-PAS8 and a signal peptide 25 amino acid residue of CspA derived from *C. ammoniagenes* ATCC 6872 strain (hereinafter referred to as "CspAss-EPO-PAS8"). The base sequence and amino acid sequence encoding the designed CspAss-EPO-PAS8 are set forth in SEQ ID NOs: 106 and 107, respectively.

```
Base sequence encoding CspAss-EPO-PAS8
                                   (SEQ ID NO: 106)
atgaaacgcatgaaatcgctggctgcggcgctcaccgtcgctggggccat

gctggccgcacctgtggcaacggcaggtggcctttacgcttgtcacatgg

gtccaatgacctgggtttgtcagcccctccgtggtgccgctcctgccgcc

cccgctcctggtggcctgtacgcatgccatatgggtccaatgacttgggt

gtgccagccactccgcggctaa

Amino acid sequence of CspAss-EPO-PAS8
                                   (SEQ ID NO: 107)
MKRMKSLAAALTVAGAMLAAPVATAGGLYACHMGPMTWVCQPLRGAAPAA

PAPGGLYACHMGPMTWVCQPLRG
```

EPO-PAS22 was secretory-expressed as a fusion protein of EPO-PAS22 and a signal peptide 25 amino acid residue of CspA derived from *C. ammoniagenes* ATCC 6872 strain (hereinafter referred to as "CspAss-EPO-PAS22"). The base sequence and amino acid sequence encoding the designed CspAss-EPO-PAS22 are set forth in SEQ ID NOs: 108 and 109, respectively.

```
Base sequence encoding CspAss-EPO-PAS22
                                   (SEQ ID NO: 108)
atgaaacgcatgaaatcgctggctgcggcgctcaccgtcgctggggccat

gctggccgcacctgtggcaacggcaggcggcctttacgcttgtcacatgg

gtccaatgacctgggtctgtcaacctctccgtggtgcagccccggcagcc

cccgctccagccgcaccagcagccccagccccagctgcaccagccgctcc

aggcggcctctacgcctgccacatgggtcctatgacctgggtgtgccaac

cacttcgcggctaa

Amino acid sequence of CspAss-EPO-PAS22
                                   (SEQ ID NO: 109)
MKRMKSLAAALTVAGAMLAAPVATAGGLYACHMGPMTWVCQPLRGAAPAA

PAPAAPAAPAPAAPAAPGGLYACHMGPMTWVCQPLRG
```

The promoter of the cspB gene derived from the *C. glutamicum* ATCC 13869 strain was linked upstream of the base sequences set forth in CspAss-EPO-PAS8 and CspAss-EPO-PAS22, and furthermore, an expression cassette of each EPO-PAS dimer peptide having a KpnI site on the 5'-side and an BamHI site on the 3'-side was designed and totally synthesized. The totally synthesized DNA fragment (EPO-PAS dimer peptide expression cassette) was inserted into the KpnI-BamHI site of pPK4 described in Japanese Patent Application Publication No. Hei 9-322774 to construct pPK4_CspAss-EPO-PAS8 and pPK4_CspAss-EPO-PAS22, a secretory expression plasmid for each EPO-PAS dimer peptide using the CspA signal sequence. As a result of determining the base sequence of the inserted fragment, it was confirmed that each EPO-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(20-5) Construction of each secretory expression plasmid of AET-EPO-PAS8 and AET-EPO-PAS22 using CspB signal sequence As the EPO-PAS dimer peptide, two types of amino acid sequences of the above (r) AET-EPO-PAS8 (which may be hereinafter referred to as "AET-EPO-PAS8") and (s) AET-EPO-PAS22 (which may be hereinafter referred to as "AET-EPO-PAS22") were designed, and the base sequences encoding these proteins were designed in consideration of the codon usage frequency of *C. glutamicum*. Furthermore, the following expression cassettes were designed to enable secretory expression by *C. glutamicum.*

AET-EPO-PAS8 was secretory-expressed as a fusion protein of AET-EPO-PAS8 and a signal peptide 30 amino acid residue of CspB derived from *C. glutamicum* ATCC 13869 strain (hereinafter referred to as "CspBss-AET-EPO-PAS8"). The base sequence and amino acid sequence encoding the designed CspBss-AET-EPO-PAS8 are set forth in SEQ ID NOs: 110 and 111, respectively.

```
Base sequence encoding CspBss-AET-EPO-PAS8
                                   (SEQ ID NO: 110)
atgtttaacaaccgtatccgcactgcagctctcgctggtgcaatcgcaat

ctccaccgcagcttccggcgtagctatcccagcattcgctgcagagaccg

gtggcctttacgcttgtcacatgggtccaatgacctgggtttgtcagccc

ctccgtggtgccgctcctgccgcccccgctcctggtggcctgtacgcatg

ccatatgggtccaatgacttgggtgtgccagccactccgcggctaa

Amino acid sequence of CspBss-AET-EPO-PAS8
                                    (SEQ ID NO: 11)
MFNNRIRTAALAGAIAISTAASGVAIPAFAAETGGLYACHMGPMTWVCQP

LRGAAPAAPAPGGLYACHMGPMTWVCQPLRG
```

AET-EPO-PAS22 was secretory-expressed as a fusion protein of AET-EPO-PAS22 and a signal peptide 30 amino acid residue of CspB derived from *C. glutamicum* ATCC 13869 strain (hereinafter referred to as "CspBss-AET-EPO-PAS22"). The base sequence and amino acid sequence encoding the designed CspBss-AET-EPO-PAS22 are set forth in SEQ ID NOs: 112 and 113, respectively.

```
Base sequence encoding CspBss-AET-EPO-PAS22
                                   (SEQ ID NO: 112)
atgtttaacaaccgtatccgcactgcagctctcgctggtgcaatcgcaat

ctccaccgcagcttccggcgtagctatcccagcattcgctgcagagaccg

gcggcctttacgcttgtcacatgggtccaatgacctgggtctgtcaacct

ctccgtggtgcagccccggcagcccccgctccagccgcaccagcagcccc

agccccagctgcaccagccgctccaggcggcctctacgcctgccacatgg
```

-continued

```
gtcctatgacctgggtgtgccaaccacttcgcggctaa

                                        (SEQ ID NO: 113)
PLRGAAPAAPAPAAPAAPAPAPAAPAAPGGLYACHMGPMTWVCQPLRG
```

The promoter of the cspB gene derived from the *C. glutamicum* ATCC 13869 strain was linked upstream of the base sequences set forth in CspBss-AET-EPO-PAS8 and CspBss-AET-EPO-PAS22, and furthermore, an expression cassette of each EPO-PAS dimer peptide having a KpnI site on the 5'-side and an BamHI site on the 3'-side was designed and totally synthesized. The totally synthesized DNA fragment (EPO-PAS dimer peptide expression cassette) was inserted into the KpnI-BamHI site of pPK4 described in Japanese Patent Application Publication No. Hei 9-322774 to construct pPK4_CspBss-AET-EPO-PAS8 and pPK4_CspBss-AET-EPO-PAS22, a secretory expression plasmid for each EPO-PAS dimer peptide using the CspB signal sequence. As a result of determining the base sequence of the inserted fragment, it was confirmed that each EPO-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(20-6) Secretory Expression of Each EPO-PAS Dimer Peptide in *C. glutamicum*

The pPK4_CspAss-EPO-PAS8, pPK4_CspAss-EPO-PAS22, pPK4_CspBss-AET-EPO-PAS8, and pPK4_CspBss-AET-EPO-PAS22 constructed above were used to transform the *C. glutamicum* YDK0107 strain described in WO2016/171224 to obtain the YDK0107/pPK4_CspAss-EPO-PAS8 strain, YDK0107/pPK4_CspAss-EPO-PAS22 strain, YDK0107/pPK4_CspBss-AET-EPO-PAS8 strain, and YDK0107/pPK4_CspBss-AET-EPO-PAS22 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 32:
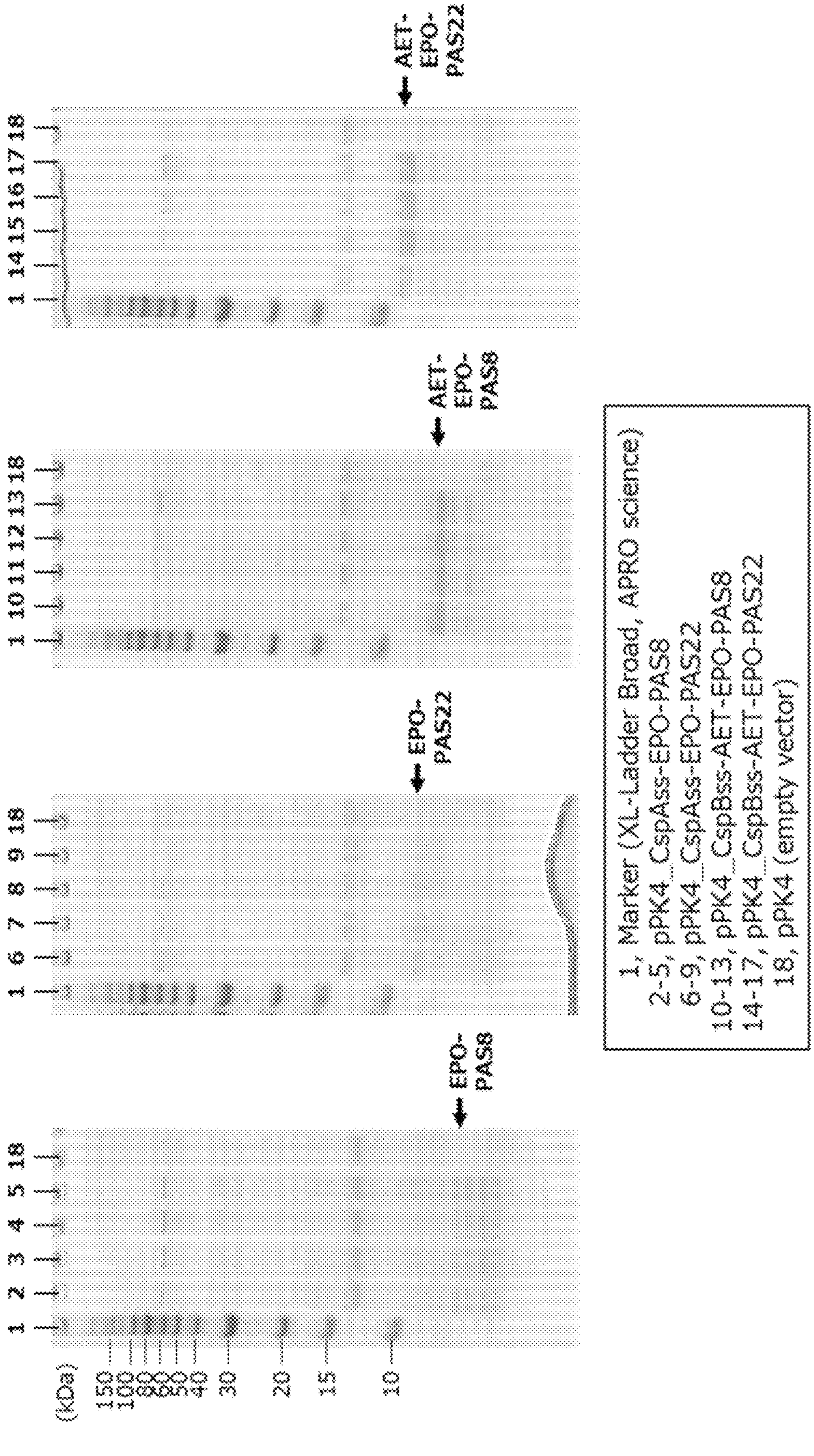
FIG. 32 shows the results of SDS-polyacrylamide electrophoresis showing the secretory expression of the dimer peptide (EPO-PAS) in *C. glutamicum*. Lane 1 is a marker (XL-Ladder Broad, APRO science), lanes 2 to 5 are ones using pPK4_CspBss-EPO-PAS8, lanes 6 to 9 are ones using pPK4_CspBss-EPO-PAS22, lanes 10 to 13 are ones using pPK4_CspBss-AET-EPO-PAS8, lanes 14 to 17 are ones using pPK4_CspBss-AET-EPO-PAS22, and lane 18 is one using pPK4 (empty vector).

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be EPO-PAS8 was detected in the culture supernatant of the YDK0107/pPK4_CspAss-EPO-PAS8 strain (FIG. 32, lanes 2 to 5), a protein band presumed to be EPO-PAS22 was detected in the culture supernatant of the YDK0107/pPK4_CspAss-EPO-PAS22 strain (FIG. 32, lanes 6 to 9), a protein band presumed to be AET-EPO-PAS8 was detected in the culture supernatant of the YDK0107/pPK4_CspBss-AET-EPO-PAS8 strain (FIG. 32, lanes 10 to 13), and a protein band presumed to be AET-EPO-PAS22 was detected in the culture supernatant of the YDK0107/pPK4_CspBss-AET-EPO-PAS22 strain (FIG. 32, lanes 14 to 17).

Example 21: Molecular Weight Analysis of EPO-PAS Dimer Peptide

Figure 33:
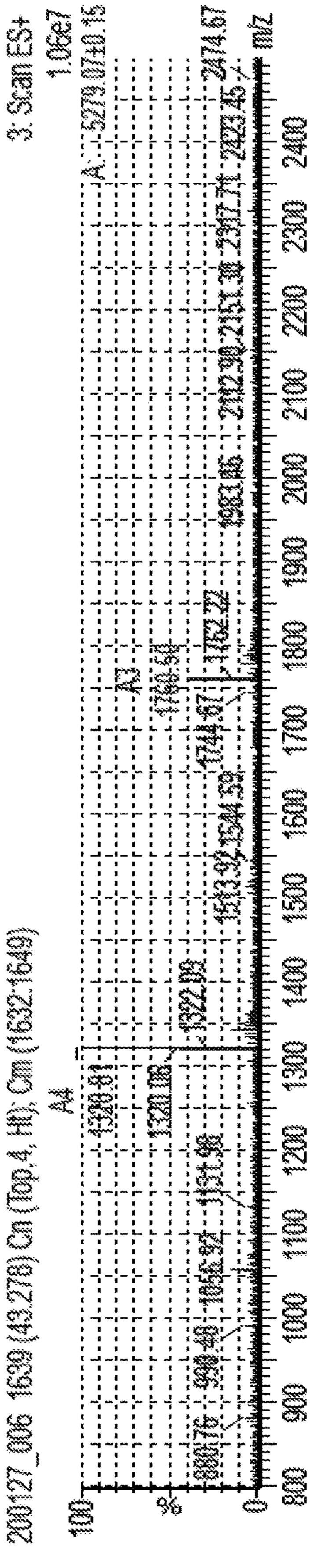
FIG. 33 shows measurement results of the dimer peptide (EPO-PAS) by LC-MS. Calc represents the theoretical value and Obs represents the measured value.
Figure 34:
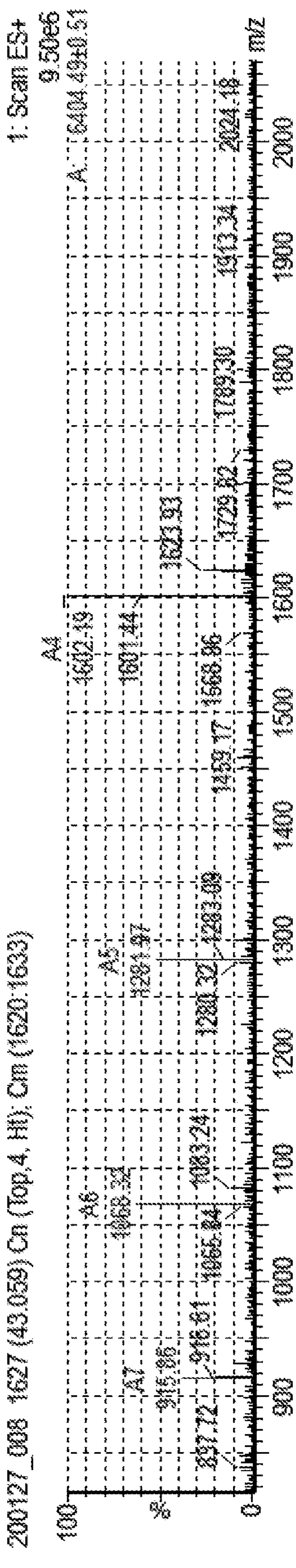
FIG. 34 shows measurement results of the dimer peptide (EPO-PAS) by LC-MS. Calc represents the theoretical value and Obs represents the measured value.

The cell filtrate of AET-EPO-PAS8 and AET-EPO-PAS22 after culturing in Example 20 was subjected to molecular weight measurement using LC-MS (Waters, ACQUITY UPLC/SQD2). The analysis conditions are shown in Table 2. As shown in FIGS. 33 and 34, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 22: Activity Evaluation of EPO-PAS Dimer Peptide

The EpoR activation ability of the EPO-PAS dimer peptide was evaluated using PathHunter (registered trademark) eXpress EpoR-JAK2 Functional Assay Kit (DiscoverX).

Cells for EPO activity evaluation included in PathHunter (registered trademark) eXpress EpoR-JAK2 Functional Assay Kit were seeded on a 96-well plate and cultured for 24 hours at 37 °C under 5% $CO_2$. To the cells, 860 pg/L to 900 μg/L recombinant human erythropoietin (rhEPO, Peprotech), or a culture supernatant containing AET-EPO-PAS8 or AET-EPO-PAS22 diluted to a predetermined concentration (cultured as described in Example 20), or the monomer peptide EMP35 (GGLYACHMGPMTWVCQPLRG, synthesized by GenScript Japan) was added. As a negative control, the culture supernatant (FIG. 32, lane 18) obtained by culturing as described in Example 20 except for using a vector containing no gene for expressing the EPO-PAS dimer peptide, diluted at the same ratio as the culture supernatant containing AET-EPO-PAS8 or AET-EPO-PAS22, was added. The prepared Substrate Reagent was added to the cells stimulated at room temperature for 3 hours, and the cells were incubated for 60 minutes. The chemiluminescence intensity was quantified with a Nivo plate reader (Perkin Elmer).

Figure 35:
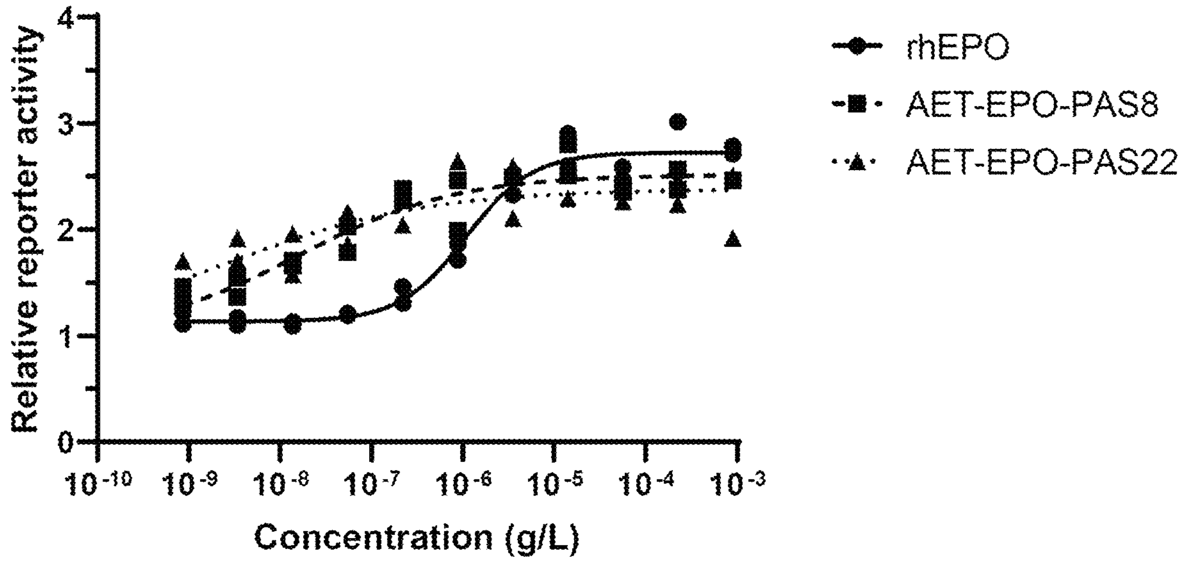
FIG. 35 is a graph showing the activity evaluation of rhEPO and dimer peptide (EPO-PAS). The vertical axis represents relative receptor activity and the horizontal axis represents concentration.
Figure 36:
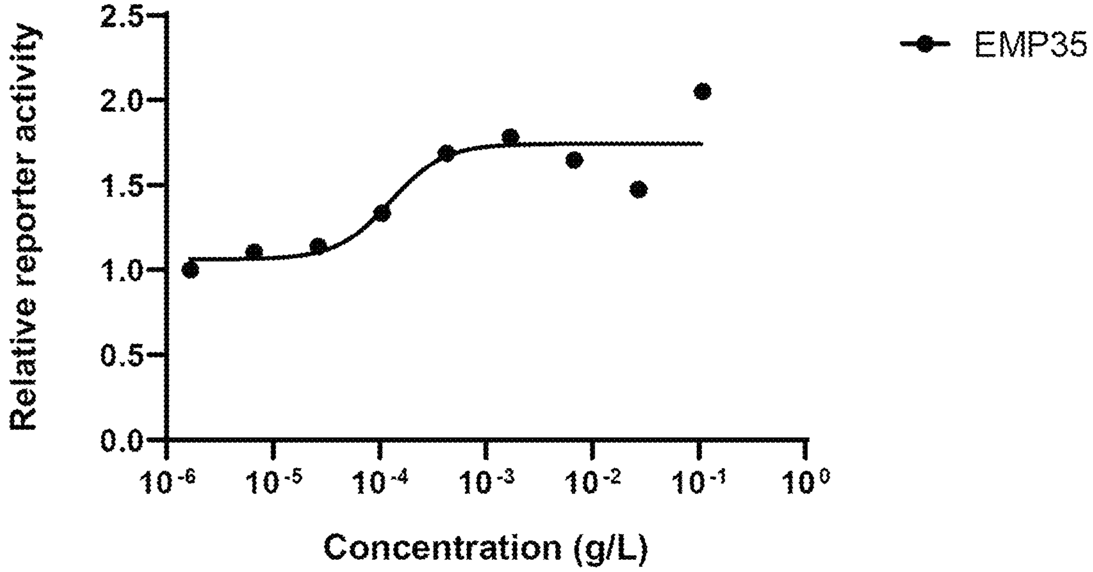
FIG. 36 is a graph showing the activity evaluation of the monomer peptide EMP35. The vertical axis represents relative receptor activity and the horizontal axis represents concentration.

As shown in FIG. 35, it was clarified that AET-EPO-PAS8 and AET-EPO-PAS22 activated EpoR in a concentration-dependent manner. The maximum activation ability was almost the same as that of rhEPO. In addition, as shown in Table 4 below, as for the EC50 values, rhEPO was found to be $1.1\times10^{-6}$ g/L, while AET-EPO-PAS8 was found to be $1.9\times10^{-7}$ g/L and AET-EPO-PAS22 was found to be $3.4\times10^{-7}$ g/L, with high activity. In addition, the monomer peptide EMP35 showed an activity of $1.1\times10^{-4}$ g/L, which was about 1000 times lower than that of the EPO-PAS dimer peptide (FIG. 36, Table 4), and it was clarified that higher agonist activity was obtained by dimerization.

TABLE 4

| Peptide | EC50 (g/L) |
| --- | --- |
| rhEPO | $1.1 \times 10^{-6}$ |
| AET-EPO-PAS8 | $1.9 \times 10^{-7}$ |
| AET-EPO-PAS22 | $3.4 \times 10^{-7}$ |
| EMP35 | $1.1 \times 10^{-4}$ |

Example 23: Design of TPO-PAS Dimer Peptide and its Secretory Expression in *C. glutamicum*

(23-1) Outline of Design

Peptide dimers that bind to the thrombopoietin receptor c-Mpl cannot be expressed in *C. glutamicum* for the following reasons. Specifically, a peptide dimer molecule (AF13948) obtained by dimerizing the straight chain c-Mpl-binding peptide AF12505 reported in S. E. Cwirla, et al. Science, 276, 1696-1699, 1997 with the α- and ε-amino groups of lysine cannot be expressed in *C. glutamicum* as a single polypeptide chain for the following reasons.

(1) Dimerization is achieved by binding the C-terminuses of the straight chain peptides AF12505 to each other via the α- and ε-amino groups of lysine, and cannot be expressed in *C. glutamicum*. (2) The non-protein amino acid β-alanine is bound to the C-terminus of AF12505 bound to the α-amino group of lysine, and peptides containing non-protein amino acids cannot be expressed in *C. glutamicum*. Therefore, the molecule was converted as follows to design an expressible form. The obstacles were dealt with by using PAS sequences instead of lysine and β-alanine and further designing the peptide sequence to be "first AF12505"-"PAS linker"-"second AF12505" so that it could be expressed as a single polypeptide chain. Specifically, the C-terminal of the first AF12505 and the N-terminal of the PAS linker are linked by an amide bond, and the N-terminal of the second AF12505 and the C-terminal of the PAS linker are linked by an amide bond, so that they can be expressed as a single polypeptide chain.

In addition, the peptide reported in WO9640750, a cyclic c-Mpl binding peptide AF12285 with biotin added to the C-terminus and multimerized with streptavidin, cannot be expressed in *C. glutamicum* as a single polypeptide chain for the following reasons.

(1) Biotin is modified at the C-terminal of the cyclic peptide AF12285 via the ε-amino group of lysine. Peptides containing biotin cannot be expressed at *C. glutamicum*.

(2) The biotinylated cyclic peptide is multimerized with streptavidin. It is impossible to express streptavidin at the same time as a peptide in *C. glutamicum*. Therefore, the molecule was converted as follows to design an expressible form. The obstacles were dealt with by using PAS sequences instead of biotin-streptavidin multimerization and further designing the peptide sequence to be "first AF12285"-"PAS linker"-"second AF12285" so that it could be expressed as a single polypeptide chain. Specifically, the C-terminal of the first AF12505 and the N-terminal of the PAS linker are linked by an amide bond, and the N-terminal of the second AF12505 and the C-terminal of the PAS linker are linked by an amide bond, so that they can be expressed as a single polypeptide chain.

(23-2) Preparation of TPO-PAS Dimer Peptides

The prepared TPO-PAS dimer peptides are as follows.

```
(t) TP02-PAS8
                                        (SEQ ID NO: 114)
GGCADGPTLREWISFCGGAAPAAPAPGGCADGPTLREWISFCGG

(u) AET-TPO1-PAS8
                                        (SEQ ID NO: 115)
AETIEGPTLRQWLAARAAAPAAPAPIEGPTLRQWLAARA

(v) AET-TPO2-PAS8
                                        (SEQ ID NO: 116)
AETGGCADGPTLREWISFCGGAAPAAPAPGGCADGPTLREWISFCGG
```

(23-3) Expression of TPO-PAS Dimer Peptides

The expression of these TPO-PAS dimer peptides was examined using Corynex (registered trademark). Hereinafter, examples of expression examinations using Corynex (registered trademark) will be described.

(23-4) Construction of Secretory Expression Plasmid of TPO2-PAS8 Using CspA Signal Sequence As the TPO-PAS dimer peptide, the amino acid sequence of the above (t) TPO2-PAS8 (which may be hereinafter referred to as "TPO2-PAS8") was designed, and the base sequence encoding this protein was designed in consideration of the codon usage frequency of *C. glutamicum*. Furthermore, the following expression cassette was designed to enable secretion expression by *C. glutamicum*.

TPO2-PAS8 was secretory-expressed as a fusion protein of TPO2-PAS8 and a signal peptide 25 amino acid residue of CspA derived from *C. ammoniagenes* ATCC 6872 strain (hereinafter referred to as "CspAss-TPO2-PAS8"). The base sequence and amino acid sequence encoding the designed CspAss-TPO2-PAS8 are set forth in SEQ ID NOs: 117 and 118, respectively.

```
Base sequence encoding CspAss-TPO2-PAS8
                                        (SEQ ID NO: 117)
atgaaacgcatgaaatcgctggctgcggcgctcaccgtcgctggggccat

gctggccgcacctgtggcaacggcaggtggttgtgctgatggtcctacct

tgcgtgaatggatttccttctgcggcggcgctgctccggctgcccctgcc

cctggcggttgcgcagatggcccaaccctgcgcgaatggatctccttctg

cggcggctaa

Amino acid sequence of CspAss-TPO2-PAS8
                                        (SEQ ID NO: 118)
MKRMKSLAAALTVAGAMLAAPVATAGGCADGPTLREWISFCGGAAPA

APAPGGCADGPTLREWISFCGG
```

The promoter of the cspB gene derived from the *C. glutamicum* ATCC 13869 strain was linked upstream of the base sequence set forth in CspAss-TPO2-PAS8, and furthermore, an expression cassette of TPO-PAS dimer peptide having a KpnI site on the 5'-side and an BamHI site on the 3'-side was designed and totally synthesized. The totally synthesized DNA fragment (TPO-PAS dimer peptide expression cassette) was inserted into the KpnI-BamHI site of pPK4 described in Japanese Patent Application Publication No. Hei 9-322774 to construct pPK4_CspAss-TPO2-PAS8, a secretory expression plasmid for the TPO-PAS dimer peptide using the CspA signal sequence. As a result of determining the base sequence of the inserted fragment, it was confirmed that the TPO-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(23-5) Construction of Each Secretory Expression Plasmid of AET-TPO1-PAS8 and AET-TPO2-PAS8 Using CspB Signal Sequence As the TPO-PAS dimer peptide, two types of amino acid sequences of the above (u) AET-TPO1-PAS8 (which may be hereinafter referred to as "AET-TPO1-PAS8") and (v) AET-TPO2-PAS8 (which may be hereinafter referred to as "AET-EPO2-PAS8") were designed, and the base sequences encoding these proteins were designed in consideration of the codon usage frequency of *C. glutamicum*. Furthermore, the following expression cassettes were designed to enable secretory expression by *C. glutamicum*.

AET-TPO1-PAS8 was secretory-expressed as a fusion protein of AET-TPO1-PAS8 and a signal peptide 30 amino acid residue of CspB derived from *C. glutamicum* ATCC 13869 strain (hereinafter referred to as "CspBss-AET-TPO1-PAS8"). The base sequence and amino acid sequence encoding the designed CspBss-AET-TPO1-PAS8 are set forth in SEQ ID NOs: 119 and 120, respectively.

```
Base sequence encoding CspBss-AET-TP01-PAS8
                                        (SEQ ID NO: 119)
atgtttaacaaccgtatccgcactgcagctctcgctggtgcaatcgcaat

ctccaccgcagcttccggcgtagctatcccagcattcgctgcagagacca

tcgaaggtcctaccctccgtcaatggctggctgctcgtgccgccgctccc

gccgctcctgctccaatcgaaggtcccaccctccgtcagtggctggcagc

ccgcgcataa

Amino acid sequence of CspBss-AET-TP01-PAS8
                                        (SEQ ID NO: 120)
MFNNRIRTAALAGAIAISTAASGVAIPAFAAETIEGPTLRQWLAARAAAP

AAPAPIEGPTLRQWLAARA
```

AET-TPO2-PAS8 was secretory-expressed as a fusion protein of AET-TPO2-PAS8 and a signal peptide 30 amino acid residue of CspB derived from *C. glutamicum* ATCC 13869 strain (hereinafter referred to as "CspBss-AET-TPO2-PAS8"). The base sequence and amino acid sequence encoding the designed CspBss-AET-TPO2-PAS8 are set forth in SEQ ID NOs: 121 and 122, respectively.

```
Base sequence encoding CspBss-AET-TPO2-PAS8
                                        (SEQ ID NO: 121)
atgtttaacaaccgtatccgcactgcagctctcgctggtgcaatcgcaat

ctccaccgcagcttccggcgtagctatcccagcattcgctgcagagaccg

gtggttgtgctgatggtcctaccttgcgtgaatggatttccttctgcggc

ggcgctgctccggctgcccctgcccctggcggttgcgcagatggcccaac

cctgcgcgaatggatctccttctgcggcggctaa

Amino acid sequence of CspBss-AET-TPO2-PAS8
                                        (SEQ ID NO: 122)
MFNNRIRTAALAGAIAISTAASGVAIPAFAAETGGCADGPTLREWISFCG

GAAPAAPAPGGCADGPTLREWISFCGG
```

The promoter of the cspB gene derived from the *C. glutamicum* ATCC 13869 strain was linked upstream of the base sequences set forth in CspBss-AET-TPO1-PAS8 and CspBss-AET-TPO2-PAS8, and furthermore, an expression cassette of each TPO-PAS dimer peptide having a KpnI site on the 5'-side and an BamHI site on the 3'-side was designed and totally synthesized. The totally synthesized DNA fragment (TPO-PAS dimer peptide expression cassette) was inserted into the KpnI-BamHI site of pPK4 described in Japanese Patent Application Publication No. Hei 9-322774 to construct pPK4_CspBss-AET-TPO1-PAS8 and pPK4_CspBss-AET-TPO2-PAS8, a secretory expression plasmid for each TPO-PAS dimer peptide using the CspB signal sequence. As a result of determining the base sequence of the inserted fragment, it was confirmed that each TPO-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(23-6) Secretory Expression of Each TPO-PAS Dimer Peptide in *C. glutamicum*

The pPK4_CspAss-TPO2-PAS8, pPK4_CspBss-AET-TPO1-PAS8, and pPK4_CspBss-AET-TPO2-PAS8 constructed above were used to transform the *C. glutamicum* YDK0107 strain described in WO2016/171224 to obtain the YDK0107/pPK4_CspAss-TPO2-PAS8 strain, YDK0107/pPK4_CspBss-AET-TPO1-PAS8 strain, and YDK0107/pPK4_CspBss-AET-TPO2-PAS8 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 37:
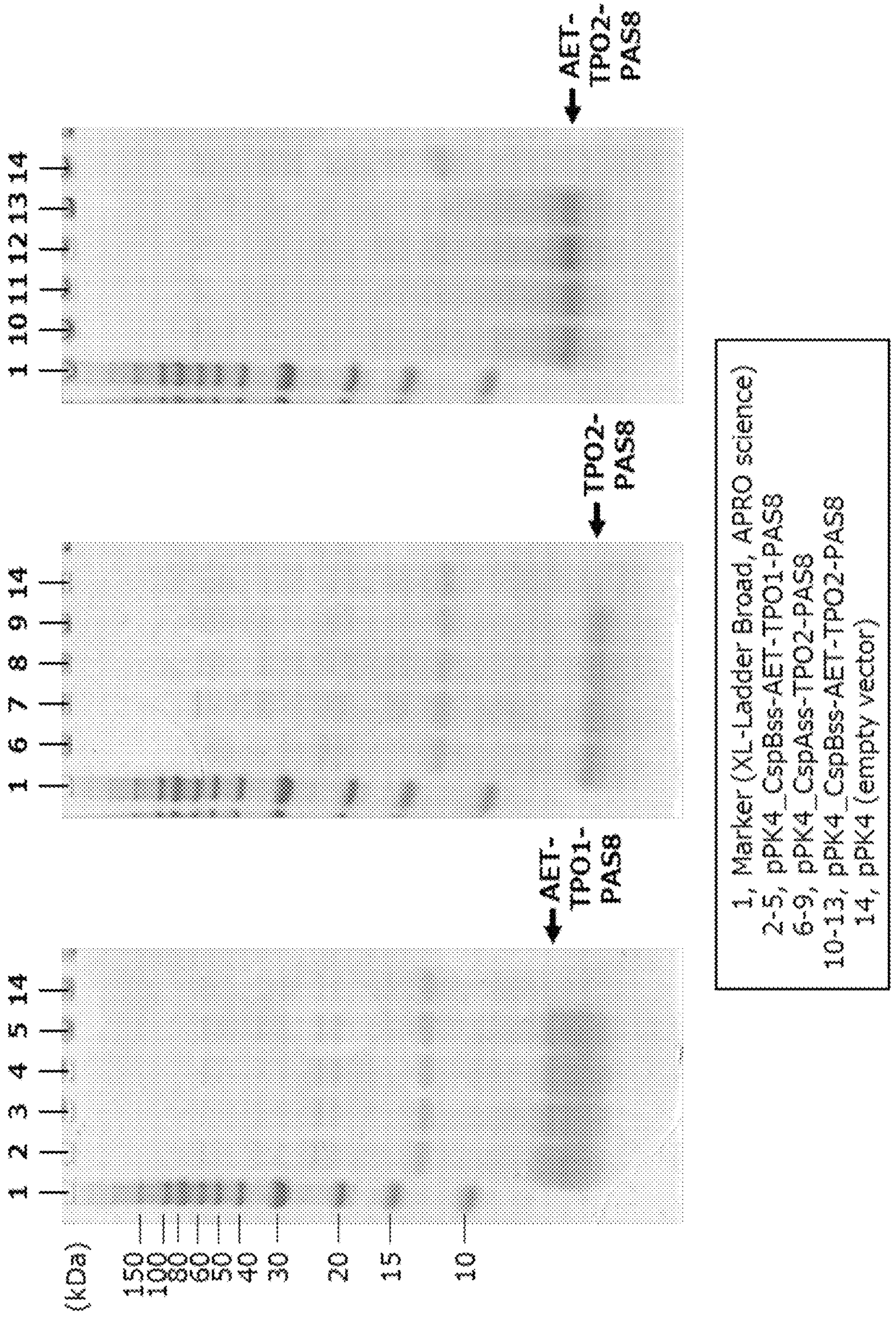
FIG. 37 is the results of SDS-polyacrylamide electrophoresis showing the secretory expression of the dimer peptide (TPO-PAS) in *C. glutamicum*. Lane 1 is a marker (XL-Ladder Broad, APRO science), lanes 2 to 5 are ones using pPK4_CspBss-AET-TPO1-PAS8, lanes 6 to 9 are ones using pPK4_CspBss-TPO2-PAS8, lanes 10 to 13 are ones using pPK4_CspBss-AET-TPO2-PAS8, and lane 14 is one using pPK4 (empty vector).

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-TPO1-PAS8 was detected in the culture supernatant of the YDK0107/pPK4_CspBss-AET-TPO1-PAS8 strain (FIG. 37, lanes 2 to 5), a protein band presumed to be TPO2-PAS8 was detected in the culture supernatant of the YDK0107/pPK4_CspAss-TPO2-PAS8 strain (FIG. 37, lanes 6 to 9), and a protein band presumed to be AET-TPO2-PAS8 was detected in the culture supernatant of the YDK0107/pPK4_CspBss-AET-TPO2-PAS8 strain (FIG. 37, lanes 10 to 13).

Example 24: Molecular Weight Analysis of TPO-PAS Dimer Peptide

Figure 38:
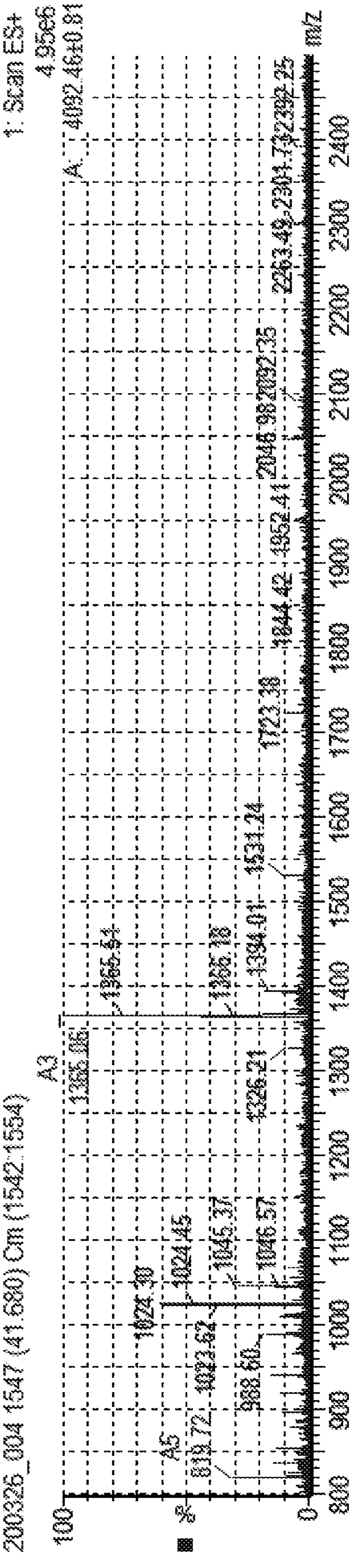
FIG. 38 shows measurement results of the dimer peptide (TPO-PAS) by LC-MS. Calc represents the theoretical value and Obs represents the measured value.
Figure 39:
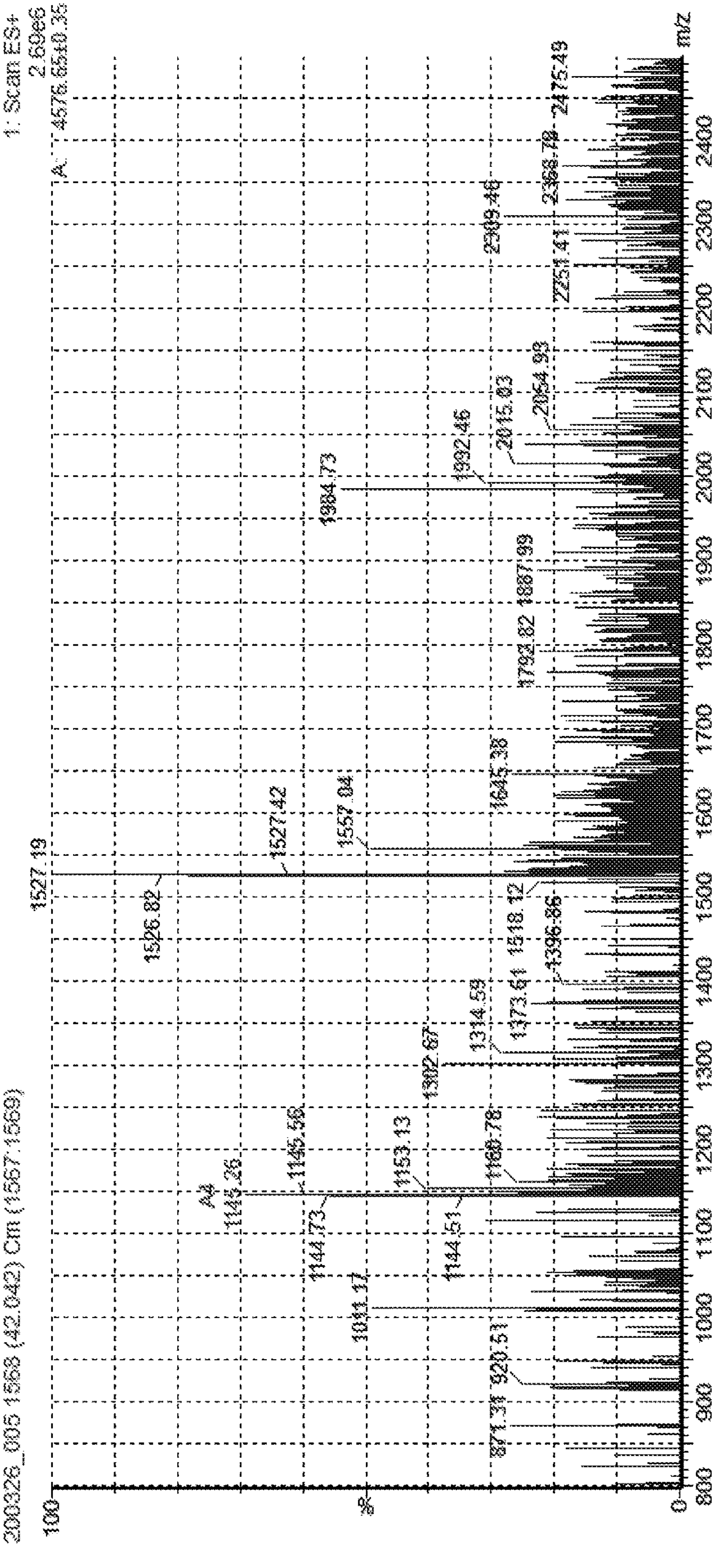
FIG. 39 shows measurement results of the dimer peptide (TPO-PAS) by LC-MS. Calc represents the theoretical value and Obs represents the measured value.
Figure 40:
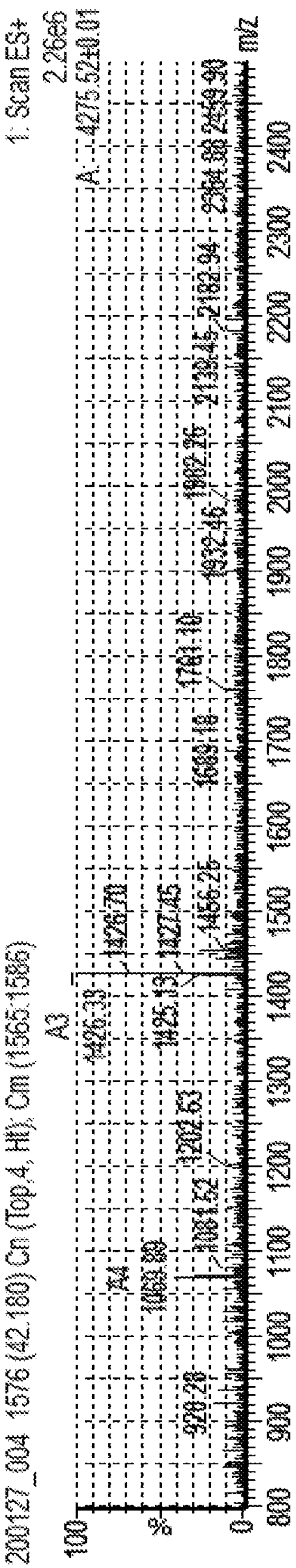
FIG. 40 shows measurement results of the dimer peptide (TPO-PAS) by LC-MS. Calc represents the theoretical value and Obs represents the measured value.

The cell filtrate of the TPO-PAS dimer peptide after culturing in Example 23 was subjected to molecular weight measurement using LC-MS (Waters, ACQUITY UPLC/SQD2). The analysis conditions are shown in Table 2. As shown in FIGS. 38 to 40, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 25: Activity Evaluation of TPO-PAS Dimer Peptide

The thrombopoietin-like activity of the TPO-PAS dimer peptide was evaluated by quantification of tyrosine phosphorylation levels in HEL cells, a human leukemia-derived blood cell line. 200,000 HEL cells were cultured in RPMI 1640 medium without FBS (Thermo Fisher Scientific) for 24 hours and starved. The cells were stimulated for 20 minutes in RPMI 1640 medium supplemented with 10 to 100 ng/mL recombinant human TPO (rhTPO, Peprotech) or a culture supernatant containing AET-TPO1-PAS8, TPO2-PAS8, or AET-TPO2-PAS8 at a predetermined dilution factor. As a negative control, PBS (Mock group) or a supernatant expressing no peptide (Empty group) by using an empty vector was added, and stimulation was performed for 20 minutes. After removing the medium and washing the cells once with PBS, the cells were lysed by adding 100 μL of Lysis buffer 17 (R&D Systems) supplemented with Protease inhibitor cocktail (Nacalai Tesque). The lysate solution was centrifuged at 14,000 G for 5 minutes to obtain the supernatant as lysate.

APVDF membrane (Immobilon-P membrane 0.45 m, Merck) was treated with methanol for 1 minute and then with ultrapure water for 5 minutes for hydrophilic treatment. The PVDF membrane was dried, and each cell lysate solution was spotted with a 1 μL pipette and dried. The PVDF membrane was blocked with PVDF Blocking Reagent for Can Get Signal (NOF) at room temperature for 1 hour, and then Can Get Signal Solution 2 (NOF), supplemented with anti-pY antibody-HGF conjugate (Cell Signaling Technology) at 1:5000, was added, followed by an antibody reaction at 4 °C for 24 hours. The membrane was washed 3 times with TBST buffer, Luminata Crescendo Western HRP Substrate (Merck) was added, and a chemiluminescence reaction was carried out. Chemiluminescence was detected using Amersham Imager 600 (GE Healthcare). The luminescence intensity of the detected dots was quantified by ImageJ.

Figure 41:
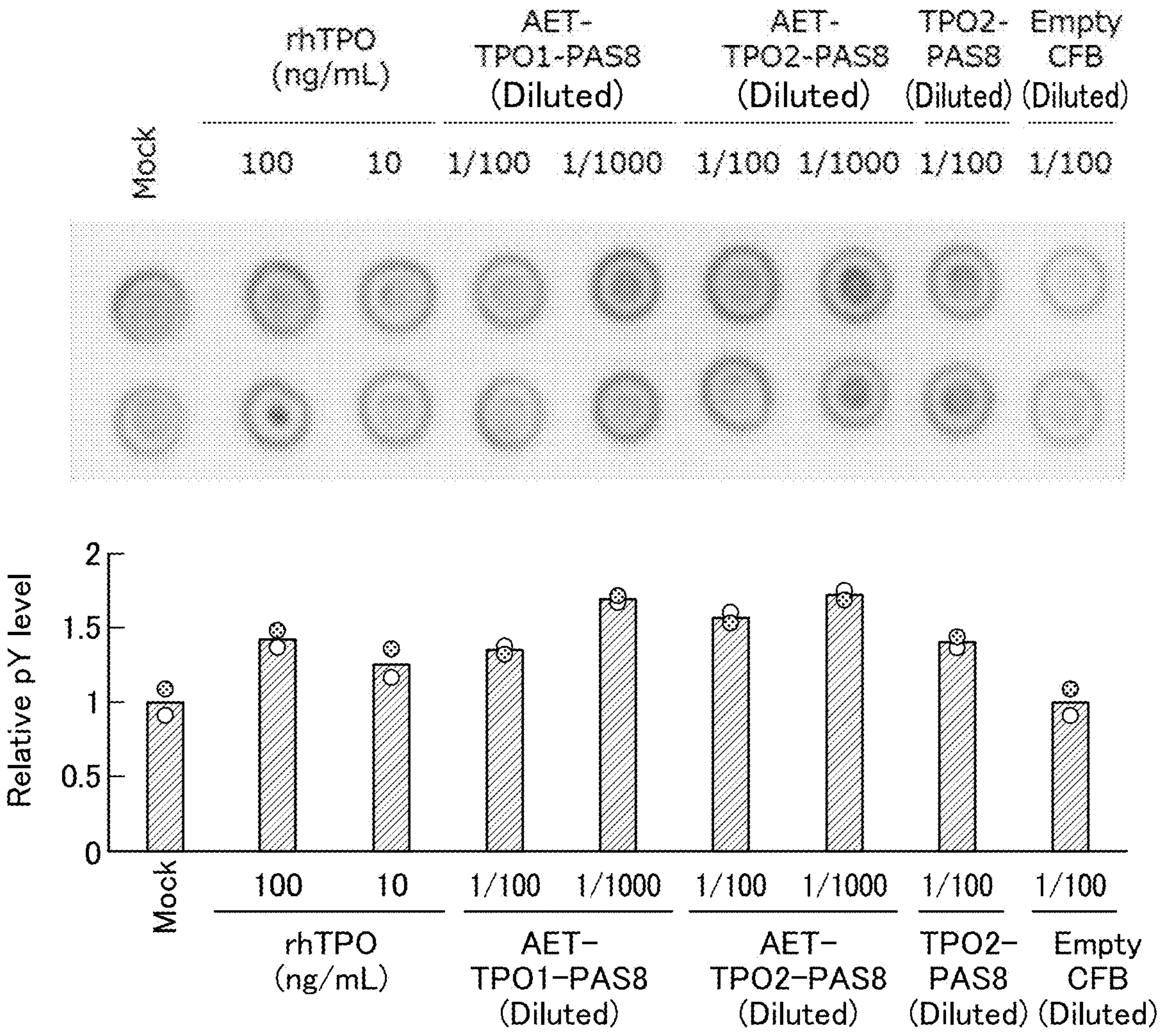
FIG. 41 is a graph showing the evaluation of tyrosine phosphorylation levels of rhTPO and dimer peptide (TPO-PAS). As shown in the upper figure, the detected dot luminescence intensity is quantified, and the quantification results are shown in the lower graph in terms of relative tyrosine phosphorylation level. The vertical axis represents the relative tyrosine phosphorylation level, and the horizontal axis represents concentration for rhTPO, and for the dimer peptide (TPO-PAS), the dilution rate of the culture supernatant containing the dimer peptide (TPO-PAS) with respect to the medium used for the activity evaluation. Empty CFB is the result for the supernatant when using an empty vector. Mock represents the PBS-added group.

As shown in FIG. 41, AET-TPO1-PAS8, AET-TPO2-PAS8, and TPO2-PAS8 were all observed to increase in tyrosine phosphorylation levels equal to or higher than that of rhTPO. From this result, it was clarified that AET-TPO1-PAS8, AET-TPO2-PAS8, and TPO2-PAS8 activated HEL cells in the same manner as TPO.

Figure 42:
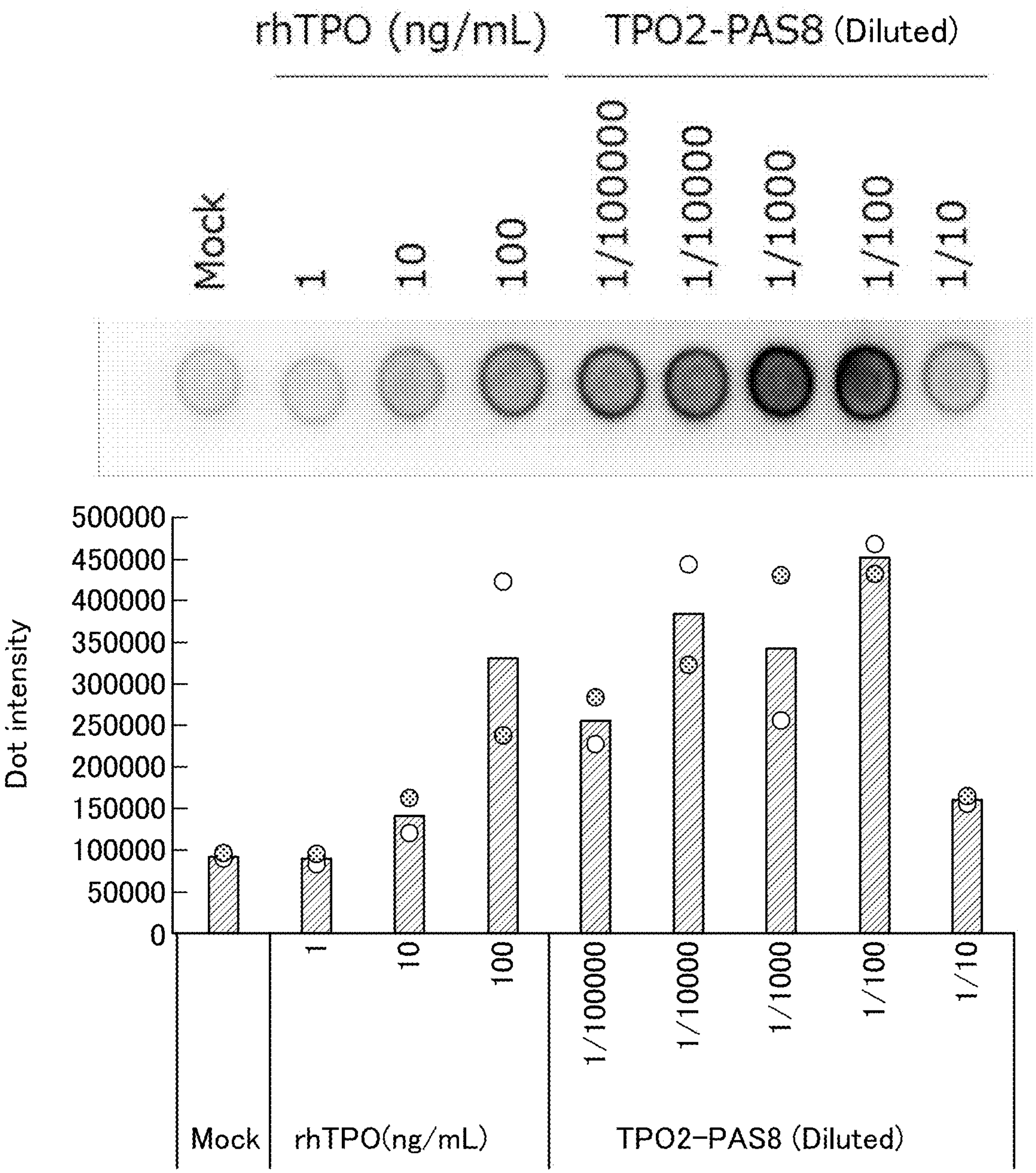
FIG. 42 is a graph showing the evaluation of cell activation ability of rhTPO and dimer peptide (TPO-PAS). As shown in the upper figure, the detected dot luminescence intensity is quantified, and the quantification results are shown in the lower graph. The vertical axis represents the dot luminescence intensity, and the horizontal axis represents concentration for rhTPO, and for the dimer peptide (TPO-PAS), the dilution rate of the culture supernatant containing the dimer peptide (TPO-PAS) with respect to the medium used for the activity evaluation. Mock represents the PBS-added group.

FIG. 42 shows the concentration-dependent ability of TPO2-PAS8 to activate HEL cells. Within the 1/100 to 1/10000 dilution range, the TPO2-PAS8 stimulation group showed luminescence intensity equal to or higher than that of the 100 ng/mL rhTPO stimulation group, and from this, it was clarified that the HEL cell activation ability was equal to or higher than that of rhTPO in this concentration range.

Example 26: Evaluation of Signal Characteristics of TPO-PAS Dimer Peptide

The signal characteristics of the TPO-PAS dimer peptide were evaluated using Proteome Profiler Human Phospho-Kinase Array Kit (R&D Systems).

1,000,000 HEL cells were cultured in RPMI 1640 medium without FBS (Thermo Fisher Scientific) for 24 hours and starved. The cells were stimulated for 20 minutes in RPMI 1640 medium supplemented with 100 ng/mL recombinant human TPO (rhTPO, Peprotech) or a culture supernatant containing TPO2-PAS8 at a dilution of 1/100 to 1/1000. As a negative control, PBS was added, and stimulation was performed for 20 minutes (Mock group). After removing the medium and washing the cells once with PBS, the cells were lysed by adding 200 μL of Lysis buffer 17 (R&D Systems) supplemented with Protease inhibitor cocktail (Nacalai Tesque). The lysate solution was centrifuged at 14,000 G for 5 minutes to obtain the supernatant as lysate.

Figure 43:
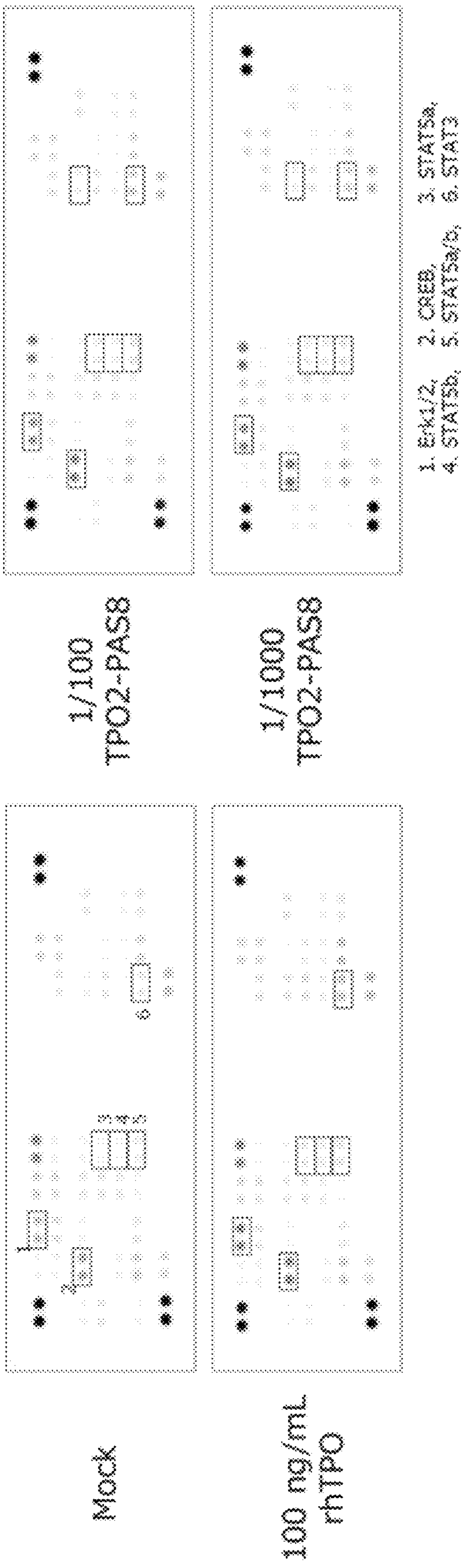
FIG. 43 is a diagram evaluating the signal activation characteristics of rhTPO and dimer peptide (TPO-PAS) using Proteome Profiler Human Phospho-Kinase Array Kit (R&D Systems). For the dimer peptide (TPO-PAS), the dilution rate of the culture supernatant containing the dimer peptide (TPO-PAS) with respect to the medium used for the activity evaluation is shown. Mock represents the PBS-added group.
Figure 44:
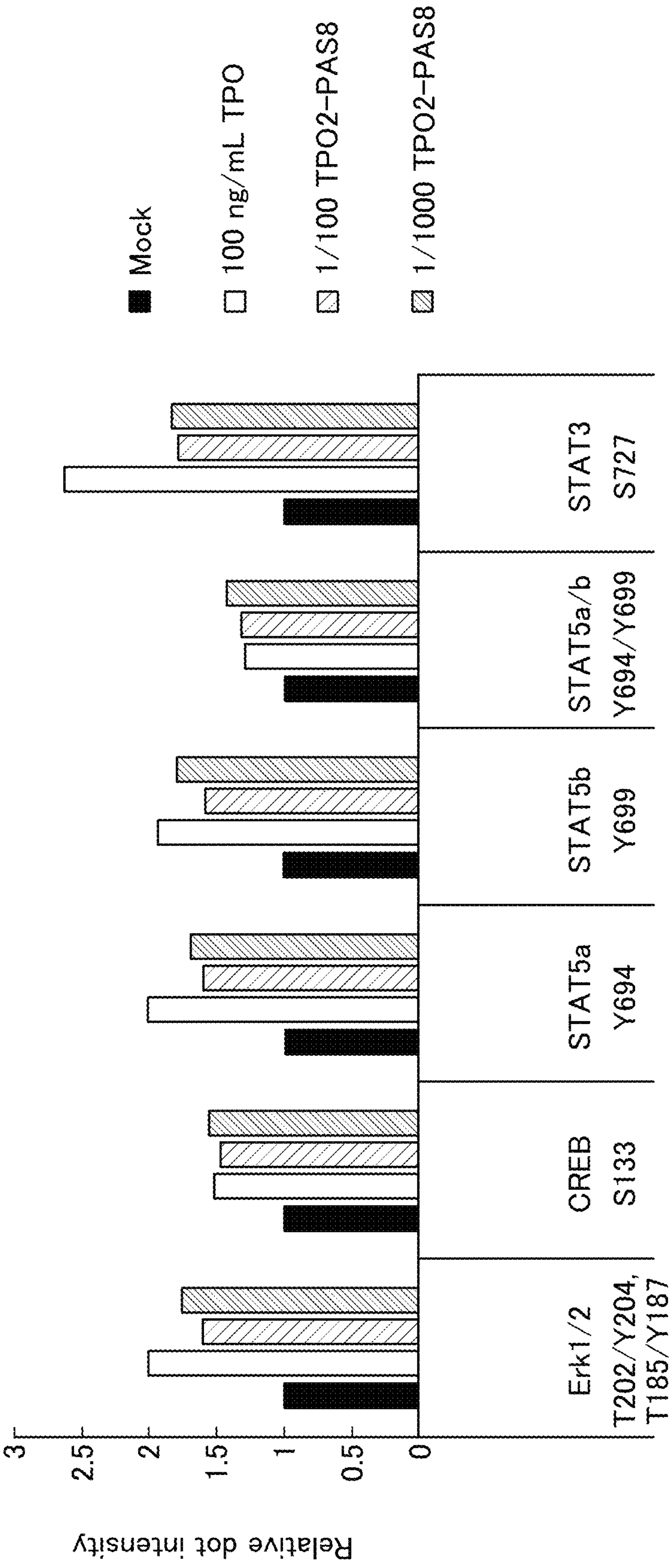
FIG. 44 is a graph showing quantitatively the phosphorylation ability of rhTPO and dimer peptide (TPO-PAS) measured using Proteome Profiler Human Phospho-Kinase Array Kit (R&D Systems). The vertical axis represents the relative dot luminescence intensity, and the horizontal axis represents the activated molecules. For the dimer peptide (TPO-PAS), the dilution rate of the culture supernatant containing the dimer peptide (TPO-PAS) with respect to the medium used for the activity evaluation is shown. Mock represents the PBS-added group.

The lysate was analyzed using Proteome Profiler Human Phospho-Kinase Array Kit. Amersham Imager 600 (GE Healthcare) was used to detect chemiluminescence. The chemiluminescence intensity of the dots was quantified using ImageJ. As shown in FIG. 43, it was confirmed that compared to the cells stimulated with PBS (Mock group), the cells stimulated with rhTPO or TPO2-PAS8 increased in phosphorylation levels of Erk, CREB, Stat3, Stat5a, and Stat5b, and their phosphorylation patterns were similar. The signal pathway stimulated by rhTPO is mainly the JAK2/Stat3,5 pathway, and all of the proteins with increased phosphorylation levels are included in the pathway. From this result, it has been confirmed that TPO2-PAS8 activates a signal similar to rhTPO.

Example 27: Design of VEGFR_D2-PAS Heterodimer Peptide and its Secretory Expression in *C. glutamicum*

(27-1) Outline of Design

It is impossible to express the VEGFR-binding cyclic peptides P-3 and P-4 reported in A. Shrivastava, et al. Protein Eng. Des. Select. 18, 417, 2005, dimerized by a glutarate linker, as a single polypeptide chain in *C. glutamicum* for the following reasons. Dimerization is achieved by binding the ε-amino groups of the lysine residues located at the C-terminus of each of the cyclic peptides P-3 and P-4 via glutaric acid, and cannot be expressed in *C. glutamicum*. Therefore, the molecule was converted as follows to design an expressible form. The obstacles were dealt with by using a PAS sequence instead of a glutarate linker and further designing the peptide sequence to be "first VEGFR-binding sequence (P-3)"-"PAS linker"-"second VEGFR-binding sequence (P-4)" so that it could be expressed as a single polypeptide chain. Specifically, the C-terminal of P-3 and the N-terminal of the PAS linker are linked by an amide bond, and the N-terminal of P-4 and the C-terminal of the PAS linker are linked by an amide bond, so that they can be expressed as a single polypeptide chain.

(27-2) Preparation of VEGFR_D2-PAS Heterodimer Peptide

The prepared VEGFR_D2-PAS heterodimer peptide is as follows.

```
(w) AET-VEGFR_D2-PAS 16
                                        (SEQ ID NO: 123)
AETAGPTWCEDDWYYCWLFGTAAPAAPAPAAPAAPAPVCWEDSWGGEVCW

LFGT
```

(27-3) Expression of VEGFR_D2-PAS Heterodimer Peptide

Corynex (registered trademark) was used to examine the expression of VEGFR_D2-PAS heterodimer peptide. Hereinafter, examples of expression examinations using Corynex (registered trademark) will be described.

(27-4) Construction of AET-VEGFR_D2-PAS16 Secretory Expression Plasmid Using CspB Signal Sequence As the VEGFR_D2-PAS heterodimer peptide, the amino acid sequence of the above (w) AET-VEGFR_D2-PAS16 (which may be hereinafter referred to as "AET-VEGFR_D2-PAS16", and may be simply referred to as "VEGFR_D2-PAS16") was designed, and the base sequence encoding this protein was designed in consideration of the codon usage frequency of *C. glutamicum*. Furthermore, the following expression cassette was designed to enable secretion expression by *C. glutamicum*.

AET-VEGFR_D2-PAS16 was secretory-expressed as a fusion protein of AET-VEGFR_D2-PAS16 and a signal peptide 30 amino acid residue of CspB derived from *C. glutamicum* ATCC 13869 strain (hereinafter referred to as "CspBss-VEGFR_D2-PAS16"). The base sequence and amino acid sequence encoding the designed CspBss-AET-VEGFR_D2-PAS16 are set forth in SEQ ID NOs: 124 and 125, respectively.

```
Base sequence encoding CspBss-AET-
VEGFR_D2-PAS16
                                        (SEQ ID NO: 124)
atgtttaacaaccgtatccgcactgcagctctcgctggtgcaatcgcaat

ctccaccgcagcttccggcgtagctatcccagcattcgctgcagagaccg
```

-continued

```
ctggtcctacctggtgtgaagacgactggtactactgctggctgtttggc

accgctgctcccgctgcccctgctcctgccgctccggcagccccagctcc

tgtgtgttgggaagattcttggggcggcgaagtttgctggctgtttggca

cctaa

Amino acid sequence of CspBss-AET-
VEGFR_D2-PAS16
                                   (SEQ ID NO: 125)
MFNNRIRTAALAGAIAISTAASGVAIPAFAAETAGPTWCEDDWYYCWLFG

TAAPAAPAPAAPAAPAPVCWEDSWGGEVCWLFGT
```

The promoter of the cspB gene derived from the *C. glutamicum* ATCC 13869 strain was linked upstream of the base sequence set forth in CspBss-AET-VEGFR_D2-PAS16, and furthermore, an expression cassette of VEGFR_D2-PAS heterodimer peptide having a KpnI site on the 5'-side and an BamHI site on the 3'-side was designed and totally synthesized. The totally synthesized DNA fragment (VEGFR_D2-PAS heterodimer peptide expression cassette) was inserted into the KpnI-BamHI site of pPK4 described in Japanese Patent Application Publication No. Hei 9-322774 to construct pPK4_CspBss-AET-VEGFR_D2-PAS16, a secretory expression plasmid for the VEGFR_D2-PAS heterodimer peptide using the CspB signal sequence. As a result of determining the base sequence of the inserted fragment, it was confirmed that the VEGFR_D2-PAS heterodimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(27-5) Secretory Expression of VEGFR_D2-PAS Heterodimer Peptide in *C. glutamicum*

The pPK4_CspBss-AET-VEGFR_D2-PAS16 constructed above was used to transform the *C. glutamicum* YDK0107 strain described in WO2016/171224 to obtain the YDK0107/pPK4_CspBss-AET-VEGFR_D2-PAS16 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

After completion of the culture, 6.5 μL of the culture supernatant obtained by centrifuging the culture solution or the culture solution containing the cells and the culture supernatant uniformly without centrifugation was each subjected to reduced SDS-PAGE using NuPAGE (registered trademark) 12% Bis-Tirs Gel (Thermo Fisher Scientific), and then stained with Quick-CBB (Wako). As a result, a very small amount of a protein band presumed to be AET-VEGFR_D2-PAS16 was detected in the culture supernatant of the YDK0107/pPK4_CspBss-AET-VEGFR_D2-PAS16 strain (FIG. 45, lane 2), whereas a protein band presumed to be AET-VEGFR_D2-PAS16 was significantly detected in the culture solution sample containing the cells (FIG. 45, lane 3).

From the above results, it was considered that after secretion, most of AET-VEGFR_D2-PAS16 was aggregated in the culture supernatant or adsorbed on the cell surface of the cultured cells.

(27-6) Solubilization of VEGFR_D2-PAS Heterodimer Peptide by Urea Treatment

To the precipitate fraction containing the cells obtained by centrifuging the culture solution of the YDK0107/pPK4_CspBss-AET-VEGFR_D2-PAS16 strain obtained above, an equal volume of 0.5 M Urea (50 mM Tris-HCl, pH 8.0) or 1.0 M Urea (50 mM Tris-HCl, pH 8.0) was added to the removed culture supernatant and mixed. 6.5 μL of the supernatant fraction obtained by centrifuging each Urea treatment solution or the mixture containing the cells and the supernatant uniformly without centrifugation was each subjected to reduced SDS-PAGE using NuPAGE (registered trademark) 12% Bis-Tirs Gel (Thermo Fisher Scientific), and then stained with Quick-CBB (Wako). As a result, in the 0.5 M Urea and 1.0 M Urea treatment samples, a protein band presumed to be AET-VEGFR_D2-PAS16 was extracted into the supernatant and obtained as a soluble fraction (FIG. 45, lanes 6 and 8).

Example 28: Molecular Weight Analysis of VEGFR_D2-PAS Heterodimer

The solution obtained by washing the cells expressing the VEGFR_D2-PAS heterodimer after culturing in Example 27 with 8 M Urea was subjected to cell filtration and then molecular weight measurement using LC-MS (Waters, ACQUITY UPLC/SQD2). The analysis conditions are shown in Table 5.

TABLE 5

| LC set up | | | |
|---|---|---|---|
| System | ACQUITYUPLC H-Class/SQD2 | | |
| Column | TMC-Triart C8 50 × 2.0 mmI.D. 1.9 um, 12 nm(TO12SP9-0502PT) | | |
| Solvent A | 0.1% TFA | | |
| B | 0.1% TFA, 80% Acetonitrile | | |
| Flow rate | 1.0 mL/min | | |
| Column temp. | 40 °C | | |
| Detection | 220 nm | | |
| Sample Vol. | 10 uL | | |
| Gradient program | Time (min) | % A | % B |
| | 0 | 100 | 0 |
| | 50 | 100 | 100 |
| | 53 | 0 | 100 |
| | 53.1 | 100 | 0 |
| | 56 | 100 | 0 |
| | 56.1 | 0 | 100 |

TABLE 5-continued

| | | | |
|---|---|---|---|
| | 59 | 0 | 100 |
| | 59.1 | 100 | 0 |
| | 65 | 100 | 0 |

MS spectrometer set up

| | |
|---|---|
| Ion mode | ESI positive |
| Range | 800-2500 m/z |
| Scan time | 0.4 amu/sec |
| Capillary Voltage | 2.0 kV |
| Cone voltage | 10 V, 20 V, 40 V |
| Desolvation temp | 500 °C |
| Desolvation Gas Flow | 1000 L/hr |
| Cone Gas Flow | 50 L/hr |
| Software | Deconvolution is performed using "MassLynx" |

Figure 46:
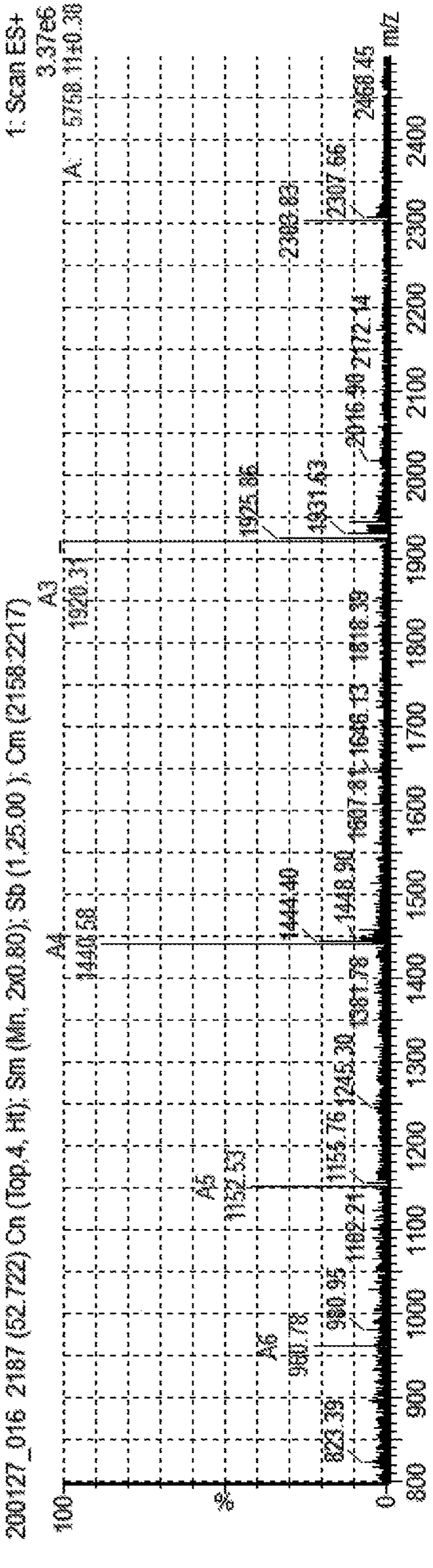
FIG. 46 shows measurement results of the heterodimer peptide (VEGFR_D2-PAS) by LC-MS. Calc represents the theoretical value and Obs represents the measured value.

As shown in FIG. 46, almost the same value as the theoretical value of the molecular weight of the oxidized dimer peptide forming two disulfide bonds in the molecule was obtained. From this, it was confirmed that a peptide having the correct amino acid sequence containing two disulfide bonds could be expressed.

Example 29: Activity Evaluation of VEGFR_D2-PAS Heterodimer

The VEGF inhibitory ability of the VEGFR_D2-PAS heterodimer peptide was evaluated by luciferase assay. 40,000 cell/well VEGFR/NFAT Reporter HEK293 cells (BPS Bioscience) were seeded and incubated overnight in a 5% $CO_2$ incubator at 37 °C. The cells were incubated overnight in Assay medium (MEM medium (Nacalai Tesque), 1×MEM Non-Essential Amino Acids Solution (Thermo Fisher Scientific), 1 mM Sodium Pyruvate (Nacalai Tesque), 1% Penicillin-Streptomycin (Sigma Aldrich), and 0.3% FBS (Thermo Fisher Scientific)) to starvation. To the Assay medium, 10 ng/mL human recombinant VEGF (R&D Systems) was added, and further, VEGFR_D2-PAS16 purified by HPLC, or a monomer peptide P3 (AGPTWCEDDWYYCWLFGT (SEQ ID NO: 71), synthesized by GenScript Japan) or Pm4 (VCWEDSWGGEVCWLFGT (SEQ ID NO: 72), synthesized by GenScript Japan) was added at a predetermined dilution factor, and 100 µL of the Assay medium was added to the cells. The cells were stimulated by culturing in a 5% $CO_2$ incubator at 37 °C for 4 hours.

One-Glo Luciferase Assay System (Promega) was used to detect the signal intensity. Medium supernatant in an amount of 50 µL was removed, 50 µL of One-Glo reagent was added, and the cells were lysed for 10 minutes at room temperature. The luminescence emitted from the cell lysate solution was detected with a Nivo plate reader (Perkin Elmer) to quantify the activation of the VEGFR-NFAT pathway, and the relative signal activity value for the sample without addition of evaluation compound was determined and used as relative receptor activity.

Figure 47:
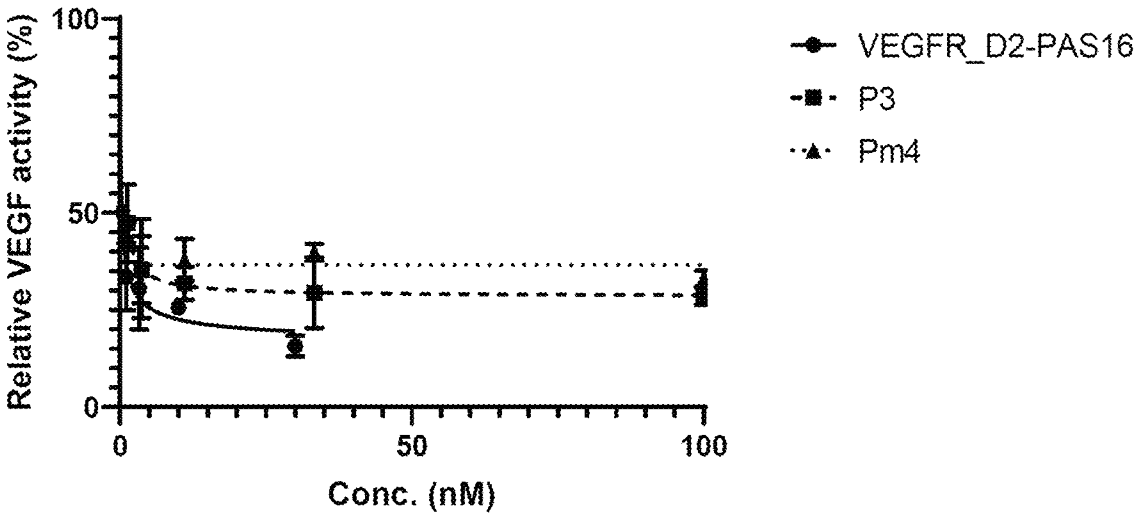
FIG. 47 is a graph showing the evaluation of the VEGF inhibitory ability of the heterodimer peptide (VEGFR_D2-PAS) and the monomeric peptides P3 and Pm4. The vertical axis represents relative VEGF activity (relative receptor activity), and the horizontal axis represents concentration.

As shown in FIG. 47, VEGFR_D2-PAS16 showed higher inhibitory activity than the monomer peptides P3 and Pm4, so that it was clarified that high inhibitory activity could be obtained by heterodimerization of cyclic peptides.

Example 30: Design of EPO-PAS Dimer Peptide Linker Variant and its Secretory Expression in *C. glutamicum*

(30-1) Outline of Linker Variant Design

The erythropoietin mimetic peptides AET-EPO-PAS8 and AET-EPO-PAS22 have a structure in which a PAS linker composed of 8 amino acids or 22 amino acids is linked between the first erythropoietin receptor-binding cyclic peptide and the second erythropoietin receptor-binding cyclic peptide. By changing the length of this PAS linker, it is expected that the erythropoietin receptor binding activity will change. Therefore, a linker variant was designed in which the PAS linker portion was changed to a PAS repeat sequence of 49 amino acids or 100 amino acids.

In addition to the PAS linker, a GS linker, which is a repeating sequence of glycine and serin, is also known as a flexible linker. Therefore, the peptide sequence was designed to be a linker variant in which an EPO cyclic peptide was bound to the N-terminus and C-terminus of the GS linker composed of a repeating sequence of 4 glycine residues and 1 serine residue (GGGGS), that is, a "first erythropoietin receptor-binding cyclic peptide"-"GS linker"-"second erythropoietin receptor-binding cyclic peptide".

(30-2) Preparation of EPO-PAS Dimer Peptide Linker Variants

The prepared EPO-PAS dimer peptide linker variants are as follows.

```
(x) AET-EPO-PAS49
                                          (SEQ ID NO: 126)
AETGGLYACHMGPMTWVCQPLRGAAPAAPAPAAPAAPAPAAPAAPAPA

APAAPAPAAPAAPAPAAPAAPAPAGGLYACHMGPMTWVCQPLRG

(y) AET-EPO-PAS49-b
                                          (SEQ ID NO: 127)
AETGGLYACHMGPMTWVCQPLRGSAPSPSSAPASASAPASPASASASA

SPASSPASASSASPAASSASPASSGGLYACHMGPMTWVCQPLRG

(z) AET-EPO-PAS100
                                         ((SEQ ID NO: 128)
AETGGLYACHMGPMTWVCQPLRGAAPAAPAPAAPAAPAPAAPAAPAPA

APAAPAPAAPAAPAPAAPAAPAPAAPAAPAPAAPAAPAPAAPAAPAPA

APAAPAPAAPAAPAPAAPAAPAPAAPAGGLYACHMGPMTWVCQPLRG

(A) AET-EPO-PAS100-b
                                          (SEQ ID NO: 129)
AETGGLYACHMGPMTWVCQPLRGSAPSPSSAPASASAPASPASASASA
```

-continued

```
SPASSPASASSASPAASSASPASSSASPSAPAAPSASAAPSASPASSS

PAPASAPSPAAAASSPSPAPSSASSAAGGLYACHMGPMTWVCQPLRG

(B) AET-EPO-GS8
                                    (SEQ ID NO: 130)
AETGGLYACHMGPMTWVCQPLRGGGGGSGGGGGLYACHMGPMTWVCQP

LRG

(C) AET-EPO-GS22
                                    (SEQ ID NO: 131)
AETGGLYACHMGPMTWVCQPLRGGGGGSGGGGSGGGGSGGGGSGGGGL

YACHMGPMTWVCQPLRG
```

(30-3) Expression of EPO-PAS Dimer Peptide Linker Variant

The expression of these EPO-PAS dimer peptide linker variants was examined using Corynex (registered trademark). Hereinafter, examples of expression examinations using Corynex (registered trademark) will be described.

(30-4) Construction of Each Secretory Expression Plasmid of AET-EPO-PAS49, AET-EPO-PAS49-b, AET-EPO-PAS100, AET-EPO-PAS100-b, AET-EPO-GS8, and AET-EPO-GS22 Using CspB Signal Sequence As the EPO-PAS dimer peptide linker variant, six types of amino acid sequences of the above (x) AET-EPO-PAS49 (which may be hereinafter referred to as "AET-EPO-PAS49"), (y) AET-EPO-PAS49-b (which may be hereinafter referred to as "AET-EPO-PAS49-b"), (z) AET-EPO-PAS100 (which may be hereinafter referred to as "AET-EPO-PAS100"), (A) AET-EPO-PAS100-b (which may be hereinafter referred to as "AET-EPO-PAS100-b"), (B) AET-EPO-GS8 (which may be hereinafter referred to as "AET-EPO-GS8"), and (C) AET-EPO-GS22 (which may be hereinafter referred to as "AET-EPO-GS22") were designed, and base sequences encoding these proteins were designed in consideration of the codon usage frequency of *C. glutamicum*. Furthermore, the following expression cassettes were designed to enable secretory expression by *C. glutamicum*.

AET-EPO-PAS49 was secretory-expressed as a fusion protein of AET-EPO-PAS49 and a signal peptide 30 amino acid residue of CspB derived from *C. glutamicum* ATCC 13869 strain (hereinafter referred to as "CspBss-AET-EPO-PAS49"). The base sequence and amino acid sequence encoding the designed CspBss-AET-EPO-PAS49 are set forth in SEQ ID NOs: 132 and 133, respectively.

```
Base sequence encoding CspBss-AET-EPO-PAS49
                                    (SEQ ID NO: 132)
atgtttaacaaccgtatccgcactgcagctctcgctggtgcaatcgca

atctccaccgcagcttccggcgtagctatcccagcattcgctgcagag

accggtggtctctacgcctgtcacatgggtcctatgacctgggtgtgc

caacctctccgtggtgccgcccccgccgcccccgcccccgccgcccca

gctgcaccagctccagcagccccagccgcaccagccccagcagctcca

gctgccccagcaccagcagcaccagccgctccagcaccagctgctcca

gcagctccagccccagccggcggcctttacgcctgccacatgggtcct

atgacctgggtttgccagcctcttcgcggttag

Amino acid sequence of CspBss-AET-EPO-PAS49
                                    (SEQ ID NO: 133)
MFNNRIRTAALAGAIAISTAASGVAIPAFAAETGGLYACHMGPMTWVC

QPLRGAAPAAPAPAAPAAPAPAAPAAPAPAAPAAPAPAAPAAPAPAAP

AAPAPAGGLYACHMGPMTWVCQPLRG
```

AET-EPO-PAS49-b was secretory-expressed as a fusion protein of AET-EPO-PAS49-b and a signal peptide 30 amino acid residue of CspB derived from *C. glutamicum* ATCC 13869 strain (hereinafter referred to as "CspBss-AET-EPO-PAS49-b"). The base sequence and amino acid sequence encoding the designed CspBss-AET-EPO-PAS49-b are set forth in SEQ ID NOs: 134 and 135, respectively.

```
Base sequence encoding CspBss-AET-EPO-PAS49-b
                                    (SEQ ID NO: 134)
atgtttaacaaccgtatccgcactgcagctctcgctggtgcaatcgca

atctccaccgcagcttccggcgtagctatcccagcattcgctgcagag

accggcggactgtacgcctgccatatggggccaatgacctgggtgtgc

caaccgttgcgtggatcagcgccatcgccctcttccgctccagcctct

gcgtctgctcccgcatccccagcgtcagcttccgcatccgcttcgcct

gcaagctcccctgctagcgcgtcctctgcctcccctgcagcatcctcg

gcttccccggcaagctcaggtggcctctatgcctgccacatgggtccg

atgacttgggtctgtcagccacttcgcggctaa

Amino acid sequence of CspBss-AET-EPO-PAS49-b
                                    (SEQ ID NO: 135)
MFNNRIRTAALAGAIAISTAASGVAIPAFAAETGGLYACHMGPMTWVC

QPLRGSAPSPSSAPASASAPASPASASASASPASSPASASSASPAASS

ASPASSGGLYACHMGPMTWVCQPLRG
```

AET-EPO-PAS100 was secretory-expressed as a fusion protein of AET-EPO-PAS100 and a signal peptide 30 amino acid residue of CspB derived from *C. glutamicum* ATCC 13869 strain (hereinafter referred to as "CspBss-AET-EPO-PAS100"). The base sequence and amino acid sequence encoding the designed CspBss-AET-EPO-PAS100 are set forth in SEQ ID NOs: 136 and 137, respectively.

```
Base sequence encoding CspBss-AET-EPO-PAS100
                                    (SEQ ID NO: 136)
atgtttaacaaccgtatccgcactgcagctctcgctggtgcaatcgca

atctccaccgcagcttccggcgtagctatcccagcattcgctgcagag

accggtggtttgtacgcttgccacatgggtcctatgacctgggtttgt

cagcctcttcgtggtgccgcccccgcagcccccgctcccgctgcacca

gccgcaccagcaccagcagctccagcagctccagcaccagctgcacca

gccgccccagcaccagcagccccagccgctccagcaccagctgcccca

gctgctccagctccagcagcaccagctgccccagccccagcagcacca

gccgctccagccccagctgccccagcagctccagctccagctgctcca

gcagccccagcaccagccgccccagcagccccagctccagctgcacca

gctgcaccagccccagccgcaccagccggcggtttgtacgcttgccac

atgggtccgatgacctgggtttgtcagccccttcgcggttag

Amino acid sequence of CspBss-AET-EPO-PAS100
                                    (SEQ ID NO: 137)
MFNNRIRTAALAGAIAISTAASGVAIPAFAAETGGLYACHMGPMTWVC
```

-continued

QPLRGAAPAAPAPAAPAAPAPAAPAAPAPAAPAAPAPAAPAAPAPAAP

AAPAPAAPAAPAPAAPAAPAPAAPAAPAPAAPAAPAPAAPAAPAPAAP

AAPAPAAPAGGLYACHMGPMTWVCQPLRG

AET-EPO-PAS100-b was secretory-expressed as a fusion protein of AET-EPO-PAS100-b and a signal peptide 30 amino acid residue of CspB derived from *C. glutamicum* ATCC 13869 strain (hereinafter referred to as "CspBss-AET-EPO-PAS100-b"). The base sequence and amino acid sequence encoding the designed CspBss-AET-EPO-PAS100-b are set forth in SEQ ID NOs: 138 and 139, respectively.

```
Base sequence encoding CspBss-AET-EPO-PAS100-b
                                    (SEQ ID NO: 138)
atgtttaacaaccgtatccgcactgcagctctcgctggtgcaatcgca

atctccaccgcagcttccggcgtagctatcccagcattcgctgcagag

accggcggcttgtacgcctgccatatggggcctatgacctgggtctgc

caaccactgcgtggaagcgcaccctcaccatcctccgcaccagctagc

gcctccgctcctgcaagcccagcgtccgcatccgcttcggcctcacca

gcgtcctctccagcttccgcttcgagcgctagcccagcggcatcctct

gcctccccagcctcctcgtctgcatccccgtccgctccagccgcacct

tctgcatctgcggctccgtccgcctccccggcatcttcctcgcctgct

cccgcgtcagcgccttccccggctgcagcggcctcctctccgtcaccc

gctccttcaagcgcgtcgtctgcagcaggaggcctctatgcctgccac

atgggtccgatgacttgggtgtgtcagccccttcgcggttaa

Amino acid sequence of CspBss-AET-EPO-PAS100-b
                                    (SEQ ID NO: 139)
MFNNRIRTAALAGAIAISTAASGVAIPAFAAETGGLYACHMGPMTWVC

QPLRGSAPSPSSAPASASAPASPASASASASPASSPASASSASPAASS

ASPASSSASPSAPAAPSASAAPSASPASSSPAPASAPSPAAAASSPSP

APSSASSAAGGLYACHMGPMTWVCQPLRG
```

AET-EPO-GS8 was secretory-expressed as a fusion protein of AET-EPO-GS8 and a signal peptide 30 amino acid residue of CspB derived from *C. glutamicum* ATCC 13869 strain (hereinafter referred to as "CspBss-AET-EPO-GS8"). The base sequence and amino acid sequence encoding the designed CspBss-AET-EPO-GS8 are set forth in SEQ ID NOs: 140 and 141, respectively.

```
Base sequence encoding CspBss-AET-EPO-GS8
                                    (SEQ ID NO: 140)
atgtttaacaaccgtatccgcactgcagctctcgctggtgcaatcgca

atctccaccgcagcttccggcgtagctatcccagcattcgctgcagag

accggcggcctctatgcatgccatatggggccaatgacctgggtctgc

caaccgttgcgtggcggaggtggcggttccggtggaggtggtggcctg

tacgcttgccacatgggacccatgacttgggtgtgtcagcctcttcgc

ggctaa

Amino acid sequence of CspBss-AET-EPO-GS8
                                    (SEQ ID NO: 141)
MFNNRIRTAALAGAIAISTAASGVAIPAFAAETGGLYACHMGPMTWVC

QPLRGGGGGSGGGGGLYACHMGPMTWVCQPLRG
```

AET-EPO-GS22 was secretory-expressed as a fusion protein of AET-EPO-GS22 and a signal peptide 30 amino acid residue of CspB derived from *C. glutamicum* ATCC 13869 strain (hereinafter referred to as "CspBss-AET-EPO-GS22"). The base sequence and amino acid sequence encoding the designed CspBss-AET-EPO-GS22 are set forth in SEQ ID NOs: 142 and 143, respectively.

```
Base sequence encoding CspBss-AET-EPO-GS22
                                    (SEQ ID NO: 142)
atgtttaacaaccgtatccgcactgcagctctcgctggtgcaatcgca

atctccaccgcagcttccggcgtagctatcccagcattcgctgcagag

accggtgggctgtatgcttgccatatggggcctatgacttgggtgtgc

caacccttgcgtggtggaggcggaggctccggcggtggtgggagcgga

ggaggcggttccggtggcggtggctctggcggaggcggcctctacgca

tgccacatgggtccgatgacctgggtctgtcagccacttcgcggctaa

Amino acid sequence of CspBss-AET-EPO-GS22
                                    (SEQ ID NO: 143)
MFNNRIRTAALAGAIAISTAASGVAIPAFAAETGGLYACHMGPMTWVC

QPLRGGGGGSGGGGSGGGGSGGGGSGGGGLYACHMGPMTWVCQPLRG
```

The promoter of the cspB gene derived from the *C. glutamicum* ATCC 13869 strain was linked upstream of the base sequences set forth in CspBss-AET-EPO-PAS49, CspBss-AET-EPO-PAS49-b, CspBss-AET-EPO-PAS100, CspBss-AET-EPO-PAS100-b, CspBss-AET-EPO-GS8, and CspBss-AET-EPO-GS22, and furthermore, an expression cassette of each EPO-PAS dimer peptide linker variant having a KpnI site on the 5'-side and an BamHI site on the 3'-side was designed and totally synthesized. The totally synthesized DNA fragment (EPO-PAS dimer peptide linker variant expression cassette) was inserted into the KpnI-BamHI site of pPK4 described in Japanese Patent Application Publication No. Hei 9-322774 to construct pPK4_CspBss-AET-EPO-PAS49, pPK4_CspBss-AET-EPO-PAS49-b, pPK4_CspBss-AET-EPO-PAS100, pPK4_CspBss-AET-EPO-PAS100-b, pPK4_CspBss-AET-EPO-GS8, and pPK4_CspBss-AET-EPO-GS22, a secretory expression plasmid for each EPO-PAS dimer peptide linker variant using the CspB signal sequence. As a result of determining the base sequence of the inserted fragment, it was confirmed that each EPO-PAS dimer peptide linker variant expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(30-5) Secretory Expression of Each EPO-PAS Dimer Peptide in *C. glutamicum*

The pPK4_CspBss-AET-EPO-PAS49, pPK4_CspBss-AET-EPO-PAS49-b, pPK4_CspBss-AET-EPO-PAS100, pPK4_CspBss-AET-EPO-PAS100-b, pPK4_CspBss-AET-EPO-GS8, and pPK4_CspBss-AET-EPO-GS22 constructed above were used to transform the *C. glutamicum* YDK0107 strain described in WO2016/171224 to obtain the YDK0107/pPK4_CspBss-AET-EPO-PAS49 strain, YDK0107/pPK4_CspBss-AET-EPO-PAS49-b strain, YDK0107/pPK4_CspBss-AET-EPO-PAS100 strain, YDK0107/pPK4_CspBss-AET-EPO-PAS100-b strain, YDK0107/pPK4_CspBss-AET-EPO-GS8 strain, and YDK0107/pPK4_CspBss-AET-EPO-GS22 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 48:
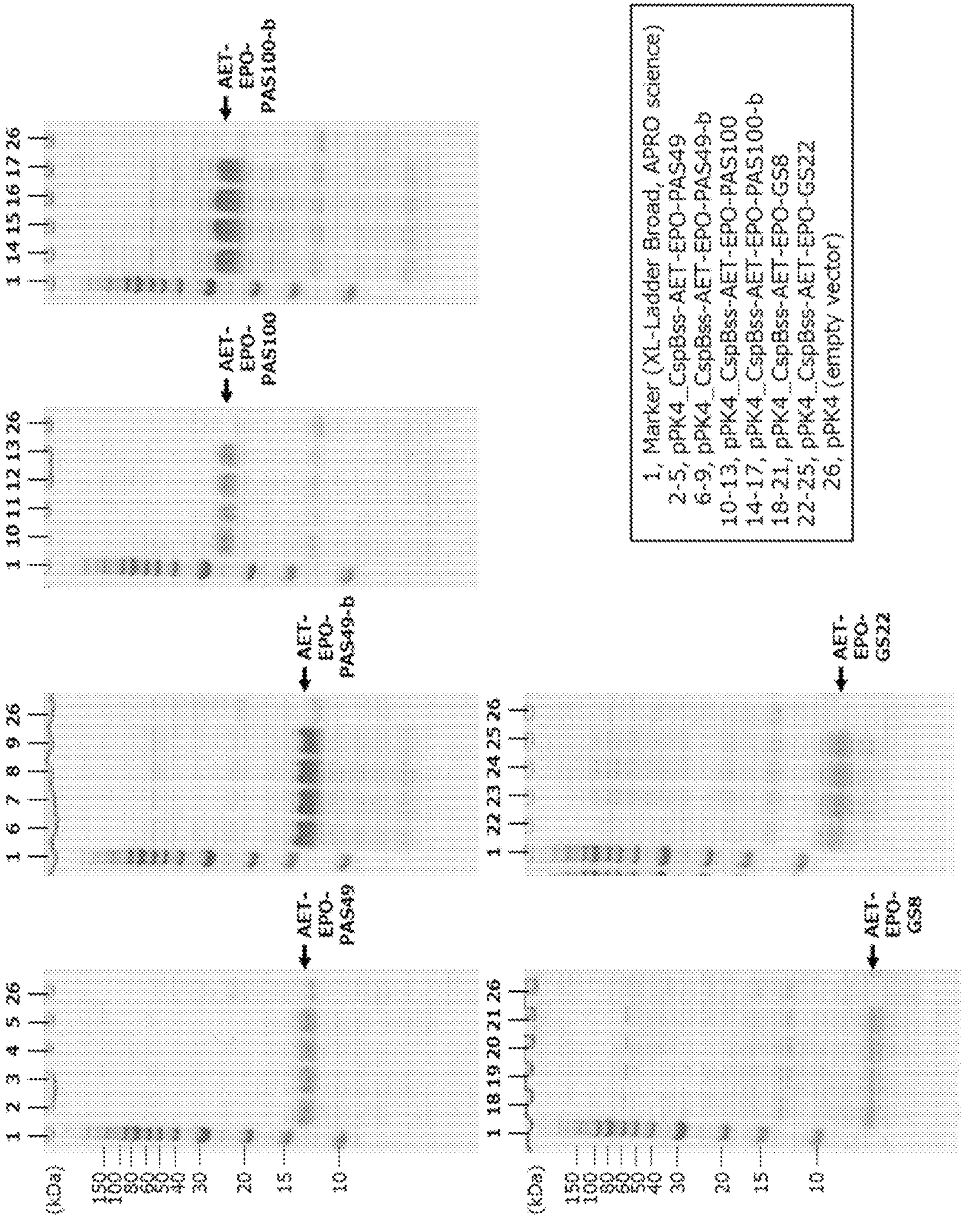
FIG. 48 shows the results of SDS-polyacrylamide electrophoresis showing the secretory expression of the dimer peptides (EPO-PAS and EPO-GS) in *C. glutamicum*. Lane 1 is a marker (XL-Ladder Broad, APRO science), lanes 2 to 5 are ones using pPK4_CspBss-AET-EPO-PAS49, lanes 6 to 9 are ones using pPK4_CspBss-AET-EPO-PAS49-b, lanes 10 to 13 are ones using pPK4_CspBss-AET-EPO-PAS100, lanes 14 to 17 are ones using pPK4_CspBss-AET-EPO-PAS100-b, lanes 18 to 21 are ones using pPK4_CspBss-AET-EPO-GS8, lanes 22 to 25 are ones using pPK4_CspBss-AET-EPO-GS22, and lane 26 is one using pPK4 (empty vector).
Figure 49:
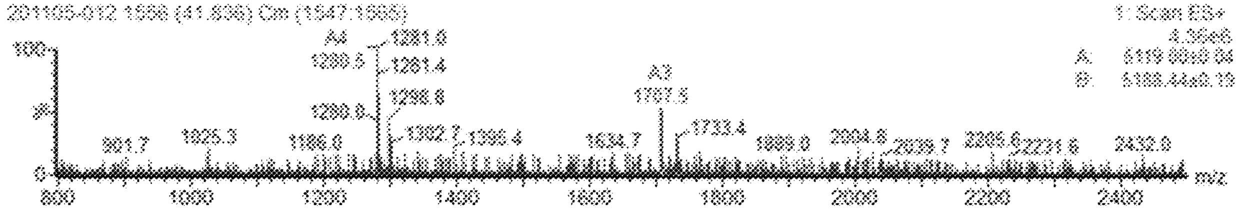
FIG. 49 shows measurement results of the dimer peptide (EPO-GS) by LC-MS. Calc represents the theoretical value and Obs represents the measured value.
Figure 50:
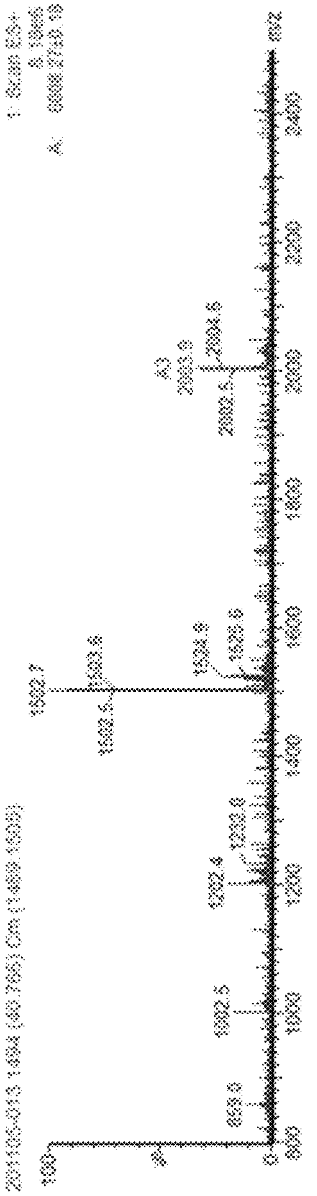
FIG. 50 shows measurement results of the dimer peptide (EPO-GS) by LC-MS. Calc represents the theoretical value and Obs represents the measured value.
Figure 51:
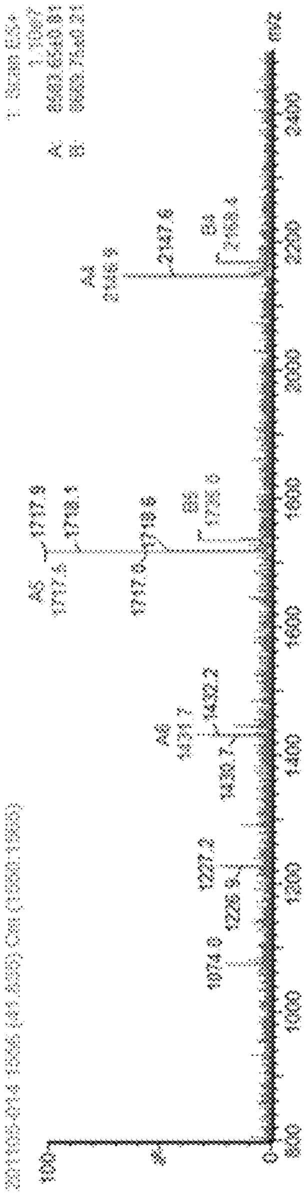
FIG. 51 shows measurement results of the dimer peptide (EPO-PAS) by LC-MS. Calc represents the theoretical value and Obs represents the measured value.
Figure 52:
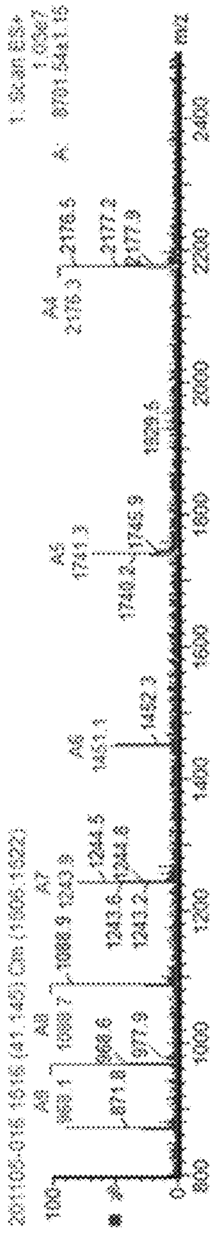
FIG. 52 shows measurement results of the dimer peptide (EPO-PAS) by LC-MS. Calc represents the theoretical value and Obs represents the measured value.
Figure 53:
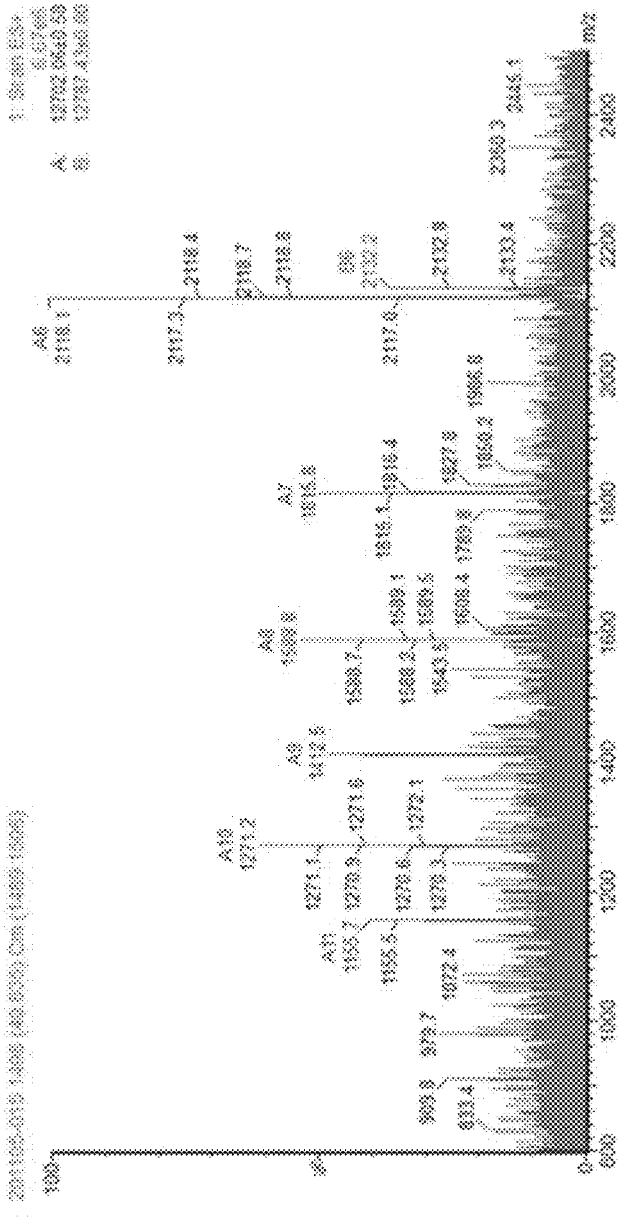
FIG. 53 shows measurement results of the dimer peptide (EPO-PAS) by LC-MS. Calc represents the theoretical value and Obs represents the measured value.
Figure 54:
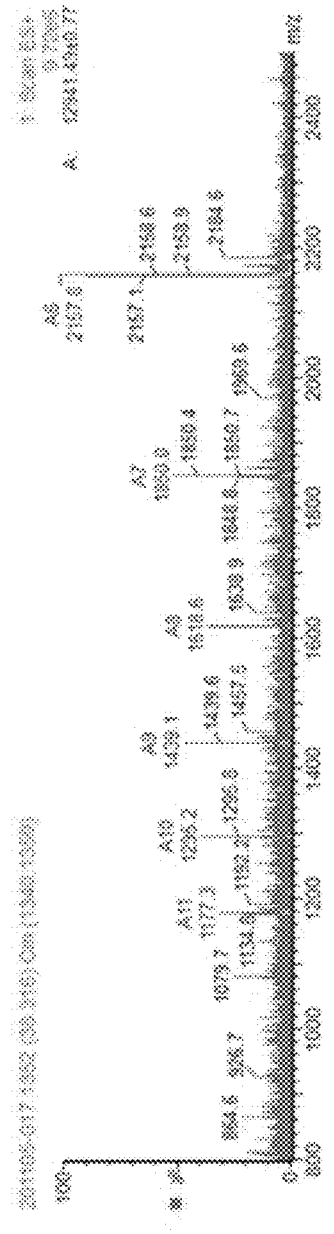
FIG. 54 shows measurement results of the dimer peptide (EPO-PAS) by LC-MS. Calc represents the theoretical value and Obs represents the measured value.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-EPO-PAS49 was detected in the culture supernatant of the YDK0107/pPK4_CspBss-AET-EPO-PAS49 strain (FIG. 48, lanes 2 to 5), a protein band presumed to be AET-EPO-PAS49-b was detected in the culture supernatant of the YDK0107/pPK4_CspBss-AET-EPO-PAS49-b strain (FIG. 48, lanes 6 to 9), a protein band presumed to be AET-EPO-PAS100 was detected in the culture supernatant of the YDK0107/pPK4_CspBss-AET-EPO-PAS100 strain (FIG. 48, lanes 10 to 13), a protein band presumed to be AET-EPO-PAS100-b was detected in the culture supernatant of the YDK0107/pPK4_CspBss-AET-EPO-PAS100-b strain (FIG. 48, lanes 14 to 17), a protein band presumed to be AET-EPO-GS8 was detected in the culture supernatant of the YDK0107/pPK4_CspBss-AET-EPO-GS8 strain (FIG. 48, lanes 18 to 21), and a protein band presumed to be AET-EPO-GS22 was detected in the culture supernatant of the YDK0107/pPK4_CspBss-AET-EPO-GS22 strain (FIG. 48, lanes 22 to 25).

Example 31: Molecular Weight Analysis of EPO-PAS Dimer Peptide Linker Variant The cell filtrate of the EPO-PAS dimer peptide linker variant after culturing in Example 30 was subjected to molecular weight measurement using LC-MS (Waters, ACQUITY UPLC/SQD2). The analysis conditions are shown in Table 2. As shown in FIGS. 49 to 54, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 32: Activity Evaluation of EPO-PAS Dimer Peptide Linker Variant

The EpoR activation ability of the EPO-PAS dimer peptide linker variant was evaluated using PathHunter (registered trademark) eXpress EpoR-JAK2 Functional Assay Kit (DiscoverX).

Cells for EPO activity evaluation included in PathHunter (registered trademark) eXpress EpoR-JAK2 Functional Assay Kit were seeded on a 96-well plate and cultured for 24 hours at 37 °C under 5% $CO_2$. To the cells, a culture supernatant containing AET-EPO-PAS8, AET-EPO-GS8, AET-EPO-PAS22, or AET-EPO-GS22 diluted to a predetermined concentration (cultured as described in Example 20 or 30), or the monomer peptide EMP35 (GGLYACHMGPMTWVCQPLRG, synthesized by GenScript Japan) was added. As a negative control, the culture supernatant (FIG. 48, lane 26) obtained by culturing as described in Example 30 except for using a vector containing no gene for expressing the EPO-PAS dimer peptide, diluted at the same ratio as the culture supernatant containing AET-EPO-PAS8 or AET-EPO-PAS22, was added. The prepared Substrate Reagent was added to the cells stimulated at room temperature for 3 hours, and the cells were incubated for 60 minutes. The chemiluminescence intensity was quantified with a Nivo plate reader (Perkin Elmer).

Figure 55:
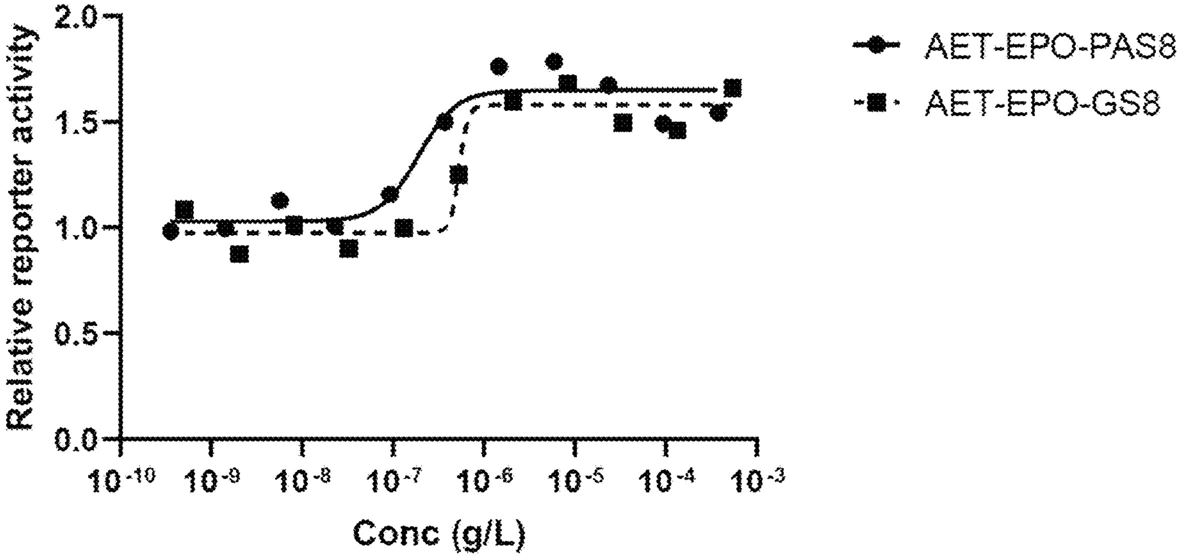
FIG. 55 is a graph showing the activity evaluation of the dimer peptides (EPO-PAS and EPO-GS). The vertical axis represents relative receptor activity and the horizontal axis represents concentration.
Figure 56:
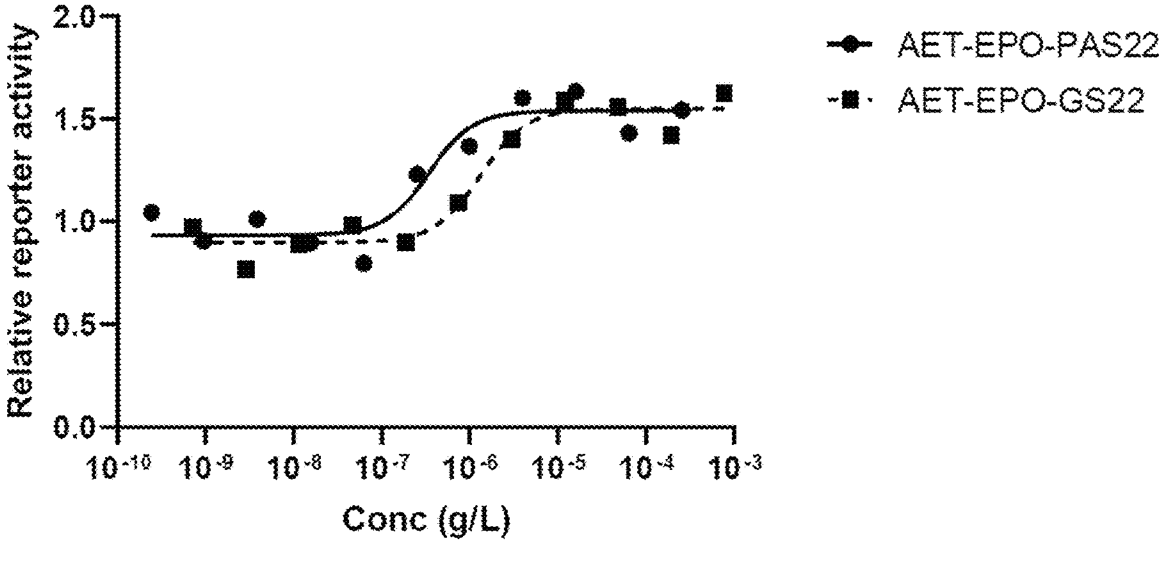
FIG. 56 is a graph showing the activity evaluation of the dimer peptides (EPO-PAS and EPO-GS). The vertical axis represents relative receptor activity and the horizontal axis represents concentration.
Figure 57:
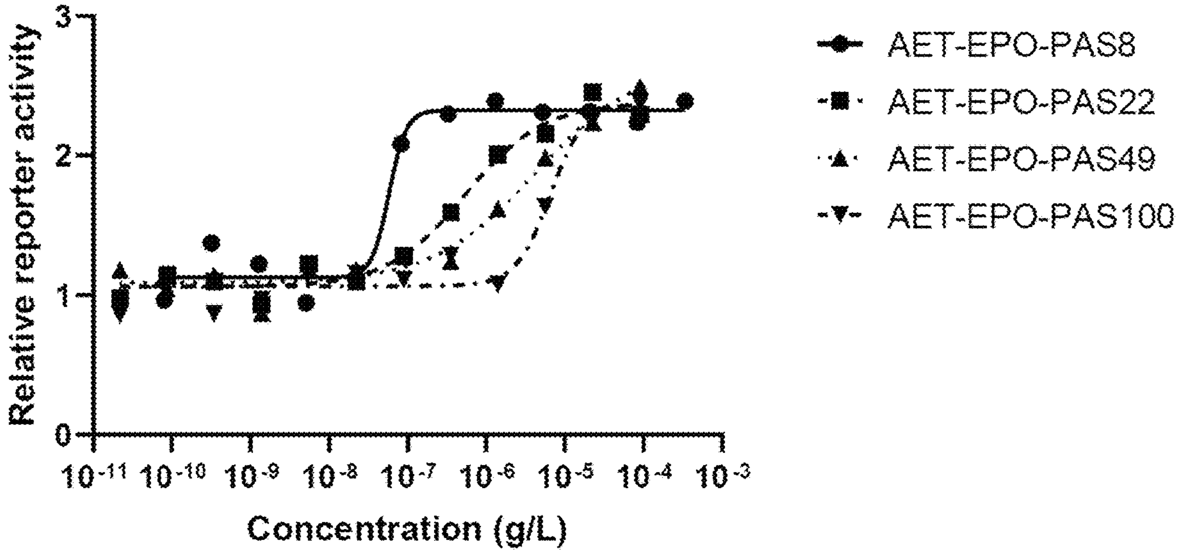
FIG. 57 is a graph showing the activity evaluation of the dimer peptide (EPO-PAS). The vertical axis represents relative receptor activity and the horizontal axis represents concentration.

As shown in FIGS. 55 to 57, it was clarified that all dimer peptides activated EpoR in a concentration-dependent manner. The EC50 value for each construct is shown in Table 6 below, and it was clarified that AET-EPO-PAS8 showed higher activity than AET-EPO-GS8, and AET-EPO-PAS22 had higher activity than AET-EPO-GS22. Note that the EC50 values of rhEPO, AET-EPO-PAS8, and AET-EPO-PAS22 are those in Example 22. It was also clarified that AET-EPO-PAS100 had lower activity than AET-EPO-PAS49, AET-EPO-PAS22, and AET-EPO-PAS8. From this, it has been clarified that a dimer peptide can be developed that has higher activity than a GS linker by using a PAS linker and that has high agonist activity by using a PAS linker of 49 amino acids or less.

TABLE 6

| Peptide | EC50 (g/L) |
|---|---|
| rhEPO | $1.1 \times 10^{-6}$ |
| AET-EPO-PAS8 | $1.9 \times 10^{-7}$ |
| AET-EPO-GS8 | $5.3 \times 10^{-7}$ |
| AET-EPO-PAS22 | $3.4 \times 10^{-7}$ |
| AET-EPO-GS22 | $1.3 \times 10^{-6}$ |
| AET-EPO-PAS49 | $4.3 \times 10^{-6}$ |
| AET-EPO-PAS100 | $6.6 \times 10^{-6}$ |

Example 33: Design of Stabilized EPO-PAS Dimer Peptide and its Secreted Expression in *C. glutamicum*

(33-1) Outline of Design

The EPO-PAS peptide with enhanced stability was designed as follows. As a method for enhancing the stability of peptides and proteins, a method for adding a long-chain PAS sequence has been reported (Published Japanese Translation of PCT International Application No. 2013-531480 and Published Japanese Translation of PCT International Application No. 2010-531139). As an EPO-PAS peptide with enhanced stability, a peptide was designed in which a PAS sequence composed of 200 amino acids (PAS200) or a PAS sequence composed of 600 amino acids (PAS600) was bound to the C-terminus of AET-EPO-PAS22. That is, the peptide sequence was designed to be "first erythropoietin receptor-binding cyclic peptide"-"PAS linker"-"second erythropoietin receptor-binding cyclic peptide"-"long-chain PAS sequence (PAS200 or PAS600)".

(33-2) Preparation of Stabilized EPO-PAS Dimer Peptides

The prepared stabilized EPO-PAS dimer peptides are as follows.

```
(D) AET-EPO-PAS22-PAS200
                                           (SEQ ID NO: 144)
AETGGLYACHMGPMTWVCQPLRGAAPAAPAPAAPAAPAPAAPAAPGGL

YACHMGPMTWVCQPLRGAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA
```

-continued

PAAPAAPAPAAPAAPAPAAPAAPAPAAPAAPAPAAPAAPAPAAPAAPA

PAAPAAPAPAAPAAPAPAAPAAPAP (E) AET-EPO-PAS22-PAS600

(SEQ ID NO: 145)

AETGGLYACHMGPMTWVCQPLRGAAPAAPAPAAPAAPAPAAPAAPGGL

YACHMGPMTWVCQPLRGAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAPAAPAAPA

PAAPAAPAPAAPAAPAPAAPAAPAPAAPAAPAPAAPAAPAP (33-3) Expression of Stabilized EPO-PAS Dimer Peptides Corynex (registered trademark) was used to examine the expression of stabilized EPO-PAS dimer peptide. Hereinafter, examples of expression examinations using Corynex (registered trademark) will be described.

(33-4) Construction of AET-EPO-PAS22-PAS200 Secretory Expression Plasmid Using CspB Signal Sequence As the stabilized EPO-PAS dimer peptide, the amino acid sequences of the above (D) AET-EPO-PAS22-PAS200 (which may be hereinafter referred to as “AET-EPO-PAS22-PAS200”) and (E)AET-EPO-PAS22-PAS600 (which may be hereinafter referred to as “AET-EPO-PAS22-PAS600”) were designed, and the base sequences encoding these proteins were designed in consideration of the codon usage frequency of *C. glutamicum*. Furthermore, the following expression cassette was designed to enable secretion expression by *C. glutamicum*.

AET-EPO-PAS22-PAS200 was secretory-expressed as a fusion protein of AET-EPO-PAS22-PAS200 and a signal peptide 30 amino acid residue of CspB derived from *C. glutamicum* ATCC 13869 strain (hereinafter referred to as “CspBss-AET-EPO-PAS22-PAS200”). The base sequence and amino acid sequence encoding the designed CspBss-AET-EPO-PAS22-PAS200 are set forth in SEQ ID NOs: 146 and 147, respectively.

Base sequence encoding CspBss-AET-EPO-PAS22-PAS200

(SEQ ID NO: 146)

atgttcaacaaccgtattcgtaccgctgccctggccggcgccattgcc atctccaccgctgcgtccggcgtcgccattcctgcgttcgcagccgaa accggcggcctgtacgcatgccacatgggtccaatgacctgggtgtgc cagccactgcgcggcgctgcaccagctgctccagcaccagcagcccca gctgcaccagcaccagctgctccagctgcaccaggcggcctgtacgct -continued tgtcatatgggtccaatgacttgggtctgccagccactccgcggcgct gcaccagcagctcctgctccagcagcacctgcagcaccagcaccagca gctccagcagcacctgccccagcagctcctgcagctcctgccccagca gcacctgccgctcctgctcctgcagctccagcagcacccgccccagca gctcccgcagctcctgcgccagcagcacctgccgcccctgctcccgca gctccagcagcaccggcacccgcagctccagcagctcctgcacctgca gcacctgccgctcccgctccggcagctccagcagcaccagcccctgca gctcctgctgcacctgctccagcagcacccgcggctcctgctccggct gctccagcagcccctgctccagcagctcccgctgcacctgcaccagca gcacctgccgcgcctgctcctgctgcccctgctgctcctgctcctgca gcccctgctgcacccgctccagcagcacctgcggctcctgctccggcc gcccctgctgctccagcaccagctgcccctgcagcccctgcccctgca gccccagctgcaccagcaccagcagcaccagcagcacccgcaccagca gccccagcagccccagccccttag Amino acid sequence of CspBss-AET-EPO-PAS22-PAS200

(SEQ ID NO: 147)

MFNNRIRTAALAGAIAISTAASGVAIPAFAAETGGLYACHMGPMTWVC

QPLRGAAPAAPAPAAPAAPAPAAPAAPGGLYACHMGPMTWVCQPLRGA

APAAPAPAAPAAPAPAAPAAPAPAAPAAPAPAAPAAPAPAAPAAPAPA

APAAPAPAAPAAPAPAAPAAPAPAAPAAPAPAAPAAPAPAAPAAPAPA

APAAPAPAAPAAPAPAAPAAPAPAAPAAPAPAAPAAPAPAAPAAPAPA

APAAPAPAAPAAPAPAAPAAPAPAAPAAPAPAAPAAPAPAAPAAPAPA

APAAPAP

AET-EPO-PAS22-PAS600 was secretory-expressed as a fusion protein of AET-EPO-PAS22-PAS600 and a signal peptide 30 amino acid residue of CspB derived from *C. glutamicum* ATCC 13869 strain (hereinafter referred to as “CspBss-AET-EPO-PAS22-PAS600”). The base sequence and amino acid sequence encoding the designed CspBss-AET-EPO-PAS22-PAS600 are set forth in SEQ ID NOs: 148 and 149, respectively.

Base sequence encoding CspBss-AET-EPO-PAS22-PAS600

(SEQ ID NO: 148)

atgtttaacaaccgtattcgtaccgctgccctcgctggtgccattgcc atctctaccgctgcgtccggcgtcgctattcctgcctttgcagccgaa accggcggcctgtacgcatgccacatgggtccaatgacctgggtgtgc cagccactccgcggcgctgcaccagcagctccagcaccagcagcccca gctgcaccagctccagctgctccagctgcaccaggcggcctgtacgct tgtcatatgggtccaatgacttgggtctgtcaacctctgcgcggcgct gctcctgcagctccagctccagcagcaccagctgcaccagcccctgct gcaccagcagcaccagcaccagcagcaccagctgcccctgcccctgct gccccagctgcaccagcccccgctgcccctgccgctcctgctcctgca gcaccagctgcccccgcccctgctgctcctgcagcccctgctcccgct gcccctgccgcccccgcccctgcagcaccagctgcgcctgcccccgct -continued

```
gcgccagctgcaccagccccggctgcccctgccgctcccgcccccgca
gcaccagctgccccggccccggctgcgcctgctgcaccagctcctgct
gcccctgccgctccggccccggcagcaccagctgccccagcacctgct
gcaccagctgcaccagcgcctgctgcccctgccgccccggcccccgca
gctcctgctgcccccgcacctgccgcaccagctgcaccagcacctgct
gctcccgccgctcctgctcccgcagcaccagctgcgcccgccccggct
gcgcccgcagcccctgctcccgccgcacctgctgctcccgcgcctgca
gcaccagctgctcctgcacctgctgctcctgccgctccagctcctgct
gccccggccgctcctgctccggcagcaccagctgcgccggcccccgct
gcccccgcagcccctgctccggctgcccctgccgcccctgctccagca
gctcctgctgccccagcacctgccgctcctgcagctcctgctccagct
gcccctgccgctccagccccagcagcaccagctgcgccagcacctgcc
gctcccgcagctcctgctccagccgcacctgctgctccggcgcccgca
gcaccagctgctcccgcacctgcggctccagcagcccctgcccctgct
gcgcctgccgctcctgctccagcagctcccgctgcacctgccccggcc
gctccagctgcaccagccccagctgctccagccgctcccgctccggca
gctcctgctgctcccgctccggctgctcctgccgcaccagctcctgca
gctccagcagcccccgctccggcagctcccgctgctcccgctccagcc
gctcctgcagccccagcaccagctgctccagccgcccccgctccggca
gcccctgctgctcccgctcccgctgctcctgcggcaccagctcccgca
gctccagcagccccggctccggcagctccggctgctcccgctcccgcc
gctcccgcagcccctgctccagctgctccagccgcgcccgctccagca
gctccagctgcacctgctccggccgcccctgccgctccagctccggca
gctccagcagccccagcgcctgcagctcctgctgctccggctccagcc
gctcccgcagcccccgctccagctgctccagcggctcccgctccagca
gcccccgccgcacctgctccagccgctccggcagccccagctccagcc
gctccagccgctccagcgcctgcagctccagcggctcccgccccagcc
gctcctgcagcgccagctccagcggctcctgccgctcctgcccctgca
gctccagcagcgcccgctccagccgccccggcagctcctgctcctgct
gctccagccgctccagcacctgcagctccagcagctcctgccccagcc
gctcccgcagcgccagctccagcagcgccggctgcaccggcccctgca
gcaccagccgctcccgctcccgctgctcccgccgcccccgcacccgcc
gcccccgctgctcccgctccctaa
```

Amino acid sequence of CspBss-AET-EPO-PAS22-PAS600

(SEQ ID NO: 149)

```
MFNNRIRTAALAGAIAISTAASGVAIPAFAAETGGLYACHMGPMTWVC
QPLRGAAPAAPAPAAPAAPAPAAPAAPGGLYACHMGPMTWVCQPLRGA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
```

-continued

```
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAPAAPAAPAPAAPAAPAPAAPAAPAPA
APAAPAPAAPAAPAPAAPAAPAP
```

The promoter of the cspB gene derived from the *C. glutamicum* ATCC 13869 strain was linked upstream of the base sequences set forth in CspBss-AET-EPO-PAS22-PAS200 and CspBss-AET-EPO-PAS22-PAS600, and furthermore, an expression cassette of each stabilized EPO-PAS dimer peptide having a KpnI site on the 5'-side and an BamHI site on the 3'-side was designed and totally synthesized. The totally synthesized DNA fragment (stabilized EPO-PAS dimer peptide expression cassette) was inserted into the KpnI-BamHI site of pPK4 described in Japanese Patent Application Publication No. Hei 9-322774 to construct pPK4_CspBss-AET-EPO-PAS22-PAS200 and pPK4_CspBss-AET-EPO-PAS22-PAS600, a secretory expression plasmid for each stabilized EPO-PAS dimer peptide using the CspB signal sequence. As a result of determining the base sequence of the inserted fragment, it was confirmed that the stabilized EPO-PAS dimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(33-5) Secretory Expression of Stabilized EPO-PAS Dimer Peptide in *C. glutamicum*

The pPK4_CspBss-AET-EPO-PAS22-PAS200 and pPK4_CspBss-AET-EPO-PAS22-PAS600 constructed above were used to transform the *C. glutamicum* YDK0107 strain described in WO2016/171224 to obtain the YDK0107/pPK4_CspBss-AET-EPO-PAS22-PAS200 strain and YDK0107/pPK4_CspBss-AET-EPO-PAS22-PAS600 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 58:
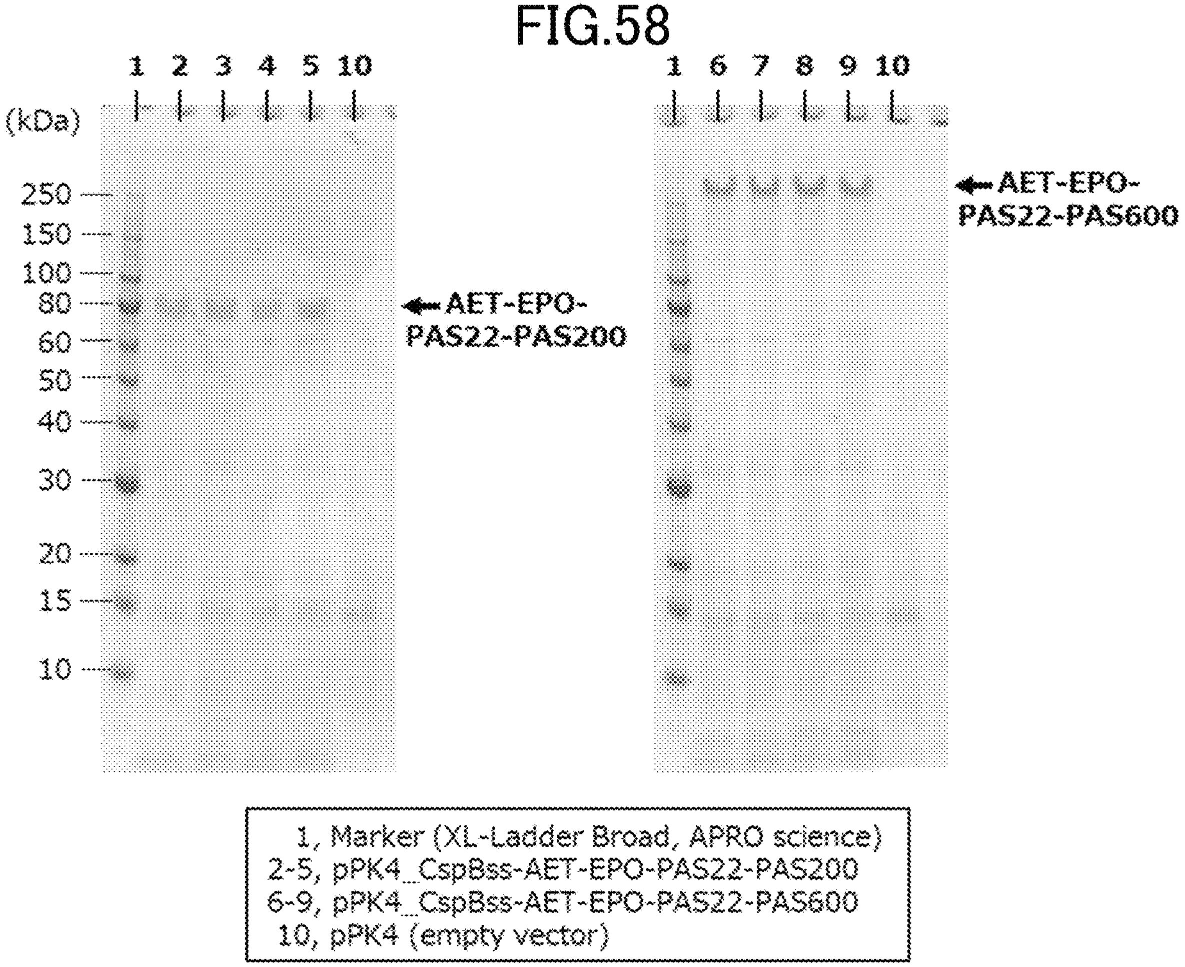
FIG. 58 shows the results of SDS-polyacrylamide electrophoresis showing the secretory expression of the dimer peptide (EPO-PAS) in *C. glutamicum*. Lane 1 is a marker (XL-Ladder Broad, APRO science), lanes 2 to 5 are ones pPK4_CspBss-AET-EPO-PAS22-PAS200, lanes 6 to 9 are ones pPK4_CspBss-AET-EPO-PAS22-PAS600, and lane 10 is one using pPK4 (empty vector).

After completion of the culture, 6.5 µL of the culture supernatant obtained by centrifuging each culture solution was subjected to reduced SDS-PAGE using NuPAGE (registered trademark) 4 to 12% Bis-Tirs Gel (Thermo Fisher Scientific), and then stained with Quick-CBB (Wako). As a result, a protein band presumed to be AET-EPO-PAS22-PAS200 was detected in the culture supernatant of the YDK0107/pPK4_CspBss-AET-EPO-PAS22-PAS200 strain (FIG. 58, lanes 2 to 5) and a protein band presumed to be AET-EPO-PAS22-PAS600 was detected in the culture supernatant of the YDK0107/pPK4_CspBss-AET-EPO-PAS22-PAS600 strain (FIG. 58, lanes 6 to 9).

Example 34: Molecular Weight Analysis of Stabilized EPO-PAS Dimer Peptide

Figure 59:
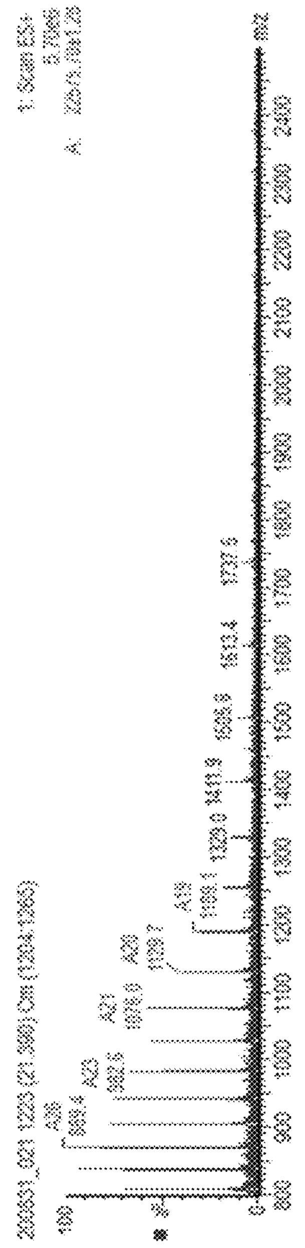
FIG. 59 shows measurement results of the dimer peptide (EPO-PAS) by LC-MS. Calc represents the theoretical value and Obs represents the measured value.
Figure 60:
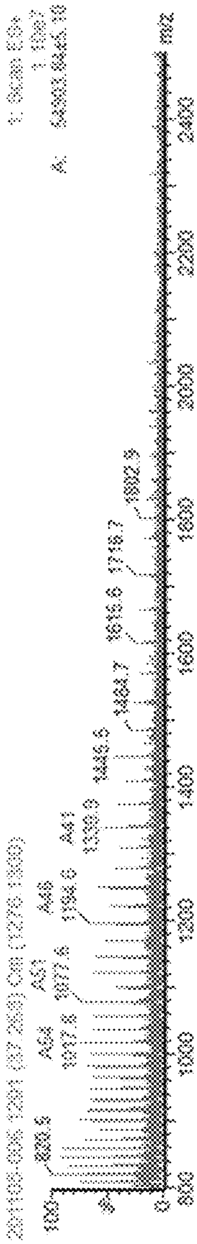
FIG. 60 shows measurement results of the dimer peptide (EPO-PAS) by LC-MS. Calc represents the theoretical value and Obs represents the measured value.

The cell filtrate of each stabilized EPO-PAS dimer peptide after culturing in Example 33 was subjected to molecular weight measurement using LC-MS (Waters, ACQUITY UPLC/SQD2). The analysis conditions are shown in Table 2. As shown in FIGS. 59 and 60, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 35: Activity Evaluation of Stabilized EPO-PAS Dimer Peptide

The EpoR activation ability of the stabilized EPO-PAS dimer peptide was evaluated using PathHunter (registered trademark) eXpress EpoR-JAK2 Functional Assay Kit (DiscoverX).

Cells for EPO activity evaluation included in PathHunter (registered trademark) eXpress EpoR-JAK2 Functional Assay Kit were seeded on a 96-well plate and cultured for 24 hours at 37 °C under 5% $CO_2$. To the cells, a culture supernatant containing 14.2 μg/L to 220 pg/L AET-EPO-PAS22, AET-EPO-PAS22-PAS200, or AET-EPO-PAS22-PAS600 (cultured as described in Example 20 or 33) was added. As a negative control, the culture supernatant (FIG. 58, lane 20) obtained by culturing as described in Example 33 except for using a vector containing no gene for expressing the EPO-PAS dimer peptide, diluted at the same ratio as the culture supernatant containing AET-EPO-PAS22, AET-EPO-PAS22-PAS200, or AET-EPO-PAS22-PAS600, was added. The prepared Substrate Reagent was added to the cells stimulated at room temperature for 3 hours, and the cells were incubated for 60 minutes. The chemiluminescence intensity was quantified with a Nivo plate reader (Perkin Elmer).

Figure 61:
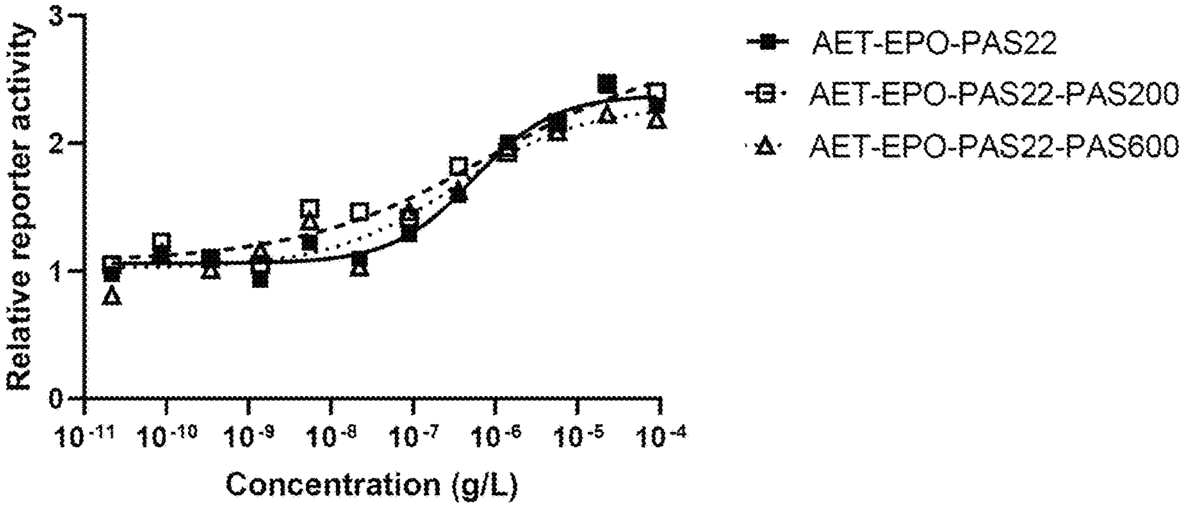
FIG. 61 is a graph showing the activity evaluation of the dimer peptide (EPO-PAS). The vertical axis represents relative receptor activity and the horizontal axis represents concentration.
Figure 62:
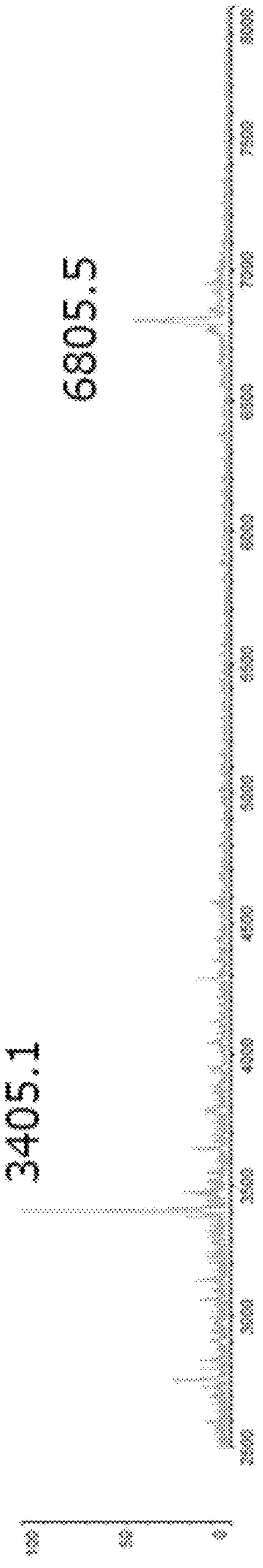
FIG. 62 shows measurement results for the dimer peptide (HGF-PAS) by MALDI-TOF-MS.
Figure 63:
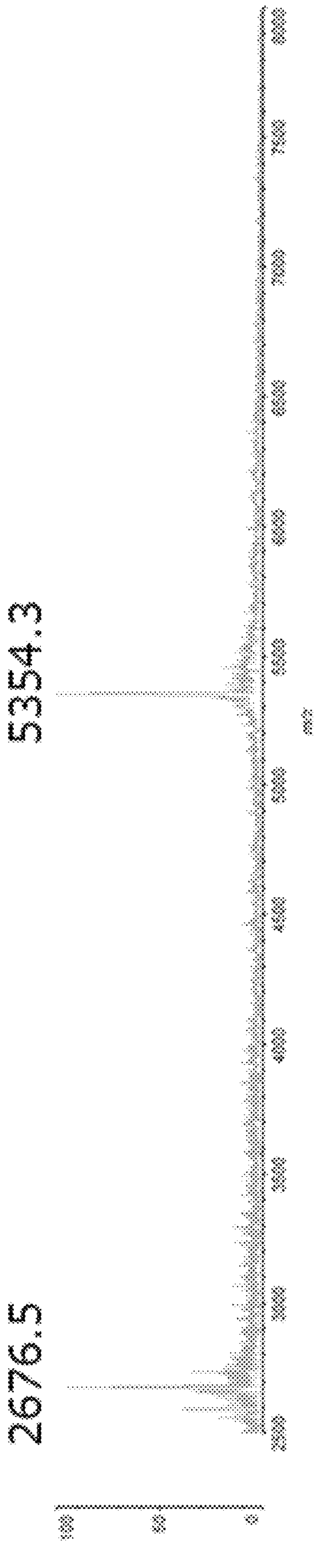
FIG. 63 shows measurement results for the dimer peptide (HGF-PAS) by MALDI-TOF-MS.
Figure 64:
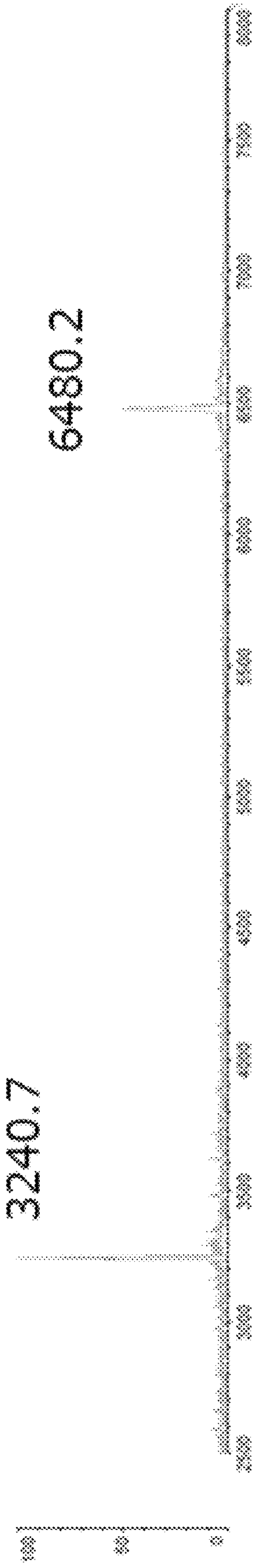
FIG. 64 shows measurement results for the dimer peptide (HGF-PAS) by MALDI-TOF-MS.
Figure 65:
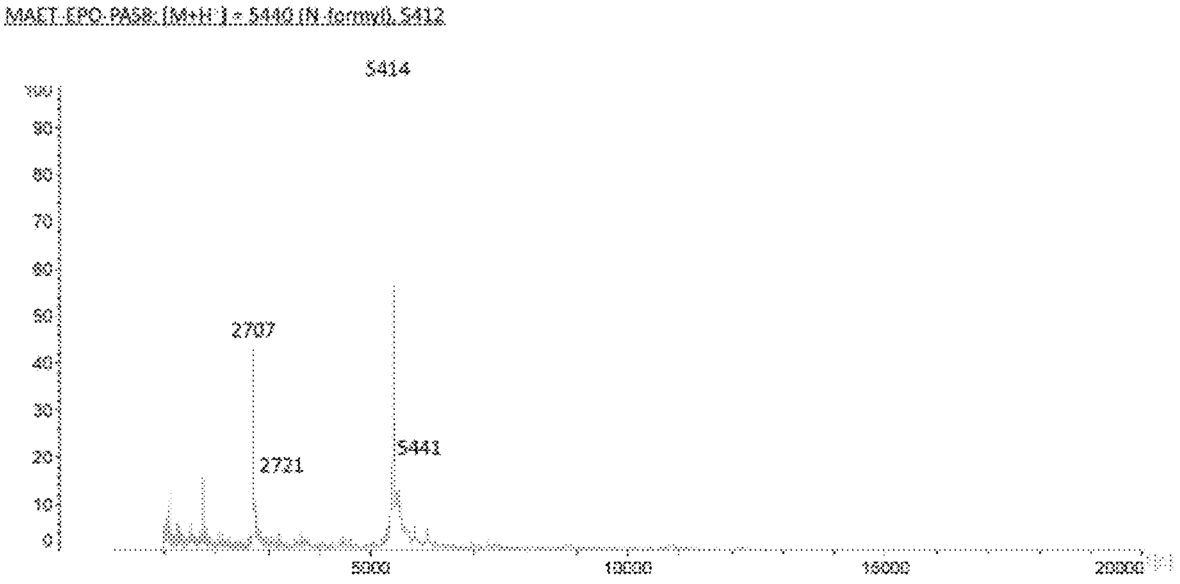
FIG. 65 shows measurement results of the dimer peptide (EPO-PAS) by MALDI-TOF-MS.
Figure 66:
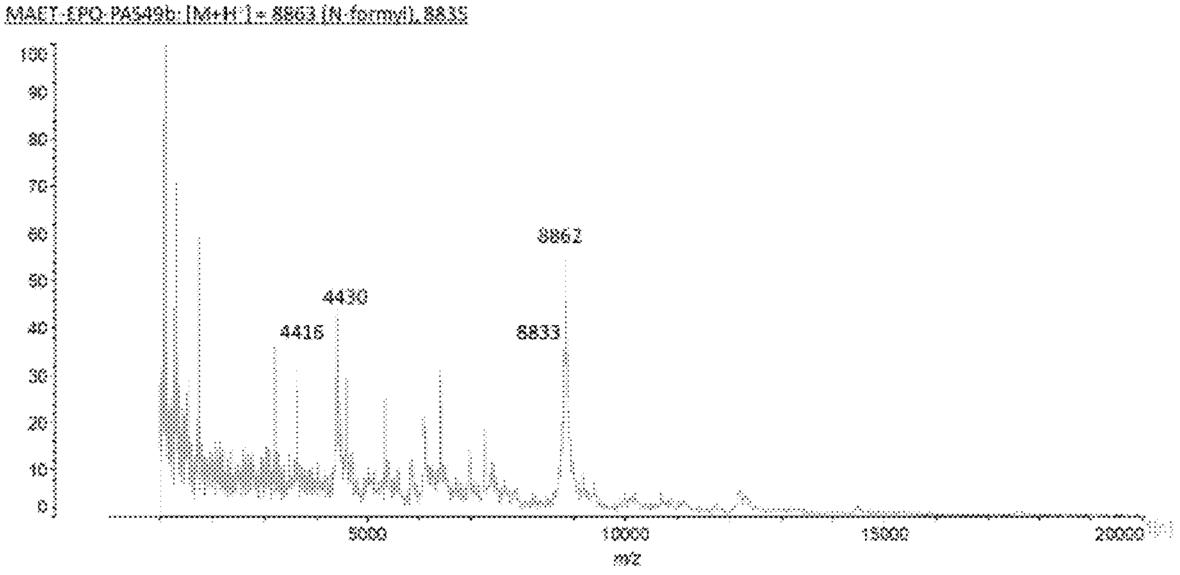
FIG. 66 shows measurement results of the dimer peptide (EPO-PAS) by MALDI-TOF-MS.
Figure 67:
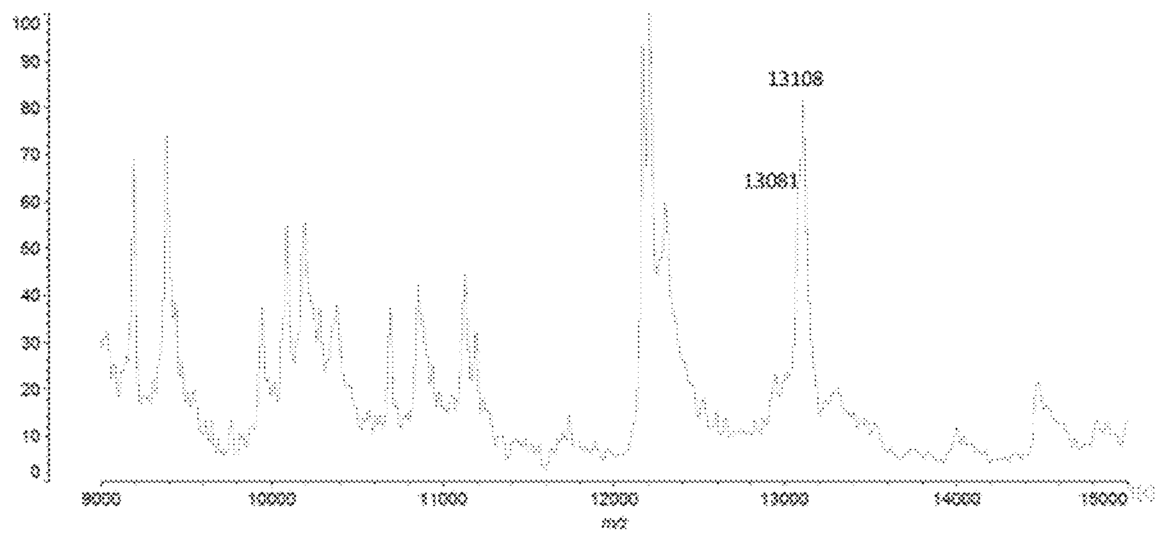
FIG. 67 shows measurement results of the dimer peptide (EPO-PAS) by MALDI-TOF-MS.
Figure 68:
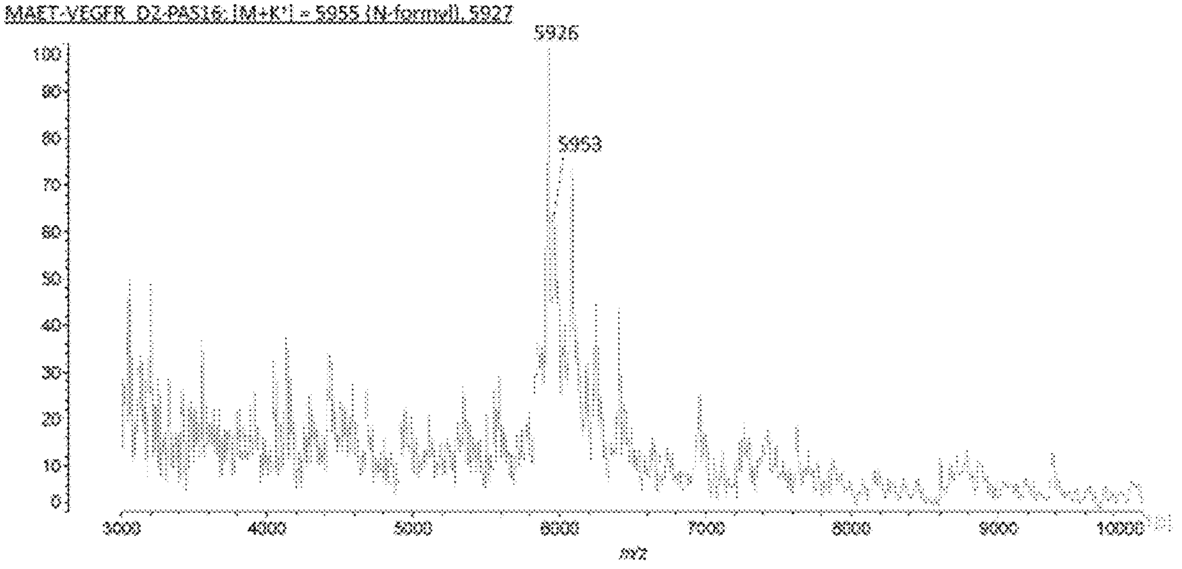
FIG. 68 shows measurement results of the dimer peptide (VEGFR_D2-PAS) by MALDI-TOF-MS.

As shown in FIG. 61, it was clarified that AET-EPO-PAS22, AET-EPO-PAS22-PAS200, or AET-EPO-PAS22-PAS600 activated EpoR in a concentration-dependent manner. In addition, the EC50 values were calculated as shown in Table 7 below, and it was clarified that the agonistic ability of the EPO-PAS dimer peptide did not decrease even if the C-terminus was stabilized and modified. Note that the EC50 value of AET-EPO-PAS22 is that of Example 22.

TABLE 7

| Peptide | EC50 (g/L) |
|---|---|
| AET-EPO-PAS22 | $3.4 \times 10^{-7}$ |
| AET-EPO-PAS22-PAS200 | $8.5 \times 10^{-7}$ |
| AET-EPO-PAS22-PAS600 | $3.2 \times 10^{-7}$ |

Example 36: Cell-Free Expression of Dimer Peptides

(36-1) Construction of Gene Construct of Cell-Free Expression Dimer Peptides The following were designed as cell-free expression dimer peptides.

```
(F) MAET-aMD4dY-PAS22
                                        (SEQ ID NO: 150)
MAETCRQFNRRTHEVWNLDCGAAPAAPAPAAPAAPAPAAPAAPGCRQF

NRRTHEVWNLDC

(G) MAET-aMD4dY-PAS8
                                        (SEQ ID NO: 151)
MAETCRQFNRRTHEVWNLDCGAAPAAPAPGCRQFNRRTHEVWNLDC

(H) MAET-aMD4-PAS22
                                        (SEQ ID NO: 152)
MAETCYRQFNRRTHEVWNLDCGAAPAAPAPAAPAAPAPAAPAAPGCRQ

FNRRTHEVWNLDC

(I) MAET-EPO-PAS8
                                        (SEQ ID NO: 153)
MAETGGLYACHMGPMTWVCQPLRGAAPAAPAPGGLYACHMGPMTWVCQ

PLRG

(J) MAET-EPO-PAS49-b
                                        (SEQ ID NO: 154)
MAETGGLYACHMGPMTWVCQPLRGSAPSPSSAPASASAPASPASASAS

ASPASSPASASSASPAASSASPASSGGLYACHMGPMTWVCQPLRG

(K) MAET-EPO-PAS100-b
                                        (SEQ ID NO: 155)
MAETGGLYACHMGPMTWVCQPLRGSAPSPSSAPASASAPASPASASAS

ASPASSPASASSASPAASSASPASSSASPSAPAAPSASAAPSASPASS

SPAPASAPSPAAAASSPSPAPSSASSAAGGLYACHMGPMTWVCQPLRG

(L) MAET-VEGFR_D2-PAS16
                                        (SEQ ID NO: 156)
MAETAGPTWCEDDWYYCWLFGTAAPAAPAPAAPAAPAPVCWEDSWGGE

VCWLFGT

(M) MAET-VEGFR_D2-PAS49-b
                                        (SEQ ID NO: 157)
MAETAGPTWCEDDWYYCWLFGTSAPSPSSAPASASAPASPASASASAS

PASSPASASSASPAASSASPASSVCWEDSWGGEVCWLFGT

(N) MAET-VEGFR_D2-PAS100-b
                                        (SEQ ID NO: 158)
MAETAGPTWCEDDWYYCWLFGTSAPSPSSAPASASAPASPASASASAS

PASSPASASSASPAASSASPASSSASPSAPAAPSASAAPSASPASSSP

APASAPSPAAAASSPSPAPSSASSAAVCWEDSWGGEVCWLFGT

(O) MAET-VEGFR_D2-GS16
                                        (SEQ ID NO: 159)
MAETAGPTWCEDDWYYCWLFGTGGGGSGGGGSGGGGSGVCWEDSWGGE

VCWLFGT
```

Base sequence encoding the amino acid sequences of the above dimer peptides were designed. Furthermore, 5'-sides were added with T7 promoter sequences and ribosome binding sequences required for cell-free expression, and their 3'-sides were added with stop codons and untranslated regions. The corresponding cell-free expression base sequences are shown below. These DNA sequences were totally synthesized and cloned into the pEX-K4J2 vector by Eurofins Genomics.

```
Base sequence encoding MAET-aMD4dY-PAS22
                                        (SEQ ID NO: 160)
gaaattaatacgactcactatagggagaccacaacggtttccctctag

aaataattttgtttaactttaagaaggagatataccaatgcagagacc
```

-continued tgtcgtcagtttaaccgtcgtacgcacgaagtttggaatctggactgt ggcgcagcccccgcagcaccagctccagcagcacccgcagctccagca ccagcagcccctgcagccccaggctgccgccaattcaatcgccgcacc catgaagtgtggaacttagattgctagtgaataactaatc Base sequence encoding MAET-aMD4dY-PAS8
(SEQ ID NO: 161)

gaaattaatacgactcactatagggagaccacaacggtttccctctag aaataattttgtttaactttaagaaggagatataccaatggcagagac ctgtcgtcagtttaaccgtcgtacgcacgaagtttggaatctggactg tggcgcagcacccgcagctccagcaccaggctgccgccaattcaatcg ccgcacccatgaagtgtggaacttagattgctagtgaataactaatcc Base sequence encoding MAET-aMD4-PAS22
(SEQ ID NO: 162)

gaaattaatacgactcactatagggagaccacaacggtttccctctag aaataattttgtttaactttaagaaggagatataccaatggcagagac ctgttatcgtcagtttaaccgtcgtacgcacgaagtttggaatctgga ctgtggcgcagcccccgcagcaccagctccagcagcacccgcagctcc agcaccagcagcccctgcagccccaggctgctatcgccaattcaatcg ccgcacccatgaagtgtggaacttagattgctagtgaataactaatcc Base sequence encoding MAET-EPO-PAS8
(SEQ ID NO: 163)

gaaattaatacgactcactatagggagaccacaacggtttccctctag aaataattttgtttaactttaagaaggagatataccaatggcagaaac tggtggtttatacgcctgtcacatgggcccgatgacttgggtttgcca gccattgcgtggcgcagcacccgcagctccagcaccaggtggcctgta tgcgtgccatatggggccaatgacctgggtgtgtcagccgttacgcgg ctagtgaataactaatcc Base sequence encoding MAET-EPO-PAS49-b
(SEQ ID NO: 164)

gaaattaatacgactcactatagggagaccacaacggtttccctctag aaataattttgtttaactttaagaaggagatataccaatggcagaaac tggtggtttatacgcctgtcacatgggcccgatgacttgggtttgcca gccattgcgtggctctgctccatcaccttcttccgcaccagcatcagc ttctgcaccagcgtcgcctgcttctgcatctgcgtctgcttcaccagc atcctcacctgcatcagcatcgtctgcttctccagcagcttcctcagc ttcacctgcttcgtctggtggcctgtatgcgtgccatatggggccaat gacctgggtgtgtcagccgttacgcggctagtgaataactaatcc Base sequence encoding MAET-EPO-PAS100-b
(SEQ ID NO: 165)

gaaattaatacgactcactatagggagaccacaacggtttccctctag aaataattttgtttaactttaagaaggagatataccaatggcagaaac tggtggtttatacgcctgtcacatgggcccgatgacttgggtttgcca gccattgcgtggctctgctccatcaccttcttccgcaccagcatcagc ttctgcaccagcgtcgcctgcttctgcatctgcgtctgcttcaccagc atcctcacctgcatcagcatcgtctgcttctccagcagcttcctcagc ttcacctgcttcgtcttccgcatccccatctgctccagcagcaccttc -continued agcttctgcagctccatctgcttcacctgcctcatcgtctccagcacc tgcgtcagctccatcccctgcagcagcggcttcatcgccatctccagc accttcttcagcgtcatccgctgcaggtggcctgtatgcgtgccatat ggggccaatgacctgggtgtgtcagccgttacgcggctagtgaataac taatcc Base sequence encoding MAET-VEGFR_D2-PAS16
(SEQ ID NO: 166)

gaaattaatacgactcactatagggagaccacaacggtttccctctag aaataattttgtttaactttaagaaggagatataccaatggcggaaac cgcgggtcccacgtggtgtgaggatgactggtactattgctggttatt cgggactgcggcccctgctgccccggctccggcagcaccggccgcacc agcgccggtttgctgggaagatagctggggtggcgaagtgtgttggct gtttggcacctagtgaataactaatcc Base sequence encoding MAET-VEGFR_D2-PAS49-b
(SEQ ID NO: 167)

gaaattaatacgactcactatagggagaccacaacggtttccctctag aaataattttgtttaactttaagaaggagatataccaatggcggaaac cgcgggtcccacgtggtgtgaggatgactggtactattgctggttatt cgggacttctgctccatcaccttcttccgcaccagcatcagcttctgc accagcgtcgcctgcttctgcatctgcgtctgcttcaccagcatcctc acctgcatcagcatcgtctgcttctccagcagcttcctcagcttcacc tgcttcgtctgtttgctgggaagatagctggggtggcgaagtgtgttg gctgtttggcacctagtgaataactaatcc Base sequence encoding MAET-VEGFR_D2-PAS100-b
(SEQ ID NO: 168)

gaaattaatacgactcactatagggagaccacaacggtttccctctag aaataattttgtttaactttaagaaggagatataccaatggcagaaac tggtggtttatacgcctgtcacatgggcccgatgacttgggtttgcca gccattgcgtggctctgctccatcaccttcttccgcaccagcatcagc ttctgcaccagcgtcgcctgcttctgcatctgcgtctgcttcaccagc atcctcacctgcatcagcatcgtctgcttctccagcagcttcctcagc ttcacctgcttcgtcttccgcatccccatctgctccagcagcaccttc agcttctgcagctccatctgcttcacctgcctcatcgtctccagcacc tgcgtcagctccatcccctgcagcagcggcttcatcgccatctccagc accttcttcagcgtcatccgctgcaggtggcctgtatgcgtgccatat ggggccaatgacctgggtgtgtcagccgttacgcggctagtgaataac taatcc Base sequence encoding MAET-VEGFR_D2-GS16
(SEQ ID NO: 169)

gaaattaatacgactcactatagggagaccacaacggtttccctctag aaataattttgtttaactttaagaaggagatataccaatggcggaaac cgcgggtcccacgtggtgtgaggatgactggtactattgctggttatt cgggactggtagcggtagcggcagcggcagcggtagtggtagtggcag -continued

```
cggcagcgtttgctgggaagatagctggggtggcgaagtgtgttggct

gtttggcacctagtgaataactaatcc
```

(36-2) Cell-Free Expression of Dimer Peptides

The genes of the dimer peptides constructed above were amplified by PCR. PCR was performed using the primers of the sequences shown below and KOD-Plus-Ver. 2 (Toyobo) as the PCR enzyme.

```
Cell-free primer Fwd:
                                    (SEQ ID NO: 170)
gaaattaatacgactcactataggg

Cell-free primer Rev:
                                    (SEQ ID NO: 171)
cactgactggattagttattcac
```

Next, the peptide dimers were expressed by a cell-free expression system based on the gene fragments amplified by PCR. PUREfrex 2.0 (GeneFrontier) was used for cell-free expression.

For cell-free expression with PUREfrex 2.0, to the gene fragments amplified by 2 nM PCR, 10 μL of Solution I, 1 μL of Solution II, 2 μL of Solution III, and 7 μL of water were added, and the mixture was incubated at 37 °C for 6 hours to carry out a translation reaction.

(36-3) Molecular Weight Analysis of Cell-Free Expression Dimer Peptides

A solution, obtained by expressing HGF-PAS dimer peptides (MAET-aMD4-PAS22, MAET-aMD4dY-PAS8, MAET-aMD4dY-PAS22), EPO-PAS dimer peptides (MAET-EPO-PAS8, MAET-EPO-PAS49-b, MAET-EPO-PAS100-b), and a VEGFR_D2-PAS dimer peptide (MAET-VEGFR_D2-PAS16) in a cell-free expression system, was mixed with α-Cyano-4-hydroxycinnamic Acid (CHCA), and subjected to molecular weight measurement with MALDI-TOF-MS (Shimadzu, AXIMA TOF 2).

As shown in FIGS. 62 to 68, for the HGF-PAS dimer peptides, values were obtained close to the molecular weight with two formed disulfide bonds and a formylated N-terminus, and for the EPO-PAS dimer peptides and VEGFR_D2-PAS dimer peptide, both the molecular weight with two formed disulfide bonds and a formylated N-terminus and the molecular weight without deformylated N-terminus were obtained, each demonstrating that dimer peptides containing two disulfide bonds could be expressed.

Example 37: Activity Evaluation of Cell-Free Expression HGF-PAS Dimer Peptides The Met activation ability of the cell-free expression HGF-PAS dimer peptides was evaluated by luciferase assay. To 25 μL of Opti-MEM medium (Thermo Fisher Scientific), 0.6 μL of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 100 ng/mL HGF was added, or a cell-free translation solution with translated AET-aMD4dY-PAS22 was added to the medium so as to be diluted at a predetermined ratio, or a cell-free translation solution with untranslated peptide was added to dilute at the same ratio, and the evaluation basal medium was added in an amount of 100 L to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 69:
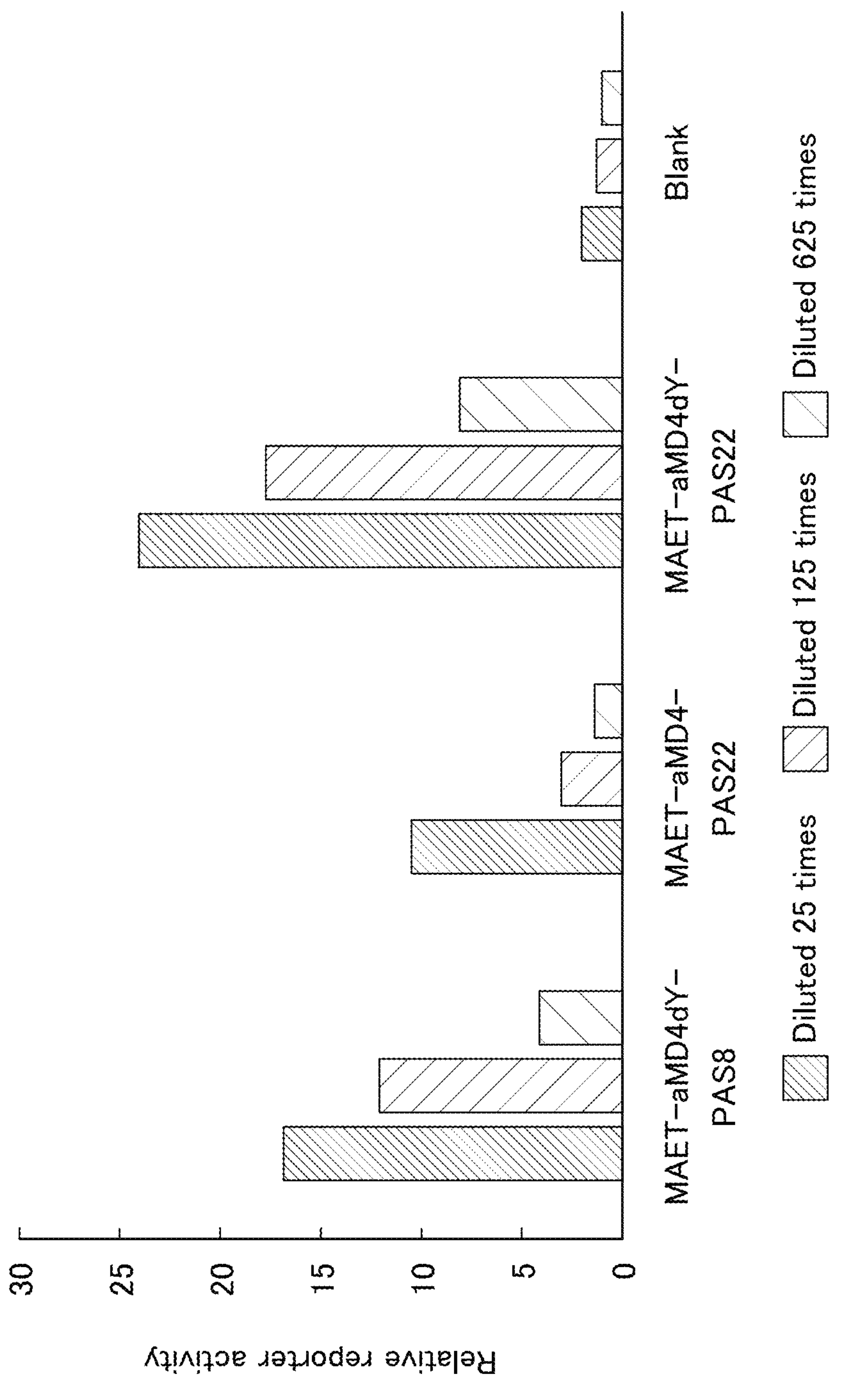
FIG. 69 is a graph showing the activity evaluation of the dimer peptide (HGF-PAS). The vertical axis represents the relative receptor activity, and the horizontal axis represents the dilution factor of the reaction solution of the cell-free expression system containing the dimer peptide (HGF-PAS) with respect to the medium used for the activity evaluation. Blank is the result of using no expression DNA in cell-free expression.

As shown in FIG. 69, it was clarified that the cell-free translations MAET-aMD4dY-PAS22, MAET-aMD4dY-PAS8, and MAET-aMD4-PAS22 had Met activation ability.

Example 38: Activity Evaluation of Cell-Free Expression EPO-PAS Dimer Peptide The EpoR activation ability of the EPO-PAS dimer peptide linker variant was evaluated using PathHunter (registered trademark) eXpress EpoR-JAK2 Functional Assay Kit (DiscoverX).

Cells for EPO activity evaluation included in PathHunter (registered trademark) eXpress EpoR-JAK2 Functional Assay Kit were seeded on a 96-well plate and cultured for 24 hours at 37 °C under 5% $CO_2$. To the cells, a cell-free translation solution with translated AET-EPO-PAS8, AET-EPO-PAS49-b, or AET-EPO-PAS100-b diluted to a predetermined concentration was added. As a negative control, a cell-free translation solution with untranslated peptide, diluted at the same ratio as the cell-free translation solution with translated AET-EPO-PAS8, AET-EPO-PAS49, or AET-EPO-PAS100, was added. The prepared Substrate Reagent was added to the cells stimulated at room temperature for 3 hours, and the cells were incubated for 60 minutes. The chemiluminescence intensity was quantified with a Nivo plate reader (Perkin Elmer).

Figure 70:
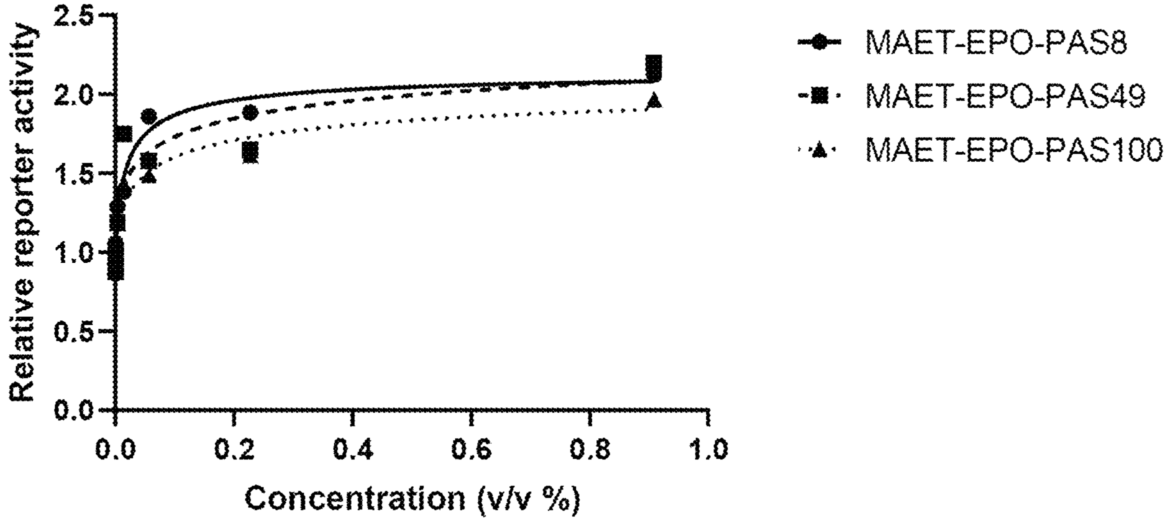
FIG. 70 is a graph showing the activity evaluation of the dimer peptide (EPO-PAS). The vertical axis represents relative receptor activity and the horizontal axis represents concentration.

As shown in FIG. 70, it was clarified that all dimer peptides activated EpoR in a concentration-dependent manner. In addition, MAET-EPO-PAS8 and MAET-EPO-PAS49-b showed higher activity than MAET-EPO-PAS100-b. From this, it was been clarified that a dimer peptide having high activity could be constructed by using a short-chain PAS linker of 49 amino acids or less.

Example 39: Activity Evaluation of Cell-Free Expression VEGFR_D2-PAS Heterodimer The VEGF inhibitory ability of the cell-free expressed VEGFR_D2-PAS heterodimer peptide was evaluated by luciferase assay. 40,000 cell/well VEGFR/NFAT Reporter HEK293 cells (BPS Bioscience) were seeded and incubated overnight in a 5% $CO_2$ incubator at 37 °C. The cells were incubated overnight in Assay medium (MEM medium (Nacalai Tesque), 1×MEM Non-Essential Amino Acids Solution (Thermo Fisher Scientific), 1 mM Sodium Pyruvate (Nacalai Tesque), 1% Penicillin-Streptomycin (Sigma Aldrich), and 0.3% FBS (Thermo Fisher Scientific)) to starvation. To the Assay medium, 100 μL of 10 ng/mL human recombinant VEGF (R&D Systems) was added, and further, MAET-VEGFR_D2-PAS16, MAET-VEGFR_D2-PAS49-b, MAET-VEGFR_D2-PAS100-b, or a cell-free expression solution containing MAET-VEGFR_D2-GS16, or a cell-free expression solution with unexpressed peptide was added at a predetermined dilution factor, and 100 μL of the Assay medium was added to the cells. The cells were stimulated by culturing in a 5% $CO_2$ incubator at 37 °C for 4 hours.

One-Glo Luciferase Assay System (Promega) was used to detect the signal intensity. Medium supernatant in an amount of 50 μL was removed, 50 μL of One-Glo reagent was added, and the cells were lysed for 10 minutes at room temperature. The luminescence emitted from the cell lysate solution was detected with a Nivo plate reader (Perkin Elmer) to quantify the activation of the VEGFR-NFAT pathway, and the relative signal activity value for the sample without addition of evaluation compound was determined and used as relative receptor activity.

Figure 71:
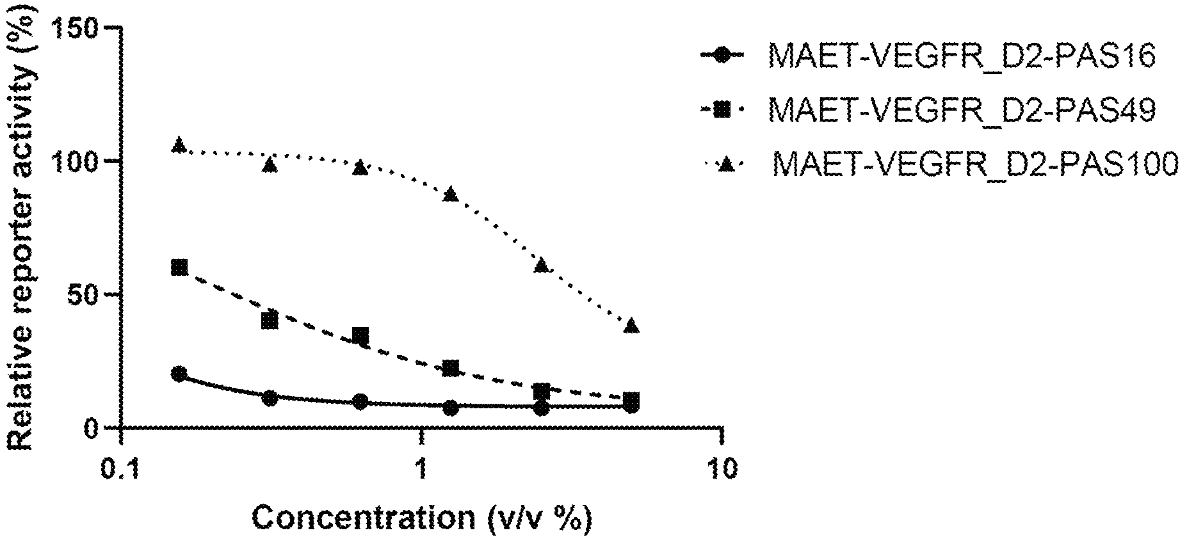
FIG. 71 is a graph showing the evaluation of the VEGF inhibitory ability of the heterodimer peptide (VEGFR_D2-PAS). The vertical axis represents relative VEGF activity (relative receptor activity), and the horizontal axis represents concentration.
Figure 72:
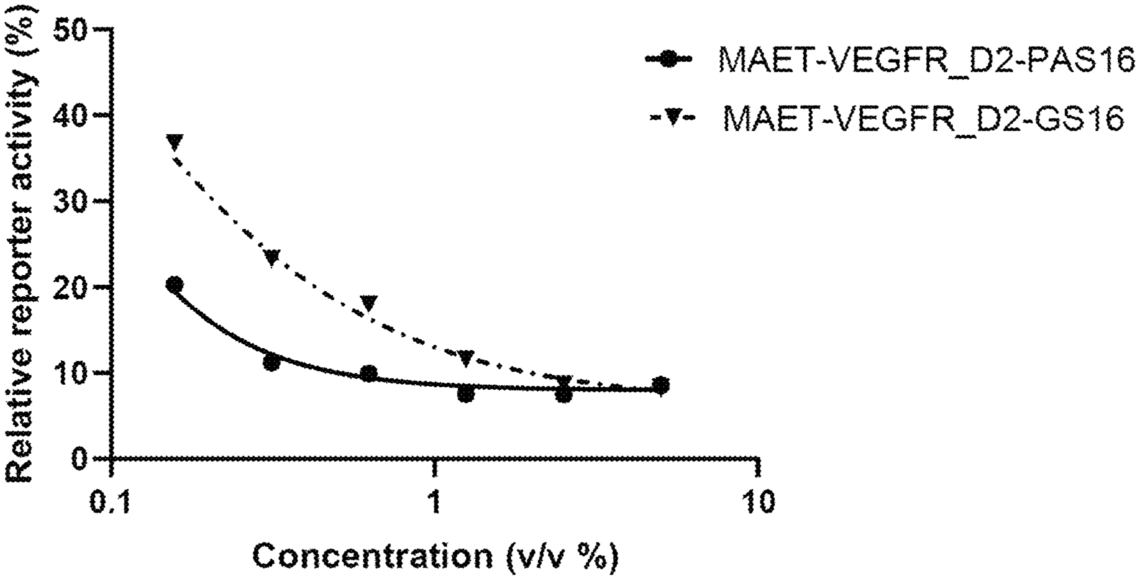
FIG. 72 is a graph showing the evaluation of VEGF inhibitory ability of the heterodimer peptides (VEGFR_D2-PAS and VEGFR_D2-GS). The vertical axis represents relative VEGF activity (relative receptor activity), and the horizontal axis represents concentration.

As shown in FIGS. 71 and 72, MAET-VEGFR_D2-PAS16 and MAET-VEGFR_D2-PAS49-b showed higher inhibitory activity than MAET-VEGFR_D2-PAS100-b, so that it was clarified that a dimer peptide having high activity could be constructed by using a short-chain PAS linker of 49 amino acids or less. In addition, MAET-VEGFR_D2-PAS16 showed higher inhibitory activity than MAET-VEGFR_D2-GS16, so that it was clarified that a dimer peptide having higher activity than a GS linker can be constructed by using a PAS linker.

Example 40: Design of HGF-PAS Trimer Peptide and its Secretory Expression in *C. glutamicum*

(40-1) Outline of Design

The HGF-PAS trimer peptide was designed as follows. A peptide was designed in which an aMD4dY sequence was further bound to the C-terminus of AET-aMD4dY-PAS22 mentioned above via a PAS linker. That is, the peptide sequence was designed to be "first aMD4dY cyclic peptide"-"PAS linker"-"second aMD4dY cyclic peptide"-"PAS linker"-"third aMD4dY cyclic peptide".

(40-2) Preparation of HGF-PAS Trimer Peptide

The prepared HGF-PAS trimer peptide is as follows.

```
(P) AET-aMD4dY-PAS22-Trimer
                                   (SEQ ID NO: 172)
AETCRQFNRRTHEVWNLDCGAAPAAPAPAAPAAPAPAAPAAPGCRQFN

RRTHEVWNLDCGAAPAAPAPAAPAAPAPAAPAAPGCRQFNRRTHEVWN

LDC
```

(40-3) Expression of HGF-PAS Trimer Peptide

Corynex (registered trademark) was used to examine the expression of stabilized HGF-PAS trimer peptide. Hereinafter, examples of expression examinations using Corynex (registered trademark) will be described.

(40-4) Construction of AET-aMD4dY-PAS22-Trimer Secretory Expression Plasmid Using CspB Signal Sequence As the stabilized HGF-PAS dimer peptide, the amino acid sequence of the above (P) AET-aMD4dY-PAS22-Trimer was designed, and the base sequence encoding this protein was designed in consideration of the codon usage frequency of *C. glutamicum*. Furthermore, the following expression cassette was designed to enable secretion expression by *C. glutamicum*.

AET-aMD4dY-PAS22-Trimer was secretory-expressed as a fusion protein of AET-aMD4dY-PAS22-Trimer and a signal peptide 30 amino acid residue of CspB derived from *C. glutamicum* ATCC 13869 strain (hereinafter referred to as "CspBss-AET-aMD4dY-PAS22-Trimer"). The base sequence and amino acid sequence encoding the designed CspBss-AET-aMD4dY-PAS22-Trimer are set forth in SEQ ID NOs: 173 and 174, respectively.

```
Base sequence encoding CspBss-AET-aMD4dY-PAS22-
Trimer
                                   (SEQ ID NO: 173)
atgtttaacaaccgtatccgcactgcagctctcgctggtgcaatcgca

atctccaccgcagcttccggcgtagctatcccagcattcgctgcagag

acctgccgccagttcaatcgccggacccacgaagtctggaatctggat

tgcggcgcagctcctgccgccccagcaccggctgcgccagctgctcca

gcgccggctgcccctgcggcaccgggttgccgtcagtttaaccgccgt

actcacgaggtttggaaccttgactgtggagcggctcccgcagcacca

gccccagccgcccctgctgcacccgcaccagcggcacccgccgctcct

ggctgtcgccaattcaaccgacgcacccatgaagtgtggaacctcgat

tgctaa

Amino acid sequence of CspBss-AET-aMD4dY-PAS22-
Trimer
                                   (SEQ ID NO: 174)
MFNNRIRTAALAGAIAISTAASGVAIPAFAAETCRQFNRRTHEVWNLD

CGAAPAAPAPAAPAAPAPAAPAAPGCRQFNRRTHEVWNLDCGAAPAAP

APAAPAAPAPAAPAAPGCRQFNRRTHEVWNLDC
```

The promoter of the cspB gene derived from the *C. glutamicum* ATCC 13869 strain was linked upstream of the base sequence set forth in CspBss-AET-aMD4dY-PAS22-Trimer, and furthermore, an expression cassette of HGF-PAS trimer peptide having a KpnI site on the 5'-side and an BamHI site on the 3'-side was designed and totally synthesized. The totally synthesized DNA fragment (HGF-PAS trimer peptide expression cassette) was inserted into the KpnI-BamHI site of pPK4 described in Japanese Patent Application Publication No. Hei 9-322774 to construct pPK4_CspBss-AET-aMD4dY-PAS22-Trimer, a secretory expression plasmid for the HGF-PAS trimer peptide using the CspB signal sequence. As a result of determining the base sequence of the inserted fragment, it was confirmed that the HGF-PAS trimer peptide expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(40-5) Secretory Expression of HGF-PAS Trimer Peptide in *C. glutamicum*

The pPK4_CspBss-AET-aMD4dY-PAS22-Trimer constructed above was used to transform the *C. glutamicum* YDK010:phoS(W302C) strain described in WO2016/171224 to obtain the YDK010:phoS(W302C)/pPK4_CspBss-AET-aMD4dY-PAS22-Trimer strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be AET-aMD4dY-PAS22-Trimer was detected in the culture supernatant of the YDK010:phoS (W302C)/pPK4_CspBss-AET-aMD4dY-PAS22-Trimer strain (FIG. 73, lanes 2 to 5).

Figure 73:
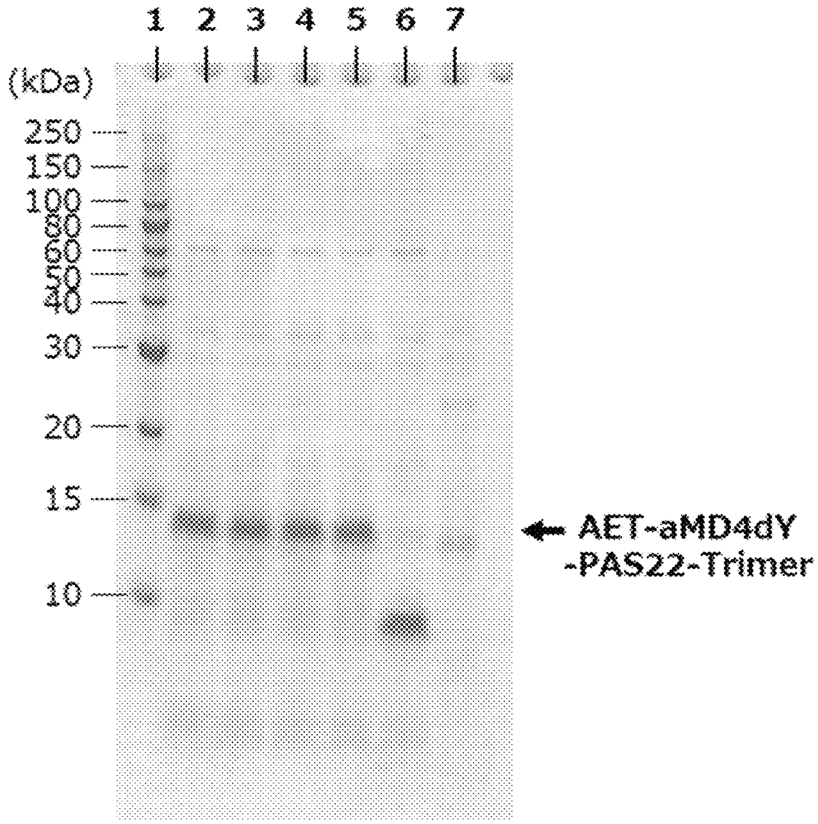
FIG. 73 shows the results of SDS-polyacrylamide electrophoresis showing the secretory expression of the dimer peptide and trimer peptide (HGF-PAS) in *C. glutamicum*. Lane 1 is a marker (XL-Ladder Broad, APRO science), lanes 2 to 5 are ones using pPK4_CspBss-AET-aMD4dY-PAS22-Trimer, lane 6 is one using pPK4_CspBss-AET-aMD4dY-PAS22, and lane 7 is one using pPK4 (empty vector).

In addition, the YDK010:phoS(W302C)/pPK4_CspBss-AET-aMD4dY-PAS22 strain obtained by the same method as above was cultured in the same manner as above, and a protein band presumed to be AET-aMD4dY-PAS22 was detected in the culture supernatant (FIG. 73, lane 6).

Example 41: Molecular Weight Analysis of HGF-PAS Trimer Peptide

Figure 74:
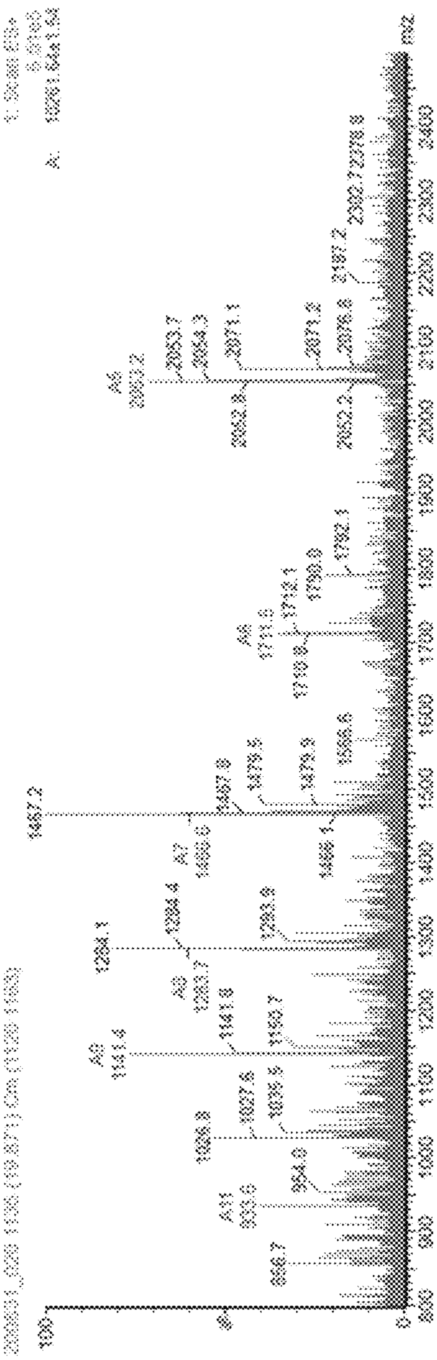
FIG. 74 shows measurement results of the trimer peptide (HGF-PAS) by LC-MS. Calc represents the theoretical value and Obs represents the measured value.

The cell filtrate of AET-aMD4dY-PAS22-Trimer after culturing in Example 40 was subjected to molecular weight measurement using LC-MS (Waters, ACQUITY UPLC/SQD2). The analysis conditions are shown in Table 2. As shown in FIG. 74, almost the same value as the theoretical value of the molecular weight of the oxidized dimer peptide forming three disulfide bonds in the molecule was obtained. From this, it was confirmed that a peptide having the correct amino acid sequence containing three disulfide bonds could be expressed.

Example 42: Activity Evaluation of HGF-PAS Trimer Peptide

The Met activation ability of the HGF-PAS trimer peptide was evaluated by luciferase assay. To 25 μL of Opti-MEM medium (Thermo Fisher Scientific), 0.6 μL of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 100 ng/mL HGF was added, or a culture supernatant containing AET-aMD4dY-PAS22 or AET-aMD4dY-PAS22-Trimer was added to the medium so as to be diluted at a predetermined ratio, and the evaluation basal medium was added in an amount of 100 μL to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 75:
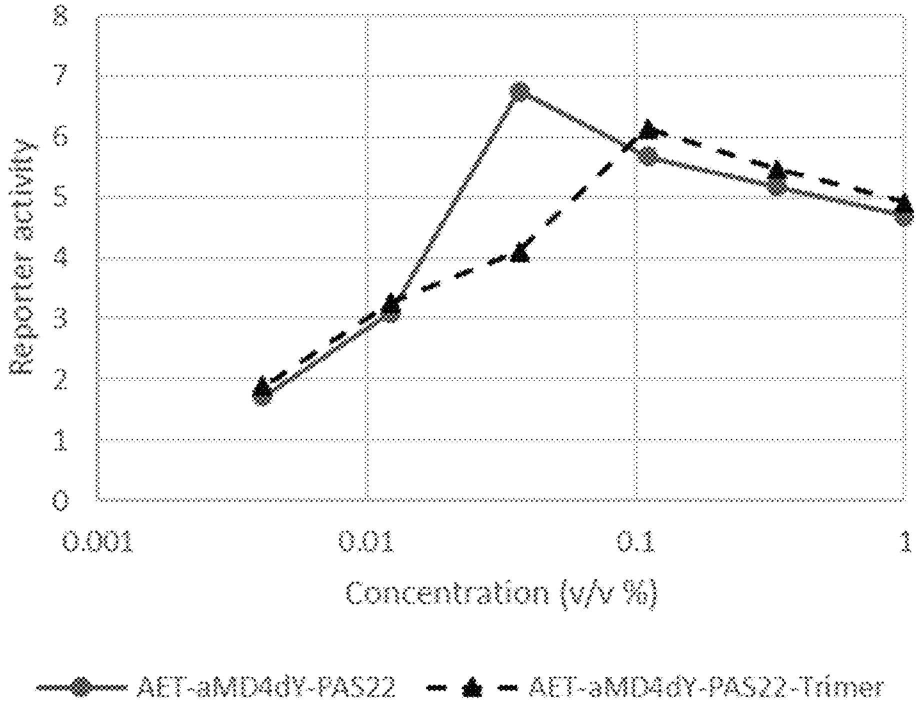
FIG. 75 is a graph showing the activity evaluation of the dimer peptide and trimer peptide (HGF-PAS). The vertical axis represents relative receptor activity and the horizontal axis represents concentration.

As shown in FIG. 75, it was clarified that the HGF-PAS trimer peptide (AET-aMD4dY-PAS22-Trimer) had a signal activation ability similar to the dimer peptide (AET-aMD4dY-PAS22).

Example 43: Comparison of Activity Between HGF-PAS Dimer Peptide and Monomer Peptide The Met activation ability of HGF-PAS dimer peptide and monomer peptide was compared by luciferase assay. To 25 μL of Opti-MEM medium (Thermo Fisher Scientific), 0.6 L of Attractene Transfection Reagent (QIAGEN) was added, and the mixture was incubated at room temperature for 5 minutes. To the above mixed solution, a mixed solution of 25 μL of Opti-MEM and 1 μL of SRE reporter vector (QIAGEN) was added, and the mixture was incubated at room temperature for 20 minutes. This mixed solution was added to a 96-well plate, over which 40,000 cell/well HEK293E cells were seeded and incubated overnight in a 5% $CO_2$ incubator at 37 °C. After transfection, all culture supernatant was removed, 100 μL of Opti-MEM medium (evaluation basal medium) containing 0.5% FBS (Thermo Fisher Scientific), 1% non-essential amino acid solution (Thermo Fisher Scientific), and penicillin-streptomycin (Nacalai Tesque) was added, and incubation was performed at 37 °C for 4 hours, and thereby the cells were starved.

To the evaluation basal medium, 0 to 100 ng/mL HGF was added, or a AET-aMD4dY-PAS22 or aMD4dY monomer peptide (CRQFNRRTHEVWNLDC (SEQ ID NO: 2), synthesized by GenScript Japan) was added at a predetermined concentration, and added in an amount of 100 μL to the cells. The cells were stimulated by culturing overnight in a 5% $CO_2$ incubator at 37 °C.

The signal intensities were detected using Dual-Luciferase Reporter Assay System (Promega). The medium supernatant in an amount of 100 μL was removed, 50 μL of Glo reagent was added, and the cells were lysed for 10 minutes at room temperature. The luminescence of Firefly luciferase emitted from the cell lysate solution was detected with a plate reader to quantify the activation of the HGF-Erk-SRE pathway. Subsequently, 50 μL of Glo & Stop reagent solution was added, and after 10 minutes, the luminescence of the internal standard *Renilla* luciferase was detected to quantify the number of cells. The signal activity of each sample was quantified as SRE activity=(Firefly luciferase luminescence intensity)/(*Renilla* luciferase luminescence intensity). The relative signal activity values for the samples without addition of the evaluation compound were determined and used as relative receptor activity.

Figure 76:
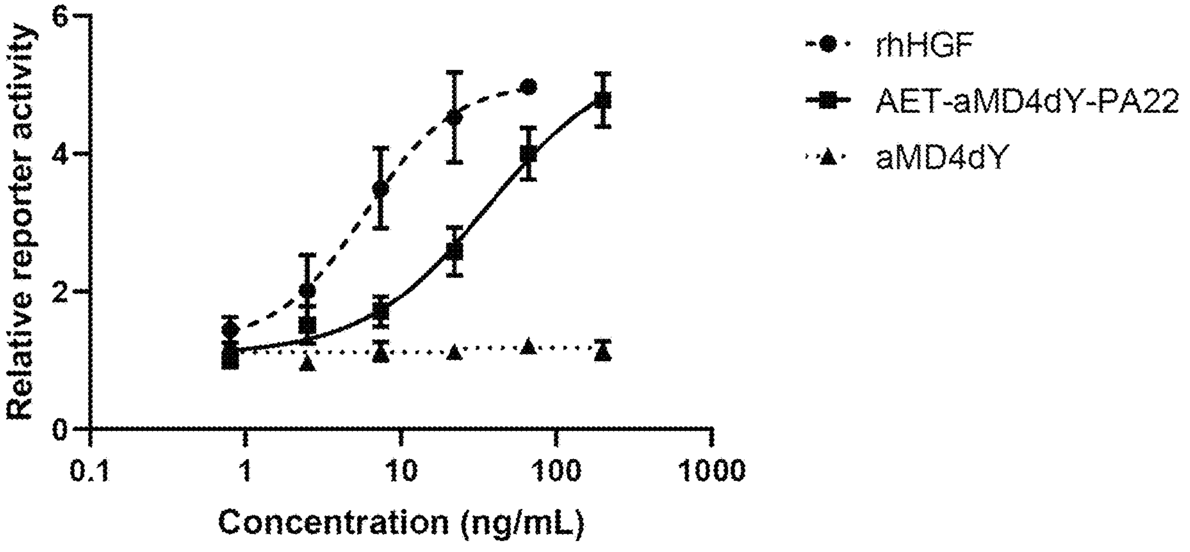
FIG. 76 is a graph showing the activity evaluation of HGF, dimer peptide (HGF-PAS), and monomer peptide aMD4dY The vertical axis represents relative receptor activity and the horizontal axis represents concentration.

As shown in FIG. 76, HGF and the dimer peptide (AET-aMD4dY-PAS22) showed signal activation ability, whereas the monomer peptide (aMD4dY) showed no signal activation ability. From this result, it was clarified that the peptide acquired the signal activation ability by dimerization.

Example 44: Design of VEGFR_D2-PAS Heterodimer Peptide Linker Variant and its Secretory Expression in *C. glutamicum*

(44-1) Outline of Linker Variant Design

AET-VEGFR_D2-PAS16 has a structure in which a PAS linker composed of 16 amino acids is linked between the first VEGFR-binding sequence (P-3) and the second VEGFR-binding sequence (P-4). By changing the length of this PAS linker, it is expected that the VEGFR-binding activity will change. Therefore, a linker variant was designed in which the PAS linker portion was changed to a PAS repeat sequence of 49 amino acids or 100 amino acids.

In addition to the PAS linker, a GS linker, which is a repeating sequence of glycine and serin, is also known as a flexible linker. Therefore, the peptide sequence was designed to be a linker variant in which a VEGFR-binding cyclic peptide was bound to the N-terminus and C-terminus of the GS linker composed of a repeating sequence of 4 glycine residues and 1 serine residue (GGGGS), that is, a "first VEGFR-binding sequence (P-3)"-"GS linker"-"second VEGFR-binding sequence (P-4)". That is, the C-terminus of P-3 and the N-terminus of the PAS linker are linked by an amide bond to the N-terminus of P-4 and the C-terminus of the PAS linker, respectively, and the peptide chain can be expressed as a single polypeptide chain.

(44-2) Preparation of VEGFR_D2-PAS Heterodimer Peptide Linker Variants

The prepared VEGFR_D2-PAS heterodimer peptide linker variants are as follows.

```
(Q) AET-VEGFR_D2-PAS49
                                        (SEQ ID NO: 175)
AETAGPTWCEDDWYYCWLFGTAAPAAPAPAAPAAPAPAAPAAPAPAAP

AAPAPAAPAAPAPAAPAAPAPAVCWEDSWGGEVCWLFGT

(R) AET-VEGFR_D2-PAS49-b
                                        (SEQ ID NO: 176)
AETAGPTWCEDDWYYCWLFGTSAPSPSSAPASASAPASPASASASASP

ASSPASASSASPAASSASPASSVCWEDSWGGEVCWLFGT

(S) AET-VEGFR_D2-PAS100
                                        (SEQ ID NO: 177)
AETAGPTWCEDDWYYCWLFGTAAPAAPAPAAPAAPAPAAPAAPAPAAP

AAPAPAAPAAPAPAAPAAPAPAAPAAPAPAAPAAPAPAAPAAPAPAAP

AAPAPAAPAAPAPAAPAAPAPAAPAVCWEDSWGGEVCWLFGT

(T) AET-VEGFR_D2-PAS100-b
                                        (SEQ ID NO: 178)
AETAGPTWCEDDWYYCWLFGTSAPSPSSAPASASAPASPASASASASP

ASSPASASSASPAASSASPASSSASPSAPAAPSASAAPSASPASSSPA

PASAPSPAAAASSPSPAPSSASSAAVCWEDSWGGEVCWLFGT

(U) AET-VEGFR_D2-GS16
                                        (SEQ ID NO: 179)
AETAGPTWCEDDWYYCWLFGTGGGGSGGGGSGGGGSGVCWEDSWGGEV

CWLFGT
```

(44-3) Expression of VEGFR_D2-PAS Heterodimer Peptide Linker Variants

Corynex (registered trademark) was used to examine the expression of VEGFR_D2-PAS heterodimer peptide linker variants. Hereinafter, examples of expression examinations using Corynex (registered trademark) will be described.

(44-4) Construction of Each Secretory Expression Plasmid of AET-VEGFR_D2-PAS49, AET-VEGFR_D2-PAS49-b, AET-VEGFR_D2-PAS100, AET-VEGFR_D2-PAS100-b, and AET-VEGFR_D2-GS16 Using CspB Signal Sequence As the VEGFR_D2-PAS heterodimer peptide linker variant, five types of amino acid sequences of the above (Q) AET-VEGFR_D2-PAS49 (which may be hereinafter referred to as "AET-VEGFR_D2-PAS49", and may be simply referred to as "VEGFR_D2-PAS49"), (R) AET-VEGFR_D2-PAS49-b (which may be hereinafter referred to as "AET-VEGFR_D2-PAS49-b", and may be simply referred to as "VEGFR_D2-PAS49-b"), (S) AET-VEGFR_D2-PAS100 (which may be hereinafter referred to as "AET-VEGFR_D2-PAS100", and may be simply referred to as "VEGFR_D2-PAS100"), (T) AET-VEGFR_D2-PAS100-b (which may be hereinafter referred to as "AET-VEGFR_D2-PAS100-b", and may be simply referred to as "VEGFR_D2-PAS100-b"), and (U) AET-VEGFR_D2-GS16 (which may be hereinafter referred to as "AET-VEGFR_D2-GS16", and may be simply referred to as "VEGFR_D2-GS16") were designed, and the base sequences encoding these proteins were designed in consideration of the codon usage frequency of *C. glutamicum*. Furthermore, the following expression cassettes were designed to enable secretory expression by *C. glutamicum*.

VEGFR_D2-PAS49 was secretory-expressed as a fusion protein of VEGFR_D2-PAS49 and a signal peptide 30 amino acid residue of CspB derived from *C. glutamicum* ATCC 13869 strain (hereinafter referred to as "CspBss-VEGFR_D2-PAS49"). The base sequence and amino acid sequence encoding the designed CspBss-VEGFR_D2-PAS49 are set forth in SEQ ID NOs: 180 and 181, respectively.

```
Base sequence encoding CspBss-VEGFR_D2-PAS49
                                        (SEQ ID NO: 180)
atgtttaacaaccgtatccgcactgcagctctcgctggtgcaatcgca

atctccaccgcagcttccggcgtagctatcccagcattcgctgcagag

accgctggccctacctggtgtgaggacgattggtactactgttggctc

tttggcaccgccgcccctgctgctcccgcccccgccgcccctgccgca

ccagctccagcagccccagctgcaccagcaccagccgctccagcagct

ccagcaccagctgctccagcagcaccagccccagcagctccagccgca

ccagctcctgcggtttgctgggaggattcttggggcggcgaagtttgc

tggctctttggcacctaa

Amino acid sequence of CspBss-VEGFR_D2-PAS49
                                        (SEQ ID NO: 181)
MFNNRIRTAALAGAIAISTAASGVAIPAFAAETAGPTWCEDDWYYCWL

FGTAAPAAPAPAAPAAPAPAAPAAPAPAAPAAPAPAAPAAPAPAAPAA

PAPAVCWEDSWGGEVCWLFGT
```

VEGFR_D2-PAS49-b was secretory-expressed as a fusion protein of VEGFR_D2-PAS49-b and a signal peptide 30 amino acid residue of CspB derived from *C. glutamicum* ATCC 13869 strain (hereinafter referred to as "CspBss-VEGFR_D2-PAS49-b"). The base sequence and amino acid sequence encoding the designed CspBss-VEGFR_D2-PAS49-b are set forth in SEQ ID NOs: 182 and 183, respectively.

Base sequence encoding CspBss-VEGFR_D2-PAS49-b
(SEQ ID NO: 182)
atgtttaacaaccgtatccgcactgcagctctcgctggtgcaatcgca atctccaccgcagcttccggcgtagctatcccagcattcgctgcagag accgcaggacccacttggtgcgaagatgactggtactattgctggctc tttggcacctcagcacccagcccatcctccgctccagcgtctgcgagc gctcctgcatccccagcctctgcctccgcatcggcatcaccggcttcc agcccagcgtcggcatcgtcagcctctccggctgcctcctccgcttct cctgcgtcctccgtgtgttgggaggattcctggggtggtgaagtctgc tggctgttcggcacctaa Amino acid sequence of CspBss-VEGFR_D2-PAS49-b
(SEQ ID NO: 183)
MFNNRIRTAALAGAIAISTAASGVAIPAFAAETAGPTWCEDDWYYCWL

FGTSAPSPSSAPASASAPASPASASASASPASSPASASSASPAASSAS

PASSVCWEDSWGGEVCWLFGT

VEGFR_D2-PAS100 was secretory-expressed as a fusion protein of VEGFR_D2-PAS100 and a signal peptide 30 amino acid residue of CspB derived from *C. glutamicum* ATCC 13869 strain (hereinafter referred to as "CspBss-VEGFR_D2-PAS100"). The base sequence and amino acid sequence encoding the designed CspBss-VEGFR_D2-PAS100 are set forth in SEQ ID NOs: 184 and 185, respectively.

Base sequence encoding CspBss-VEGFR_D2-PAS100
(SEQ ID NO: 184)
atgtttaacaaccgtatccgcactgcagctctcgctggtgcaatcgca atctccaccgcagcttccggcgtagctatcccagcattcgctgcagag accgccggtccaacctggtgtgaggatgactggtactactgctggctc tttggcaccgctgctcccgctgctcccgcccctgctgctccagctgcc ccagccccagctgccccagctgctccagcaccagccgctccagctgcc ccagcaccagctgcaccagcagcaccagcaccagcagctccagccgct ccagccccagccgctccagcagcaccagccccagcagctccagctgca ccagctccagccgccccagcagcaccagctccagcagccccagcagct ccagctccagccgcaccagctgctccagccccagccgcaccagcagcc ccagctccagctgctcctgctgtctgttgggaggactcttggggcggc gaagtttgttggttgtttggcacctaa Amino acid sequence of CspBss-VEGFR_D2-PAS100
(SEQ ID NO: 185)
MFNNRIRTAALAGAIAISTAASGVAIPAFAAETAGPTWCEDDWYYCWL

FGTAAPAAPAPAAPAAPAPAAPAAPAPAAPAAPAPAAPAAPAPAAPAA

PAPAAPAAPAPAAPAAPAPAAPAAPAPAAPAAPAPAAPAAPAPAAPAA

PAPAAPAVCWEDSWGGEVCWLFGT

VEGFR_D2-PAS100-b was secretory-expressed as a fusion protein of VEGFR_D2-PAS100-b and a signal peptide 30 amino acid residue of CspB derived from *C. glutamicum* ATCC 13869 strain (hereinafter referred to as "CspBss-VEGFR_D2-PAS100-b"). The base sequence and amino acid sequence encoding the designed CspBss-VEGFR_D2-PAS100-b are set forth in SEQ ID NOs: 186 and 187, respectively.

Base sequence encoding CspBss-VEGFR_D2-PAS100-b
(SEQ ID NO: 186)
atgtttaacaaccgtatccgcactgcagctctcgctggtgcaatcgca atctccaccgcagcttccggcgtagctatcccagcattcgctgcagag accgccggacctacctggtgtgaggatgactggtactattgctggctc ttcggcacttccgccccttccccttccagcgcaccagcgagcgcttcg gctccggcctccccagcgtccgcatctgcgtctgcatcccctgcgtcg tcacccgcttcagcctcctcagcctcccctgcggcttcatccgcctcg cccgcatccagctccgcatcaccctctgcgccagcagctccatccgct tctgctgccccatcggcctctccggcttccagctctcccgcaccggca tccgctccgagcccagcagcagctgcatcctccccatctccggcacca tcctcggcctctagcgcggctgtgtgctgggaagattcctggggtggt gaagtctgctggctgtttggcacctaa Amino acid sequence of CspBss-VEGFR_D2-PAS100-b
(SEQ ID NO: 187)
MFNNRIRTAALAGAIAISTAASGVAIPAFAAETAGPTWCEDDWYYCWL

FGTSAPSPSSAPASASAPASPASASASASPASSPASASSASPAASSAS

PASSSASPSAPAAPSASAAPSASPASSSPAPASAPSPAAAASSPSPAP

SSASSAAVCWEDSWGGEVCWLFGT

VEGFR_D2-GS16 was secretory-expressed as a fusion protein of VEGFR_D2-GS16 and a signal peptide 30 amino acid residue of CspB derived from *C. glutamicum* ATCC 13869 strain (hereinafter referred to as "CspBss-VEGFR_D2-GS16"). The base sequence and amino acid sequence encoding the designed CspBss-VEGFR_D2-GS16 are set forth in SEQ ID NOs: 188 and 189, respectively.

Base sequence encoding CspBss-VEGFR_D2-GS16
(SEQ ID NO: 188)
atgtttaacaaccgtatccgcactgcagctctcgctggtgcaatcgca atctccaccgcagcttccggcgtagctatcccagcattcgctgcagag accgcgggtccgacctggtgtgaggatgactggtactactgttggttg ttcggcaccggcggcggcggctccggcggcggcggctctggcggcggc ggctctggcgtttgttgggaggactcttggggcggcgaagtttgctgg ctgtttggcacctaa Amino acid sequence of CspBss-VEGFR_D2-GS16
(SEQ ID NO: 189)
MFNNRIRTAALAGAIAISTAASGVAIPAFAAETAGPTWCEDDWYYCWL

FGTGGGGSGGGGSGGGGSGVCWEDSWGGEVCWLFGT

The promoter of the cspB gene derived from the *C. glutamicum* ATCC 13869 strain was linked upstream of the base sequences set forth in CspBss-VEGFR_D2-PAS49, CspBss-VEGFR_D2-PAS49-b, CspBss-VEGFR_D2-PAS100, CspBss-VEGFR_D2-PAS100-b, and CspBss-VEGFR_D2-GS16, and furthermore, an expression cassette of each VEGFR_D2-PAS heterodimer peptide linker variant having a KpnI site on the 5'-side and an BamHI site on the 3'-side was designed and totally synthesized. The totally synthesized DNA fragment (VEGFR_D2-PAS heterodimer peptide linker variant expression cassette) was inserted into the KpnI-BamHI site of pPK4 described in Japanese Patent Application Publication No. Hei 9-322774 to construct pPK4_CspBss-VEGFR_D2-PAS49, pPK4_CspBss-VEG- FR_D2-PAS49-b, pPK4_CspBss-VEGFR_D2-PAS100, pPK4_CspBss-VEGFR_D2-PAS100-b, and pPK4_CspBss-VEGFR_D2-GS16, a secretory expression plasmid for each VEGFR_D2-PAS heterodimer peptide linker variant using the CspB signal sequence. As a result of determining the base sequence of the inserted fragment, it was confirmed that each VEGFR_D2-PAS heterodimer peptide linker variant expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(44-5) Secretory Expression of Each VEGFR_D2-PAS Heterodimer Peptide Linker Variant in *C. glutamicum*

The pPK4_CspBss-VEGFR_D2-PAS49, pPK4_CspBss-VEGFR_D2-PAS49-b, pPK4_CspBss-VEGFR_D2-PAS100, pPK4_CspBss-VEGFR_D2-PAS100-b, and pPK4_CspBss-VEGFR_D2-GS16 constructed above were used to transform the *C. glutamicum* YDK0107 strain described in WO2016/171224 to obtain the YDK0107/pPK4_CspBss-VEGFR_D2-PAS49 strain, YDK0107/pPK4_CspBss-VEGFR_D2-PAS49-b strain, YDK0107/pPK4_CspBss-VEGFR_D2-PAS100 strain, YDK0107/pPK4_CspBss-VEGFR_D2-PAS100-b strain, and YDK0107/pPK4_CspBss-VEGFR_D2-GS16 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 77:
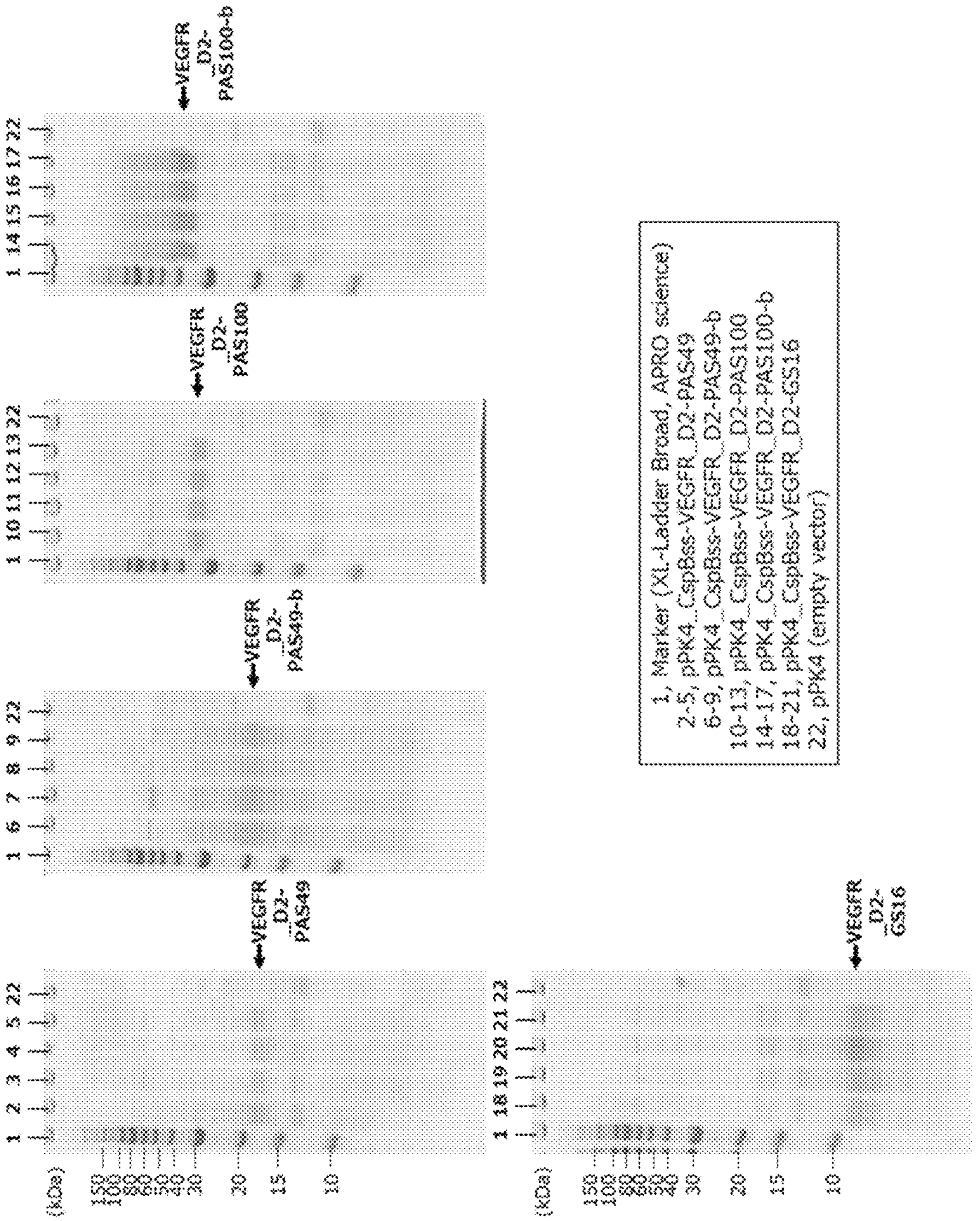
FIG. 77 shows the results of SDS-polyacrylamide electrophoresis showing the secretory expression of the heterodimer peptides (VEGFR_D2-PAS and VEGFR_D2-GS) in *C. glutamicum*. Lane 1 is a marker (XL-Ladder Broad, APRO science), lanes 2 to 5 are ones using pPK4_CspBss-VEGFR_D2-PAS49, lanes 6 to 9 are ones using pPK4_CspBss-VEGFR_D2-PAS49-b, lanes 10 to 13 are ones using pPK4_CspBss-VEGFR_D2-PAS100, lanes 14 to 17 are ones using pPK4_CspBss-VEGFR_D2-PAS100-b, lanes 18 to 21 are ones using pPK4_CspBss-VEGFR_D2-GS16, and lane 22 is one using pPK4 (empty vector).
Figure 78:
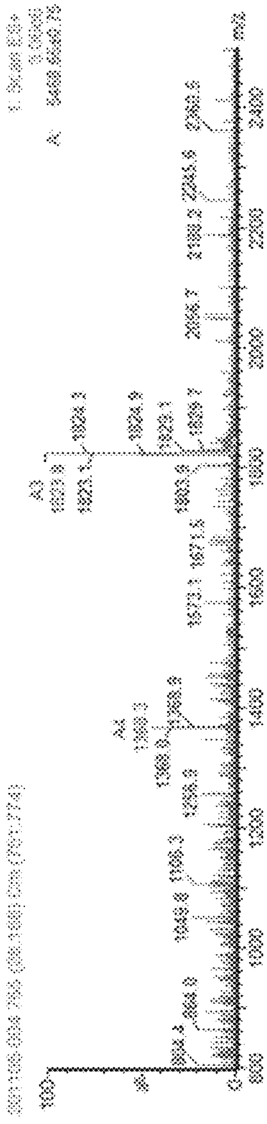
FIG. 78 shows measurement results of the heterodimer peptide (VEGFR_D2-GS) by LC-MS. Calc represents the theoretical value and Obs represents the measured value.
Figure 79:
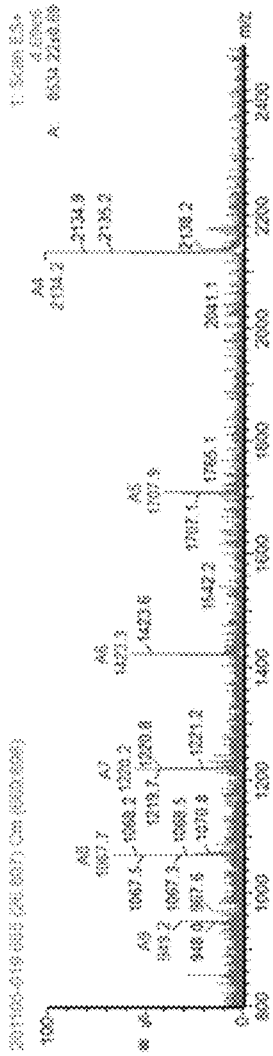
FIG. 79 shows measurement results of the heterodimer peptide (VEGFR_D2-PAS) by LC-MS. Calc represents the theoretical value and Obs represents the measured value.
Figure 80:
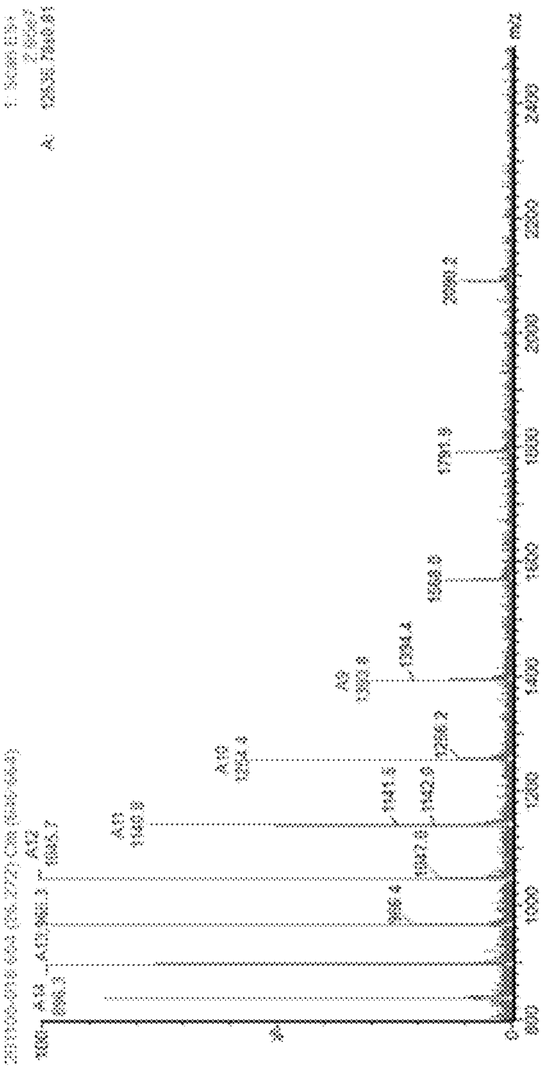
FIG. 80 shows measurement results of the heterodimer peptide (VEGFR_D2-PAS) by LC-MS. Calc represents the theoretical value and Obs represents the measured value.
Figure 81:
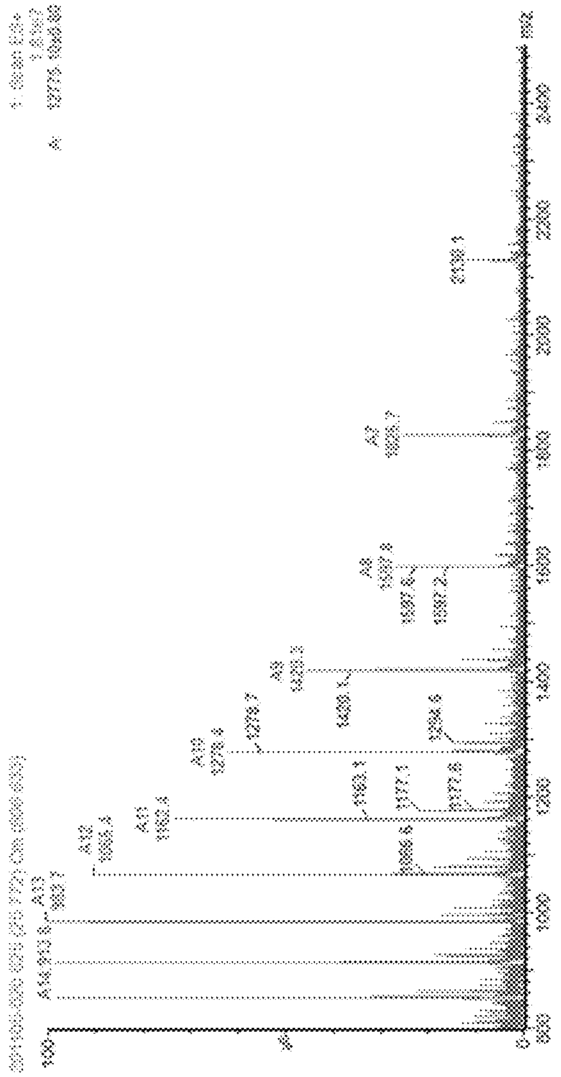
FIG. 81 shows measurement results of the heterodimer peptide (VEGFR_D2-PAS) by LC-MS. Calc represents the theoretical value and Obs represents the measured value.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be VEGFR_D2-PAS49 was detected in the culture supernatant of the YDK0107/pPK4_CspBss-VEGFR_D2-PAS49 strain (FIG. 77, lanes 2 to 5), a protein band presumed to be VEGFR_D2-PAS49-b was detected in the culture supernatant of the YDK0107/pPK4_CspBss-VEGFR_D2-PAS49-b strain (FIG. 77, lanes 6 to 9), a protein band presumed to be VEGFR_D2-PAS100 was detected in the culture supernatant of the YDK0107/pPK4_CspBss-VEGFR_D2-PAS100 strain (FIG. 77, lanes 10 to 13), a protein band presumed to be VEGFR_D2-PAS100-b was detected in the culture supernatant of the YDK0107/pPK4_CspBss-VEGFR_D2-PAS100-b strain (FIG. 77, lanes 14 to 17), and a protein band presumed to be VEGFR_D2-GS16 was detected in the culture supernatant of the YDK0107/pPK4_CspBss-VEGFR_D2-GS16 strain (FIG. 77, lanes 18 to 21).

Example 45: Molecular Weight Analysis of VEGFR_D2-PAS Heterodimer Peptide Linker Variant The cell filtrate with expressed VEGFR_D2-PAS heterodimer variant after culturing in Example 44 was subjected to cell filtration and then molecular weight measurement using LC-MS (Waters, ACQUITY UPLC/SQD2). The analysis conditions are shown in Table 5. As shown in FIGS. 78 to 81, almost the same value as the theoretical value of the molecular weight of the oxidized dimer peptide forming two disulfide bonds in the molecule was obtained. From this, it was confirmed that a peptide having the correct amino acid sequence containing two disulfide bonds could be expressed.

Example 46: Activity Evaluation of VEGFR_D2-PAS Heterodimer Peptide Linker Variant The VEGF inhibitory ability of the VEGFR_D2-PAS heterodimer peptide linker variant was evaluated by luciferase assay. 40,000 cell/well VEGFR/NFAT Reporter HEK293 cells (BPS Bioscience) were seeded and incubated overnight in a 5% $CO_2$ incubator at 37 °C. The cells were incubated overnight in Assay medium (MEM medium (Nacalai Tesque), 1×MEM Non-Essential Amino Acids Solution (Thermo Fisher Scientific), 1 mM Sodium Pyruvate (Nacalai Tesque), 1% Penicillin-Streptomycin (Sigma Aldrich), and 0.3% FBS (Thermo Fisher Scientific)) to starvation. To the Assay medium, 10 ng/mL human recombinant VEGF (R&D Systems) was added, and further, a culture supernatant containing VEGFR_D2-PAS16, VEGFR_D2-PAS49, or VEGFR_D2-PAS100 at a predetermined concentration was added, and 100 μL of the Assay medium was added to the cells. The cells were stimulated by culturing in a 5% $CO_2$ incubator at 37 °C for 4 hours. Note that VEGFR_D2-PAS16 was obtained according to the method described in Example 27.

One-Glo Luciferase Assay System (Promega) was used to detect the signal intensity. Medium supernatant in an amount of 50 μL was removed, 50 μL of One-Glo reagent was added, and the cells were lysed for 10 minutes at room temperature. The luminescence emitted from the cell lysate solution was detected with a Nivo plate reader (Perkin Elmer) to quantify the activation of the VEGFR-NFAT pathway, and the relative signal activity value for the sample without addition of evaluation compound was determined and used as relative receptor activity.

Figure 82:
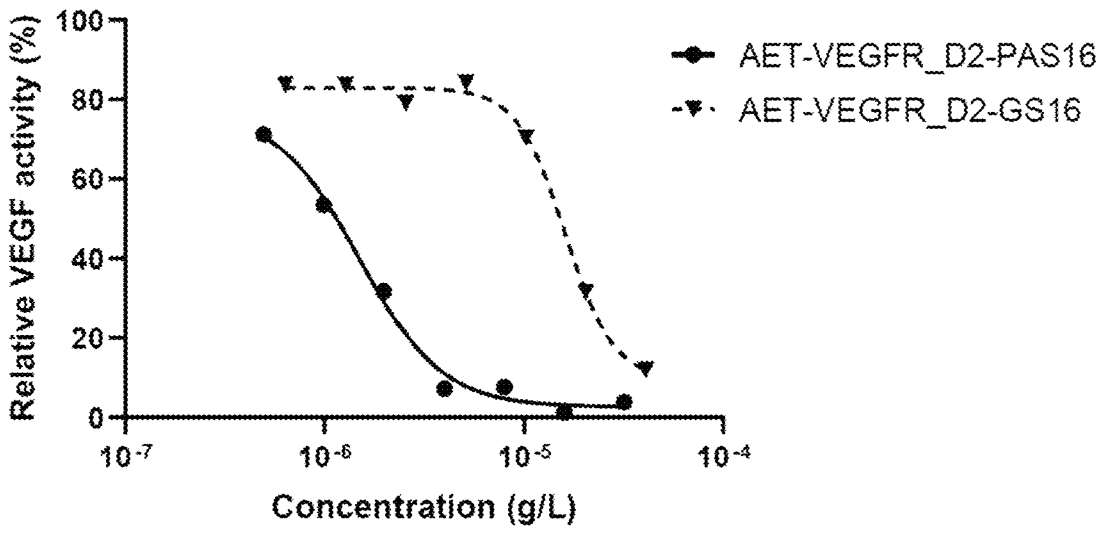
FIG. 82 is a graph showing the evaluation of VEGF inhibitory ability of the heterodimer peptides (VEGFR_D2-PAS and VEGFR_D2-GS). The vertical axis represents relative VEGF activity (relative receptor activity), and the horizontal axis represents concentration.
Figure 83:
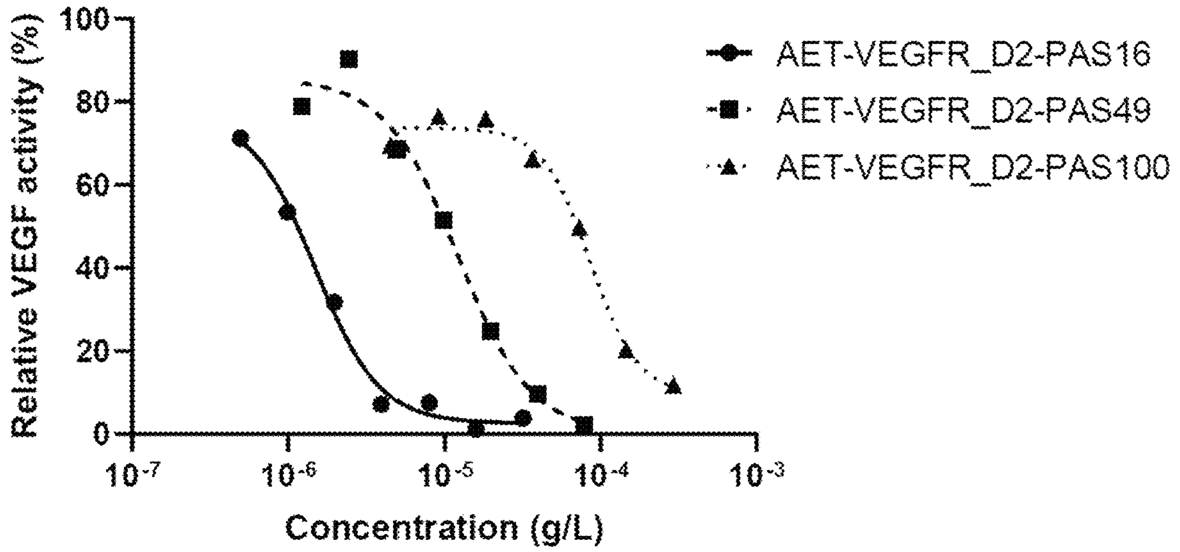
FIG. 83 is a graph showing the evaluation of VEGF inhibitory ability of the heterodimer peptide (VEGFR_D2-PAS). The vertical axis represents relative VEGF activity (relative receptor activity), and the horizontal axis represents concentration.

The evaluation results are shown in FIGS. 82 and 83, and the results of calculating the IC50 value of each peptide dimer are shown in Table 8 below. VEGFR_D2-PAS16 showed higher inhibitory activity than VEGFR_D2-GS16. In addition, VEGFR_D2-PAS16 and VEGFR_D2-PAS49 showed higher inhibitory activity than VEGFR_D2-PAS100, so that it has been clarified that a dimer peptide can be developed that has higher inhibitory activity than a GS linker by using a PAS linker and that has high inhibitory activity by using a PAS linker of 49 amino acids or less.

TABLE 8

| Peptide | IC50 (g/L) |
|---|---|
| AET-VEGFR_D2-PAS16 | $1.5 \times 10^{-6}$ |
| AET-VEGFR_D2-GS16 | $1.6 \times 10^{-5}$ |
| AET-VEGFR_D2-PAS49 | $1.2 \times 10^{-5}$ |
| AET-VEGFR_D2-PAS100 | $8.6 \times 10^{-5}$ |

Example 47: Design of TPO-PAS Dimer Peptide Linker Variant and its Secretory Expression in *C. glutamicum*

(47-1) Outline of Linker Variant Design

TPO2-PAS8, which has thrombopoietin-like activity, has a structure in which a PAS linker composed of 8 amino acids is linked between the first AF12285 peptide and the second AF12285 peptide. By changing the length of this PAS linker, it is expected that the thrombopoietin-like activity will change. Therefore, a linker variant was designed in which the PAS linker portion was changed to a PAS repeat sequence of 49 amino acids or 100 amino acids.

In addition to the PAS linker, a GS linker, which is a repeating sequence of glycine and serin, is also known as a flexible linker. Therefore, the peptide sequence was designed to be a linker variant in which EPO cyclic peptide was bound to the N-terminus and C-terminus of the GS linker composed of a repeating sequence of 4 glycine residues and 1 serine residue (GGGGS), that is, a "first AF12285 peptide"-"GS linker"-"first AF12285 peptide".

(47-2) Preparation of TPO-PAS Dimer Peptide Linker Variant

The prepared TPO-PAS dimer peptide linker variants are as follows.

```
(V) TPO2-PAS49
                                        (SEQ ID NO: 190)
GGCADGPTLREWISFCGGAAPAAPAPAAPAAPAPAAPAAPAPAAPAAP

APAAPAAPAPAAPAAPAPAGGCADGPTLREWISFCGG

(W) TPO2-PAS49-b
                                        (SEQ ID NO: 191)
GGCADGPTLREWISFCGGSAPSPSSAPASASAPASPASASASASPASS

PASASSASPAASSASPASSGGCADGPTLREWISFCGG

(X) TPO2-PAS100
                                        (SEQ ID NO: 192)
GGCADGPTLREWISFCGGAAPAAPAPAAPAAPAPAAPAAPAPAAPAAP

APAAPAAPAPAAPAAPAPAAPAAPAPAAPAAPAPAAPAAPAPAAPAAP

APAAPAAPAPAAPAAPAPAAPAGGCADGPTLREWISFCGG

(Y) TPO2-PAS100-b
                                        (SEQ ID NO: 193)
GGCADGPTLREWISFCGGSAPSPSSAPASASAPASPASASASASPASS

PASASSASPAASSASPASSSASPSAPAAPSASAAPSASPASSSPAPAS

APSPAAAASSPSPAPSSASSAAGGCADGPTLREWISFCGG

(Z) TPO2-GS8
                                        (SEQ ID NO: 194)
GGCADGPTLREWISFCGGGGGGSGGGGGCADGPTLREWISFCGG
```

(47-3) Expression of TPO-PAS Dimer Peptide Linker Variants

Corynex (registered trademark) was used to examine the expression of these TPO-PAS dimer peptide linker variants. Hereinafter, examples of expression examinations using Corynex (registered trademark) will be described.

(47-4) Construction of Each Secretory Expression Plasmid of TPO2-PAS49, TPO2-PAS49-b, TPO2-PAS100, TPO2-PAS100-b, and TPO2-GS8 Using CspA Signal Sequence.

As the TPO-PAS dimer peptide linker variant, five types of amino acid sequences of the above (V) TPO2-PAS49 (which may be hereinafter referred to as "TPO2-PAS49"), (W) TPO2-PAS49-b (which may be hereinafter referred to as "TPO2-PAS49-b"), (X) TPO2-PAS100 (which may be hereinafter referred to as "TPO2-PAS100"), (Y) TPO2-PAS100-b (which may be hereinafter referred to as "TPO2-PAS100-b"), and (Z) TPO2-GS8 (which may be hereinafter referred to as "TPO2-GS8") were designed, and the base sequences encoding these proteins were designed in consideration of the codon usage frequency of *C. glutamicum*. Furthermore, the following expression cassettes were designed to enable secretory expression by *C. glutamicum*.

TPO2-PAS49 was secretory-expressed as a fusion protein of TPO2-PAS49 and a signal peptide 25 amino acid residue of CspA derived from *C. ammoniagenes* ATCC 6872 strain (hereinafter referred to as "CspAss-TPO2-PAS49"). The base sequence and amino acid sequence encoding the designed CspAss-TPO2-PAS49 are set forth in SEQ ID NOs: 195 and 196, respectively.

```
Base sequence encoding CspAss-TP02-PAS49
                                        (SEQ ID NO: 195)
atgaaacgcatgaaatcgctggctgcggcgctcaccgtcgctggggcc

atgctggccgcacctgtggcaacggcaggtggctgtgctgacggtcct

acccttcgtgagtggatttctttttgcggcggtgctgctcctgctgcc

cctgctcctgctgctcctgcagcaccagccccagcagctccagccgcc

ccagctccagccgcaccagctgccccagcaccagccgctccagcagca

ccagctccagcagccccagctgcaccagccccagcgggcggttgtgct

gacggtcctacccttcgtgagtggatttccttctgtggtggctaa

Amino acid sequence of CspAss-TPO2-PAS49
                                        (SEQ ID NO: 196)
MKRMKSLAAALTVAGAMLAAPVATAGGCADGPTLREWISFCGGAAPAA

PAPAAPAAPAPAAPAAPAPAAPAAPAPAAPAAPAPAAPAAPAPAGGCA

DGPTLREWISFCGG
```

TPO2-PAS49-b was secretory-expressed as a fusion protein of TPO2-PAS49-b and a signal peptide 25 amino acid residue of CspA derived from *C. ammoniagenes* ATCC 6872 strain (hereinafter referred to as "CspAss-TPO2-PAS49-b"). The base sequence and amino acid sequence encoding the designed CspAss-TPO2-PAS49-b are set forth in SEQ ID NOs: 197 and 198, respectively.

```
Base sequence encoding CspAss-TPO2-PAS49-b
                                        (SEQ ID NO: 197)
atgaaacgcatgaaatcgctggctgcggcgctcaccgtcgctggggcc

atgctggccgcacctgtggcaacggcaggcgggtgtgcagacggaccc

actctgcgcgaatggatctccttttgcggcggttccgctccgtcgcca

tcctctgctccggcatccgcgtctgcgccagcatccccagccagcgct

tcagcctcagcgtcccctgcctcctctccagcatccgccagcagcgca

tctcctgcggctagctcggcatcacccgcttcgtccggaggttgcgct

gatggccctaccctccgtgagtggatttccttctgcggtggctaa

Amino acid sequence of CspAss-TPO2-PAS49-b
                                        (SEQ ID NO: 198)
MKRMKSLAAALTVAGAMLAAPVATAGGCADGPTLREWISFCGGSAPSP

SSAPASASAPASPASASASASPASSPASASSASPAASSASPASSGGCA

DGPTLREWISFCGG
```

TPO2-PAS100 was secretory-expressed as a fusion protein of TPO2-PAS100 and a signal peptide 25 amino acid residue of CspA derived from *C. ammoniagenes* ATCC 6872 strain (hereinafter referred to as "CspAss-TPO2-PAS100"). The base sequence and amino acid sequence encoding the designed CspAss-TPO2-PAS100 are set forth in SEQ ID NOs: 199 and 200, respectively.

Base sequence encoding CspAss-TPO2-PAS100
(SEQ ID NO: 199)
atgaaacgcatgaaatcgctggctgcggcgctcaccgtcgctggggcc atgctggccgcacctgtggcaacggcaggcggttgtgctgacggtcct accttgcgtgaatggatttctttctgtggtggtgcggctccggctgct ccggctcctgcggctccggctgcaccagcaccagccgcaccagctgca ccagccccagctgcaccagccgctccagcaccagctgccccagctgca ccagctccagccgcaccagcagccccagctccagcagccccagcagct ccagcaccagccgctccagctgccccagcaccagctgctccagcagct ccagcaccagcagctccagctgctccagccccagccgccccagccgct ccagccccagcagcaccagccgccccagctccagccgccccagcaggt ggctgtgctgatggtcctacccttcgtgaatggatttccttttgtggc ggttag Amino acid sequence of CspAss-TPO2-PAS 100
(SEQ ID NO: 200)
MKRMKSLAAALTVAGAMLAAPVATAGGCADGPTLREWISFCGGAAPAA

PAPAAPAAPAPAAPAAPAPAAPAAPAPAAPAAPAPAAPAAPAPAAPAA

PAPAAPAAPAPAAPAAPAPAAPAAPAPAAPAAPAPAAPAAPAPAAPAG

GCADGPTLREWISFCGG

TPO2-PAS100-b was secretory-expressed as a fusion protein of TPO2-PAS100-b and a signal peptide 25 amino acid residue of CspA derived from *C. ammoniagenes* ATCC 6872 strain (hereinafter referred to as "CspAss-TPO2-PAS100-b"). The base sequence and amino acid sequence encoding the designed CspAss-TPO2-PAS100-b are set forth in SEQ ID NOs: 201 and 202, respectively.

Base sequence encoding CspAss-TPO2-PAS 100-b
(SEQ ID NO: 201)
atgaaacgcatgaaatcgctggctgcggcgctcaccgtcgctggggcc atgctggccgcacctgtggcaacggcaggcgggtgtgcagacggtccc actctccgcgaatggatctccttttgcggcggaagcgcgccctccccg tcatctgcccctgcatctgcgtccgcaccagcatccccagcctctgcg tctgcttctgcatcaccggcctcgtccccagcaagcgcatcgtccgcg tcaccagctgcgtcctcagcctcccctgcttcctcgtccgcttcgcct tcggctcctgccgctccctctgcatccgctgccccatccgcctcacca gccagctcctctccggcaccagcgtccgctccttcccctgcagctgcg gcgagctctccaagcccggctccctcctccgcatccagcgctgccggt ggatgcgcagatggcccgaccctgcgtgagtggattagcttctgcggc ggttaa Amino acid sequence of CspAss-TPO2-PAS100-b
(SEQ ID NO: 202)
MKRMKSLAAALTVAGAMLAAPVATAGGCADGPTLREWISFCGGSAPSP

SSAPASASAPASPASASASASPASSPASASSASPAASSASPASSSASP

SAPAAPSASAAPSASPASSSPAPASAPSPAAAASSPSPAPSSASSAAG

GCADGPTLREWISFCGG

TPO2-GS8 was secretory-expressed as a fusion protein of TPO2-GS8 and a signal peptide 25 amino acid residue of CspA derived from *C. ammoniagenes* ATCC 6872 strain (hereinafter referred to as "CspAss-TPO2-GS8"). The base sequence and amino acid sequence encoding the designed CspAss-TPO2-GS8 are set forth in SEQ ID NOs: 203 and 204, respectively.

Base sequence encoding CspAss-TPO2-GS8
(SEQ ID NO: 203)
atgaaacgcatgaaatcgctggctgcggcgctcaccgtcgctggggcc atgctggccgcacctgtggcaacggcaggtggctgtgcggatggtcct accttgcgtgagtggatttctttctgtggcggtggtggtggtggttct ggtggtggtggtggttgcgcagatggcccaaccctgcgcgaatggatc tccttctgcggcggctaa Amino acid sequence of CspAss-TPO2-GS8
(SEQ ID NO: 204)
MKRMKSLAAALTVAGAMLAAPVATAGGCADGPTLREWISFCGGGGGGS

GGGGGCADGPTLREWISFCGG

The promoter of the cspB gene derived from the *C. glutamicum* ATCC 13869 strain was linked upstream of the base sequences set forth in CspAss-TPO2-PAS49, CspAss-TPO2-PAS49-b, CspAss-TPO2-PAS100, CspAss-TPO2-PAS100-b, and CspAss-TPO2-GS8, and furthermore, an expression cassette of each TPO-PAS dimer peptide linker variant having a KpnI site on the 5'-side and an BamHI site on the 3'-side was designed and totally synthesized. The totally synthesized DNA fragment (TPO-PAS dimer peptide linker variant expression cassette) was inserted into the KpnI-BamHI site of pPK4 described in Japanese Patent Application Publication No. Hei 9-322774 to construct pPK4_CspAss-TPO2-PAS49, pPK4_CspAss-TPO2-PAS49-b, pPK4_CspAss-TPO2-PAS100, pPK4_CspAss-TPO2-PAS100-b, and pPK4_CspAss-TPO2-GS8, a secretory expression plasmid for each TPO-PAS dimer peptide linker variant using the CspA signal sequence. As a result of determining the base sequence of the inserted fragment, it was confirmed that each TPO-PAS dimer peptide linker variant expression cassette as designed had been constructed. Base sequences were determined using BigDye (registered trademark) Terminator v3.1 Cycle Sequencing Kit (Applied Biosystems) and 3500xL Genetic Analyzer (Applied Biosystems).

(47-5) Secretory Expression of Each TPO-PAS Dimer Peptide Linker Variant in *C. glutamicum*

The pPK4_CspAss-TPO2-PAS49, pPK4_CspAss-TPO2-PAS49-b, pPK4_CspAss-TPO2-PAS100, pPK4_CspAss-TPO2-PAS100-b, and pPK4_CspAss-TPO2-GS8 constructed above were used to transform the *C. glutamicum* YDK0107 strain described in WO2016/171224 to obtain the YDK0107/pPK4_CspAss-TPO2-PAS49 strain, YDK0107/pPK4_CspAss-TPO2-PAS49-b strain, YDK0107/pPK4_CspAss-TPO2-PAS100 strain, YDK0107/pPK4_CspAss-TPO2-PAS100-b strain, and YDK0107/pPK4_CspAss-TPO2-GS8 strain.

The obtained transformants were each cultured in MMTG liquid medium containing 25 mg/L kanamycin (glucose at 120 g, magnesium sulfate heptahydrate at 3 g, ammonium sulfate at 30 g, potassium dihydrogen phosphate at 1.5 g, iron heptahydrate at 0.03 g, manganese sulfate pentahydrate at 0.03 g, thiamine hydrochloride at 0.45 mg, biotin at 0.45 mg, DL-methionine at 0.15 g, soybean hydrochloric acid hydrolyzate (total nitrogen amount at 0.2 g), calcium carbonate at 50 g, adjusted to pH 7.0 with 1 L of water) at 30 °C for 72 hours.

Figure 84:
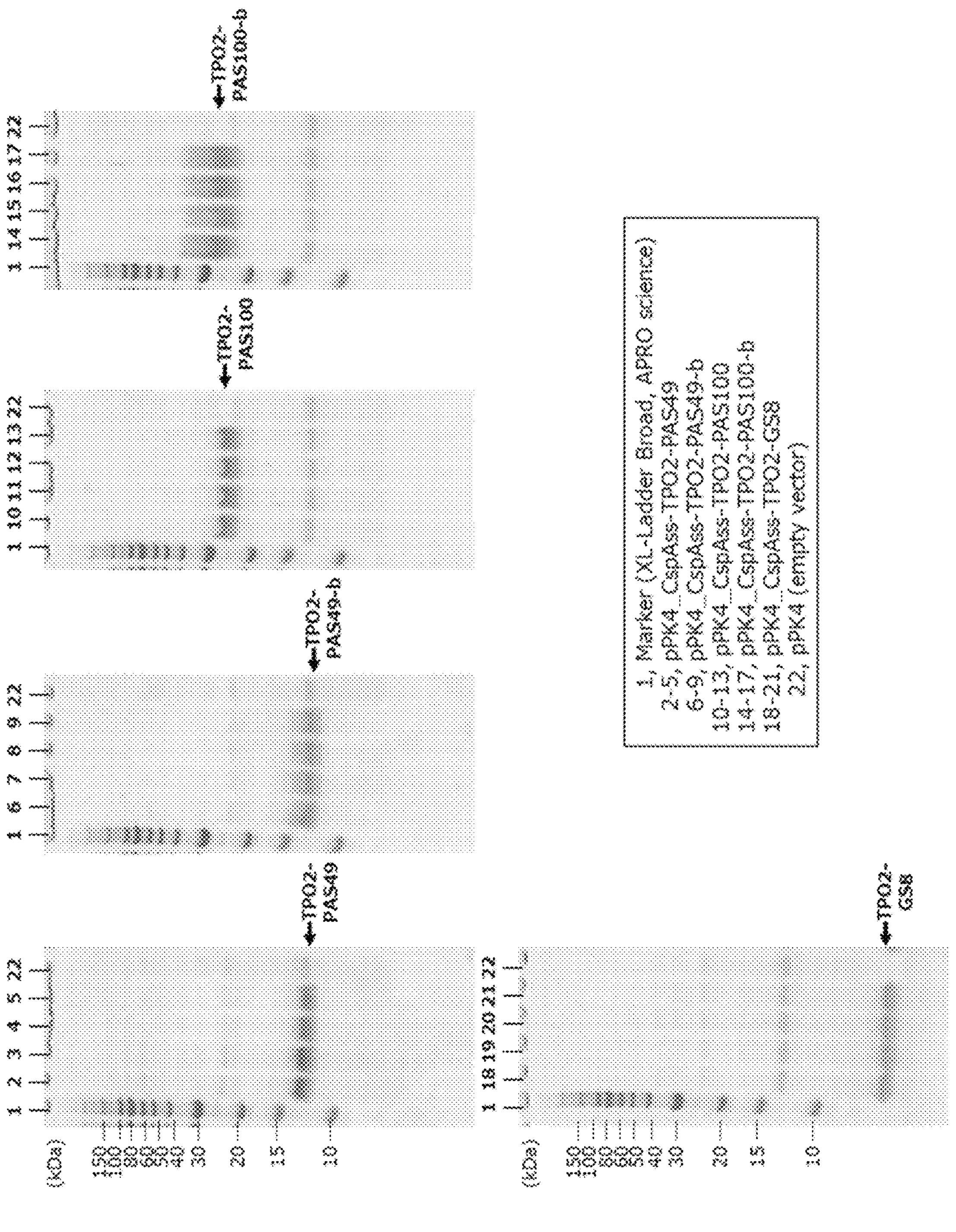
FIG. 84 shows the results of SDS-polyacrylamide electrophoresis showing the secretory expression of the dimer peptides (TPO-PAS and TPO-GS) in *C. glutamicum*. Lane 1 is a marker (XL-Ladder Broad, APRO science), lanes 2 to 5 are ones using pPK4_CspBss-TPO2-PAS49, lanes 6 to 9 are ones using pPK4_CspBss-TPO2-PAS49-b, lanes 10 to 13 are ones using pPK4_CspBss-TPO2-PAS100, lanes 14 to 17 are ones using pPK4_CspBss-TPO2-PAS100-b, lanes 18 to 21 are ones using pPK4_CspBss-TPO2-GS8, and lane 22 is one using pPK4 (empty vector).
Figure 85:
FIG. 85 shows measurement results of the dimer peptide (TPO-GS) by LC-MS. Calc represents the theoretical value and Obs represents the measured value.
Figure 86:
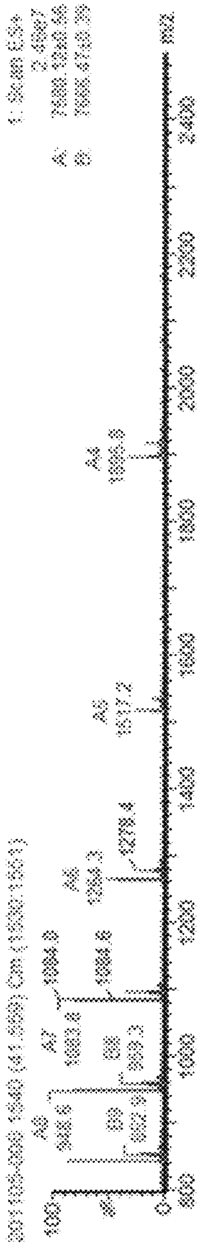
FIG. 86 shows measurement results of the dimer peptide (TPO-PAS) by LC-MS. Calc represents the theoretical value and Obs represents the measured value.
Figure 87:
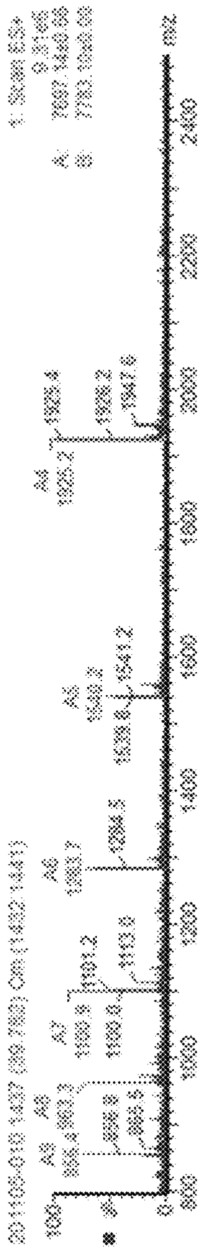
FIG. 87 shows measurement results of the dimer peptide (TPO-PAS) by LC-MS. Calc represents the theoretical value and Obs represents the measured value.
Figure 88:
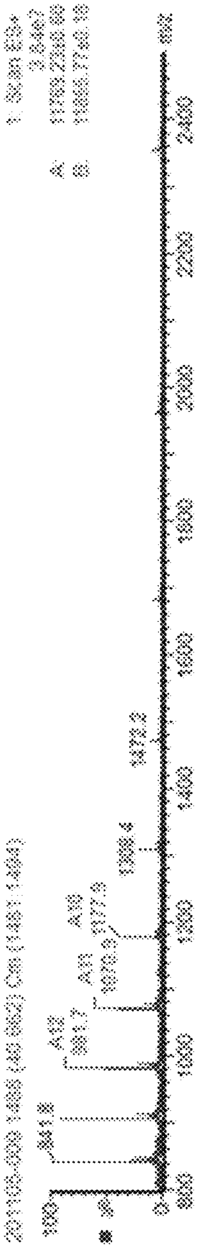
FIG. 88 shows measurement results of the dimer peptide (TPO-PAS) by LC-MS. Calc represents the theoretical value and Obs represents the measured value.
Figure 89:
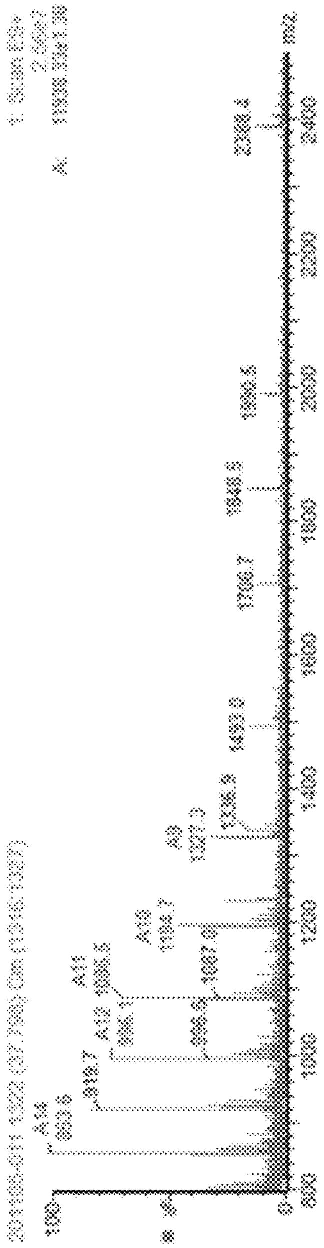
FIG. 89 shows measurement results of the dimer peptide (TPO-PAS) by LC-MS. Calc represents the theoretical value and Obs represents the measured value.

After completion of the culture, 6.5 μL of the culture supernatant obtained by centrifuging each culture solution was subjected to reduced SDS-PAGE using NuPAGE (registered trademark) 12% Bis-Tirs Gel (Thermo Fisher Scientific), and then stained with Quick-CBB (Wako). As a result, a protein band presumed to be TPO2-PAS49 was detected in the culture supernatant of the YDK0107/pPK4_CspAss-TPO2-PAS49 strain (FIG. 84, lanes 2 to 5), a protein band presumed to be TPO2-PAS49-b was detected in the culture supernatant of the YDK0107/pPK4_CspAss-TPO2-PAS49-b strain (FIG. 84, lanes 6 to 9), a protein band presumed to be TPO2-PAS100 was detected in the culture supernatant of the YDK0107/pPK4_CspAss-TPO2-PAS100 strain (FIG. 84, lanes 10 to 13), a protein band presumed to be TPO2-PAS49-b was detected in the culture supernatant of the YDK0107/pPK4_CspAss-TPO2-PAS49-b strain (FIG. 84, lanes 14 to 17), and a protein band presumed to be TPO2-GS8 was detected in the culture supernatant of the YDK0107/pPK4_CspAss-TPO2-GS8 strain (FIG. 84, lanes 18 to 21).

Example 48: Molecular Weight Analysis of TPO-PAS Dimer Peptide Linker Variant The cell filtrate of the TPO-PAS dimer peptide linker variant after culturing in Example 47 was subjected to molecular weight measurement using LC-MS (Waters, ACQUITY UPLC/SQD2). The analysis conditions are shown in Table 2. As shown in FIGS. 85 to 89, almost the same value as the theoretical value of the molecular weight of each oxidized dimer peptide forming two disulfide bonds in the molecule was obtained. From this, it was confirmed that a peptide having the correct amino acid sequence containing two disulfide bonds could be expressed.

Example 49: Activity Evaluation of TPO-PAS Dimer Peptide Linker Variant

The thrombopoietin-like activity of the TPO-PAS dimer peptide variant was evaluated by quantification of CREB phosphorylation levels in HEL cells, a human leukemia-derived blood cell line. 200,000 HEL cells were cultured in RPMI 1640 medium without FBS (Thermo Fisher Scientific) for 24 hours and starved. The cells were stimulated for 20 minutes in RPMI 1640 medium supplemented with 100 ng/mL recombinant human TPO (rhTPO, Peprotech) or a culture supernatant containing each dimer peptide of TPO2-PAS8, TPO2-PAS49, TPO2-PAS100, or TPO2-GS8 diluted to a final concentration of 20-40 ng/mL. As a negative control, PBS was added, and stimulation was performed for 20 minutes (Mock group). After removing the medium and washing the cells once with PBS, the cells were lysed by adding 100 μL of Lysis buffer 17 (R&D Systems) supplemented with Protease inhibitor cocktail (Nacalai Tesque). The lysate solution was centrifuged at 14,000 G for 5 minutes to obtain the supernatant as lysate. Note that TPO2-PAS8 was obtained according to the method described in Example 23.

Phospho-CREB (Ser133) and Total CREB ELISA kit (RayBio) were used to quantify phosphorylated CREB (pCREB) levels in the lysates. Each lysate was diluted 25-fold with Assay Diluent, and 100 μL each was added to CREB Pan CREB Microplate, and shaken overnight at 4 °C. After washing the Microplate 3 times with a washing buffer, 100 μL of Phospho Detection Antibody CREB (Ser133) was added, and the mixture was allowed to stand at 37 °C for 30 minutes for an antigen-antibody reaction. Furthermore, after washing the Microplate 3 times with a washing buffer, 100 μL of 100 μL anti-rabbit antibody HRP conjugate was added, and the mixture was allowed to stand at 37 °C for 30 minutes for an antigen-antibody reaction. After further washing the Microplate 3 times with a washing buffer, 100 μL of TMB solution was added, and a color reaction was carried out at room temperature for 30 minutes. Phosphorylation levels were quantified by adding 50 μL of Stop solution and measuring the absorbance at a wavelength of 450 nm on a microplate.

Figure 90:
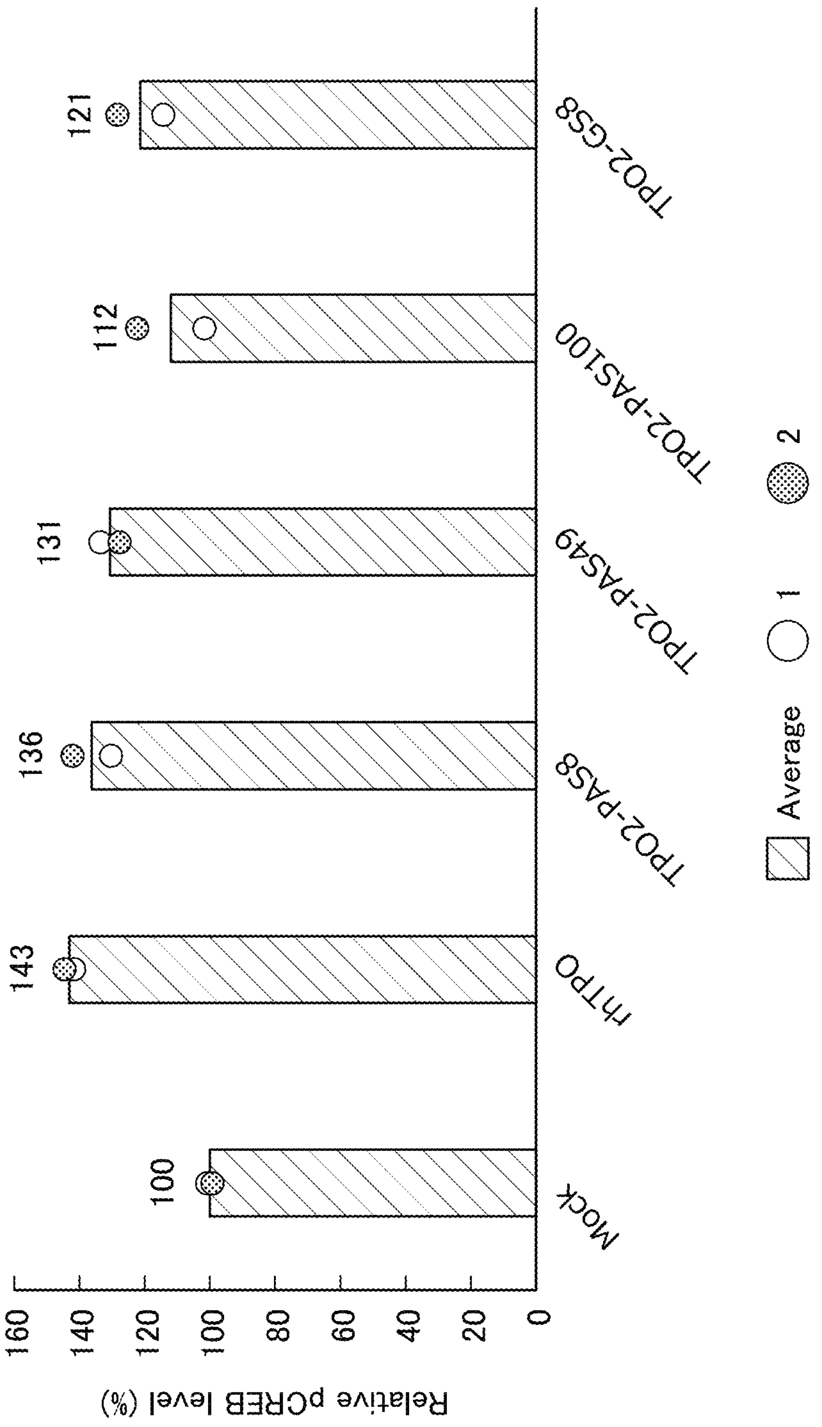
FIG. 90 is a graph showing quantitatively the phosphorylation ability of rhTPO and dimer peptides (TPO-PAS and TPO-GS) measured using Phospho-CREB (Ser133) and Total CREB ELISA kit (RayBio). The vertical axis represents relative CREB phosphorylation levels and the horizontal axis represents activated molecules. Mock represents the PBS-added group.

FIG. 90 shows the results. Higher pCREB levels were confirmed in all groups supplemented with dimer peptides compared to the Mock group. TPO2-PAS8 and TPO2-PAS49 showed pCREB levels of 136% and 131%, respectively, close to the rhTPO stimulation group (143%), while TPO2-PAS100 had a low pCREB level of 112%. In addition, TPO2-GS8 was 121%, which was a lower pCREB level than TPO2-PAS8. From these, it was clarified that the use of the short-chain PAS linker provided higher agonist activity than the long-chain PAS linker and GS linker.

What is claimed is:

1. A peptide molecule comprising:

(I) one first physiologically active peptide portion;

(II) one linker portion composed of 49 or less amino acid residues; and (III) one second physiologically active peptide portion located on the opposite side of the linker portion from the first physiologically active peptide portion, wherein the first physiologically active peptide portion and the second physiologically active peptide portion may be the same as or different from each other, and at least 90% of an amino acid sequence of the linker portion is composed of amino acid residues selected from alanine (A), proline (P), and serine(S), the linker portion comprises repeats of a two or more amino acid sequences selected from the group consisting of AP, AAP, AS, ASP, and ASS, and the first physiologically active peptide portion and the second physiologically active peptide portion each independently constitutes a target-binding peptide, a target-inhibiting peptide, a target-activating peptide, or an enzyme-recognizing peptide, the first physiologically active peptide portion and the second physiologically active peptide portion each independently constitutes a cyclic peptide, and the first physiologically active peptide portion and the second physiologically active peptide portion each independently is from 3 to 50 amino acids in length.

2. The peptide molecule according to claim 1, wherein the first physiologically active peptide portion and the second physiologically active peptide portion each has a cyclic structure formed by a disulfide bond.

3. The peptide molecule according to claim 1, wherein the first physiologically active peptide portion and the second physiologically active peptide portion each constitute a cyclic peptide that binds to a c-Met protein, and may be the same as or different from each other.

4. The peptide molecule according to claim 3, wherein the cyclic peptide has a cyclic structure formed by a disulfide bond and contains an amino acid sequence selected from the group consisting of:

(a) (SEQ ID NO: 1)
CYRQFNRRTHEVWNLDC;

-continued (b) (SEQ ID NO: 2)
CRQFNRRTHEVWNLDC;

(c) (SEQ ID NO: 3)
CYWYYAWDQTYKAFPC;

(d) (SEQ ID NO: 4)
CWYYAWDQTYKAFPC;

(e) (SEQ ID NO: 5)
CYISWNEFNSPNWRFITC;

(f) (SEQ ID NO: 6)
CISWNEFNSPNWRFITC;

(g) an amino acid sequence in which one or two amino acid residues other than a cysteine residue are substituted, deleted, or added in any of the amino acid sequences (a) to (f), and which binds to a c-Met protein;

(h) an amino acid sequence which is composed of an amino acid sequence having 90% or more sequence identity with any of the amino acid sequences (a) to (f), but having cysteine residues at both ends, and which binds to a c-Met protein; and (i) an amino acid sequence in which at least one amino acid other than the cysteine residues at both ends in any of the amino acid sequences (a) to (h) is modified, wherein the amino acid modification is phosphorylation, methylation, acetylation, adenylylation, ADP-ribosylation, or glycosylation.

5. The peptide molecule according to claim 1, wherein the first physiologically active peptide portion and the second physiologically active peptide portion each constitute a cyclic peptide that binds to an erythropoietin receptor, and may be the same as or different from each other.

6. The peptide molecule according to claim 5, wherein the cyclic peptide has a cyclic structure formed by a disulfide bond and contains an amino acid sequence selected from the group consisting of:

(j)

(SEQ ID NO: 65)
GGLYACHMGPMTWVCQPLRG;

(k)

(SEQ ID NO: 66)
CISWNEFNSPNWRFITC;

(l) an amino acid sequence in which one or two amino acid residues other than a cysteine residue are substituted, deleted, or added in the amino acid sequence of (j) or (k), and which binds to an erythropoietin receptor;

(m) an amino acid sequence which is composed of an amino acid sequence having 90% or more sequence identity with either the amino acid sequence of (j) or (k), but having a cysteine residue at the same position in (j) or (k), and which binds to an erythropoietin receptor; and (n) an amino acid sequence in which at least one amino acid other than the cysteine residue in any of the amino acid sequences (j) to (m) is modified, wherein the amino acid modification is phosphorylation, methylation, acetylation, adenylylation, ADP-ribosylation, or glycosylation.

7. The peptide molecule according to claim 1, wherein the first physiologically active peptide portion and the second physiologically active peptide portion are each composed of a physiologically active peptide that binds to a thrombopoietin receptor, and may be the same as or different from each other.

8. The peptide molecule according to claim 7, wherein the physiologically active peptide contains an amino acid sequence selected from the group consisting of:

(o)

(SEQ ID NO: 67)
IEGPTLRQWLAARA;

(p)

(SEQ ID NO: 68)
GGCADGPTLREWISFCGG;

(q)

(SEQ ID NO: 69)
GGCTLREWLHGGFCGG;

(r)

(SEQ ID NO: 70)
LAIEGPTLRQWLHGNGRDT;

(s) an amino acid sequence in which one or two amino acid residues other than a cysteine residue are substituted, deleted, or added in any of the amino acid sequences (o) to (r), and which binds to a thrombopoietin receptor; and (t) an amino acid sequence in which at least one amino acid other than the cysteine residue in any of the amino acid sequences (o) to(s) is modified (the amino acid modification is phosphorylation, methylation, acetylation, adenylylation, ADP-ribosylation, or glycosylation).

9. A method for producing the peptide molecule of claim 1, comprising the steps of:

producing the peptide molecule by expressing a polynucleotide in a host cell containing the polynucleotide encoding the peptide molecule or by expressing a polynucleotide encoding the peptide molecule in a cell-free expression system, wherein the peptide molecule is the peptide molecule according to claim 1.

10. The peptide molecule according to claim 1, wherein the target is a receptor activated by dimerization.

* * * * *

SEQUENCE LISTING

```
<160> NUMBER OF SEQ ID NOS: 204

<210> SEQ ID NO 1
<211> LENGTH: 17
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(17)
<223> OTHER INFORMATION: Disulfid bridge between Cys-1 and Cys-17

<400> SEQUENCE: 1

Cys Tyr Arg Gln Phe Asn Arg Arg Thr His Glu Val Trp Asn Leu Asp
1               5                   10                  15

Cys


<210> SEQ ID NO 2
```

```
<211> LENGTH: 16
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(16)
<223> OTHER INFORMATION: Disulfid bridge between Cys-1 and Cys-16

<400> SEQUENCE: 2

Cys Arg Gln Phe Asn Arg Arg Thr His Glu Val Trp Asn Leu Asp Cys
1               5                   10                  15


<210> SEQ ID NO 3
<211> LENGTH: 16
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(16)
<223> OTHER INFORMATION: Disulfid bridge between Cys-1 and Cys-16

<400> SEQUENCE: 3

Cys Tyr Trp Tyr Tyr Ala Trp Asp Gln Thr Tyr Lys Ala Phe Pro Cys
1               5                   10                  15


<210> SEQ ID NO 4
<211> LENGTH: 15
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(15)
<223> OTHER INFORMATION: Disulfid bridge between Cys-1 and Cys-15

<400> SEQUENCE: 4

Cys Trp Tyr Tyr Ala Trp Asp Gln Thr Tyr Lys Ala Phe Pro Cys
1               5                   10                  15


<210> SEQ ID NO 5
<211> LENGTH: 18
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(18)
<223> OTHER INFORMATION: Disulfid bridge between Cys-1 and Cys-18

<400> SEQUENCE: 5

Cys Tyr Ile Ser Trp Asn Glu Phe Asn Ser Pro Asn Trp Arg Phe Ile
1               5                   10                  15

Thr Cys


<210> SEQ ID NO 6
<211> LENGTH: 17
<212> TYPE: PRT
<213> ORGANISM: Artificial Sequence
<220> FEATURE:
<223> OTHER INFORMATION: Met binding peptide
<220> FEATURE:
<221> NAME/KEY: DISULFID
<222> LOCATION: (1)..(17)
<223> OTHER INFORMATION: Disulfid bridge between Cys-1 and Cys-17
```

<400> SEQUENCE: 6

Cys Ile Ser Trp Asn Glu Phe Asn Ser Pro Asn Trp Arg Phe Ile Thr
1 5 10 15

Cys

<210> SEQ ID NO 7
<211> LENGTH: 20
<212> TYPE: PRT
<213> ORGANISM: Artificial Sequence
<220> FEATURE:
<223> OTHER INFORMATION: PAS Linker

<400> SEQUENCE: 7

Ala Ala Pro Ala Ala Pro Ala Pro Ala Ala Pro Ala Ala Pro Ala Pro
1 5 10 15

Ala Ala Pro Ala
20

<210> SEQ ID NO 8
<211> LENGTH: 22
<212> TYPE: PRT
<213> ORGANISM: Artificial Sequence
<220> FEATURE:
<223> OTHER INFORMATION: PAS Linker

<400> SEQUENCE: 8

Ala Ala Pro Ala Ala Pro Ala Pro Ala Ala Pro Ala Ala Pro Ala Pro
1 5 10 15

Ala Ala Pro Ala Ala Pro
20

<210> SEQ ID NO 9
<211> LENGTH: 14
<212> TYPE: PRT
<213> ORGANISM: Artificial Sequence
<220> FEATURE:
<223> OTHER INFORMATION: PAS Linker

<400> SEQUENCE: 9

Ala Ala Pro Ala Ala Pro Ala Pro Ala Ala Pro Ala Ala Pro
1 5 10

<210> SEQ ID NO 10
<211> LENGTH: 20
<212> TYPE: PRT
<213> ORGANISM: Artificial Sequence
<220> FEATURE:
<223> OTHER INFORMATION: PAS Linker

<400> SEQUENCE: 10

Ala Ala Pro Ala Ala Ala Pro Ala Pro Ala Ala Pro Ala Ala Pro Ala
1 5 10 15

Pro Ala Ala Pro
20

<210> SEQ ID NO 11
<211> LENGTH: 20
<212> TYPE: PRT
<213> ORGANISM: Artificial Sequence
<220> FEATURE:
<223> OTHER INFORMATION: PAS Linker

<400> SEQUENCE: 11

Ala Ala Ala Pro Ala Ala Ala Pro Ala Ala Ala Pro Ala Ala Ala Pro
1 5 10 15

Ala Ala Ala Pro
20

<210> SEQ ID NO 12
<211> LENGTH: 24
<212> TYPE: PRT
<213> ORGANISM: Artificial Sequence
<220> FEATURE:
<223> OTHER INFORMATION: PAS Linker

<400> SEQUENCE: 12

Ala Ala Pro Ala Ala Pro Ala Ala Pro Ala Ala Pro Ala Ala Pro Ala
1 5 10 15

Ala Pro Ala Ala Pro Ala Ala Pro
20

<210> SEQ ID NO 13
<211> LENGTH: 24
<212> TYPE: PRT
<213> ORGANISM: Artificial Sequence
<220> FEATURE:
<223> OTHER INFORMATION: PAS Linker

<400> SEQUENCE: 13

Ala Pro Ala Ala Ala Pro Ala Pro Ala Ala Ala Pro Ala Pro Ala Ala
1 5 10 15

Ala Pro Ala Pro Ala Ala Ala Pro
20

<210> SEQ ID NO 14
<211> LENGTH: 24
<212> TYPE: PRT
<213> ORGANISM: Artificial Sequence
<220> FEATURE:
<223> OTHER INFORMATION: PAS Linker

<400> SEQUENCE: 14

Ala Ala Ala Pro Ala Ala Pro Ala Ala Pro Pro Ala Ala Ala Ala Pro
1 5 10 15

Ala Ala Pro Ala Ala Pro Pro Ala
20

<210> SEQ ID NO 15
<211> LENGTH: 20
<212> TYPE: PRT
<213> ORGANISM: Artificial Sequence
<220> FEATURE:
<223> OTHER INFORMATION: PAS Linker

<400> SEQUENCE: 15

Ala Pro Ala Pro Ala Pro Ala Pro Ala Pro Ala Pro Ala Pro Ala Pro
1 5 10 15

Ala Pro Ala Pro
20

<210> SEQ ID NO 16
<211> LENGTH: 20
<212> TYPE: PRT
<213> ORGANISM: Artificial Sequence
<220> FEATURE:
<223> OTHER INFORMATION: PAS Linker

<400> SEQUENCE: 16

Ala Ser Pro Ala Ala Pro Ala Pro Ala Ser Pro Ala Ala Pro Ala Pro
1 5 10 15

Ser Ala Pro Ala
20

<210> SEQ ID NO 17
<211> LENGTH: 20
<212> TYPE: PRT
<213> ORGANISM: Artificial Sequence
<220> FEATURE:
<223> OTHER INFORMATION: PAS Linker

<400> SEQUENCE: 17

Ala Ala Pro Ala Ser Pro Ala Pro Ala Ala Pro Ser Ala Pro Ala Pro
1 5 10 15

Ala Ala Pro Ser
20

<210> SEQ ID NO 18
<211> LENGTH: 20
<212> TYPE: PRT
<213> ORGANISM: Artificial Sequence
<220> FEATURE:
<223> OTHER INFORMATION: PAS Linker

<400> SEQUENCE: 18

Ala Pro Ser Ser Pro Ser Pro Ser Ala Pro Ser Ser Pro Ser Pro Ala
1 5 10 15

Ser Pro Ser Ser
20

<210> SEQ ID NO 19
<211> LENGTH: 20
<212> TYPE: PRT
<213> ORGANISM: Artificial Sequence
<220> FEATURE:
<223> OTHER INFORMATION: PAS Linker

<400> SEQUENCE: 19

Ser Ala Pro Ser Ser Pro Ser Pro Ser Ala Pro Ser Ser Pro Ser Pro
1 5 10 15

Ala Ser Pro Ser
20

<210> SEQ ID NO 20
<211> LENGTH: 20
<212> TYPE: PRT
<213> ORGANISM: Artificial Sequence
<220> FEATURE:
<223> OTHER INFORMATION: PAS Linker

<400> SEQUENCE: 20

Ser Ser Pro Ser Ala Pro Ser Pro Ser Ser Pro Ala Ser Pro Ser Pro
1 5 10 15

Ser Ser Pro Ala
20

<210> SEQ ID NO 21
<211> LENGTH: 24
<212> TYPE: PRT
<213> ORGANISM: Artificial Sequence
<220> FEATURE:
<223> OTHER INFORMATION: PAS Linker

<400> SEQUENCE: 21

Ala Ala Ser Pro Ala Ala Pro Ser Ala Pro Pro Ala Ala Ala Ser Pro
1 5 10 15

Ala Ala Pro Ser Ala Pro Pro Ala
20

<210> SEQ ID NO 22
<211> LENGTH: 20
<212> TYPE: PRT
<213> ORGANISM: Artificial Sequence
<220> FEATURE:
<223> OTHER INFORMATION: PAS Linker

<400> SEQUENCE: 22

Ala Ser Ala Ala Ala Pro Ala Ala Ala Ser Ala Ala Ala Ser Ala Pro
1 5 10 15

Ser Ala Ala Ala
20

<210> SEQ ID NO 23
<211> LENGTH: 20
<212> TYPE: PRT
<213> ORGANISM: Artificial Sequence
<220> FEATURE:
<223> OTHER INFORMATION: PAS Linker

<400> SEQUENCE: 23

Ala Pro Ala Ala Pro Ala Pro Ala Ala Pro Ala Ala Pro Ala Pro Ala
1 5 10 15

Ala Pro Ala Ala
20

<210> SEQ ID NO 24
<211> LENGTH: 20
<212> TYPE: PRT
<213> ORGANISM: Artificial Sequence
<220> FEATURE:
<223> OTHER INFORMATION: PAS Linker

<400> SEQUENCE: 24

Pro Ala Ala Pro Ala Pro Ala Ala Pro Ala Ala Pro Ala Pro Ala Ala
1 5 10 15

Pro Ala Ala Ala
20

<210> SEQ ID NO 25
<211> LENGTH: 20
<212> TYPE: PRT
<213> ORGANISM: Artificial Sequence
<220> FEATURE:
<223> OTHER INFORMATION: PAS Linker

<400> SEQUENCE: 25

Ala Ala Pro Ala Pro Ala Ala Pro Ala Ala Pro Ala Pro Ala Ala Pro
1 5 10 15

Ala Ala Ala Pro
20

<210> SEQ ID NO 26
<211> LENGTH: 20
<212> TYPE: PRT
<213> ORGANISM: Artificial Sequence
<220> FEATURE:
<223> OTHER INFORMATION: PAS Linker

<400> SEQUENCE: 26

Ala Pro Ala Pro Ala Ala Pro Ala Ala Pro Ala Pro Ala Ala Pro Ala
1 5 10 15

Ala Ala Pro Ala
20

<210> SEQ ID NO 27
<211> LENGTH: 20
<212> TYPE: PRT
<213> ORGANISM: Artificial Sequence
<220> FEATURE:
<223> OTHER INFORMATION: PAS Linker

<400> SEQUENCE: 27

Pro Ala Pro Ala Ala Pro Ala Ala Pro Ala Pro Ala Ala Pro Ala Ala
1 5 10 15

Ala Pro Ala Ala
20

<210> SEQ ID NO 28
<211> LENGTH: 20
<212> TYPE: PRT
<213> ORGANISM: Artificial Sequence
<220> FEATURE:
<223> OTHER INFORMATION: PAS Linker

<400> SEQUENCE: 28

Ala Pro Ala Ala Pro Ala Ala Pro Ala Pro Ala Ala Pro Ala Ala Ala
1 5 10 15

Pro Ala Ala Pro
20

<210> SEQ ID NO 29
<211> LENGTH: 20
<212> TYPE: PRT
<213> ORGANISM: Artificial Sequence
<220> FEATURE:
<223> OTHER INFORMATION: PAS Linker

<400> SEQUENCE: 29

Pro Ala Ala Pro Ala Ala Pro Ala Pro Ala Ala Pro Ala Ala Ala Pro
1 5 10 15

Ala Ala Pro Ala
20

<210> SEQ ID NO 30
<211> LENGTH: 20
<212> TYPE: PRT
<213> ORGANISM: Artificial Sequence
<220> FEATURE:
<223> OTHER INFORMATION: PAS Linker

<400> SEQUENCE: 30

Ala Ala Pro Ala Ala Pro Ala Pro Ala Ala Pro Ala Ala Ala Pro Ala
1 5 10 15

Ala Pro Ala Pro
20

<210> SEQ ID NO 31
<211> LENGTH: 20
<212> TYPE: PRT
<213> ORGANISM: Artificial Sequence
<220> FEATURE:

<223> OTHER INFORMATION: PAS Linker

<400> SEQUENCE: 31

Ala Pro Ala Ala Pro Ala Pro Ala Ala Pro Ala Ala Ala Pro Ala Ala
1 5 10 15

Pro Ala Pro Ala
20

<210> SEQ ID NO 32
<211> LENGTH: 20
<212> TYPE: PRT
<213> ORGANISM: Artificial Sequence
<220> FEATURE:
<223> OTHER INFORMATION: PAS Linker

<400> SEQUENCE: 32

Pro Ala Ala Pro Ala Pro Ala Ala Pro Ala Ala Ala Pro Ala Ala Pro
1 5 10 15

Ala Pro Ala Ala
20

<210> SEQ ID NO 33
<211> LENGTH: 34
<212> TYPE: DNA
<213> ORGANISM: Artificial Sequence
<220> FEATURE:
<223> OTHER INFORMATION: Primer

<400> SEQUENCE: 33
tcagaggaat gtcgactgct cgcaaccggc ccgt 34

<210> SEQ ID NO 34
<211> LENGTH: 33
<212> TYPE: DNA
<213> ORGANISM: Artificial Sequence
<220> FEATURE:
<223> OTHER INFORMATION: Primer

<400> SEQUENCE: 34
cctacattca gcgcaggttc ccctagagca cgt 33

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
tgcgctgaat gtagggaag 19

<210> SEQ ID NO 36
<211> LENGTH: 34
<212> TYPE: DNA
<213> ORGANISM: Artificial Sequence
<220> FEATURE:
<223> OTHER INFORMATION: Primer

<400> SEQUENCE: 36
atcgctgcag gtcgactcta gaggatcccc ggaa 34

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
cttcccatac aatcgataga ttgtcgcacc tgattg 36

<210> SEQ ID NO 38
<211> LENGTH: 33
<212> TYPE: DNA
<213> ORGANISM: Artificial Sequence
<220> FEATURE:
<223> OTHER INFORMATION: Primer

<400> SEQUENCE: 38
cctcaggctg gtgttgggcg agctcgaatt cgt 33

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
aacaccagcc tgaggcaa 18

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
gatcttcggg actagttact ttcaaatgct cagcatg 37

<210> SEQ ID NO 41
<211> LENGTH: 58
<212> TYPE: PRT
<213> ORGANISM: Artificial Sequence
<220> FEATURE:
<223> OTHER INFORMATION: FBP-PAS
<220> FEATURE:
<221> NAME/KEY: DISULFID
<222> LOCATION: (4)..(15)
<223> OTHER INFORMATION: Disulfid bridge between Cys-4 and Cys-15
<220> FEATURE:
<221> NAME/KEY: DISULFID
<222> LOCATION: (44)..(55)
<223> OTHER INFORMATION: Disulfid bridge between Cys-44 and Cys-55

<400> SEQUENCE: 41

Arg Pro Gly Cys Gly Pro Arg Lys Pro Arg Thr Pro Lys Lys Cys Gly
1 5 10 15

Ser His Gly Ala Ala Pro Ala Ala Pro Ala Pro Ala Ala Pro Ala Ala
20 25 30

Pro Ala Pro Ala Ala Pro Ala Gly Arg Pro Gly Cys Gly Pro Arg Lys
35 40 45

Pro Arg Thr Pro Lys Lys Cys Gly Ser His
50 55

<210> SEQ ID NO 42
<211> LENGTH: 294
<212> TYPE: DNA
<213> ORGANISM: Artificial Sequence
<220> FEATURE:

<223> OTHER INFORMATION: TorAss-FBP-PAS

<400> SEQUENCE: 42
atgaacaata acgatctctt tcaggcatca cgtcggcgtt ttctggcaca actcggcggc 60
ttaaccgtcg ccgggatgct ggggccgtca ttgttaacgc cgcgacgtgc gactgcgcgt 120
cctggttgtg gtcctcgcaa gccccgcacc cctaagaaat gtggttctca cggcgccgct 180
cctgccgcac ccgcacccgc tgctccagca gccccagccc cagctgcacc agcaggtcgc 240
ccaggctgtg gtccccgcaa accccgcacc cctaagaaat gtggctctca ctaa 294

<210> SEQ ID NO 43
<211> LENGTH: 97
<212> TYPE: PRT
<213> ORGANISM: Artificial Sequence
<220> FEATURE:
<223> OTHER INFORMATION: TorAss-FBP-PAS
<220> FEATURE:
<221> NAME/KEY: DISULFID
<222> LOCATION: (43)..(54)
<223> OTHER INFORMATION: Disulfid bridge between Cys-43 and Cys-54
<220> FEATURE:
<221> NAME/KEY: DISULFID
<222> LOCATION: (83)..(94)
<223> OTHER INFORMATION: Disulfid bridge between Cys-83 and Cys-94

<400> SEQUENCE: 43

Met Asn Asn Asn Asp Leu Phe Gln Ala Ser Arg Arg Arg Phe Leu Ala
1 5 10 15

Gln Leu Gly Gly Leu Thr Val Ala Gly Met Leu Gly Pro Ser Leu Leu
20 25 30

Thr Pro Arg Arg Ala Thr Ala Arg Pro Gly Cys Gly Pro Arg Lys Pro
35 40 45

Arg Thr Pro Lys Lys Cys Gly Ser His Gly Ala Ala Pro Ala Ala Pro
50 55 60

Ala Pro Ala Ala Pro Ala Ala Pro Ala Pro Ala Ala Pro Ala Gly Arg
65 70 75 80

Pro Gly Cys Gly Pro Arg Lys Pro Arg Thr Pro Lys Lys Cys Gly Ser
85 90 95

His

<210> SEQ ID NO 44
<211> LENGTH: 58
<212> TYPE: PRT
<213> ORGANISM: Artificial Sequence
<220> FEATURE:
<223> OTHER INFORMATION: PAS-aMD4-PEG11
<220> FEATURE:
<221> NAME/KEY: DISULFID
<222> LOCATION: (1)..(17)
<223> OTHER INFORMATION: Disulfid bridge between Cys-1 and Cys-17
<220> FEATURE:
<221> NAME/KEY: DISULFID
<222> LOCATION: (42)..(58)
<223> OTHER INFORMATION: Disulfid bridge between Cys-42 and Cys-58

<400> SEQUENCE: 44

Cys Tyr Arg Gln Phe Asn Arg Arg Thr His Glu Val Trp Asn Leu Asp
1 5 10 15

Cys Gly Ala Ala Pro Ala Ala Pro Ala Pro Ala Ala Pro Ala Ala Pro
20 25 30

Ala Pro Ala Ala Pro Ala Ala Pro Gly Cys Tyr Arg Gln Phe Asn Arg
35 40 45

Arg Thr His Glu Val Trp Asn Leu Asp Cys
50 55

<210> SEQ ID NO 45
<211> LENGTH: 56
<212> TYPE: PRT
<213> ORGANISM: Artificial Sequence
<220> FEATURE:
<223> OTHER INFORMATION: PAS-aMD4dY-PEG11
<220> FEATURE:
<221> NAME/KEY: DISULFID
<222> LOCATION: (1)..(16)
<223> OTHER INFORMATION: Disulfid bridge between Cys-1 and Cys-16
<220> FEATURE:
<221> NAME/KEY: DISULFID
<222> LOCATION: (41)..(56)
<223> OTHER INFORMATION: Disulfid bridge between Cys-41 and Cys-56

<400> SEQUENCE: 45

Cys Arg Gln Phe Asn Arg Arg Thr His Glu Val Trp Asn Leu Asp Cys
1 5 10 15

Gly Ala Ala Pro Ala Ala Pro Ala Pro Ala Ala Pro Ala Ala Pro Ala
20 25 30

Pro Ala Ala Pro Ala Ala Pro Gly Cys Arg Gln Phe Asn Arg Arg Thr
35 40 45

His Glu Val Trp Asn Leu Asp Cys
50 55

<210> SEQ ID NO 46
<211> LENGTH: 50
<212> TYPE: PRT
<213> ORGANISM: Artificial Sequence
<220> FEATURE:
<223> OTHER INFORMATION: PAS-aMD4-PEG3
<220> FEATURE:
<221> NAME/KEY: DISULFID
<222> LOCATION: (1)..(17)
<223> OTHER INFORMATION: Disulfid bridge between Cys-1 and Cys-17
<220> FEATURE:
<221> NAME/KEY: DISULFID
<222> LOCATION: (34)..(50)
<223> OTHER INFORMATION: Disulfid bridge between Cys-34 and Cys-50

<400> SEQUENCE: 46

Cys Tyr Arg Gln Phe Asn Arg Arg Thr His Glu Val Trp Asn Leu Asp
1 5 10 15

Cys Gly Ala Ala Pro Ala Ala Pro Ala Pro Ala Ala Pro Ala Ala Pro
20 25 30

Gly Cys Tyr Arg Gln Phe Asn Arg Arg Thr His Glu Val Trp Asn Leu
35 40 45

Asp Cys
50

<210> SEQ ID NO 47
<211> LENGTH: 61
<212> TYPE: PRT
<213> ORGANISM: Artificial Sequence
<220> FEATURE:
<223> OTHER INFORMATION: AET-PAS-aMD4-PEG11
<220> FEATURE:
<221> NAME/KEY: DISULFID
<222> LOCATION: (4)..(20)
<223> OTHER INFORMATION: Disulfid bridge between Cys-4 and Cys-20
<220> FEATURE:
<221> NAME/KEY: DISULFID
<222> LOCATION: (45)..(61)
<223> OTHER INFORMATION: Disulfid bridge between Cys-45 and Cys-61

<400> SEQUENCE: 47

Ala Glu Thr Cys Tyr Arg Gln Phe Asn Arg Arg Thr His Glu Val Trp
1 5 10 15

Asn Leu Asp Cys Gly Ala Ala Pro Ala Ala Pro Ala Pro Ala Ala Pro
20 25 30

Ala Ala Pro Ala Pro Ala Ala Pro Ala Ala Pro Gly Cys Tyr Arg Gln
35 40 45

Phe Asn Arg Arg Thr His Glu Val Trp Asn Leu Asp Cys
50 55 60

<210> SEQ ID NO 48
<211> LENGTH: 59
<212> TYPE: PRT
<213> ORGANISM: Artificial Sequence
<220> FEATURE:
<223> OTHER INFORMATION: AET-PAS-aMD4dY-PEG11
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (44)..(59)
<223> OTHER INFORMATION: Disulfid bridge between Cys-44 and Cys-59

<400> SEQUENCE: 48

Ala Glu Thr Cys Arg Gln Phe Asn Arg Arg Thr His Glu Val Trp Asn
1 5 10 15

Leu Asp Cys Gly Ala Ala Pro Ala Ala Pro Ala Pro Ala Ala Pro Ala
20 25 30

Ala Pro Ala Pro Ala Ala Pro Ala Ala Pro Gly Cys Arg Gln Phe Asn
35 40 45

Arg Arg Thr His Glu Val Trp Asn Leu Asp Cys
50 55

<210> SEQ ID NO 49
<211> LENGTH: 53
<212> TYPE: PRT
<213> ORGANISM: Artificial Sequence
<220> FEATURE:
<223> OTHER INFORMATION: AET-PAS-aMD4-PEG3
<220> FEATURE:
<221> NAME/KEY: DISULFID
<222> LOCATION: (4)..(20)
<223> OTHER INFORMATION: Disulfid bridge between Cys-4 and Cys-20
<220> FEATURE:
<221> NAME/KEY: DISULFID
<222> LOCATION: (37)..(53)
<223> OTHER INFORMATION: Disulfid bridge between Cys-37 and Cys-53

<400> SEQUENCE: 49

Ala Glu Thr Cys Tyr Arg Gln Phe Asn Arg Arg Thr His Glu Val Trp
1 5 10 15

Asn Leu Asp Cys Gly Ala Ala Pro Ala Ala Pro Ala Pro Ala Ala Pro
20 25 30

Ala Ala Pro Gly Cys Tyr Arg Gln Phe Asn Arg Arg Thr His Glu Val
35 40 45

Trp Asn Leu Asp Cys
50

<210> SEQ ID NO 50
<211> LENGTH: 294
<212> TYPE: DNA
<213> ORGANISM: Artificial Sequence
<220> FEATURE:
<223> OTHER INFORMATION: TorAss-PAS-aMD4-PEG11

<400> SEQUENCE: 50
atgaacaata acgatctctt tcaggcatca cgtcggcgtt ttctggcaca actcggcggc 60
ttaaccgtcg ccgggatgct ggggccgtca ttgttaacgc cgcgacgtgc gactgcgtgt 120
taccgtcaat tcaaccgtcg cacccacgaa gtttggaacc tggactgtgg cgcagcaccc 180
gcagccccag cccccgcagc acctgcagcc ccagcaccag ctgcaccagc cgctccaggc 240
tgctaccgtc agttcaaccg ccgcacccac gaagtttgga atttggattg ctaa 294

<210> SEQ ID NO 51
<211> LENGTH: 97
<212> TYPE: PRT
<213> ORGANISM: Artificial Sequence
<220> FEATURE:
<223> OTHER INFORMATION: TorAss-PAS-aMD4-PEG11
<220> FEATURE:
<221> NAME/KEY: DISULFID
<222> LOCATION: (40)..(56)
<223> OTHER INFORMATION: Disulfid bridge between Cys-40 and Cys-56
<220> FEATURE:
<221> NAME/KEY: DISULFID
<222> LOCATION: (81)..(97)
<223> OTHER INFORMATION: Disulfid bridge between Cys-81 and Cys-97

<400> SEQUENCE: 51

Met Asn Asn Asn Asp Leu Phe Gln Ala Ser Arg Arg Arg Phe Leu Ala
1 5 10 15

Gln Leu Gly Gly Leu Thr Val Ala Gly Met Leu Gly Pro Ser Leu Leu
20 25 30

Thr Pro Arg Arg Ala Thr Ala Cys Tyr Arg Gln Phe Asn Arg Arg Thr
35 40 45

His Glu Val Trp Asn Leu Asp Cys Gly Ala Ala Pro Ala Ala Pro Ala
50 55 60

Pro Ala Ala Pro Ala Ala Pro Ala Pro Ala Ala Pro Ala Ala Pro Gly
65 70 75 80

Cys Tyr Arg Gln Phe Asn Arg Arg Thr His Glu Val Trp Asn Leu Asp
85 90 95

Cys

<210> SEQ ID NO 52
<211> LENGTH: 288
<212> TYPE: DNA
<213> ORGANISM: Artificial Sequence
<220> FEATURE:
<223> OTHER INFORMATION: TorAss-PAS-aMD4dY-PEG11

<400> SEQUENCE: 52
atgaacaata acgatctctt tcaggcatca cgtcggcgtt ttctggcaca actcggcggc 60
ttaaccgtcg ccgggatgct ggggccgtca ttgttaacgc cgcgacgtgc gactgcgtgc 120
cgtcagttca accgtcgcac ccacgaagtt tggaatctgg actgtggcgc agcccccgca 180
gcacccgctc ccgcagcacc cgcagctcca gcaccagcag ccccagcagc accaggctgc 240
cgccagttca accgtcgcac ccacgaagtt tggaatttgg attgttag 288

<210> SEQ ID NO 53
<211> LENGTH: 95
<212> TYPE: PRT
<213> ORGANISM: Artificial Sequence
<220> FEATURE:

<223> OTHER INFORMATION: TorAss-PAS-aMD4dY-PEG11
<220> FEATURE:
<221> NAME/KEY: DISULFID
<222> LOCATION: (40)..(55)
<223> OTHER INFORMATION: Disulfid bridge between Cys-40 and Cys-55
<220> FEATURE:
<221> NAME/KEY: DISULFID
<222> LOCATION: (80)..(95)
<223> OTHER INFORMATION: Disulfid bridge between Cys-80 and Cys-95

<400> SEQUENCE: 53

Met Asn Asn Asn Asp Leu Phe Gln Ala Ser Arg Arg Arg Phe Leu Ala
1 5 10 15

Gln Leu Gly Gly Leu Thr Val Ala Gly Met Leu Gly Pro Ser Leu Leu
20 25 30

Thr Pro Arg Arg Ala Thr Ala Cys Arg Gln Phe Asn Arg Arg Thr His
35 40 45

Glu Val Trp Asn Leu Asp Cys Gly Ala Ala Pro Ala Ala Pro Ala Pro
50 55 60

Ala Ala Pro Ala Ala Pro Ala Pro Ala Ala Pro Ala Ala Pro Gly Cys
65 70 75 80

Arg Gln Phe Asn Arg Arg Thr His Glu Val Trp Asn Leu Asp Cys
85 90 95

<210> SEQ ID NO 54
<211> LENGTH: 270
<212> TYPE: DNA
<213> ORGANISM: Artificial Sequence
<220> FEATURE:
<223> OTHER INFORMATION: TorAss-PAS-aMD4-PEG3

<400> SEQUENCE: 54
atgaacaata acgatctctt tcaggcatca cgtcggcgtt ttctggcaca actcggcggc 60
ttaaccgtcg ccgggatgct ggggccgtca ttgttaacgc cgcgacgtgc gactgcgtgt 120
taccgtcagt tcaaccgccg tacccacgaa gtctggaacc tggattgtgg tgccgccccc 180
gccgctcccg ctcccgccgc tccggcagcc cctggctgct accgtcagtt taaccgtcgc 240
acccacgaag tctggaacct ggattgctaa 270

<210> SEQ ID NO 55
<211> LENGTH: 89
<212> TYPE: PRT
<213> ORGANISM: Artificial Sequence
<220> FEATURE:
<223> OTHER INFORMATION: TorAss-PAS-aMD4-PEG3
<220> FEATURE:
<221> NAME/KEY: DISULFID
<222> LOCATION: (40)..(56)
<223> OTHER INFORMATION: Disulfid bridge between Cys-40 and Cys-56
<220> FEATURE:
<221> NAME/KEY: DISULFID
<222> LOCATION: (73)..(89)
<223> OTHER INFORMATION: Disulfid bridge between Cys-73 and Cys-89

<400> SEQUENCE: 55

Met Asn Asn Asn Asp Leu Phe Gln Ala Ser Arg Arg Arg Phe Leu Ala
1 5 10 15

Gln Leu Gly Gly Leu Thr Val Ala Gly Met Leu Gly Pro Ser Leu Leu
20 25 30

Thr Pro Arg Arg Ala Thr Ala Cys Tyr Arg Gln Phe Asn Arg Arg Thr
35 40 45

His Glu Val Trp Asn Leu Asp Cys Gly Ala Ala Pro Ala Ala Pro Ala
50 55 60

```
Pro Ala Ala Pro Ala Ala Pro Gly Cys Tyr Arg Gln Phe Asn Arg Arg
65                  70                  75                  80

Thr His Glu Val Trp Asn Leu Asp Cys
                85


<210> SEQ ID NO 56
<211> LENGTH: 276
<212> TYPE: DNA
<213> ORGANISM: Artificial Sequence
<220> FEATURE:
<223> OTHER INFORMATION: CspBss-AET-PAS-aMD4-PEG11

<400> SEQUENCE: 56

atgtttaaca accgtatccg cactgcagct ctcgctggtg caatcgcaat ctccaccgca      60

gcttccggcg tagctatccc agcattcgct gcagagacct gttaccgtca attcaaccgt     120

cgcacccacg aagtttggaa cctggactgt ggcgcagcac ccgcagcccc agcccccgca     180

gcacctgcag ccccagcacc agctgcacca gccgctccag gctgctaccg tcagttcaac     240

cgccgcaccc acgaagtttg gaatttggat tgctaa                               276


<210> SEQ ID NO 57
<211> LENGTH: 91
<212> TYPE: PRT
<213> ORGANISM: Artificial Sequence
<220> FEATURE:
<223> OTHER INFORMATION: CspBss-AET-PAS-aMD4-PEG11
<220> FEATURE:
<221> NAME/KEY: DISULFID
<222> LOCATION: (34)..(50)
<223> OTHER INFORMATION: Disulfid bridge between Cys-34 and Cys-50
<220> FEATURE:
<221> NAME/KEY: DISULFID
<222> LOCATION: (75)..(91)
<223> OTHER INFORMATION: Disulfid bridge between Cys-75 and Cys-91

<400> SEQUENCE: 57

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Tyr Arg Gln Phe Asn Arg Arg Thr His Glu Val Trp Asn Leu
        35                  40                  45

Asp Cys Gly Ala Ala Pro Ala Ala Pro Ala Pro Ala Ala Pro Ala Ala
    50                  55                  60

Pro Ala Pro Ala Ala Pro Ala Ala Pro Gly Cys Tyr Arg Gln Phe Asn
65                  70                  75                  80

Arg Arg Thr His Glu Val Trp Asn Leu Asp Cys
                85                  90


<210> SEQ ID NO 58
<211> LENGTH: 270
<212> TYPE: DNA
<213> ORGANISM: Artificial Sequence
<220> FEATURE:
<223> OTHER INFORMATION: CspBss-AET-PAS-aMD4dY-PEG11

<400> SEQUENCE: 58

atgtttaaca accgtatccg cactgcagct ctcgctggtg caatcgcaat ctccaccgca      60

gcttccggcg tagctatccc agcattcgct gcagagacct gccgtcagtt caaccgtcgc     120

acccacgaag tttggaatct ggactgtggc gcagcccccg cagcacccgc tcccgcagca     180
```

cccgcagctc cagcaccagc agccccagca gcaccaggct gccgccagtt caaccgtcgc 240
acccacgaag tttggaattt ggattgttag 270

<210> SEQ ID NO 59
<211> LENGTH: 89
<212> TYPE: PRT
<213> ORGANISM: Artificial Sequence
<220> FEATURE:
<223> OTHER INFORMATION: CspBss-AET-PAS-aMD4dY-PEG11
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (74)..(89)
<223> OTHER INFORMATION: Disulfid bridge between Cys-74 and Cys-89

<400> SEQUENCE: 59

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Ala Ala Pro Ala Ala Pro
    50                  55                  60

Ala Pro Ala Ala Pro Ala Ala Pro Gly Cys Arg Gln Phe Asn Arg Arg
65                  70                  75                  80

Thr His Glu Val Trp Asn Leu Asp Cys
                85
```

<210> SEQ ID NO 60
<211> LENGTH: 252
<212> TYPE: DNA
<213> ORGANISM: Artificial Sequence
<220> FEATURE:
<223> OTHER INFORMATION: CspBss-AET-PAS-aMD4-PEG3

<400> SEQUENCE: 60
atgtttaaca accgtatccg cactgcagct ctcgctggtg caatcgcaat ctccaccgca 60
gcttccggcg tagctatccc agcattcgct gcagagacct gttaccgtca gttcaaccgc 120
cgtacccacg aagtctggaa cctggattgt ggtgccgccc ccgccgctcc cgctcccgcc 180
gctccggcag cccctggctg ctaccgtcag tttaaccgtc gcacccacga agtctggaac 240
ctggattgct aa 252

<210> SEQ ID NO 61
<211> LENGTH: 83
<212> TYPE: PRT
<213> ORGANISM: Artificial Sequence
<220> FEATURE:
<223> OTHER INFORMATION: CspBss-AET-PAS-aMD4-PEG3
<220> FEATURE:
<221> NAME/KEY: DISULFID
<222> LOCATION: (34)..(50)
<223> OTHER INFORMATION: Disulfid bridge between Cys-34 and Cys-50
<220> FEATURE:
<221> NAME/KEY: DISULFID
<222> LOCATION: (67)..(83)
<223> OTHER INFORMATION: Disulfid bridge between Cys-67 and Cys-83

<400> SEQUENCE: 61

```
Met Phe Asn Asn Arg Ile Arg Thr Ala Ala Leu Ala Gly Ala Ile Ala
```

```
1               5                   10                  15

Ile Ser Thr Ala Ala Ser Gly Val Ala Ile Pro Ala Phe Ala Ala Glu
            20                  25                  30

Thr Cys Tyr Arg Gln Phe Asn Arg Arg Thr His Glu Val Trp Asn Leu
        35                  40                  45

Asp Cys Gly Ala Ala Pro Ala Ala Pro Ala Pro Ala Ala Pro Ala Ala
    50                  55                  60

Pro Gly Cys Tyr Arg Gln Phe Asn Arg Arg Thr His Glu Val Trp Asn
65                  70                  75                  80

Leu Asp Cys
```

<210> SEQ ID NO 62
<211> LENGTH: 60
<212> TYPE: PRT
<213> ORGANISM: Artificial Sequence
<220> FEATURE:
<223> OTHER INFORMATION: AET-PAS-aMD4_aMD5-PEG11
<220> FEATURE:
<221> NAME/KEY: DISULFID
<222> LOCATION: (4)..(20)
<223> OTHER INFORMATION: Disulfid bridge between Cys-4 and Cys-20
<220> FEATURE:
<221> NAME/KEY: DISULFID
<222> LOCATION: (45)..(60)
<223> OTHER INFORMATION: Disulfid bridge between Cys-45 and Cys-60

<400> SEQUENCE: 62

```
Ala Glu Thr Cys Tyr Arg Gln Phe Asn Arg Arg Thr His Glu Val Trp
1               5                   10                  15

Asn Leu Asp Cys Gly Ala Ala Pro Ala Ala Pro Ala Pro Ala Ala Pro
            20                  25                  30

Ala Ala Pro Ala Pro Ala Ala Pro Ala Ala Pro Gly Cys Tyr Trp Tyr
        35                  40                  45

Tyr Ala Trp Asp Gln Thr Tyr Lys Ala Phe Pro Cys
    50                  55                  60
```

<210> SEQ ID NO 63
<211> LENGTH: 273
<212> TYPE: DNA
<213> ORGANISM: Artificial Sequence
<220> FEATURE:
<223> OTHER INFORMATION: CspBss-AET-PAS-aMD4_aMD5-PEG11

<400> SEQUENCE: 63

```
atgtttaaca accgtatccg cactgcagct ctcgctggtg caatcgcaat ctccaccgca     60

gcttccggcg tagctatccc agcattcgct gcagagacct gttaccgtca gttcaaccgt    120

cgcacccacg aagtttggaa cctggattgt ggcgcagccc ccgcagcccc cgcacccgca    180

gcccctgcag ccccagcccc agctgcacca gcagcacctg gctgttactg gtattatgcg    240

tgggatcaga cctacaaagc gtttccgtgt tag                                 273
```

<210> SEQ ID NO 64
<211> LENGTH: 90
<212> TYPE: PRT
<213> ORGANISM: Artificial Sequence
<220> FEATURE:
<223> OTHER INFORMATION: CspBss-AET-PAS-aMD4_aMD5-PEG11
<220> FEATURE:
<221> NAME/KEY: DISULFID
<222> LOCATION: (34)..(50)
<223> OTHER INFORMATION: Disulfid bridge between Cys-34 and Cys-50
<220> FEATURE:
<221> NAME/KEY: DISULFID
<222> LOCATION: (75)..(90)
<223> OTHER INFORMATION: Disulfid bridge between Cys-75 and Cys-90

<400> SEQUENCE: 64

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Cys Tyr Arg Gln Phe Asn Arg Arg Thr His Glu Val Trp Asn Leu
35 40 45

Asp Cys Gly Ala Ala Pro Ala Ala Pro Ala Pro Ala Ala Pro Ala Ala
50 55 60

Pro Ala Pro Ala Ala Pro Ala Ala Pro Gly Cys Tyr Trp Tyr Tyr Ala
65 70 75 80

Trp Asp Gln Thr Tyr Lys Ala Phe Pro Cys
85 90

<210> SEQ ID NO 65
<211> LENGTH: 20
<212> TYPE: PRT
<213> ORGANISM: Artificial Sequence
<220> FEATURE:
<223> OTHER INFORMATION: EpoR binding peptide
<220> FEATURE:
<221> NAME/KEY: DISULFID
<222> LOCATION: (6)..(15)
<223> OTHER INFORMATION: Disulfid bridge between Cys-6 and Cys-15

<400> SEQUENCE: 65

Gly Gly Leu Tyr Ala Cys His Met Gly Pro Met Thr Trp Val Cys Gln
1 5 10 15

Pro Leu Arg Gly
20

<210> SEQ ID NO 66
<211> LENGTH: 17
<212> TYPE: PRT
<213> ORGANISM: Artificial Sequence
<220> FEATURE:
<223> OTHER INFORMATION: EpoR binding peptide
<220> FEATURE:
<221> NAME/KEY: DISULFID
<222> LOCATION: (1)..(17)
<223> OTHER INFORMATION: Disulfid bridge between Cys-1 and Cys-17

<400> SEQUENCE: 66

Cys Ile Ser Trp Asn Glu Phe Asn Ser Pro Asn Trp Arg Phe Ile Thr
1 5 10 15

Cys

<210> SEQ ID NO 67
<211> LENGTH: 14
<212> TYPE: PRT
<213> ORGANISM: Artificial Sequence
<220> FEATURE:
<223> OTHER INFORMATION: TPO recepter binding peptide

<400> SEQUENCE: 67

Ile Glu Gly Pro Thr Leu Arg Gln Trp Leu Ala Ala Arg Ala
1 5 10

<210> SEQ ID NO 68
<211> LENGTH: 18
<212> TYPE: PRT

```
<213> ORGANISM: Artificial Sequence
<220> FEATURE:
<223> OTHER INFORMATION: TPO receptor binding peptide
<220> FEATURE:
<221> NAME/KEY: DISULFID
<222> LOCATION: (3)..(16)
<223> OTHER INFORMATION: Disulfid bridge between Cys-3 and Cys-16

<400> SEQUENCE: 68

Gly Gly Cys Ala Asp Gly Pro Thr Leu Arg Glu Trp Ile Ser Phe Cys
1               5                   10                  15

Gly Gly


<210> SEQ ID NO 69
<211> LENGTH: 16
<212> TYPE: PRT
<213> ORGANISM: Artificial Sequence
<220> FEATURE:
<223> OTHER INFORMATION: TPO receptor binding peptide
<220> FEATURE:
<221> NAME/KEY: DISULFID
<222> LOCATION: (3)..(14)
<223> OTHER INFORMATION: Disulfid bridge between Cys-3 and Cys-14

<400> SEQUENCE: 69

Gly Gly Cys Thr Leu Arg Glu Trp Leu His Gly Gly Phe Cys Gly Gly
1               5                   10                  15


<210> SEQ ID NO 70
<211> LENGTH: 19
<212> TYPE: PRT
<213> ORGANISM: Artificial Sequence
<220> FEATURE:
<223> OTHER INFORMATION: TPO receptor binding peptide

<400> SEQUENCE: 70

Leu Ala Ile Glu Gly Pro Thr Leu Arg Gln Trp Leu His Gly Asn Gly
1               5                   10                  15

Arg Asp Thr


<210> SEQ ID NO 71
<211> LENGTH: 18
<212> TYPE: PRT
<213> ORGANISM: Artificial Sequence
<220> FEATURE:
<223> OTHER INFORMATION: VEGFR binding peptide
<220> FEATURE:
<221> NAME/KEY: DISULFID
<222> LOCATION: (6)..(13)
<223> OTHER INFORMATION: Disulfid bridge between Cys-6 and Cys-13

<400> SEQUENCE: 71

Ala Gly Pro Thr Trp Cys Glu Asp Asp Trp Tyr Tyr Cys Trp Leu Phe
1               5                   10                  15

Gly Thr


<210> SEQ ID NO 72
<211> LENGTH: 17
<212> TYPE: PRT
<213> ORGANISM: Artificial Sequence
<220> FEATURE:
<223> OTHER INFORMATION: VEGFR binding peptide
<220> FEATURE:
<221> NAME/KEY: DISULFID
<222> LOCATION: (2)..(12)
<223> OTHER INFORMATION: Disulfid bridge between Cys-2 and Cys-12

<400> SEQUENCE: 72
```

Val Cys Trp Glu Asp Ser Trp Gly Gly Glu Val Cys Trp Leu Phe Gly
1 5 10 15

Thr

<210> SEQ ID NO 73
<211> LENGTH: 17
<212> TYPE: PRT
<213> ORGANISM: Artificial Sequence
<220> FEATURE:
<223> OTHER INFORMATION: VEGFR binding peptide
<220> FEATURE:
<221> NAME/KEY: DISULFID
<222> LOCATION: (2)..(12)
<223> OTHER INFORMATION: Disulfid bridge between Cys-2 and Cys-12

<400> SEQUENCE: 73

Val Cys Trp Glu Asp Ser Trp Gly Gly Glu Val Cys Phe Arg Tyr Asp
1 5 10 15

Pro

<210> SEQ ID NO 74
<211> LENGTH: 8
<212> TYPE: PRT
<213> ORGANISM: Artificial Sequence
<220> FEATURE:
<223> OTHER INFORMATION: PAS Linker

<400> SEQUENCE: 74

Ala Ala Pro Ala Ala Pro Ala Pro
1 5

<210> SEQ ID NO 75
<211> LENGTH: 16
<212> TYPE: PRT
<213> ORGANISM: Artificial Sequence
<220> FEATURE:
<223> OTHER INFORMATION: PAS Linker

<400> SEQUENCE: 75

Ala Ala Pro Ala Ala Pro Ala Pro Ala Ala Pro Ala Ala Pro Ala Pro
1 5 10 15

<210> SEQ ID NO 76
<211> LENGTH: 49
<212> TYPE: PRT
<213> ORGANISM: Artificial Sequence
<220> FEATURE:
<223> OTHER INFORMATION: PAS Linker

<400> SEQUENCE: 76

Ala Ala Pro Ala Ala Pro Ala Pro Ala Ala Pro Ala Ala Pro Ala Pro
1 5 10 15

Ala Ala Pro Ala Ala Pro Ala Pro Ala Ala Pro Ala Ala Pro Ala Pro
20 25 30

Ala Ala Pro Ala Ala Pro Ala Pro Ala Ala Pro Ala Ala Pro Ala Pro
35 40 45

Ala

<210> SEQ ID NO 77
<211> LENGTH: 49
<212> TYPE: PRT
<213> ORGANISM: Artificial Sequence
<220> FEATURE:
<223> OTHER INFORMATION: PAS Linker

<400> SEQUENCE: 77

Ser Ala Pro Ser Pro Ser Ser Ala Pro Ala Ser Ala Ser Ala Pro Ala
1 5 10 15

Ser Pro Ala Ser Ala Ser Ala Ser Ala Ser Pro Ala Ser Ser Pro Ala
20 25 30

Ser Ala Ser Ser Ala Ser Pro Ala Ala Ser Ser Ala Ser Pro Ala Ser
35 40 45

Ser

<210> SEQ ID NO 78
<211> LENGTH: 100
<212> TYPE: PRT
<213> ORGANISM: Artificial Sequence
<220> FEATURE:
<223> OTHER INFORMATION: PAS Linker

<400> SEQUENCE: 78

Ala Ala Pro Ala Ala Pro Ala Pro Ala Ala Pro Ala Ala Pro Ala Pro
1 5 10 15

Ala Ala Pro Ala Ala Pro Ala Pro Ala Ala Pro Ala Ala Pro Ala Pro
20 25 30

Ala Ala Pro Ala Ala Pro Ala Pro Ala Ala Pro Ala Ala Pro Ala Pro
35 40 45

Ala Ala Pro Ala Ala Pro Ala Pro Ala Ala Pro Ala Ala Pro Ala Pro
50 55 60

Ala Ala Pro Ala Ala Pro Ala Pro Ala Ala Pro Ala Ala Pro Ala Pro
65 70 75 80

Ala Ala Pro Ala Ala Pro Ala Pro Ala Ala Pro Ala Ala Pro Ala Pro
85 90 95

Ala Ala Pro Ala
100

<210> SEQ ID NO 79
<211> LENGTH: 100
<212> TYPE: PRT
<213> ORGANISM: Artificial Sequence
<220> FEATURE:
<223> OTHER INFORMATION: PAS Linker

<400> SEQUENCE: 79

Ser Ala Pro Ser Pro Ser Ser Ala Pro Ala Ser Ala Ser Ala Pro Ala
1 5 10 15

Ser Pro Ala Ser Ala Ser Ala Ser Ala Ser Pro Ala Ser Ser Pro Ala
20 25 30

Ser Ala Ser Ser Ala Ser Pro Ala Ala Ser Ser Ala Ser Pro Ala Ser
35 40 45

Ser Ser Ala Ser Pro Ser Ala Pro Ala Ala Pro Ser Ala Ser Ala Ala
50 55 60

Pro Ser Ala Ser Pro Ala Ser Ser Ser Pro Ala Pro Ala Ser Ala Pro
65 70 75 80

Ser Pro Ala Ala Ala Ala Ser Ser Pro Ser Pro Ala Pro Ser Ser Ala
85 90 95

Ser Ser Ala Ala
100

<210> SEQ ID NO 80
<211> LENGTH: 200

<212> TYPE: PRT
<213> ORGANISM: Artificial Sequence
<220> FEATURE:
<223> OTHER INFORMATION: PAS Linker

<400> SEQUENCE: 80

```
Ala Ala Pro Ala Ala Pro Ala Pro Ala Ala Pro Ala Ala Pro Ala Pro
1               5                   10                  15

Ala Ala Pro Ala Ala Pro Ala Pro Ala Ala Pro Ala Ala Pro Ala Pro
            20                  25                  30

Ala Ala Pro Ala Ala Pro Ala Pro Ala Ala Pro Ala Ala Pro Ala Pro
        35                  40                  45

Ala Ala Pro Ala Ala Pro Ala Pro Ala Ala Pro Ala Ala Pro Ala Pro
    50                  55                  60

Ala Ala Pro Ala Ala Pro Ala Pro Ala Ala Pro Ala Ala Pro Ala Pro
65                  70                  75                  80

Ala Ala Pro Ala Ala Pro Ala Pro Ala Ala Pro Ala Ala Pro Ala Pro
                85                  90                  95

Ala Ala Pro Ala Ala Pro Ala Pro Ala Ala Pro Ala Ala Pro Ala Pro
            100                 105                 110

Ala Ala Pro Ala Ala Pro Ala Pro Ala Ala Pro Ala Ala Pro Ala Pro
        115                 120                 125

Ala Ala Pro Ala Ala Pro Ala Pro Ala Ala Pro Ala Ala Pro Ala Pro
    130                 135                 140

Ala Ala Pro Ala Ala Pro Ala Pro Ala Ala Pro Ala Ala Pro Ala Pro
145                 150                 155                 160

Ala Ala Pro Ala Ala Pro Ala Pro Ala Ala Pro Ala Ala Pro Ala Pro
                165                 170                 175

Ala Ala Pro Ala Ala Pro Ala Pro Ala Ala Pro Ala Ala Pro Ala Pro
            180                 185                 190

Ala Ala Pro Ala Ala Pro Ala Pro
        195                 200
```

<210> SEQ ID NO 81
<211> LENGTH: 45
<212> TYPE: PRT
<213> ORGANISM: Artificial Sequence
<220> FEATURE:
<223> OTHER INFORMATION: AET-aMD4dY-PAS8
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (30)..(45)
<223> OTHER INFORMATION: Disulfid bridge between Cys-30 and Cys-45

<400> SEQUENCE: 81

```
Ala Glu Thr Cys Arg Gln Phe Asn Arg Arg Thr His Glu Val Trp Asn
1               5                   10                  15

Leu Asp Cys Gly Ala Ala Pro Ala Ala Pro Ala Pro Gly Cys Arg Gln
            20                  25                  30

Phe Asn Arg Arg Thr His Glu Val Trp Asn Leu Asp Cys
        35                  40                  45
```

<210> SEQ ID NO 82
<211> LENGTH: 86
<212> TYPE: PRT
<213> ORGANISM: Artificial Sequence
<220> FEATURE:

<223> OTHER INFORMATION: AET-aMD4dY-PAS49
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (71)..(86)
<223> OTHER INFORMATION: Disulfid bridge between Cys-71 and Cys-86

<400> SEQUENCE: 82

```
Ala Glu Thr Cys Arg Gln Phe Asn Arg Arg Thr His Glu Val Trp Asn
1               5                   10                  15

Leu Asp Cys Gly Ala Ala Pro Ala Ala Pro Ala Pro Ala Ala Pro Ala
            20                  25                  30

Ala Pro Ala Pro Ala Ala Pro Ala Ala Pro Ala Pro Ala Ala Pro Ala
        35                  40                  45

Ala Pro Ala Pro Ala Ala Pro Ala Ala Pro Ala Pro Ala Ala Pro Ala
    50                  55                  60

Ala Pro Ala Pro Ala Gly Cys Arg Gln Phe Asn Arg Arg Thr His Glu
65                  70                  75                  80

Val Trp Asn Leu Asp Cys
                85
```

<210> SEQ ID NO 83
<211> LENGTH: 137
<212> TYPE: PRT
<213> ORGANISM: Artificial Sequence
<220> FEATURE:
<223> OTHER INFORMATION: AET-aMD4dY-PAS100
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (122)..(137)
<223> OTHER INFORMATION: Disulfid bridge between Cys-122 and Cys-137

<400> SEQUENCE: 83

```
Ala Glu Thr Cys Arg Gln Phe Asn Arg Arg Thr His Glu Val Trp Asn
1               5                   10                  15

Leu Asp Cys Gly Ala Ala Pro Ala Ala Pro Ala Pro Ala Ala Pro Ala
            20                  25                  30

Ala Pro Ala Pro Ala Ala Pro Ala Ala Pro Ala Pro Ala Ala Pro Ala
        35                  40                  45

Ala Pro Ala Pro Ala Ala Pro Ala Ala Pro Ala Pro Ala Ala Pro Ala
    50                  55                  60

Ala Pro Ala Pro Ala Ala Pro Ala Ala Pro Ala Pro Ala Ala Pro Ala
65                  70                  75                  80

Ala Pro Ala Pro Ala Ala Pro Ala Ala Pro Ala Pro Ala Ala Pro Ala
                85                  90                  95

Ala Pro Ala Pro Ala Ala Pro Ala Ala Pro Ala Pro Ala Ala Pro Ala
            100                 105                 110

Ala Pro Ala Pro Ala Ala Pro Ala Gly Cys Arg Gln Phe Asn Arg Arg
        115                 120                 125

Thr His Glu Val Trp Asn Leu Asp Cys
    130                 135
```

<210> SEQ ID NO 84
<211> LENGTH: 237
<212> TYPE: PRT

<213> ORGANISM: Artificial Sequence
<220> FEATURE:
<223> OTHER INFORMATION: AET-aMD4dY-PAS200
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (222)..(237)
<223> OTHER INFORMATION: Disulfid bridge between Cys-222 and Cys-237

<400> SEQUENCE: 84

Ala Glu Thr Cys Arg Gln Phe Asn Arg Arg Thr His Glu Val Trp Asn
1 5 10 15

Leu Asp Cys Gly Ala Ala Pro Ala Ala Pro Ala Pro Ala Ala Pro Ala
20 25 30

Ala Pro Ala Pro Ala Ala Pro Ala Ala Pro Ala Pro Ala Ala Pro Ala
35 40 45

Ala Pro Ala Pro Ala Ala Pro Ala Ala Pro Ala Pro Ala Ala Pro Ala
50 55 60

Ala Pro Ala Pro Ala Ala Pro Ala Ala Pro Ala Pro Ala Ala Pro Ala
65 70 75 80

Ala Pro Ala Pro Ala Ala Pro Ala Ala Pro Ala Pro Ala Ala Pro Ala
85 90 95

Ala Pro Ala Pro Ala Ala Pro Ala Ala Pro Ala Pro Ala Ala Pro Ala
100 105 110

Ala Pro Ala Pro Ala Ala Pro Ala Ala Pro Ala Pro Ala Ala Pro Ala
115 120 125

Ala Pro Ala Pro Ala Ala Pro Ala Ala Pro Ala Pro Ala Ala Pro Ala
130 135 140

Ala Pro Ala Pro Ala Ala Pro Ala Ala Pro Ala Pro Ala Ala Pro Ala
145 150 155 160

Ala Pro Ala Pro Ala Ala Pro Ala Ala Pro Ala Pro Ala Ala Pro Ala
165 170 175

Ala Pro Ala Pro Ala Ala Pro Ala Ala Pro Ala Pro Ala Ala Pro Ala
180 185 190

Ala Pro Ala Pro Ala Ala Pro Ala Ala Pro Ala Pro Ala Ala Pro Ala
195 200 205

Ala Pro Ala Pro Ala Ala Pro Ala Ala Pro Ala Pro Gly Cys Arg Gln
210 215 220

Phe Asn Arg Arg Thr His Glu Val Trp Asn Leu Asp Cys
225 230 235

<210> SEQ ID NO 85
<211> LENGTH: 52
<212> TYPE: PRT
<213> ORGANISM: Artificial Sequence
<220> FEATURE:
<223> OTHER INFORMATION: AET-aMD4dY-GS15
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (37)..(52)
<223> OTHER INFORMATION: Disulfid bridge between Cys-37 and Cys-52

<400> SEQUENCE: 85

Ala Glu Thr Cys Arg Gln Phe Asn Arg Arg Thr His Glu Val Trp Asn
1 5 10 15

Leu Asp Cys Gly Gly Gly Gly Gly Ser Gly Gly Gly Gly Ser Gly Gly
            20                  25                  30

Gly Gly Ser Gly Cys Arg Gln Phe Asn Arg Arg Thr His Glu Val Trp
        35                  40                  45

Asn Leu Asp Cys
    50

<210> SEQ ID NO 86
<211> LENGTH: 59
<212> TYPE: PRT
<213> ORGANISM: Artificial Sequence
<220> FEATURE:
<223> OTHER INFORMATION: AET-aMD4dY-GS22
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (44)..(59)
<223> OTHER INFORMATION: Disulfid bridge between Cys-44 and Cys-59

<400> SEQUENCE: 86

Ala Glu Thr Cys Arg Gln Phe Asn Arg Arg Thr His Glu Val Trp Asn
1               5                   10                  15

Leu Asp Cys Gly Gly Gly Gly Gly Ser Gly Gly Gly Gly Ser Gly Gly
            20                  25                  30

Gly Gly Ser Gly Gly Gly Gly Ser Gly Gly Gly Cys Arg Gln Phe Asn
        35                  40                  45

Arg Arg Thr His Glu Val Trp Asn Leu Asp Cys
    50                  55

<210> SEQ ID NO 87
<211> LENGTH: 228
<212> TYPE: DNA
<213> ORGANISM: Artificial Sequence
<220> FEATURE:
<223> OTHER INFORMATION: CspBss-AET-aMD4dY-PAS8

<400> SEQUENCE: 87
atgtttaaca accgtatccg cactgcagct ctcgctggtg caatcgcaat ctccaccgca 60
gcttccggcg tagctatccc agcattcgct gcagagacct gccgccagtt caaccgccgc 120
acccacgaag tgtggaacct ggattgcggc gctgcaccag ccgctccagc accaggctgc 180
cgccagttca accgccgcac ccacgaagtg tggaacctgg attgctaa 228

<210> SEQ ID NO 88
<211> LENGTH: 75
<212> TYPE: PRT
<213> ORGANISM: Artificial Sequence
<220> FEATURE:
<223> OTHER INFORMATION: CspBss-AET-aMD4dY-PAS8
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (60)..(75)
<223> OTHER INFORMATION: Disulfid bridge between Cys-60 and Cys-75

<400> SEQUENCE: 88

Met Phe Asn Asn Arg Ile Arg Thr Ala Ala Leu Ala Gly Ala Ile Ala
1               5                   10                  15

```
Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Gly Cys Arg Gln Phe Asn
    50                  55                  60

Arg Arg Thr His Glu Val Trp Asn Leu Asp Cys
65                  70                  75


<210> SEQ ID NO 89
<211> LENGTH: 351
<212> TYPE: DNA
<213> ORGANISM: Artificial Sequence
<220> FEATURE:
<223> OTHER INFORMATION: CspBss-AET-aMD4dY-PAS49

<400> SEQUENCE: 89

atgtttaaca accgtatccg cactgcagct ctcgctggtg caatcgcaat ctccaccgca     60

gcttccggcg tagctatccc agcattcgct gcagagacct gtcgtcagtt caaccgtcgc    120

acccacgaag tttggaattt ggactgtggc gcagcaccag cggcaccagc accagcagcc    180

ccagcggcac cagccccagc tgcaccagcc gctccagcac cagcagcacc cgcagccccc    240

gctcccgcag cccccgccgc accagcaccc gcagcaccag cagcacccgc tccagcaggt    300

tgtcgccaat tcaaccgccg cacccacgaa gtgtggaacc tggattgcta a             351


<210> SEQ ID NO 90
<211> LENGTH: 116
<212> TYPE: PRT
<213> ORGANISM: Artificial Sequence
<220> FEATURE:
<223> OTHER INFORMATION: CspBss-AET-aMD4dY-PAS49
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (101)..(116)
<223> OTHER INFORMATION: Disulfid bridge between Cys-101 and Cys-116

<400> SEQUENCE: 90

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Ala Ala Pro Ala Ala Pro
    50                  55                  60

Ala Pro Ala Ala Pro Ala Ala Pro Ala Pro Ala Ala Pro Ala Ala Pro
65                  70                  75                  80

Ala Pro Ala Ala Pro Ala Ala Pro Ala Pro Ala Ala Pro Ala Ala Pro
                85                  90                  95

Ala Pro Ala Gly Cys Arg Gln Phe Asn Arg Arg Thr His Glu Val Trp
            100                 105                 110

Asn Leu Asp Cys
        115


<210> SEQ ID NO 91
<211> LENGTH: 504
```

<212> TYPE: DNA
<213> ORGANISM: Artificial Sequence
<220> FEATURE:
<223> OTHER INFORMATION: CspBss-AET-aMD4dY-PAS100

<400> SEQUENCE: 91

```
atgtttaaca accgtatccg cactgcagct ctcgctggtg caatcgcaat ctccaccgca      60

gcttccggcg tagctatccc agcattcgct gcagagacct gtcgtcagtt caaccgtcgc     120

acccacgaag tttggaattt ggactgtggc gcagcaccag cggcaccagc accagcagcc     180

ccagcggcac cagccccagc tgcaccagcc gctccagcac cagcagcccc agcagccccc     240

gctccagcag cacccgcagc accagctccc gcagccccag cagccccagc cccagcagca     300

ccagcagccc cagctccagc agccccagct gcaccagctc cagccgcacc agcagctcca     360

gccccagccg ctcccgccgc cccagccccc gccgcaccag ccgcccctgc tcccgccgcc     420

ccagccgctc ccgctccagc cgctcctgcc ggttgccgcc agttcaaccg ccgcacccac     480

gaagtgtgga acctggattg ctaa                                            504
```

<210> SEQ ID NO 92
<211> LENGTH: 167
<212> TYPE: PRT
<213> ORGANISM: Artificial Sequence
<220> FEATURE:
<223> OTHER INFORMATION: CspBss-AET-aMD4dY-PAS100
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (152)..(167)
<223> OTHER INFORMATION: Disulfid bridge between Cys-152 and Cys-167

<400> SEQUENCE: 92

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Ala Ala Pro Ala Ala Pro
    50                  55                  60

Ala Pro Ala Ala Pro Ala Ala Pro Ala Pro Ala Ala Pro Ala Ala Pro
65                  70                  75                  80

Ala Pro Ala Ala Pro Ala Ala Pro Ala Pro Ala Ala Pro Ala Ala Pro
                85                  90                  95

Ala Pro Ala Ala Pro Ala Ala Pro Ala Pro Ala Ala Pro Ala Ala Pro
            100                 105                 110

Ala Pro Ala Ala Pro Ala Ala Pro Ala Pro Ala Ala Pro Ala Ala Pro
        115                 120                 125

Ala Pro Ala Ala Pro Ala Ala Pro Ala Pro Ala Ala Pro Ala Ala Pro
    130                 135                 140

Ala Pro Ala Ala Pro Ala Gly Cys Arg Gln Phe Asn Arg Arg Thr His
145                 150                 155                 160

Glu Val Trp Asn Leu Asp Cys
                165
```

<210> SEQ ID NO 93
<211> LENGTH: 804

<212> TYPE: DNA
<213> ORGANISM: Artificial Sequence
<220> FEATURE:
<223> OTHER INFORMATION: CspBss-AET-aMD4dY-PAS200

<400> SEQUENCE: 93
atgtttaaca accgtatccg cactgcagct ctcgctggtg caatcgcaat ctccaccgca 60
gcttccggcg tagctatccc agcattcgct gcagagacct gtcgtcagtt caaccgtcgc 120
acccacgaag tttggaattt ggactgtggc gcagcaccag cggcaccagc accagcagcc 180
ccagcggcac cagccccagc tgcaccagcc gctccagcac cagccgcccc cgccgccccc 240
gcccctgctg ctcctgctgc tcccgctccc gctgctcccg ctgcccctgc tcctgctgct 300
cccgctgcgc cagccccagc agcaccagct gccccagcac cagctgcacc agccgcacca 360
gctccagcag ccccagctgc tccagcacca gcagcaccag cagcaccagc tccagcggca 420
ccagcagcac cagcacctgc ggcaccagcg gctccagccc cagcagcacc agcagcgcca 480
gcaccagcag ctccagcagc accagcacca gcagcaccag cggcaccagc cccagctgca 540
ccagccgctc cagcaccagc tgccccagca gctccagccc cagccgcacc tgccgcacct 600
gcccctgccg ctcctgctgc cccgctcct gccgctcctg ctgcccctgc ccctgctgct 660
cctgctgctc cagctccagc cgcaccagcc gctccagcac cagctgcacc agcagctcca 720
gccccagctg ccccagcagc tccagcccct ggttgccgcc aatttaatcg ccgcacccac 780
gaggtctgga atcttgactg ctaa 804

<210> SEQ ID NO 94
<211> LENGTH: 267
<212> TYPE: PRT
<213> ORGANISM: Artificial Sequence
<220> FEATURE:
<223> OTHER INFORMATION: CspBss-AET-aMD4dY-PAS200
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (252)..(267)
<223> OTHER INFORMATION: Disulfid bridge between Cys-252 and Cys-267

<400> SEQUENCE: 94

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Cys Arg Gln Phe Asn Arg Arg Thr His Glu Val Trp Asn Leu Asp
35 40 45

Cys Gly Ala Ala Pro Ala Ala Pro Ala Pro Ala Ala Pro Ala Ala Pro
50 55 60

Ala Pro Ala Ala Pro Ala Ala Pro Ala Pro Ala Ala Pro Ala Ala Pro
65 70 75 80

Ala Pro Ala Ala Pro Ala Ala Pro Ala Pro Ala Ala Pro Ala Ala Pro
85 90 95

Ala Pro Ala Ala Pro Ala Ala Pro Ala Pro Ala Ala Pro Ala Ala Pro
100 105 110

Ala Pro Ala Ala Pro Ala Ala Pro Ala Pro Ala Ala Pro Ala Ala Pro
115 120 125

Ala Pro Ala Ala Pro Ala Ala Pro Ala Pro Ala Ala Pro Ala Ala Pro
130 135 140

Ala Pro Ala Ala Pro Ala Ala Pro Ala Pro Ala Ala Pro Ala Ala Pro
145 150 155 160

Ala Pro Ala Ala Pro Ala Ala Pro Ala Pro Ala Ala Pro Ala Ala Pro
165 170 175

Ala Pro Ala Ala Pro Ala Ala Pro Ala Pro Ala Ala Pro Ala Ala Pro
180 185 190

Ala Pro Ala Ala Pro Ala Ala Pro Ala Pro Ala Ala Pro Ala Ala Pro
195 200 205

Ala Pro Ala Ala Pro Ala Ala Pro Ala Pro Ala Ala Pro Ala Ala Pro
210 215 220

Ala Pro Ala Ala Pro Ala Ala Pro Ala Pro Ala Ala Pro Ala Ala Pro
225 230 235 240

Ala Pro Ala Ala Pro Ala Ala Pro Ala Pro Gly Cys Arg Gln Phe Asn
245 250 255

Arg Arg Thr His Glu Val Trp Asn Leu Asp Cys
260 265

<210> SEQ ID NO 95
<211> LENGTH: 249
<212> TYPE: DNA
<213> ORGANISM: Artificial Sequence
<220> FEATURE:
<223> OTHER INFORMATION: CspBss-AET-aMD4dY-GS15

<400> SEQUENCE: 95
atgtttaaca accgtatccg cactgcagct ctcgctggtg caatcgcaat ctccaccgca 60
gcttccggcg tagctatccc agcattcgct gcagagacct gccgccagtt caaccgccgc 120
acccacgaag tgtggaacct ggattgcggc ggcggcggcg gctccggcgg cggcggctcc 180
ggcggcggcg gctccggctg ccgccagttc aaccgccgca cccacgaagt gtggaacctg 240
gattgctaa 249

<210> SEQ ID NO 96
<211> LENGTH: 82
<212> TYPE: PRT
<213> ORGANISM: Artificial Sequence
<220> FEATURE:
<223> OTHER INFORMATION: CspBss-AET-aMD4dY-GS15
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (67)..(82)
<223> OTHER INFORMATION: Disulfid bridge between Cys-67 and Cys-82

<400> SEQUENCE: 96

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Cys Arg Gln Phe Asn Arg Arg Thr His Glu Val Trp Asn Leu Asp
35 40 45

Cys Gly Gly Gly Gly Gly Ser Gly Gly Gly Gly Ser Gly Gly Gly Gly
50 55 60

Ser Gly Cys Arg Gln Phe Asn Arg Arg Thr His Glu Val Trp Asn Leu
65 70 75 80

Asp Cys

<210> SEQ ID NO 97
<211> LENGTH: 270
<212> TYPE: DNA
<213> ORGANISM: Artificial Sequence
<220> FEATURE:
<223> OTHER INFORMATION: CspBss-AET-aMD4dY-GS22

<400> SEQUENCE: 97
atgtttaaca accgtatccg cactgcagct ctcgctggtg caatcgcaat ctccaccgca 60
gcttccggcg tagctatccc agcattcgct gcagagacct gccgccagtt caaccgccgc 120
acccacgaag tgtggaacct ggattgcggc ggcggcggcg gctccggcgg cggcggttct 180
ggcggtggcg gttctggcgg cggcggttct ggcggcggtt gtcgtcagtt caatcgtcgc 240
acccacgaag tctggaatct cgactgctaa 270

<210> SEQ ID NO 98
<211> LENGTH: 89
<212> TYPE: PRT
<213> ORGANISM: Artificial Sequence
<220> FEATURE:
<223> OTHER INFORMATION: CspBss-AET-aMD4dY-GS22
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (74)..(89)
<223> OTHER INFORMATION: Disulfid bridge between Cys-74 and Cys-89

<400> SEQUENCE: 98

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Cys Arg Gln Phe Asn Arg Arg Thr His Glu Val Trp Asn Leu Asp
35 40 45

Cys Gly Gly Gly Gly Gly Ser Gly Gly Gly Gly Ser Gly Gly Gly Gly
50 55 60

Ser Gly Gly Gly Gly Ser Gly Gly Gly Cys Arg Gln Phe Asn Arg Arg
65 70 75 80

Thr His Glu Val Trp Asn Leu Asp Cys
85

<210> SEQ ID NO 99
<211> LENGTH: 259
<212> TYPE: PRT
<213> ORGANISM: Artificial Sequence
<220> FEATURE:
<223> OTHER INFORMATION: AET-aMD4dY-PAS22-PAS200
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (44)..(59)
<223> OTHER INFORMATION: Disulfid bridge between Cys-44 and Cys-59

<400> SEQUENCE: 99

Ala Glu Thr Cys Arg Gln Phe Asn Arg Arg Thr His Glu Val Trp Asn
1 5 10 15

Leu Asp Cys Gly Ala Ala Pro Ala Ala Pro Ala Pro Ala Ala Pro Ala

```
            20                  25                  30

Ala Pro Ala Pro Ala Ala Pro Ala Ala Pro Gly Cys Arg Gln Phe Asn
        35                  40                  45

Arg Arg Thr His Glu Val Trp Asn Leu Asp Cys Ala Ala Pro Ala Ala
    50                  55                  60

Pro Ala Pro Ala Ala Pro Ala Ala Pro Ala Pro Ala Ala Pro Ala Ala
65                  70                  75                  80

Pro Ala Pro Ala Ala Pro Ala Ala Pro Ala Pro Ala Ala Pro Ala Ala
                85                  90                  95

Pro Ala Pro Ala Ala Pro Ala Ala Pro Ala Pro Ala Ala Pro Ala Ala
            100                 105                 110

Pro Ala Pro Ala Ala Pro Ala Ala Pro Ala Pro Ala Ala Pro Ala Ala
        115                 120                 125

Pro Ala Pro Ala Ala Pro Ala Ala Pro Ala Pro Ala Ala Pro Ala Ala
    130                 135                 140

Pro Ala Pro Ala Ala Pro Ala Ala Pro Ala Pro Ala Ala Pro Ala Ala
145                 150                 155                 160

Pro Ala Pro Ala Ala Pro Ala Ala Pro Ala Pro Ala Ala Pro Ala Ala
                165                 170                 175

Pro Ala Pro Ala Ala Pro Ala Ala Pro Ala Pro Ala Ala Pro Ala Ala
            180                 185                 190

Pro Ala Pro Ala Ala Pro Ala Ala Pro Ala Pro Ala Ala Pro Ala Ala
        195                 200                 205

Pro Ala Pro Ala Ala Pro Ala Ala Pro Ala Pro Ala Ala Pro Ala Ala
    210                 215                 220

Pro Ala Pro Ala Ala Pro Ala Ala Pro Ala Pro Ala Ala Pro Ala Ala
225                 230                 235                 240

Pro Ala Pro Ala Ala Pro Ala Ala Pro Ala Pro Ala Ala Pro Ala Ala
                245                 250                 255

Pro Ala Pro


<210> SEQ ID NO 100
<211> LENGTH: 870
<212> TYPE: DNA
<213> ORGANISM: Artificial Sequence
<220> FEATURE:
<223> OTHER INFORMATION: CspBss-AET-aMD4dY-PAS22-PAS200

<400> SEQUENCE: 100

atgtttaaca accgtatccg cactgcagct ctcgctggtg caatcgcaat ctccaccgca      60

gcttccggcg tagctatccc agcattcgct gcagagacct gccgtcagtt caaccgccgt     120

acccacgaag tttggaatct cgactgtggt gccgcccctg ccgctcctgc ccctgccgcc     180

ccagccgctc cagcaccagc cgctccagca gccccaggct gccgccagtt caaccgccgc     240

acccacgaag tgtggaacct ggattgcgca gctccagcag cccctgcccc cgccgcccca     300

gccgcccctg cccccgccgc ccccgccgca cccgcccctg ccgcccccgc cgcccccgcc     360

cctgctgctc ctgctgctcc cgctcccgct gctcccgctg cccctgctcc tgctgctccc     420

gctgcgccag ccccagcagc accagctgcc ccagcaccag ctgcaccagc cgcaccagct     480

ccagcagccc cagctgctcc agcaccagca gcaccagcag caccagctcc agcggcacca     540

gcagcaccag cacctgcggc accagcggct ccagccccag cagcaccagc agcgccagca     600

ccagcagctc cagcagcacc agcaccagca gcaccagcgg caccagcccc agctgcacca     660

gccgctccag caccagctgc cccagcagct ccagccccag ctgcccctgc tgcccccgct     720
```

```
cctgccgctc ccgctgcccc tgcccctgct gctcctgctg ctcccgctcc tgccgctccc    780

gctgcgccag ctccagcagc cccagctgca ccagccccag ccgcaccagc cgccccagcc    840

cccgcagcac ccgcagcacc agccccataa                                      870


<210> SEQ ID NO 101
<211> LENGTH: 289
<212> TYPE: PRT
<213> ORGANISM: Artificial Sequence
<220> FEATURE:
<223> OTHER INFORMATION: CspBss-AET-aMD4dY-PAS22-PAS200
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (74)..(89)
<223> OTHER INFORMATION: Disulfid bridge between Cys-74 and Cys-89

<400> SEQUENCE: 101

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Ala Ala Pro Ala Ala Pro
    50                  55                  60

Ala Pro Ala Ala Pro Ala Ala Pro Gly Cys Arg Gln Phe Asn Arg Arg
65                  70                  75                  80

Thr His Glu Val Trp Asn Leu Asp Cys Ala Ala Pro Ala Ala Pro Ala
                85                  90                  95

Pro Ala Ala Pro Ala Ala Pro Ala Pro Ala Ala Pro Ala Ala Pro Ala
            100                 105                 110

Pro Ala Ala Pro Ala Ala Pro Ala Pro Ala Ala Pro Ala Ala Pro Ala
        115                 120                 125

Pro Ala Ala Pro Ala Ala Pro Ala Pro Ala Ala Pro Ala Ala Pro Ala
    130                 135                 140

Pro Ala Ala Pro Ala Ala Pro Ala Pro Ala Ala Pro Ala Ala Pro Ala
145                 150                 155                 160

Pro Ala Ala Pro Ala Ala Pro Ala Pro Ala Ala Pro Ala Ala Pro Ala
                165                 170                 175

Pro Ala Ala Pro Ala Ala Pro Ala Pro Ala Ala Pro Ala Ala Pro Ala
            180                 185                 190

Pro Ala Ala Pro Ala Ala Pro Ala Pro Ala Ala Pro Ala Ala Pro Ala
        195                 200                 205

Pro Ala Ala Pro Ala Ala Pro Ala Pro Ala Ala Pro Ala Ala Pro Ala
    210                 215                 220

Pro Ala Ala Pro Ala Ala Pro Ala Pro Ala Ala Pro Ala Ala Pro Ala
225                 230                 235                 240

Pro Ala Ala Pro Ala Ala Pro Ala Pro Ala Ala Pro Ala Ala Pro Ala
                245                 250                 255

Pro Ala Ala Pro Ala Ala Pro Ala Pro Ala Ala Pro Ala Ala Pro Ala
            260                 265                 270

Pro Ala Ala Pro Ala Ala Pro Ala Pro Ala Ala Pro Ala Ala Pro Ala
        275                 280                 285
```

Pro

<210> SEQ ID NO 102
<211> LENGTH: 48
<212> TYPE: PRT
<213> ORGANISM: Artificial Sequence
<220> FEATURE:
<223> OTHER INFORMATION: EPO-PAS8
<220> FEATURE:
<221> NAME/KEY: DISULFID
<222> LOCATION: (6)..(15)
<223> OTHER INFORMATION: Disulfid bridge between Cys-6 and Cys-15
<220> FEATURE:
<221> NAME/KEY: DISULFID
<222> LOCATION: (34)..(43)
<223> OTHER INFORMATION: Disulfid bridge between Cys-34 and Cys-43

<400> SEQUENCE: 102

```
Gly Gly Leu Tyr Ala Cys His Met Gly Pro Met Thr Trp Val Cys Gln
1               5                   10                  15

Pro Leu Arg Gly Ala Ala Pro Ala Ala Pro Ala Pro Gly Gly Leu Tyr
            20                  25                  30

Ala Cys His Met Gly Pro Met Thr Trp Val Cys Gln Pro Leu Arg Gly
        35                  40                  45
```

<210> SEQ ID NO 103
<211> LENGTH: 62
<212> TYPE: PRT
<213> ORGANISM: Artificial Sequence
<220> FEATURE:
<223> OTHER INFORMATION: EPO-PAS22
<220> FEATURE:
<221> NAME/KEY: DISULFID
<222> LOCATION: (6)..(15)
<223> OTHER INFORMATION: Disulfid bridge between Cys-6 and Cys-15
<220> FEATURE:
<221> NAME/KEY: DISULFID
<222> LOCATION: (48)..(57)
<223> OTHER INFORMATION: Disulfid bridge between Cys-48 and Cys-57

<400> SEQUENCE: 103

```
Gly Gly Leu Tyr Ala Cys His Met Gly Pro Met Thr Trp Val Cys Gln
1               5                   10                  15

Pro Leu Arg Gly Ala Ala Pro Ala Ala Pro Ala Pro Ala Ala Pro Ala
            20                  25                  30

Ala Pro Ala Pro Ala Ala Pro Ala Ala Pro Gly Gly Leu Tyr Ala Cys
        35                  40                  45

His Met Gly Pro Met Thr Trp Val Cys Gln Pro Leu Arg Gly
    50                  55                  60
```

<210> SEQ ID NO 104
<211> LENGTH: 51
<212> TYPE: PRT
<213> ORGANISM: Artificial Sequence
<220> FEATURE:
<223> OTHER INFORMATION: AET-EPO-PAS8
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (37)..(46)
<223> OTHER INFORMATION: Disulfid bridge between Cys-37 and Cys-46

<400> SEQUENCE: 104

```
Ala Glu Thr Gly Gly Leu Tyr Ala Cys His Met Gly Pro Met Thr Trp
1               5                   10                  15
```

```
Val Cys Gln Pro Leu Arg Gly Ala Ala Pro Ala Ala Pro Ala Pro Gly
            20                  25                  30

Gly Leu Tyr Ala Cys His Met Gly Pro Met Thr Trp Val Cys Gln Pro
        35                  40                  45

Leu Arg Gly
    50


<210> SEQ ID NO 105
<211> LENGTH: 65
<212> TYPE: PRT
<213> ORGANISM: Artificial Sequence
<220> FEATURE:
<223> OTHER INFORMATION: AET-EPO-PAS22
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (51)..(60)
<223> OTHER INFORMATION: Disulfid bridge between Cys-51 and Cys-60

<400> SEQUENCE: 105

Ala Glu Thr Gly Gly Leu Tyr Ala Cys His Met Gly Pro Met Thr Trp
1               5                   10                  15

Val Cys Gln Pro Leu Arg Gly Ala Ala Pro Ala Ala Pro Ala Pro Ala
            20                  25                  30

Ala Pro Ala Ala Pro Ala Pro Ala Ala Pro Ala Ala Pro Gly Gly Leu
        35                  40                  45

Tyr Ala Cys His Met Gly Pro Met Thr Trp Val Cys Gln Pro Leu Arg
    50                  55                  60

Gly
65


<210> SEQ ID NO 106
<211> LENGTH: 222
<212> TYPE: DNA
<213> ORGANISM: Artificial Sequence
<220> FEATURE:
<223> OTHER INFORMATION: CspAss-EPO-PAS8

<400> SEQUENCE: 106

atgaaacgca tgaaatcgct ggctgcggcg ctcaccgtcg ctggggccat gctggccgca      60

cctgtggcaa cggcaggtgg cctttacgct tgtcacatgg gtccaatgac ctgggtttgt     120

cagcccctcc gtggtgccgc tcctgccgcc cccgctcctg gtggcctgta cgcatgccat     180

atgggtccaa tgacttgggt gtgccagcca ctccgcggct aa                        222


<210> SEQ ID NO 107
<211> LENGTH: 73
<212> TYPE: PRT
<213> ORGANISM: Artificial Sequence
<220> FEATURE:
<223> OTHER INFORMATION: CspAss-EPO-PAS8
<220> FEATURE:
<221> NAME/KEY: DISULFID
<222> LOCATION: (31)..(40)
<223> OTHER INFORMATION: Disulfid bridge between Cys-31 and Cys-40
<220> FEATURE:
<221> NAME/KEY: DISULFID
<222> LOCATION: (59)..(68)
<223> OTHER INFORMATION: Disulfid bridge between Cys-59 and Cys-68

<400> SEQUENCE: 107
```

```
Met Lys Arg Met Lys Ser Leu Ala Ala Ala Leu Thr Val Ala Gly Ala
1               5                   10                  15

Met Leu Ala Ala Pro Val Ala Thr Ala Gly Gly Leu Tyr Ala Cys His
            20                  25                  30

Met Gly Pro Met Thr Trp Val Cys Gln Pro Leu Arg Gly Ala Ala Pro
        35                  40                  45

Ala Ala Pro Ala Pro Gly Gly Leu Tyr Ala Cys His Met Gly Pro Met
    50                  55                  60

Thr Trp Val Cys Gln Pro Leu Arg Gly
65                  70
```

<210> SEQ ID NO 108
<211> LENGTH: 264
<212> TYPE: DNA
<213> ORGANISM: Artificial Sequence
<220> FEATURE:
<223> OTHER INFORMATION: CspAss-EPO-PAS22

<400> SEQUENCE: 108

```
atgaaacgca tgaaatcgct ggctgcggcg ctcaccgtcg ctggggccat gctggccgca     60

cctgtggcaa cggcaggcgg cctttacgct tgtcacatgg gtccaatgac ctgggtctgt    120

caacctctcc gtggtgcagc cccggcagcc cccgctccag ccgcaccagc agccccagcc    180

ccagctgcac cagccgctcc aggcggcctc tacgcctgcc acatgggtcc tatgacctgg    240

gtgtgccaac cacttcgcgg ctaa                                           264
```

<210> SEQ ID NO 109
<211> LENGTH: 87
<212> TYPE: PRT
<213> ORGANISM: Artificial Sequence
<220> FEATURE:
<223> OTHER INFORMATION: CspAss-EPO-PAS22
<220> FEATURE:
<221> NAME/KEY: DISULFID
<222> LOCATION: (31)..(40)
<223> OTHER INFORMATION: Disulfid bridge between Cys-31 and Cys-40
<220> FEATURE:
<221> NAME/KEY: DISULFID
<222> LOCATION: (73)..(82)
<223> OTHER INFORMATION: Disulfid bridge between Cys-73 and Cys-82

<400> SEQUENCE: 109

```
Met Lys Arg Met Lys Ser Leu Ala Ala Ala Leu Thr Val Ala Gly Ala
1               5                   10                  15

Met Leu Ala Ala Pro Val Ala Thr Ala Gly Gly Leu Tyr Ala Cys His
            20                  25                  30

Met Gly Pro Met Thr Trp Val Cys Gln Pro Leu Arg Gly Ala Ala Pro
        35                  40                  45

Ala Ala Pro Ala Pro Ala Ala Pro Ala Ala Pro Ala Pro Ala Ala Pro
    50                  55                  60

Ala Ala Pro Gly Gly Leu Tyr Ala Cys His Met Gly Pro Met Thr Trp
65                  70                  75                  80

Val Cys Gln Pro Leu Arg Gly
                85
```

<210> SEQ ID NO 110
<211> LENGTH: 246
<212> TYPE: DNA
<213> ORGANISM: Artificial Sequence
<220> FEATURE:
<223> OTHER INFORMATION: CspBss-AET-EPO-PAS8

<400> SEQUENCE: 110
atgtttaaca accgtatccg cactgcagct ctcgctggtg caatcgcaat ctccaccgca 60
gcttccggcg tagctatccc agcattcgct gcagagaccg gtggccttta cgcttgtcac 120
atgggtccaa tgacctgggt ttgtcagccc ctccgtggtg ccgctcctgc cgcccccgct 180
cctggtggcc tgtacgcatg ccatatgggt ccaatgactt gggtgtgcca gccactccgc 240
ggctaa 246

<210> SEQ ID NO 111
<211> LENGTH: 81
<212> TYPE: PRT
<213> ORGANISM: Artificial Sequence
<220> FEATURE:
<223> OTHER INFORMATION: CspBss-AET-EPO-PAS8
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (67)..(76)
<223> OTHER INFORMATION: Disulfid bridge between Cys-67 and Cys-76

<400> SEQUENCE: 111

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Gly Gly Leu
    50                  55                  60

Tyr Ala Cys His Met Gly Pro Met Thr Trp Val Cys Gln Pro Leu Arg
65                  70                  75                  80

Gly

<210> SEQ ID NO 112
<211> LENGTH: 288
<212> TYPE: DNA
<213> ORGANISM: Artificial Sequence
<220> FEATURE:
<223> OTHER INFORMATION: CspBss-AET-EPO-PAS22

<400> SEQUENCE: 112
atgtttaaca accgtatccg cactgcagct ctcgctggtg caatcgcaat ctccaccgca 60
gcttccggcg tagctatccc agcattcgct gcagagaccg gcggccttta cgcttgtcac 120
atgggtccaa tgacctgggt ctgtcaacct ctccgtggtg cagccccggc agcccccgct 180
ccagccgcac cagcagcccc agccccagct gcaccagccg ctccaggcgg cctctacgcc 240
tgccacatgg gtcctatgac ctgggtgtgc caaccacttc gcggctaa 288

<210> SEQ ID NO 113
<211> LENGTH: 95
<212> TYPE: PRT
<213> ORGANISM: Artificial Sequence
<220> FEATURE:
<223> OTHER INFORMATION: CspBss-AET-EPO-PAS22
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:

<221> NAME/KEY: DISULFID
<222> LOCATION: (81)..(90)
<223> OTHER INFORMATION: Disulfid bridge between Cys-81 and Cys-90

<400> SEQUENCE: 113

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Ala Ala Pro
    50                  55                  60

Ala Ala Pro Ala Pro Ala Ala Pro Ala Ala Pro Gly Gly Leu Tyr Ala
65                  70                  75                  80

Cys His Met Gly Pro Met Thr Trp Val Cys Gln Pro Leu Arg Gly
                85                  90                  95
```

<210> SEQ ID NO 114
<211> LENGTH: 44
<212> TYPE: PRT
<213> ORGANISM: Artificial Sequence
<220> FEATURE:
<223> OTHER INFORMATION: TPO2-PAS8
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (29)..(42)
<223> OTHER INFORMATION: Disulfid bridge between Cys-29 and Cys-42

<400> SEQUENCE: 114

```
Gly Gly Cys Ala Asp Gly Pro Thr Leu Arg Glu Trp Ile Ser Phe Cys
1               5                   10                  15

Gly Gly Ala Ala Pro Ala Ala Pro Ala Pro Gly Gly Cys Ala Asp Gly
            20                  25                  30

Pro Thr Leu Arg Glu Trp Ile Ser Phe Cys Gly Gly
        35                  40
```

<210> SEQ ID NO 115
<211> LENGTH: 39
<212> TYPE: PRT
<213> ORGANISM: Artificial Sequence
<220> FEATURE:
<223> OTHER INFORMATION: AET-TPO1-PAS8

<400> SEQUENCE: 115

```
Ala Glu Thr Ile Glu Gly Pro Thr Leu Arg Gln Trp Leu Ala Ala Arg
1               5                   10                  15

Ala Ala Ala Pro Ala Ala Pro Ala Pro Ile Glu Gly Pro Thr Leu Arg
            20                  25                  30

Gln Trp Leu Ala Ala Arg Ala
        35
```

<210> SEQ ID NO 116
<211> LENGTH: 47
<212> TYPE: PRT
<213> ORGANISM: Artificial Sequence
<220> FEATURE:
<223> OTHER INFORMATION: AET-TPO2-PAS8
<220> FEATURE:
<221> NAME/KEY: DISULFID
<222> LOCATION: (6)..(19)
<223> OTHER INFORMATION: Disulfid bridge between Cys-6 and Cys-19
<220> FEATURE:
<221> NAME/KEY: DISULFID
<222> LOCATION: (32)..(45)
<223> OTHER INFORMATION: Disulfid bridge between Cys-32 and Cys-45

<400> SEQUENCE: 116

Ala Glu Thr Gly Gly Cys Ala Asp Gly Pro Thr Leu Arg Glu Trp Ile
1               5                   10                  15

Ser Phe Cys Gly Gly Ala Ala Pro Ala Ala Pro Ala Pro Gly Gly Cys
            20                  25                  30

Ala Asp Gly Pro Thr Leu Arg Glu Trp Ile Ser Phe Cys Gly Gly
        35                  40                  45

<210> SEQ ID NO 117
<211> LENGTH: 210
<212> TYPE: DNA
<213> ORGANISM: Artificial Sequence
<220> FEATURE:
<223> OTHER INFORMATION: CspAss-TPO2-PAS8

<400> SEQUENCE: 117
atgaaacgca tgaaatcgct ggctgcggcg ctcaccgtcg ctggggccat gctggccgca 60
cctgtggcaa cggcaggtgg ttgtgctgat ggtcctacct tgcgtgaatg gatttccttc 120
tgcggcggcg ctgctccggc tgcccctgcc cctggcggtt gcgcagatgg cccaaccctg 180
cgcgaatgga tctccttctg cggcggctaa 210

<210> SEQ ID NO 118
<211> LENGTH: 69
<212> TYPE: PRT
<213> ORGANISM: Artificial Sequence
<220> FEATURE:
<223> OTHER INFORMATION: CspAss-TPO2-PAS8
<220> FEATURE:
<221> NAME/KEY: DISULFID
<222> LOCATION: (28)..(41)
<223> OTHER INFORMATION: Disulfid bridge between Cys-28 and Cys-41
<220> FEATURE:
<221> NAME/KEY: DISULFID
<222> LOCATION: (54)..(67)
<223> OTHER INFORMATION: Disulfid bridge between Cys-54 and Cys-67

<400> SEQUENCE: 118

Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Ala Ala Pro Ala Ala
        35                  40                  45

Pro Ala Pro Gly Gly Cys Ala Asp Gly Pro Thr Leu Arg Glu Trp Ile
    50                  55                  60

Ser Phe Cys Gly Gly
65

<210> SEQ ID NO 119
<211> LENGTH: 210
<212> TYPE: DNA
<213> ORGANISM: Artificial Sequence
<220> FEATURE:
<223> OTHER INFORMATION: CspBss-AET-TPO1-PAS8

<400> SEQUENCE: 119

```
atgtttaaca accgtatccg cactgcagct ctcgctggtg caatcgcaat ctccaccgca     60

gcttccggcg tagctatccc agcattcgct gcagagacca tcgaaggtcc taccctccgt    120

caatggctgg ctgctcgtgc cgccgctccc gccgctcctg ctccaatcga aggtcccacc    180

ctccgtcagt ggctggcagc ccgcgcataa                                     210
```

<210> SEQ ID NO 120
<211> LENGTH: 69
<212> TYPE: PRT
<213> ORGANISM: Artificial Sequence
<220> FEATURE:
<223> OTHER INFORMATION: CspBss-AET-TPO1-PAS8

<400> SEQUENCE: 120

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Ile Glu Gly Pro Thr Leu Arg Gln Trp Leu Ala Ala Arg Ala Ala
        35                  40                  45

Ala Pro Ala Ala Pro Ala Pro Ile Glu Gly Pro Thr Leu Arg Gln Trp
    50                  55                  60

Leu Ala Ala Arg Ala
65
```

<210> SEQ ID NO 121
<211> LENGTH: 234
<212> TYPE: DNA
<213> ORGANISM: Artificial Sequence
<220> FEATURE:
<223> OTHER INFORMATION: CspBss-AET-TPO2-PAS8

<400> SEQUENCE: 121

```
atgtttaaca accgtatccg cactgcagct ctcgctggtg caatcgcaat ctccaccgca     60

gcttccggcg tagctatccc agcattcgct gcagagaccg gtggttgtgc tgatggtcct    120

accttgcgtg aatggatttc cttctgcggc ggcgctgctc cggctgcccc tgcccctggc    180

ggttgcgcag atggcccaac cctgcgcgaa tggatctcct tctgcggcgg ctaa          234
```

<210> SEQ ID NO 122
<211> LENGTH: 77
<212> TYPE: PRT
<213> ORGANISM: Artificial Sequence
<220> FEATURE:
<223> OTHER INFORMATION: CspBss-AET-TPO2-PAS8
<220> FEATURE:
<221> NAME/KEY: DISULFID
<222> LOCATION: (36)..(49)
<223> OTHER INFORMATION: Disulfid bridge between Cys-36 and Cys-49
<220> FEATURE:
<221> NAME/KEY: DISULFID
<222> LOCATION: (62)..(75)
<223> OTHER INFORMATION: Disulfid bridge between Cys-62 and Cys-75

<400> SEQUENCE: 122

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Cys Ala Asp Gly Pro Thr Leu Arg Glu Trp Ile Ser Phe
        35                  40                  45

Cys Gly Gly Ala Ala Pro Ala Ala Pro Ala Pro Gly Gly Cys Ala Asp
```

```
    50                  55                  60

Gly Pro Thr Leu Arg Glu Trp Ile Ser Phe Cys Gly Gly
65                  70                  75


<210> SEQ ID NO 123
<211> LENGTH: 54
<212> TYPE: PRT
<213> ORGANISM: Artificial Sequence
<220> FEATURE:
<223> OTHER INFORMATION: AET-VEGFR_D2-PAS16
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (39)..(49)
<223> OTHER INFORMATION: Disulfid bridge between Cys-39 and Cys-49

<400> SEQUENCE: 123

Ala Glu Thr Ala Gly Pro Thr Trp Cys Glu Asp Asp Trp Tyr Tyr Cys
1               5                   10                  15

Trp Leu Phe Gly Thr Ala Ala Pro Ala Ala Pro Ala Pro Ala Ala Pro
            20                  25                  30

Ala Ala Pro Ala Pro Val Cys Trp Glu Asp Ser Trp Gly Gly Glu Val
        35                  40                  45

Cys Trp Leu Phe Gly Thr
    50


<210> SEQ ID NO 124
<211> LENGTH: 255
<212> TYPE: DNA
<213> ORGANISM: Artificial Sequence
<220> FEATURE:
<223> OTHER INFORMATION: CspBss-AET-VEGFR_D2-PAS16

<400> SEQUENCE: 124

atgtttaaca accgtatccg cactgcagct ctcgctggtg caatcgcaat ctccaccgca      60

gcttccggcg tagctatccc agcattcgct gcagagaccg ctggtcctac ctggtgtgaa     120

gacgactggt actactgctg gctgtttggc accgctgctc ccgctgcccc tgctcctgcc     180

gctccggcag ccccagctcc tgtgtgttgg gaagattctt ggggcggcga agtttgctgg     240

ctgtttggca cctaa                                                      255


<210> SEQ ID NO 125
<211> LENGTH: 84
<212> TYPE: PRT
<213> ORGANISM: Artificial Sequence
<220> FEATURE:
<223> OTHER INFORMATION: CspBss-AET-VEGFR_D2-PAS16
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (69)..(79)
<223> OTHER INFORMATION: Disulfid bridge between Cys-69 and Cys-79

<400> SEQUENCE: 125

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30
```

Thr Ala Gly Pro Thr Trp Cys Glu Asp Asp Trp Tyr Tyr Cys Trp Leu
35 40 45

Phe Gly Thr Ala Ala Pro Ala Ala Pro Ala Pro Ala Ala Pro Ala Ala
50 55 60

Pro Ala Pro Val Cys Trp Glu Asp Ser Trp Gly Gly Glu Val Cys Trp
65 70 75 80

Leu Phe Gly Thr

<210> SEQ ID NO 126
<211> LENGTH: 92
<212> TYPE: PRT
<213> ORGANISM: Artificial Sequence
<220> FEATURE:
<223> OTHER INFORMATION: AET-EPO-PAS49
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (78)..(87)
<223> OTHER INFORMATION: Disulfid bridge between Cys-78 and Cys-87

<400> SEQUENCE: 126

Ala Glu Thr Gly Gly Leu Tyr Ala Cys His Met Gly Pro Met Thr Trp
1 5 10 15

Val Cys Gln Pro Leu Arg Gly Ala Ala Pro Ala Ala Pro Ala Pro Ala
20 25 30

Ala Pro Ala Ala Pro Ala Pro Ala Ala Pro Ala Ala Pro Ala Pro Ala
35 40 45

Ala Pro Ala Ala Pro Ala Pro Ala Ala Pro Ala Ala Pro Ala Pro Ala
50 55 60

Ala Pro Ala Ala Pro Ala Pro Ala Gly Gly Leu Tyr Ala Cys His Met
65 70 75 80

Gly Pro Met Thr Trp Val Cys Gln Pro Leu Arg Gly
85 90

<210> SEQ ID NO 127
<211> LENGTH: 92
<212> TYPE: PRT
<213> ORGANISM: Artificial Sequence
<220> FEATURE:
<223> OTHER INFORMATION: AET-EPO-PAS49-b
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (78)..(87)
<223> OTHER INFORMATION: Disulfid bridge between Cys-78 and Cys-87

<400> SEQUENCE: 127

Ala Glu Thr Gly Gly Leu Tyr Ala Cys His Met Gly Pro Met Thr Trp
1 5 10 15

Val Cys Gln Pro Leu Arg Gly Ser Ala Pro Ser Pro Ser Ser Ala Pro
20 25 30

Ala Ser Ala Ser Ala Pro Ala Ser Pro Ala Ser Ala Ser Ala Ser Ala
35 40 45

Ser Pro Ala Ser Ser Pro Ala Ser Ala Ser Ser Ala Ser Pro Ala Ala
50 55 60

Ser Ser Ala Ser Pro Ala Ser Ser Gly Gly Leu Tyr Ala Cys His Met
65 70 75 80

```
Gly Pro Met Thr Trp Val Cys Gln Pro Leu Arg Gly
                85                  90


<210> SEQ ID NO 128
<211> LENGTH: 143
<212> TYPE: PRT
<213> ORGANISM: Artificial Sequence
<220> FEATURE:
<223> OTHER INFORMATION: AET-EPO-PAS100
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (129)..(138)
<223> OTHER INFORMATION: Disulfid bridge between Cys-129 and Cys-138

<400> SEQUENCE: 128

Ala Glu Thr Gly Gly Leu Tyr Ala Cys His Met Gly Pro Met Thr Trp
1               5                   10                  15

Val Cys Gln Pro Leu Arg Gly Ala Ala Pro Ala Ala Pro Ala Pro Ala
            20                  25                  30

Ala Pro Ala Ala Pro Ala Pro Ala Ala Pro Ala Ala Pro Ala Pro Ala
        35                  40                  45

Ala Pro Ala Ala Pro Ala Pro Ala Ala Pro Ala Ala Pro Ala Pro Ala
    50                  55                  60

Ala Pro Ala Ala Pro Ala Pro Ala Ala Pro Ala Ala Pro Ala Pro Ala
65                  70                  75                  80

Ala Pro Ala Ala Pro Ala Pro Ala Ala Pro Ala Ala Pro Ala Pro Ala
                85                  90                  95

Ala Pro Ala Ala Pro Ala Pro Ala Ala Pro Ala Ala Pro Ala Pro Ala
            100                 105                 110

Ala Pro Ala Ala Pro Ala Pro Ala Ala Pro Ala Gly Gly Leu Tyr Ala
        115                 120                 125

Cys His Met Gly Pro Met Thr Trp Val Cys Gln Pro Leu Arg Gly
    130                 135                 140


<210> SEQ ID NO 129
<211> LENGTH: 143
<212> TYPE: PRT
<213> ORGANISM: Artificial Sequence
<220> FEATURE:
<223> OTHER INFORMATION: AET-EPO-PAS100-b
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (129)..(138)
<223> OTHER INFORMATION: Disulfid bridge between Cys-129 and Cys-138

<400> SEQUENCE: 129

Ala Glu Thr Gly Gly Leu Tyr Ala Cys His Met Gly Pro Met Thr Trp
1               5                   10                  15

Val Cys Gln Pro Leu Arg Gly Ser Ala Pro Ser Pro Ser Ser Ala Pro
            20                  25                  30

Ala Ser Ala Ser Ala Pro Ala Ser Pro Ala Ser Ala Ser Ala Ser Ala
        35                  40                  45

Ser Pro Ala Ser Ser Pro Ala Ser Ala Ser Ser Ala Ser Pro Ala Ala
    50                  55                  60
```

Ser Ser Ala Ser Pro Ala Ser Ser Ser Ala Ser Pro Ser Ala Pro Ala
65 70 75 80

Ala Pro Ser Ala Ser Ala Ala Pro Ser Ala Ser Pro Ala Ser Ser Ser
85 90 95

Pro Ala Pro Ala Ser Ala Pro Ser Pro Ala Ala Ala Ala Ser Ser Pro
100 105 110

Ser Pro Ala Pro Ser Ser Ala Ser Ser Ala Ala Gly Gly Leu Tyr Ala
115 120 125

Cys His Met Gly Pro Met Thr Trp Val Cys Gln Pro Leu Arg Gly
130 135 140

<210> SEQ ID NO 130
<211> LENGTH: 51
<212> TYPE: PRT
<213> ORGANISM: Artificial Sequence
<220> FEATURE:
<223> OTHER INFORMATION: AET-EPO-GS8
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (37)..(46)
<223> OTHER INFORMATION: Disulfid bridge between Cys-37 and Cys-46

<400> SEQUENCE: 130

Ala Glu Thr Gly Gly Leu Tyr Ala Cys His Met Gly Pro Met Thr Trp
1 5 10 15

Val Cys Gln Pro Leu Arg Gly Gly Gly Gly Gly Ser Gly Gly Gly Gly
20 25 30

Gly Leu Tyr Ala Cys His Met Gly Pro Met Thr Trp Val Cys Gln Pro
35 40 45

Leu Arg Gly
50

<210> SEQ ID NO 131
<211> LENGTH: 65
<212> TYPE: PRT
<213> ORGANISM: Artificial Sequence
<220> FEATURE:
<223> OTHER INFORMATION: AET-EPO-GS22
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (51)..(60)
<223> OTHER INFORMATION: Disulfid bridge between Cys-51 and Cys-60

<400> SEQUENCE: 131

Ala Glu Thr Gly Gly Leu Tyr Ala Cys His Met Gly Pro Met Thr Trp
1 5 10 15

Val Cys Gln Pro Leu Arg Gly Gly Gly Gly Gly Ser Gly Gly Gly Gly
20 25 30

Ser Gly Gly Gly Gly Ser Gly Gly Gly Gly Ser Gly Gly Gly Gly Leu
35 40 45

Tyr Ala Cys His Met Gly Pro Met Thr Trp Val Cys Gln Pro Leu Arg
50 55 60

Gly
65

<210> SEQ ID NO 132
<211> LENGTH: 369
<212> TYPE: DNA
<213> ORGANISM: Artificial Sequence
<220> FEATURE:
<223> OTHER INFORMATION: CspBss-AET-EPO-PAS49

<400> SEQUENCE: 132

```
atgtttaaca accgtatccg cactgcagct ctcgctggtg caatcgcaat ctccaccgca     60

gcttccggcg tagctatccc agcattcgct gcagagaccg gtggtctcta cgcctgtcac    120

atgggtccta tgacctgggt gtgccaacct ctccgtggtg ccgcccccgc cgcccccgcc    180

cccgccgccc cagctgcacc agctccagca gccccagccg caccagcccc agcagctcca    240

gctgccccag caccagcagc accagccgct ccagcaccag ctgctccagc agctccagcc    300

ccagccggcg gcctttacgc ctgccacatg ggtcctatga cctgggtttg ccagcctctt    360

cgcggttag                                                            369
```

<210> SEQ ID NO 133
<211> LENGTH: 122
<212> TYPE: PRT
<213> ORGANISM: Artificial Sequence
<220> FEATURE:
<223> OTHER INFORMATION: CspBss-AET-EPO-PAS49
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (108)..(117)
<223> OTHER INFORMATION: Disulfid bridge between Cys-108 and Cys-117

<400> SEQUENCE: 133

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Ala Ala Pro
    50                  55                  60

Ala Ala Pro Ala Pro Ala Ala Pro Ala Ala Pro Ala Pro Ala Ala Pro
65                  70                  75                  80

Ala Ala Pro Ala Pro Ala Ala Pro Ala Ala Pro Ala Pro Ala Ala Pro
                85                  90                  95

Ala Ala Pro Ala Pro Ala Gly Gly Leu Tyr Ala Cys His Met Gly Pro
            100                 105                 110

Met Thr Trp Val Cys Gln Pro Leu Arg Gly
        115                 120
```

<210> SEQ ID NO 134
<211> LENGTH: 369
<212> TYPE: DNA
<213> ORGANISM: Artificial Sequence
<220> FEATURE:
<223> OTHER INFORMATION: CspBss-AET-EPO-PAS49-b

<400> SEQUENCE: 134

```
atgtttaaca accgtatccg cactgcagct ctcgctggtg caatcgcaat ctccaccgca     60

gcttccggcg tagctatccc agcattcgct gcagagaccg gcggactgta cgcctgccat    120
```

```
atggggccaa tgacctgggt gtgccaaccg ttgcgtggat cagcgccatc gccctcttcc    180

gctccagcct ctgcgtctgc tcccgcatcc ccagcgtcag cttccgcatc cgcttcgcct    240

gcaagctccc ctgctagcgc gtcctctgcc tcccctgcag catcctcggc ttccccggca    300

agctcaggtg gcctctatgc ctgccacatg ggtccgatga cttgggtctg tcagccactt    360

cgcggctaa                                                            369
```

<210> SEQ ID NO 135
<211> LENGTH: 122
<212> TYPE: PRT
<213> ORGANISM: Artificial Sequence
<220> FEATURE:
<223> OTHER INFORMATION: CspBss-AET-EPO-PAS49-b
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (108)..(117)
<223> OTHER INFORMATION: Disulfid bridge between Cys-108 and Cys-117

<400> SEQUENCE: 135

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ser Ala Pro Ser Pro Ser Ser Ala Pro Ala Ser
    50                  55                  60

Ala Ser Ala Pro Ala Ser Pro Ala Ser Ala Ser Ala Ser Ala Ser Pro
65                  70                  75                  80

Ala Ser Ser Pro Ala Ser Ala Ser Ser Ala Ser Pro Ala Ala Ser Ser
                85                  90                  95

Ala Ser Pro Ala Ser Ser Gly Gly Leu Tyr Ala Cys His Met Gly Pro
            100                 105                 110

Met Thr Trp Val Cys Gln Pro Leu Arg Gly
        115                 120
```

<210> SEQ ID NO 136
<211> LENGTH: 522
<212> TYPE: DNA
<213> ORGANISM: Artificial Sequence
<220> FEATURE:
<223> OTHER INFORMATION: CspBss-AET-EPO-PAS100

<400> SEQUENCE: 136

```
atgtttaaca accgtatccg cactgcagct ctcgctggtg caatcgcaat ctccaccgca     60

gcttccggcg tagctatccc agcattcgct gcagagaccg gtggtttgta cgcttgccac    120

atgggtccta tgacctgggt ttgtcagcct cttcgtggtg ccgcccccgc agcccccgct    180

cccgctgcac cagccgcacc agcaccagca gctccagcag ctccagcacc agctgcacca    240

gccgccccag caccagcagc cccagccgct ccagcaccag ctgccccagc tgctccagct    300

ccagcagcac cagctgcccc agccccagca gcaccagccg ctccagcccc agctgcccca    360

gcagctccag ctccagctgc tccagcagcc ccagcaccag ccgccccagc agccccagct    420

ccagctgcac cagctgcacc agccccagcc gcaccagccg gcggtttgta cgcttgccac    480

atgggtccga tgacctgggt ttgtcagccc cttcgcggtt ag                       522
```

<210> SEQ ID NO 137
<211> LENGTH: 173
<212> TYPE: PRT
<213> ORGANISM: Artificial Sequence
<220> FEATURE:
<223> OTHER INFORMATION: CspBss-AET-EPO-PAS100
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (159)..(168)
<223> OTHER INFORMATION: Disulfid bridge between Cys-159 and Cys-168

<400> SEQUENCE: 137

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Ala Ala Pro
    50                  55                  60

Ala Ala Pro Ala Pro Ala Ala Pro Ala Ala Pro Ala Pro Ala Ala Pro
65                  70                  75                  80

Ala Ala Pro Ala Pro Ala Ala Pro Ala Ala Pro Ala Pro Ala Ala Pro
                85                  90                  95

Ala Ala Pro Ala Pro Ala Ala Pro Ala Ala Pro Ala Pro Ala Ala Pro
            100                 105                 110

Ala Ala Pro Ala Pro Ala Ala Pro Ala Ala Pro Ala Pro Ala Ala Pro
        115                 120                 125

Ala Ala Pro Ala Pro Ala Ala Pro Ala Ala Pro Ala Pro Ala Ala Pro
    130                 135                 140

Ala Ala Pro Ala Pro Ala Ala Pro Ala Gly Gly Leu Tyr Ala Cys His
145                 150                 155                 160

Met Gly Pro Met Thr Trp Val Cys Gln Pro Leu Arg Gly
                165                 170
```

<210> SEQ ID NO 138
<211> LENGTH: 522
<212> TYPE: DNA
<213> ORGANISM: Artificial Sequence
<220> FEATURE:
<223> OTHER INFORMATION: CspBss-AET-EPO-PAS100-b

<400> SEQUENCE: 138

```
atgtttaaca accgtatccg cactgcagct ctcgctggtg caatcgcaat ctccaccgca     60

gcttccggcg tagctatccc agcattcgct gcagagaccg gcggcttgta cgcctgccat    120

atggggccta tgacctgggt ctgccaacca ctgcgtggaa gcgcaccctc accatcctcc    180

gcaccagcta gcgcctccgc tcctgcaagc ccagcgtccg catccgcttc ggcctcacca    240

gcgtcctctc cagcttccgc ttcgagcgct agcccagcgg catcctctgc ctccccagcc    300

tcctcgtctg catccccgtc cgctccagcc gcaccttctg catctgcggc tccgtccgcc    360

tccccggcat cttcctcgcc tgctcccgcg tcagcgcctt ccccggctgc agcggcctcc    420

tctccgtcac ccgctccttc aagcgcgtcg tctgcagcag gaggcctcta tgcctgccac    480

atgggtccga tgacttgggt gtgtcagccc cttcgcggtt aa                       522
```

<210> SEQ ID NO 139
<211> LENGTH: 173
<212> TYPE: PRT
<213> ORGANISM: Artificial Sequence
<220> FEATURE:
<223> OTHER INFORMATION: CspBss-AET-EPO-PAS100-b
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (159)..(168)
<223> OTHER INFORMATION: Disulfid bridge between Cys-159 and Cys-168

<400> SEQUENCE: 139

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ser Ala Pro Ser Pro Ser Ser Ala Pro Ala Ser
    50                  55                  60

Ala Ser Ala Pro Ala Ser Pro Ala Ser Ala Ser Ala Ser Ala Ser Pro
65                  70                  75                  80

Ala Ser Ser Pro Ala Ser Ala Ser Ser Ala Ser Pro Ala Ala Ser Ser
                85                  90                  95

Ala Ser Pro Ala Ser Ser Ser Ala Ser Pro Ser Ala Pro Ala Ala Pro
            100                 105                 110

Ser Ala Ser Ala Ala Pro Ser Ala Ser Pro Ala Ser Ser Ser Pro Ala
        115                 120                 125

Pro Ala Ser Ala Pro Ser Pro Ala Ala Ala Ala Ser Ser Pro Ser Pro
    130                 135                 140

Ala Pro Ser Ser Ala Ser Ser Ala Ala Gly Gly Leu Tyr Ala Cys His
145                 150                 155                 160

Met Gly Pro Met Thr Trp Val Cys Gln Pro Leu Arg Gly
                165                 170
```

<210> SEQ ID NO 140
<211> LENGTH: 246
<212> TYPE: DNA
<213> ORGANISM: Artificial Sequence
<220> FEATURE:
<223> OTHER INFORMATION: CspBss-AET-EPO-GS8

<400> SEQUENCE: 140

```
atgtttaaca accgtatccg cactgcagct ctcgctggtg caatcgcaat ctccaccgca     60

gcttccggcg tagctatccc agcattcgct gcagagaccg gcggcctcta tgcatgccat    120

atggggccaa tgacctgggt ctgccaaccg ttgcgtggcg gaggtggcgg ttccggtgga    180

ggtggtggcc tgtacgcttg ccacatggga cccatgactt gggtgtgtca gcctcttcgc    240

ggctaa                                                               246
```

<210> SEQ ID NO 141
<211> LENGTH: 81
<212> TYPE: PRT
<213> ORGANISM: Artificial Sequence
<220> FEATURE:
<223> OTHER INFORMATION: CspBss-AET-EPO-GS8

```
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (67)..(76)
<223> OTHER INFORMATION: Disulfid bridge between Cys-67 and Cys-76

<400> SEQUENCE: 141

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Gly Gly Gly Gly Ser Gly Gly Gly Gly Gly Leu
    50                  55                  60

Tyr Ala Cys His Met Gly Pro Met Thr Trp Val Cys Gln Pro Leu Arg
65                  70                  75                  80

Gly


<210> SEQ ID NO 142
<211> LENGTH: 288
<212> TYPE: DNA
<213> ORGANISM: Artificial Sequence
<220> FEATURE:
<223> OTHER INFORMATION: CspBss-AET-EPO-GS22

<400> SEQUENCE: 142

atgtttaaca accgtatccg cactgcagct ctcgctggtg caatcgcaat ctccaccgca      60

gcttccggcg tagctatccc agcattcgct gcagagaccg gtgggctgta tgcttgccat     120

atggggccta tgacttgggt gtgccaaccc ttgcgtggtg gaggcggagg ctccggcggt     180

ggtgggagcg gaggaggcgg ttccggtggc ggtggctctg gcggaggcgg cctctacgca     240

tgccacatgg gtccgatgac ctgggtctgt cagccacttc gcggctaa                  288


<210> SEQ ID NO 143
<211> LENGTH: 95
<212> TYPE: PRT
<213> ORGANISM: Artificial Sequence
<220> FEATURE:
<223> OTHER INFORMATION: CspBss-AET-EPO-GS22
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (81)..(90)
<223> OTHER INFORMATION: Disulfid bridge between Cys-81 and Cys-90

<400> SEQUENCE: 143

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Gly Gly Gly Gly Ser Gly Gly Gly Gly Ser Gly
    50                  55                  60

Gly Gly Gly Ser Gly Gly Gly Gly Ser Gly Gly Gly Gly Leu Tyr Ala
```

```
65                  70                  75                  80

Cys His Met Gly Pro Met Thr Trp Val Cys Gln Pro Leu Arg Gly
                85                  90                  95


<210> SEQ ID NO 144
<211> LENGTH: 265
<212> TYPE: PRT
<213> ORGANISM: Artificial Sequence
<220> FEATURE:
<223> OTHER INFORMATION: AET-EPO-PAS22-PAS200
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (51)..(60)
<223> OTHER INFORMATION: Disulfid bridge between Cys-51 and Cys-60

<400> SEQUENCE: 144

Ala Glu Thr Gly Gly Leu Tyr Ala Cys His Met Gly Pro Met Thr Trp
1               5                   10                  15

Val Cys Gln Pro Leu Arg Gly Ala Ala Pro Ala Ala Pro Ala Pro Ala
            20                  25                  30

Ala Pro Ala Ala Pro Ala Pro Ala Ala Pro Ala Ala Pro Gly Gly Leu
        35                  40                  45

Tyr Ala Cys His Met Gly Pro Met Thr Trp Val Cys Gln Pro Leu Arg
    50                  55                  60

Gly Ala Ala Pro Ala Ala Pro Ala Pro Ala Ala Pro Ala Ala Pro Ala
65                  70                  75                  80

Pro Ala Ala Pro Ala Ala Pro Ala Pro Ala Ala Pro Ala Ala Pro Ala
                85                  90                  95

Pro Ala Ala Pro Ala Ala Pro Ala Pro Ala Ala Pro Ala Ala Pro Ala
            100                 105                 110

Pro Ala Ala Pro Ala Ala Pro Ala Pro Ala Ala Pro Ala Ala Pro Ala
        115                 120                 125

Pro Ala Ala Pro Ala Ala Pro Ala Pro Ala Ala Pro Ala Ala Pro Ala
    130                 135                 140

Pro Ala Ala Pro Ala Ala Pro Ala Pro Ala Ala Pro Ala Ala Pro Ala
145                 150                 155                 160

Pro Ala Ala Pro Ala Ala Pro Ala Pro Ala Ala Pro Ala Ala Pro Ala
                165                 170                 175

Pro Ala Ala Pro Ala Ala Pro Ala Pro Ala Ala Pro Ala Ala Pro Ala
            180                 185                 190

Pro Ala Ala Pro Ala Ala Pro Ala Pro Ala Ala Pro Ala Ala Pro Ala
        195                 200                 205

Pro Ala Ala Pro Ala Ala Pro Ala Pro Ala Ala Pro Ala Ala Pro Ala
    210                 215                 220

Pro Ala Ala Pro Ala Ala Pro Ala Pro Ala Ala Pro Ala Ala Pro Ala
225                 230                 235                 240

Pro Ala Ala Pro Ala Ala Pro Ala Pro Ala Ala Pro Ala Ala Pro Ala
                245                 250                 255

Pro Ala Ala Pro Ala Ala Pro Ala Pro
            260                 265


<210> SEQ ID NO 145
<211> LENGTH: 665
<212> TYPE: PRT
<213> ORGANISM: Artificial Sequence
```

```
<220> FEATURE:
<223> OTHER INFORMATION: AET-EPO-PAS22-PAS600
<220> FEATURE:
<221> NAME/KEY: DISULFID
<222> LOCATION: (9)..(18)
<223> OTHER INFORMATION: Disulfid bridge between Cys-9 and Cys-18
<220> FEATURE:
<221> NAME/KEY: DISULFID
<222> LOCATION: (51)..(60)
<223> OTHER INFORMATION: Disulfid bridge between Cys-51 and Cys-60

<400> SEQUENCE: 145

Ala Glu Thr Gly Gly Leu Tyr Ala Cys His Met Gly Pro Met Thr Trp
1               5                   10                  15

Val Cys Gln Pro Leu Arg Gly Ala Ala Pro Ala Ala Pro Ala Pro Ala
            20                  25                  30

Ala Pro Ala Ala Pro Ala Pro Ala Ala Pro Ala Ala Pro Gly Gly Leu
        35                  40                  45

Tyr Ala Cys His Met Gly Pro Met Thr Trp Val Cys Gln Pro Leu Arg
    50                  55                  60

Gly Ala Ala Pro Ala Ala Pro Ala Pro Ala Ala Pro Ala Ala Pro Ala
65                  70                  75                  80

Pro Ala Ala Pro Ala Ala Pro Ala Pro Ala Ala Pro Ala Ala Pro Ala
                85                  90                  95

Pro Ala Ala Pro Ala Ala Pro Ala Pro Ala Ala Pro Ala Ala Pro Ala
            100                 105                 110

Pro Ala Ala Pro Ala Ala Pro Ala Pro Ala Ala Pro Ala Ala Pro Ala
        115                 120                 125

Pro Ala Ala Pro Ala Ala Pro Ala Pro Ala Ala Pro Ala Ala Pro Ala
    130                 135                 140

Pro Ala Ala Pro Ala Ala Pro Ala Pro Ala Ala Pro Ala Ala Pro Ala
145                 150                 155                 160

Pro Ala Ala Pro Ala Ala Pro Ala Pro Ala Ala Pro Ala Ala Pro Ala
                165                 170                 175

Pro Ala Ala Pro Ala Ala Pro Ala Pro Ala Ala Pro Ala Ala Pro Ala
            180                 185                 190

Pro Ala Ala Pro Ala Ala Pro Ala Pro Ala Ala Pro Ala Ala Pro Ala
        195                 200                 205

Pro Ala Ala Pro Ala Ala Pro Ala Pro Ala Ala Pro Ala Ala Pro Ala
    210                 215                 220

Pro Ala Ala Pro Ala Ala Pro Ala Pro Ala Ala Pro Ala Ala Pro Ala
225                 230                 235                 240

Pro Ala Ala Pro Ala Ala Pro Ala Pro Ala Ala Pro Ala Ala Pro Ala
                245                 250                 255

Pro Ala Ala Pro Ala Ala Pro Ala Pro Ala Ala Pro Ala Ala Pro Ala
            260                 265                 270

Pro Ala Ala Pro Ala Ala Pro Ala Pro Ala Ala Pro Ala Ala Pro Ala
        275                 280                 285

Pro Ala Ala Pro Ala Ala Pro Ala Pro Ala Ala Pro Ala Ala Pro Ala
    290                 295                 300

Pro Ala Ala Pro Ala Ala Pro Ala Pro Ala Ala Pro Ala Ala Pro Ala
305                 310                 315                 320

Pro Ala Ala Pro Ala Ala Pro Ala Pro Ala Ala Pro Ala Ala Pro Ala
                325                 330                 335

Pro Ala Ala Pro Ala Ala Pro Ala Pro Ala Ala Pro Ala Ala Pro Ala
            340                 345                 350
```

```
Pro Ala Ala Pro Ala Ala Pro Ala Pro Ala Ala Pro Ala Ala Pro Ala
        355                 360                 365

Pro Ala Ala Pro Ala Ala Pro Ala Pro Ala Ala Pro Ala Ala Pro Ala
    370                 375                 380

Pro Ala Ala Pro Ala Ala Pro Ala Pro Ala Ala Pro Ala Ala Pro Ala
385                 390                 395                 400

Pro Ala Ala Pro Ala Ala Pro Ala Pro Ala Ala Pro Ala Ala Pro Ala
                405                 410                 415

Pro Ala Ala Pro Ala Ala Pro Ala Pro Ala Ala Pro Ala Ala Pro Ala
            420                 425                 430

Pro Ala Ala Pro Ala Ala Pro Ala Pro Ala Ala Pro Ala Ala Pro Ala
        435                 440                 445

Pro Ala Ala Pro Ala Ala Pro Ala Pro Ala Ala Pro Ala Ala Pro Ala
    450                 455                 460

Pro Ala Ala Pro Ala Ala Pro Ala Pro Ala Ala Pro Ala Ala Pro Ala
465                 470                 475                 480

Pro Ala Ala Pro Ala Ala Pro Ala Pro Ala Ala Pro Ala Ala Pro Ala
                485                 490                 495

Pro Ala Ala Pro Ala Ala Pro Ala Pro Ala Ala Pro Ala Ala Pro Ala
            500                 505                 510

Pro Ala Ala Pro Ala Ala Pro Ala Pro Ala Ala Pro Ala Ala Pro Ala
        515                 520                 525

Pro Ala Ala Pro Ala Ala Pro Ala Pro Ala Ala Pro Ala Ala Pro Ala
    530                 535                 540

Pro Ala Ala Pro Ala Ala Pro Ala Pro Ala Ala Pro Ala Ala Pro Ala
545                 550                 555                 560

Pro Ala Ala Pro Ala Ala Pro Ala Pro Ala Ala Pro Ala Ala Pro Ala
                565                 570                 575

Pro Ala Ala Pro Ala Ala Pro Ala Pro Ala Ala Pro Ala Ala Pro Ala
            580                 585                 590

Pro Ala Ala Pro Ala Ala Pro Ala Pro Ala Ala Pro Ala Ala Pro Ala
        595                 600                 605

Pro Ala Ala Pro Ala Ala Pro Ala Pro Ala Ala Pro Ala Ala Pro Ala
    610                 615                 620

Pro Ala Ala Pro Ala Ala Pro Ala Pro Ala Ala Pro Ala Ala Pro Ala
625                 630                 635                 640

Pro Ala Ala Pro Ala Ala Pro Ala Pro Ala Ala Pro Ala Ala Pro Ala
                645                 650                 655

Pro Ala Ala Pro Ala Ala Pro Ala Pro
            660                 665
```

<210> SEQ ID NO 146
<211> LENGTH: 888
<212> TYPE: DNA
<213> ORGANISM: Artificial Sequence
<220> FEATURE:
<223> OTHER INFORMATION: CspBss-AET-EPO-PAS22-PAS200

<400> SEQUENCE: 146

```
atgttcaaca accgtattcg taccgctgcc ctggccggcg ccattgccat ctccaccgct     60

gcgtccggcg tcgccattcc tgcgttcgca gccgaaaccg gcggcctgta cgcatgccac    120

atgggtccaa tgacctgggt gtgccagcca ctgcgcggcg ctgcaccagc tgctccagca    180

ccagcagccc cagctgcacc agcaccagct gctccagctg caccaggcgg cctgtacgct    240

tgtcatatgg gtccaatgac ttgggtctgc cagccactcc gcggcgctgc accagcagct    300
```

```
cctgctccag cagcacctgc agcaccagca ccagcagctc cagcagcacc tgccccagca    360

gctcctgcag ctcctgcccc agcagcacct gccgctcctg ctcctgcagc tccagcagca    420

cccgccccag cagctcccgc agctcctgcg ccagcagcac ctgccgcccc tgctcccgca    480

gctccagcag caccggcacc cgcagctcca gcagctcctg cacctgcagc acctgccgct    540

cccgctccgg cagctccagc agcaccagcc cctgcagctc ctgctgcacc tgctccagca    600

gcacccgcgg ctcctgctcc ggctgctcca gcagcccctg ctccagcagc tcccgctgca    660

cctgcaccag cagcacctgc cgcgcctgct cctgctgccc ctgctgctcc tgctcctgca    720

gcccctgctg cacccgctcc agcagcacct gcggctcctg ctccggccgc ccctgctgct    780

ccagcaccag ctgcccctgc agcccctgcc cctgcagccc cagctgcacc agcaccagca    840

gcaccagcag cacccgcacc agcagcccca gcagccccag ccccttag                 888
```

```
<210> SEQ ID NO 147
<211> LENGTH: 295
<212> TYPE: PRT
<213> ORGANISM: Artificial Sequence
<220> FEATURE:
<223> OTHER INFORMATION: CspBss-AET-EPO-PAS22-PAS200
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (81)..(90)
<223> OTHER INFORMATION: Disulfid bridge between Cys-81 and Cys-90

<400> SEQUENCE: 147

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Ala Ala Pro
    50                  55                  60

Ala Ala Pro Ala Pro Ala Ala Pro Ala Ala Pro Gly Gly Leu Tyr Ala
65                  70                  75                  80

Cys His Met Gly Pro Met Thr Trp Val Cys Gln Pro Leu Arg Gly Ala
                85                  90                  95

Ala Pro Ala Ala Pro Ala Pro Ala Ala Pro Ala Ala Pro Ala Pro Ala
            100                 105                 110

Ala Pro Ala Ala Pro Ala Pro Ala Ala Pro Ala Ala Pro Ala Pro Ala
        115                 120                 125

Ala Pro Ala Ala Pro Ala Pro Ala Ala Pro Ala Ala Pro Ala Pro Ala
    130                 135                 140

Ala Pro Ala Ala Pro Ala Pro Ala Ala Pro Ala Ala Pro Ala Pro Ala
145                 150                 155                 160

Ala Pro Ala Ala Pro Ala Pro Ala Ala Pro Ala Ala Pro Ala Pro Ala
                165                 170                 175

Ala Pro Ala Ala Pro Ala Pro Ala Ala Pro Ala Ala Pro Ala Pro Ala
            180                 185                 190

Ala Pro Ala Ala Pro Ala Pro Ala Ala Pro Ala Ala Pro Ala Pro Ala
        195                 200                 205

Ala Pro Ala Ala Pro Ala Pro Ala Ala Pro Ala Ala Pro Ala Pro Ala
```

```
    210                 215                 220

Ala Pro Ala Ala Pro Ala Pro Ala Ala Pro Ala Ala Pro Ala Pro Ala
225                 230                 235                 240

Ala Pro Ala Ala Pro Ala Pro Ala Ala Pro Ala Ala Pro Ala Pro Ala
                245                 250                 255

Ala Pro Ala Ala Pro Ala Pro Ala Ala Pro Ala Ala Pro Ala Pro Ala
            260                 265                 270

Ala Pro Ala Ala Pro Ala Pro Ala Ala Pro Ala Ala Pro Ala Pro Ala
        275                 280                 285

Ala Pro Ala Ala Pro Ala Pro
    290                 295


<210> SEQ ID NO 148
<211> LENGTH: 2088
<212> TYPE: DNA
<213> ORGANISM: Artificial Sequence
<220> FEATURE:
<223> OTHER INFORMATION: CspBss-AET-EPO-PAS22-PAS600

<400> SEQUENCE: 148

atgtttaaca accgtattcg taccgctgcc ctcgctggtg ccattgccat ctctaccgct     60

gcgtccggcg tcgctattcc tgcctttgca gccgaaaccg gcggcctgta cgcatgccac    120

atgggtccaa tgacctgggt gtgccagcca ctccgcggcg ctgcaccagc agctccagca    180

ccagcagccc cagctgcacc agctccagct gctccagctg caccaggcgg cctgtacgct    240

tgtcatatgg gtccaatgac ttgggtctgt caacctctgc gcggcgctgc tcctgcagct    300

ccagctccag cagcaccagc tgcaccagcc cctgctgcac cagcagcacc agcaccagca    360

gcaccagctg cccctgcccc tgctgcccca gctgcaccag cccccgctgc ccctgccgct    420

cctgctcctg cagcaccagc tgcccccgcc cctgctgctc ctgcagcccc tgctcccgct    480

gcccctgccg cccccgcccc tgcagcacca gctgcgcctg cccccgctgc gccagctgca    540

ccagccccgg ctgcccctgc cgctcccgcc cccgcagcac cagctgcccc ggccccggct    600

gcgcctgctg caccagctcc tgctgcccct gccgctccgg ccccggcagc accagctgcc    660

ccagcacctg ctgcaccagc tgcaccagcg cctgctgccc ctgccgcccc ggcccccgca    720

gctcctgctg cccccgcacc tgccgcacca gctgcaccag cacctgctgc tcccgccgct    780

cctgctcccg cagcaccagc tgcgcccgcc ccggctgcgc ccgcagcccc tgctcccgcc    840

gcacctgctg ctcccgcgcc tgcagcacca gctgctcctg cacctgctgc tcctgccgct    900

ccagctcctg ctgccccggc cgctcctgct ccggcagcac cagctgcgcc ggcccccgct    960

gcccccgcag cccctgctcc ggctgcccct gccgcccctg ctccagcagc tcctgctgcc   1020

ccagcacctg ccgctcctgc agctcctgct ccagctgccc ctgccgctcc agccccagca   1080

gcaccagctg cgccagcacc tgccgctccc gcagctcctg ctccagccgc acctgctgct   1140

ccggcgcccg cagcaccagc tgctcccgca cctgcggctc cagcagcccc tgcccctgct   1200

gcgcctgccg ctcctgctcc agcagctccc gctgcacctg ccccggccgc tccagctgca   1260

ccagccccag ctgctccagc cgctcccgct ccggcagctc ctgctgctcc cgctccggct   1320

gctcctgccg caccagctcc tgcagctcca gcagcccccg ctccggcagc tcccgctgct   1380

cccgctccag ccgctcctgc agccccagca ccagctgctc cagccgcccc cgctccggca   1440

gcccctgctg ctcccgctcc cgctgctcct gcggcaccag ctcccgcagc tccagcagcc   1500

ccggctccgg cagctccggc tgctcccgct cccgccgctc ccgcagcccc tgctccagct   1560
```

```
gctccagccg cgcccgctcc agcagctcca gctgcacctg ctccggccgc ccctgccgct   1620

ccagctccgg cagctccagc agccccagcg cctgcagctc ctgctgctcc ggctccagcc   1680

gctcccgcag cccccgctcc agctgctcca gcggctcccg ctccagcagc ccccgccgca   1740

cctgctccag ccgctccggc agccccagct ccagccgctc cagccgctcc agcgcctgca   1800

gctccagcgg ctcccgcccc agccgctcct gcagcgccag ctccagcggc tcctgccgct   1860

cctgcccctg cagctccagc agcgcccgct ccagccgccc cggcagctcc tgctcctgct   1920

gctccagccg ctccagcacc tgcagctcca gcagctcctg ccccagccgc tcccgcagcg   1980

ccagctccag cagcgccggc tgcaccggcc cctgcagcac cagccgctcc cgctcccgct   2040

gctcccgccg cccccgcacc cgccgccccc gctgctcccg ctccctaa                2088
```

```
<210> SEQ ID NO 149
<211> LENGTH: 695
<212> TYPE: PRT
<213> ORGANISM: Artificial Sequence
<220> FEATURE:
<223> OTHER INFORMATION: CspBss-AET-EPO-PAS22-PAS600
<220> FEATURE:
<221> NAME/KEY: DISULFID
<222> LOCATION: (39)..(48)
<223> OTHER INFORMATION: Disulfid bridge between Cys-39 and Cys-48
<220> FEATURE:
<221> NAME/KEY: DISULFID
<222> LOCATION: (81)..(90)
<223> OTHER INFORMATION: Disulfid bridge between Cys-81 and Cys-90

<400> SEQUENCE: 149

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Gly Gly Leu Tyr Ala Cys His Met Gly Pro Met Thr Trp Val Cys
        35                  40                  45

Gln Pro Leu Arg Gly Ala Ala Pro Ala Ala Pro Ala Pro Ala Ala Pro
    50                  55                  60

Ala Ala Pro Ala Pro Ala Ala Pro Ala Ala Pro Gly Gly Leu Tyr Ala
65                  70                  75                  80

Cys His Met Gly Pro Met Thr Trp Val Cys Gln Pro Leu Arg Gly Ala
                85                  90                  95

Ala Pro Ala Ala Pro Ala Pro Ala Ala Pro Ala Ala Pro Ala Pro Ala
            100                 105                 110

Ala Pro Ala Ala Pro Ala Pro Ala Ala Pro Ala Ala Pro Ala Pro Ala
        115                 120                 125

Ala Pro Ala Ala Pro Ala Pro Ala Ala Pro Ala Ala Pro Ala Pro Ala
    130                 135                 140

Ala Pro Ala Ala Pro Ala Pro Ala Ala Pro Ala Ala Pro Ala Pro Ala
145                 150                 155                 160

Ala Pro Ala Ala Pro Ala Pro Ala Ala Pro Ala Ala Pro Ala Pro Ala
                165                 170                 175

Ala Pro Ala Ala Pro Ala Pro Ala Ala Pro Ala Ala Pro Ala Pro Ala
            180                 185                 190

Ala Pro Ala Ala Pro Ala Pro Ala Ala Pro Ala Ala Pro Ala Pro Ala
        195                 200                 205

Ala Pro Ala Ala Pro Ala Pro Ala Ala Pro Ala Ala Pro Ala Pro Ala
    210                 215                 220

Ala Pro Ala Ala Pro Ala Pro Ala Ala Pro Ala Ala Pro Ala Pro Ala
```

```
225                 230                 235                 240

Ala Pro Ala Ala Pro Ala Pro Ala Ala Pro Ala Ala Pro Ala Pro Ala
                245                 250                 255

Ala Pro Ala Ala Pro Ala Pro Ala Ala Pro Ala Ala Pro Ala Pro Ala
            260                 265                 270

Ala Pro Ala Ala Pro Ala Pro Ala Ala Pro Ala Ala Pro Ala Pro Ala
        275                 280                 285

Ala Pro Ala Ala Pro Ala Pro Ala Ala Pro Ala Ala Pro Ala Pro Ala
    290                 295                 300

Ala Pro Ala Ala Pro Ala Pro Ala Ala Pro Ala Ala Pro Ala Pro Ala
305                 310                 315                 320

Ala Pro Ala Ala Pro Ala Pro Ala Ala Pro Ala Ala Pro Ala Pro Ala
                325                 330                 335

Ala Pro Ala Ala Pro Ala Pro Ala Ala Pro Ala Ala Pro Ala Pro Ala
            340                 345                 350

Ala Pro Ala Ala Pro Ala Pro Ala Ala Pro Ala Ala Pro Ala Pro Ala
        355                 360                 365

Ala Pro Ala Ala Pro Ala Pro Ala Ala Pro Ala Ala Pro Ala Pro Ala
    370                 375                 380

Ala Pro Ala Ala Pro Ala Pro Ala Ala Pro Ala Ala Pro Ala Pro Ala
385                 390                 395                 400

Ala Pro Ala Ala Pro Ala Pro Ala Ala Pro Ala Ala Pro Ala Pro Ala
                405                 410                 415

Ala Pro Ala Ala Pro Ala Pro Ala Ala Pro Ala Ala Pro Ala Pro Ala
            420                 425                 430

Ala Pro Ala Ala Pro Ala Pro Ala Ala Pro Ala Ala Pro Ala Pro Ala
        435                 440                 445

Ala Pro Ala Ala Pro Ala Pro Ala Ala Pro Ala Ala Pro Ala Pro Ala
    450                 455                 460

Ala Pro Ala Ala Pro Ala Pro Ala Ala Pro Ala Ala Pro Ala Pro Ala
465                 470                 475                 480

Ala Pro Ala Ala Pro Ala Pro Ala Ala Pro Ala Ala Pro Ala Pro Ala
                485                 490                 495

Ala Pro Ala Ala Pro Ala Pro Ala Ala Pro Ala Ala Pro Ala Pro Ala
            500                 505                 510

Ala Pro Ala Ala Pro Ala Pro Ala Ala Pro Ala Ala Pro Ala Pro Ala
        515                 520                 525

Ala Pro Ala Ala Pro Ala Pro Ala Ala Pro Ala Ala Pro Ala Pro Ala
    530                 535                 540

Ala Pro Ala Ala Pro Ala Pro Ala Ala Pro Ala Ala Pro Ala Pro Ala
545                 550                 555                 560

Ala Pro Ala Ala Pro Ala Pro Ala Ala Pro Ala Ala Pro Ala Pro Ala
                565                 570                 575

Ala Pro Ala Ala Pro Ala Pro Ala Ala Pro Ala Ala Pro Ala Pro Ala
            580                 585                 590

Ala Pro Ala Ala Pro Ala Pro Ala Ala Pro Ala Ala Pro Ala Pro Ala
        595                 600                 605

Ala Pro Ala Ala Pro Ala Pro Ala Ala Pro Ala Ala Pro Ala Pro Ala
    610                 615                 620

Ala Pro Ala Ala Pro Ala Pro Ala Ala Pro Ala Ala Pro Ala Pro Ala
625                 630                 635                 640

Ala Pro Ala Ala Pro Ala Pro Ala Ala Pro Ala Ala Pro Ala Pro Ala
                645                 650                 655
```

Ala Pro Ala Ala Pro Ala Pro Ala Ala Pro Ala Ala Pro Ala Pro Ala
660 665 670

Ala Pro Ala Ala Pro Ala Pro Ala Ala Pro Ala Ala Pro Ala Pro Ala
675 680 685

Ala Pro Ala Ala Pro Ala Pro
690 695

<210> SEQ ID NO 150
<211> LENGTH: 60
<212> TYPE: PRT
<213> ORGANISM: Artificial Sequence
<220> FEATURE:
<223> OTHER INFORMATION: MAET-aMD4dY-PAS22
<220> FEATURE:
<221> NAME/KEY: DISULFID
<222> LOCATION: (5)..(20)
<223> OTHER INFORMATION: Disulfid bridge between Cys-5 and Cys-20
<220> FEATURE:
<221> NAME/KEY: DISULFID
<222> LOCATION: (45)..(60)
<223> OTHER INFORMATION: Disulfid bridge between Cys-45 and Cys-60

<400> SEQUENCE: 150

Met Ala Glu Thr Cys Arg Gln Phe Asn Arg Arg Thr His Glu Val Trp
1 5 10 15

Asn Leu Asp Cys Gly Ala Ala Pro Ala Ala Pro Ala Pro Ala Ala Pro
20 25 30

Ala Ala Pro Ala Pro Ala Ala Pro Ala Ala Pro Gly Cys Arg Gln Phe
35 40 45

Asn Arg Arg Thr His Glu Val Trp Asn Leu Asp Cys
50 55 60

<210> SEQ ID NO 151
<211> LENGTH: 46
<212> TYPE: PRT
<213> ORGANISM: Artificial Sequence
<220> FEATURE:
<223> OTHER INFORMATION: MAET-aMD4dY-PAS8
<220> FEATURE:
<221> NAME/KEY: DISULFID
<222> LOCATION: (5)..(20)
<223> OTHER INFORMATION: Disulfid bridge between Cys-5 and Cys-20
<220> FEATURE:
<221> NAME/KEY: DISULFID
<222> LOCATION: (31)..(46)
<223> OTHER INFORMATION: Disulfid bridge between Cys-31 and Cys-46

<400> SEQUENCE: 151

Met Ala Glu Thr Cys Arg Gln Phe Asn Arg Arg Thr His Glu Val Trp
1 5 10 15

Asn Leu Asp Cys Gly Ala Ala Pro Ala Ala Pro Ala Pro Gly Cys Arg
20 25 30

Gln Phe Asn Arg Arg Thr His Glu Val Trp Asn Leu Asp Cys
35 40 45

<210> SEQ ID NO 152
<211> LENGTH: 61
<212> TYPE: PRT
<213> ORGANISM: Artificial Sequence
<220> FEATURE:
<223> OTHER INFORMATION: MAET-aMD4-PAS22
<220> FEATURE:
<221> NAME/KEY: DISULFID
<222> LOCATION: (5)..(21)
<223> OTHER INFORMATION: Disulfid bridge between Cys-5 and Cys-21
<220> FEATURE:

<221> NAME/KEY: DISULFID
<222> LOCATION: (46)..(61)
<223> OTHER INFORMATION: Disulfid bridge between Cys-46 and Cys-61

<400> SEQUENCE: 152

Met Ala Glu Thr Cys Tyr Arg Gln Phe Asn Arg Arg Thr His Glu Val
1               5                   10                  15

Trp Asn Leu Asp Cys Gly Ala Ala Pro Ala Ala Pro Ala Pro Ala Ala
            20                  25                  30

Pro Ala Ala Pro Ala Pro Ala Ala Pro Ala Ala Pro Gly Cys Arg Gln
        35                  40                  45

Phe Asn Arg Arg Thr His Glu Val Trp Asn Leu Asp Cys
    50                  55                  60

<210> SEQ ID NO 153
<211> LENGTH: 52
<212> TYPE: PRT
<213> ORGANISM: Artificial Sequence
<220> FEATURE:
<223> OTHER INFORMATION: MAET-EPO-PAS8
<220> FEATURE:
<221> NAME/KEY: DISULFID
<222> LOCATION: (10)..(19)
<223> OTHER INFORMATION: Disulfid bridge between Cys-10 and Cys-19
<220> FEATURE:
<221> NAME/KEY: DISULFID
<222> LOCATION: (38)..(47)
<223> OTHER INFORMATION: Disulfid bridge between Cys-38 and Cys-47

<400> SEQUENCE: 153

Met Ala Glu Thr Gly Gly Leu Tyr Ala Cys His Met Gly Pro Met Thr
1               5                   10                  15

Trp Val Cys Gln Pro Leu Arg Gly Ala Ala Pro Ala Ala Pro Ala Pro
            20                  25                  30

Gly Gly Leu Tyr Ala Cys His Met Gly Pro Met Thr Trp Val Cys Gln
        35                  40                  45

Pro Leu Arg Gly
    50

<210> SEQ ID NO 154
<211> LENGTH: 93
<212> TYPE: PRT
<213> ORGANISM: Artificial Sequence
<220> FEATURE:
<223> OTHER INFORMATION: MAET-EPO-PAS49-b
<220> FEATURE:
<221> NAME/KEY: DISULFID
<222> LOCATION: (10)..(19)
<223> OTHER INFORMATION: Disulfid bridge between Cys-10 and Cys-19
<220> FEATURE:
<221> NAME/KEY: DISULFID
<222> LOCATION: (79)..(88)
<223> OTHER INFORMATION: Disulfid bridge between Cys-79 and Cys-88

<400> SEQUENCE: 154

Met Ala Glu Thr Gly Gly Leu Tyr Ala Cys His Met Gly Pro Met Thr
1               5                   10                  15

Trp Val Cys Gln Pro Leu Arg Gly Ser Ala Pro Ser Pro Ser Ser Ala
            20                  25                  30

Pro Ala Ser Ala Ser Ala Pro Ala Ser Pro Ala Ser Ala Ser Ala Ser
        35                  40                  45

Ala Ser Pro Ala Ser Ser Pro Ala Ser Ala Ser Ser Ala Ser Pro Ala
    50                  55                  60

Ala Ser Ser Ala Ser Pro Ala Ser Ser Gly Gly Leu Tyr Ala Cys His

```
65                  70                  75                  80

Met Gly Pro Met Thr Trp Val Cys Gln Pro Leu Arg Gly
                85                  90


<210> SEQ ID NO 155
<211> LENGTH: 144
<212> TYPE: PRT
<213> ORGANISM: Artificial Sequence
<220> FEATURE:
<223> OTHER INFORMATION: MAET-EPO-PAS100-b
<220> FEATURE:
<221> NAME/KEY: DISULFID
<222> LOCATION: (10)..(19)
<223> OTHER INFORMATION: Disulfid bridge between Cys-10 and Cys-19
<220> FEATURE:
<221> NAME/KEY: DISULFID
<222> LOCATION: (130)..(139)
<223> OTHER INFORMATION: Disulfid bridge between Cys-130 and Cys-139

<400> SEQUENCE: 155

Met Ala Glu Thr Gly Gly Leu Tyr Ala Cys His Met Gly Pro Met Thr
1               5                   10                  15

Trp Val Cys Gln Pro Leu Arg Gly Ser Ala Pro Ser Pro Ser Ser Ala
            20                  25                  30

Pro Ala Ser Ala Ser Ala Pro Ala Ser Pro Ala Ser Ala Ser Ala Ser
        35                  40                  45

Ala Ser Pro Ala Ser Ser Pro Ala Ser Ala Ser Ser Ala Ser Pro Ala
    50                  55                  60

Ala Ser Ser Ala Ser Pro Ala Ser Ser Ser Ala Ser Pro Ser Ala Pro
65                  70                  75                  80

Ala Ala Pro Ser Ala Ser Ala Ala Pro Ser Ala Ser Pro Ala Ser Ser
                85                  90                  95

Ser Pro Ala Pro Ala Ser Ala Pro Ser Pro Ala Ala Ala Ala Ser Ser
            100                 105                 110

Pro Ser Pro Ala Pro Ser Ser Ala Ser Ser Ala Ala Gly Gly Leu Tyr
        115                 120                 125

Ala Cys His Met Gly Pro Met Thr Trp Val Cys Gln Pro Leu Arg Gly
    130                 135                 140


<210> SEQ ID NO 156
<211> LENGTH: 55
<212> TYPE: PRT
<213> ORGANISM: Artificial Sequence
<220> FEATURE:
<223> OTHER INFORMATION: MAET-VEGFR_D2-PAS16
<220> FEATURE:
<221> NAME/KEY: DISULFID
<222> LOCATION: (10)..(17)
<223> OTHER INFORMATION: Disulfid bridge between Cys-10 and Cys-17
<220> FEATURE:
<221> NAME/KEY: DISULFID
<222> LOCATION: (40)..(50)
<223> OTHER INFORMATION: Disulfid bridge between Cys-40 and Cys-50

<400> SEQUENCE: 156

Met Ala Glu Thr Ala Gly Pro Thr Trp Cys Glu Asp Asp Trp Tyr Tyr
1               5                   10                  15

Cys Trp Leu Phe Gly Thr Ala Ala Pro Ala Ala Pro Ala Pro Ala Ala
            20                  25                  30

Pro Ala Ala Pro Ala Pro Val Cys Trp Glu Asp Ser Trp Gly Gly Glu
        35                  40                  45

Val Cys Trp Leu Phe Gly Thr
    50                  55
```

<210> SEQ ID NO 157
<211> LENGTH: 88
<212> TYPE: PRT
<213> ORGANISM: Artificial Sequence
<220> FEATURE:
<223> OTHER INFORMATION: MAET-VEGFR_D2-PAS49-b
<220> FEATURE:
<221> NAME/KEY: DISULFID
<222> LOCATION: (10)..(17)
<223> OTHER INFORMATION: Disulfid bridge between Cys-10 and Cys-17
<220> FEATURE:
<221> NAME/KEY: DISULFID
<222> LOCATION: (73)..(83)
<223> OTHER INFORMATION: Disulfid bridge between Cys-73 and Cys-83

<400> SEQUENCE: 157

```
Met Ala Glu Thr Ala Gly Pro Thr Trp Cys Glu Asp Asp Trp Tyr Tyr
1               5                   10                  15

Cys Trp Leu Phe Gly Thr Ser Ala Pro Ser Pro Ser Ser Ala Pro Ala
            20                  25                  30

Ser Ala Ser Ala Pro Ala Ser Pro Ala Ser Ala Ser Ala Ser Ala Ser
        35                  40                  45

Pro Ala Ser Ser Pro Ala Ser Ala Ser Ser Ala Ser Pro Ala Ala Ser
    50                  55                  60

Ser Ala Ser Pro Ala Ser Ser Val Cys Trp Glu Asp Ser Trp Gly Gly
65                  70                  75                  80

Glu Val Cys Trp Leu Phe Gly Thr
                85
```

<210> SEQ ID NO 158
<211> LENGTH: 139
<212> TYPE: PRT
<213> ORGANISM: Artificial Sequence
<220> FEATURE:
<223> OTHER INFORMATION: MAET-VEGFR_D2-PAS100-b
<220> FEATURE:
<221> NAME/KEY: DISULFID
<222> LOCATION: (10)..(17)
<223> OTHER INFORMATION: Disulfid bridge between Cys-10 and Cys-17
<220> FEATURE:
<221> NAME/KEY: DISULFID
<222> LOCATION: (124)..(134)
<223> OTHER INFORMATION: Disulfid bridge between Cys-124 and Cys-134

<400> SEQUENCE: 158

```
Met Ala Glu Thr Ala Gly Pro Thr Trp Cys Glu Asp Asp Trp Tyr Tyr
1               5                   10                  15

Cys Trp Leu Phe Gly Thr Ser Ala Pro Ser Pro Ser Ser Ala Pro Ala
            20                  25                  30

Ser Ala Ser Ala Pro Ala Ser Pro Ala Ser Ala Ser Ala Ser Ala Ser
        35                  40                  45

Pro Ala Ser Ser Pro Ala Ser Ala Ser Ser Ala Ser Pro Ala Ala Ser
    50                  55                  60

Ser Ala Ser Pro Ala Ser Ser Ser Ala Ser Pro Ser Ala Pro Ala Ala
65                  70                  75                  80

Pro Ser Ala Ser Ala Ala Pro Ser Ala Ser Pro Ala Ser Ser Ser Pro
                85                  90                  95

Ala Pro Ala Ser Ala Pro Ser Pro Ala Ala Ala Ala Ser Ser Pro Ser
            100                 105                 110

Pro Ala Pro Ser Ser Ala Ser Ser Ala Ala Val Cys Trp Glu Asp Ser
        115                 120                 125
```

Trp Gly Gly Glu Val Cys Trp Leu Phe Gly Thr
    130                 135

<210> SEQ ID NO 159
<211> LENGTH: 55
<212> TYPE: PRT
<213> ORGANISM: Artificial Sequence
<220> FEATURE:
<223> OTHER INFORMATION: MAET-VEGFR_D2-GS16
<220> FEATURE:
<221> NAME/KEY: DISULFID
<222> LOCATION: (10)..(17)
<223> OTHER INFORMATION: Disulfid bridge between Cys-10 and Cys-17
<220> FEATURE:
<221> NAME/KEY: DISULFID
<222> LOCATION: (40)..(50)
<223> OTHER INFORMATION: Disulfid bridge between Cys-40 and Cys-50

<400> SEQUENCE: 159

Met Ala Glu Thr Ala Gly Pro Thr Trp Cys Glu Asp Asp Trp Tyr Tyr
1               5                   10                  15

Cys Trp Leu Phe Gly Thr Gly Gly Gly Gly Ser Gly Gly Gly Gly Ser
            20                  25                  30

Gly Gly Gly Gly Ser Gly Val Cys Trp Glu Asp Ser Trp Gly Gly Glu
        35                  40                  45

Val Cys Trp Leu Phe Gly Thr
    50                  55

<210> SEQ ID NO 160
<211> LENGTH: 281
<212> TYPE: DNA
<213> ORGANISM: Artificial Sequence
<220> FEATURE:
<223> OTHER INFORMATION: MAET-aMD4dY-PAS22

<400> SEQUENCE: 160
gaaattaata cgactcacta tagggagacc acaacggttt ccctctagaa ataattttgt 60
ttaactttaa gaaggagata taccaatgca gagacctgtc gtcagtttaa ccgtcgtacg 120
cacgaagttt ggaatctgga ctgtggcgca gcccccgcag caccagctcc agcagcaccc 180
gcagctccag caccagcagc ccctgcagcc ccaggctgcc gccaattcaa tcgccgcacc 240
catgaagtgt ggaacttaga ttgctagtga ataactaatc c 281

<210> SEQ ID NO 161
<211> LENGTH: 240
<212> TYPE: DNA
<213> ORGANISM: Artificial Sequence
<220> FEATURE:
<223> OTHER INFORMATION: MAET-aMD4dY-PAS8

<400> SEQUENCE: 161
gaaattaata cgactcacta tagggagacc acaacggttt ccctctagaa ataattttgt 60
ttaactttaa gaaggagata taccaatggc agagacctgt cgtcagttta accgtcgtac 120
gcacgaagtt tggaatctgg actgtggcgc agcacccgca gctccagcac caggctgccg 180
ccaattcaat cgccgcaccc atgaagtgtg gaacttagat tgctagtgaa taactaatcc 240

<210> SEQ ID NO 162
<211> LENGTH: 288
<212> TYPE: DNA
<213> ORGANISM: Artificial Sequence
<220> FEATURE:
<223> OTHER INFORMATION: MAET-aMD4-PAS22

<400> SEQUENCE: 162
gaaattaata cgactcacta tagggagacc acaacggttt ccctctagaa ataattttgt 60
ttaactttaa gaaggagata taccaatggc agagacctgt tatcgtcagt ttaaccgtcg 120
tacgcacgaa gtttggaatc tggactgtgg cgcagccccc gcagcaccag ctccagcagc 180
acccgcagct ccagcaccag cagcccctgc agccccaggc tgctatcgcc aattcaatcg 240
ccgcacccat gaagtgtgga acttagattg ctagtgaata actaatcc 288

<210> SEQ ID NO 163
<211> LENGTH: 258
<212> TYPE: DNA
<213> ORGANISM: Artificial Sequence
<220> FEATURE:
<223> OTHER INFORMATION: MAET-EPO-PAS8

<400> SEQUENCE: 163
gaaattaata cgactcacta tagggagacc acaacggttt ccctctagaa ataattttgt 60
ttaactttaa gaaggagata taccaatggc agaaactggt ggtttatacg cctgtcacat 120
gggcccgatg acttgggttt gccagccatt gcgtggcgca gcacccgcag ctccagcacc 180
aggtggcctg tatgcgtgcc atatggggcc aatgacctgg gtgtgtcagc cgttacgcgg 240
ctagtgaata actaatcc 258

<210> SEQ ID NO 164
<211> LENGTH: 381
<212> TYPE: DNA
<213> ORGANISM: Artificial Sequence
<220> FEATURE:
<223> OTHER INFORMATION: MAET-EPO-PAS49-b

<400> SEQUENCE: 164
gaaattaata cgactcacta tagggagacc acaacggttt ccctctagaa ataattttgt 60
ttaactttaa gaaggagata taccaatggc agaaactggt ggtttatacg cctgtcacat 120
gggcccgatg acttgggttt gccagccatt gcgtggctct gctccatcac cttcttccgc 180
accagcatca gcttctgcac cagcgtcgcc tgcttctgca tctgcgtctg cttcaccagc 240
atcctcacct gcatcagcat cgtctgcttc tccagcagct tcctcagctt cacctgcttc 300
gtctggtggc ctgtatgcgt gccatatggg gccaatgacc tgggtgtgtc agccgttacg 360
cggctagtga ataactaatc c 381

<210> SEQ ID NO 165
<211> LENGTH: 534
<212> TYPE: DNA
<213> ORGANISM: Artificial Sequence
<220> FEATURE:
<223> OTHER INFORMATION: MAET-EPO-PAS100-b

<400> SEQUENCE: 165
gaaattaata cgactcacta tagggagacc acaacggttt ccctctagaa ataattttgt 60
ttaactttaa gaaggagata taccaatggc agaaactggt ggtttatacg cctgtcacat 120
gggcccgatg acttgggttt gccagccatt gcgtggctct gctccatcac cttcttccgc 180
accagcatca gcttctgcac cagcgtcgcc tgcttctgca tctgcgtctg cttcaccagc 240
atcctcacct gcatcagcat cgtctgcttc tccagcagct tcctcagctt cacctgcttc 300
gtcttccgca tccccatctg ctccagcagc accttcagct tctgcagctc catctgcttc 360
acctgcctca tcgtctccag cacctgcgtc agctccatcc cctgcagcag cggcttcatc 420
gccatctcca gcaccttctt cagcgtcatc cgctgcaggt ggcctgtatg cgtgccatat 480
ggggccaatg acctgggtgt gtcagccgtt acgcggctag tgaataacta atcc 534

<210> SEQ ID NO 166
<211> LENGTH: 267
<212> TYPE: DNA
<213> ORGANISM: Artificial Sequence
<220> FEATURE:
<223> OTHER INFORMATION: MAET-VEGFR_D2-PAS16

<400> SEQUENCE: 166
gaaattaata cgactcacta tagggagacc acaacggttt ccctctagaa ataattttgt 60
ttaactttaa gaaggagata taccaatggc ggaaaccgcg ggtcccacgt ggtgtgagga 120
tgactggtac tattgctggt tattcgggac tgcggcccct gctgccccgg ctccggcagc 180
accggccgca ccagcgccgg tttgctggga agatagctgg ggtggcgaag tgtgttggct 240
gtttggcacc tagtgaataa ctaatcc 267

<210> SEQ ID NO 167
<211> LENGTH: 366
<212> TYPE: DNA
<213> ORGANISM: Artificial Sequence
<220> FEATURE:
<223> OTHER INFORMATION: MAET-VEGFR_D2-PAS49-b

<400> SEQUENCE: 167
gaaattaata cgactcacta tagggagacc acaacggttt ccctctagaa ataattttgt 60
ttaactttaa gaaggagata taccaatggc ggaaaccgcg ggtcccacgt ggtgtgagga 120
tgactggtac tattgctggt tattcgggac ttctgctcca tcaccttctt ccgcaccagc 180
atcagcttct gcaccagcgt cgcctgcttc tgcatctgcg tctgcttcac cagcatcctc 240
acctgcatca gcatcgtctg cttctccagc agcttcctca gcttcacctg cttcgtctgt 300
ttgctgggaa gatagctggg gtggcgaagt gtgttggctg tttggcacct agtgaataac 360
taatcc 366

<210> SEQ ID NO 168
<211> LENGTH: 534
<212> TYPE: DNA
<213> ORGANISM: Artificial Sequence
<220> FEATURE:
<223> OTHER INFORMATION: MAET-VEGFR_D2-PAS100-b

<400> SEQUENCE: 168
gaaattaata cgactcacta tagggagacc acaacggttt ccctctagaa ataattttgt 60
ttaactttaa gaaggagata taccaatggc agaaactggt ggtttatacg cctgtcacat 120
gggcccgatg acttgggttt gccagccatt gcgtggctct gctccatcac cttcttccgc 180
accagcatca gcttctgcac cagcgtcgcc tgcttctgca tctgcgtctg cttcaccagc 240
atcctcacct gcatcagcat cgtctgcttc tccagcagct tcctcagctt cacctgcttc 300
gtcttccgca tccccatctg ctccagcagc accttcagct tctgcagctc catctgcttc 360
acctgcctca tcgtctccag cacctgcgtc agctccatcc cctgcagcag cggcttcatc 420
gccatctcca gcaccttctt cagcgtcatc cgctgcaggt ggcctgtatg cgtgccatat 480
ggggccaatg acctgggtgt gtcagccgtt acgcggctag tgaataacta atcc 534

<210> SEQ ID NO 169

<211> LENGTH: 267
<212> TYPE: DNA
<213> ORGANISM: Artificial Sequence
<220> FEATURE:
<223> OTHER INFORMATION: MAET-VEGFR_D2-GS16

<400> SEQUENCE: 169
gaaattaata cgactcacta tagggagacc acaacggttt ccctctagaa ataattttgt 60
ttaactttaa gaaggagata taccaatggc ggaaaccgcg ggtcccacgt ggtgtgagga 120
tgactggtac tattgctggt tattcgggac tggtagcggt agcggcagcg gcagcggtag 180
tggtagtggc agcggcagcg tttgctggga agatagctgg ggtggcgaag tgtgttggct 240
gtttggcacc tagtgaataa ctaatcc 267

<210> SEQ ID NO 170
<211> LENGTH: 25
<212> TYPE: DNA
<213> ORGANISM: Artificial Sequence
<220> FEATURE:
<223> OTHER INFORMATION: Cell-free primer Fwd

<400> SEQUENCE: 170
gaaattaata cgactcacta taggg 25

<210> SEQ ID NO 171
<211> LENGTH: 23
<212> TYPE: DNA
<213> ORGANISM: Artificial Sequence
<220> FEATURE:
<223> OTHER INFORMATION: Cell-free primer Rev

<400> SEQUENCE: 171
cactgactgg attagttatt cac 23

<210> SEQ ID NO 172
<211> LENGTH: 99
<212> TYPE: PRT
<213> ORGANISM: Artificial Sequence
<220> FEATURE:
<223> OTHER INFORMATION: AET-aMD4dY-PAS22-Trimer
<220> FEATURE:
<221> NAME/KEY: DISULFID
<222> LOCATION: (4)..(19)
<223> OTHER INFORMATION: Disulfid bridge between Cys-4 and Cys-19
<220> FEATURE:
<221> NAME/KEY: DISULFID
<222> LOCATION: (44)..(59)
<223> OTHER INFORMATION: Disulfid bridge between Cys-44 and Cys-59
<220> FEATURE:
<221> NAME/KEY: DISULFID
<222> LOCATION: (84)..(99)
<223> OTHER INFORMATION: Disulfid bridge between Cys-84 and Cys-99

<400> SEQUENCE: 172

```
Ala Glu Thr Cys Arg Gln Phe Asn Arg Arg Thr His Glu Val Trp Asn
1               5                   10                  15

Leu Asp Cys Gly Ala Ala Pro Ala Ala Pro Ala Pro Ala Ala Pro Ala
            20                  25                  30

Ala Pro Ala Pro Ala Ala Pro Ala Ala Pro Gly Cys Arg Gln Phe Asn
        35                  40                  45

Arg Arg Thr His Glu Val Trp Asn Leu Asp Cys Gly Ala Ala Pro Ala
    50                  55                  60

Ala Pro Ala Pro Ala Ala Pro Ala Ala Pro Ala Pro Ala Ala Pro Ala
65                  70                  75                  80
```

```
Ala Pro Gly Cys Arg Gln Phe Asn Arg Arg Thr His Glu Val Trp Asn
                85                  90                  95

Leu Asp Cys


<210> SEQ ID NO 173
<211> LENGTH: 390
<212> TYPE: DNA
<213> ORGANISM: Artificial Sequence
<220> FEATURE:
<223> OTHER INFORMATION: CspBss-AET-aMD4dY-PAS22-Trimer

<400> SEQUENCE: 173

atgtttaaca accgtatccg cactgcagct ctcgctggtg caatcgcaat ctccaccgca      60

gcttccggcg tagctatccc agcattcgct gcagagacct gccgccagtt caatcgccgg     120

acccacgaag tctggaatct ggattgcggc gcagctcctg ccgccccagc accggctgcg     180

ccagctgctc cagcgccggc tgcccctgcg gcaccgggtt gccgtcagtt taaccgccgt     240

actcacgagg tttggaacct tgactgtgga gcggctcccg cagcaccagc cccagccgcc     300

cctgctgcac ccgcaccagc ggcacccgcc gctcctggct gtcgccaatt caaccgacgc     360

acccatgaag tgtggaacct cgattgctaa                                      390


<210> SEQ ID NO 174
<211> LENGTH: 129
<212> TYPE: PRT
<213> ORGANISM: Artificial Sequence
<220> FEATURE:
<223> OTHER INFORMATION: CspBss-AET-aMD4dY-PAS22-Trimer
<220> FEATURE:
<221> NAME/KEY: DISULFID
<222> LOCATION: (34)..(49)
<223> OTHER INFORMATION: Disulfid bridge between Cys-34 and Cys-49
<220> FEATURE:
<221> NAME/KEY: DISULFID
<222> LOCATION: (74)..(89)
<223> OTHER INFORMATION: Disulfid bridge between Cys-74 and Cys-89
<220> FEATURE:
<221> NAME/KEY: DISULFID
<222> LOCATION: (114)..(129)
<223> OTHER INFORMATION: Disulfid bridge between Cys-114 and Cys-129

<400> SEQUENCE: 174

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Cys Arg Gln Phe Asn Arg Arg Thr His Glu Val Trp Asn Leu Asp
        35                  40                  45

Cys Gly Ala Ala Pro Ala Ala Pro Ala Pro Ala Ala Pro Ala Ala Pro
    50                  55                  60

Ala Pro Ala Ala Pro Ala Ala Pro Gly Cys Arg Gln Phe Asn Arg Arg
65                  70                  75                  80

Thr His Glu Val Trp Asn Leu Asp Cys Gly Ala Ala Pro Ala Ala Pro
                85                  90                  95

Ala Pro Ala Ala Pro Ala Ala Pro Ala Pro Ala Ala Pro Ala Ala Pro
            100                 105                 110

Gly Cys Arg Gln Phe Asn Arg Arg Thr His Glu Val Trp Asn Leu Asp
        115                 120                 125

Cys


<210> SEQ ID NO 175
```

<211> LENGTH: 87
<212> TYPE: PRT
<213> ORGANISM: Artificial Sequence
<220> FEATURE:
<223> OTHER INFORMATION: AET-VEGFR_D2-PAS49
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (72)..(82)
<223> OTHER INFORMATION: Disulfid bridge between Cys-72 and Cys-82

<400> SEQUENCE: 175

```
Ala Glu Thr Ala Gly Pro Thr Trp Cys Glu Asp Asp Trp Tyr Tyr Cys
1               5                   10                  15

Trp Leu Phe Gly Thr Ala Ala Pro Ala Ala Pro Ala Pro Ala Ala Pro
            20                  25                  30

Ala Ala Pro Ala Pro Ala Ala Pro Ala Ala Pro Ala Pro Ala Ala Pro
        35                  40                  45

Ala Ala Pro Ala Pro Ala Ala Pro Ala Ala Pro Ala Pro Ala Ala Pro
    50                  55                  60

Ala Ala Pro Ala Pro Ala Val Cys Trp Glu Asp Ser Trp Gly Gly Glu
65                  70                  75                  80

Val Cys Trp Leu Phe Gly Thr
                85
```

<210> SEQ ID NO 176
<211> LENGTH: 87
<212> TYPE: PRT
<213> ORGANISM: Artificial Sequence
<220> FEATURE:
<223> OTHER INFORMATION: AET-VEGFR_D2-PAS49-b
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (72)..(82)
<223> OTHER INFORMATION: Disulfid bridge between Cys-72 and Cys-82

<400> SEQUENCE: 176

```
Ala Glu Thr Ala Gly Pro Thr Trp Cys Glu Asp Asp Trp Tyr Tyr Cys
1               5                   10                  15

Trp Leu Phe Gly Thr Ser Ala Pro Ser Pro Ser Ser Ala Pro Ala Ser
            20                  25                  30

Ala Ser Ala Pro Ala Ser Pro Ala Ser Ala Ser Ala Ser Ala Ser Pro
        35                  40                  45

Ala Ser Ser Pro Ala Ser Ala Ser Ser Ala Ser Pro Ala Ala Ser Ser
    50                  55                  60

Ala Ser Pro Ala Ser Ser Val Cys Trp Glu Asp Ser Trp Gly Gly Glu
65                  70                  75                  80

Val Cys Trp Leu Phe Gly Thr
                85
```

<210> SEQ ID NO 177
<211> LENGTH: 138
<212> TYPE: PRT
<213> ORGANISM: Artificial Sequence
<220> FEATURE:
<223> OTHER INFORMATION: AET-VEGFR_D2-PAS100
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (123)..(133)
<223> OTHER INFORMATION: Disulfid bridge between Cys-123 and Cys-133

<400> SEQUENCE: 177

```
Ala Glu Thr Ala Gly Pro Thr Trp Cys Glu Asp Asp Trp Tyr Tyr Cys
1               5                   10                  15

Trp Leu Phe Gly Thr Ala Ala Pro Ala Ala Pro Ala Pro Ala Ala Pro
            20                  25                  30

Ala Ala Pro Ala Pro Ala Ala Pro Ala Ala Pro Ala Pro Ala Ala Pro
        35                  40                  45

Ala Ala Pro Ala Pro Ala Ala Pro Ala Ala Pro Ala Pro Ala Ala Pro
    50                  55                  60

Ala Ala Pro Ala Pro Ala Ala Pro Ala Ala Pro Ala Pro Ala Ala Pro
65                  70                  75                  80

Ala Ala Pro Ala Pro Ala Ala Pro Ala Ala Pro Ala Pro Ala Ala Pro
                85                  90                  95

Ala Ala Pro Ala Pro Ala Ala Pro Ala Ala Pro Ala Pro Ala Ala Pro
            100                 105                 110

Ala Ala Pro Ala Pro Ala Ala Pro Ala Val Cys Trp Glu Asp Ser Trp
        115                 120                 125

Gly Gly Glu Val Cys Trp Leu Phe Gly Thr
    130                 135
```

<210> SEQ ID NO 178
<211> LENGTH: 138
<212> TYPE: PRT
<213> ORGANISM: Artificial Sequence
<220> FEATURE:
<223> OTHER INFORMATION: AET-VEGFR_D2-PAS100-b
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (123)..(133)
<223> OTHER INFORMATION: Disulfid bridge between Cys-123 and Cys-133

<400> SEQUENCE: 178

```
Ala Glu Thr Ala Gly Pro Thr Trp Cys Glu Asp Asp Trp Tyr Tyr Cys
1               5                   10                  15

Trp Leu Phe Gly Thr Ser Ala Pro Ser Pro Ser Ser Ala Pro Ala Ser
            20                  25                  30

Ala Ser Ala Pro Ala Ser Pro Ala Ser Ala Ser Ala Ser Ala Ser Pro
        35                  40                  45

Ala Ser Ser Pro Ala Ser Ala Ser Ser Ala Ser Pro Ala Ala Ser Ser
    50                  55                  60

Ala Ser Pro Ala Ser Ser Ser Ala Ser Pro Ser Ala Pro Ala Ala Pro
65                  70                  75                  80

Ser Ala Ser Ala Ala Pro Ser Ala Ser Pro Ala Ser Ser Ser Pro Ala
                85                  90                  95

Pro Ala Ser Ala Pro Ser Pro Ala Ala Ala Ala Ser Ser Pro Ser Pro
            100                 105                 110

Ala Pro Ser Ser Ala Ser Ser Ala Ala Val Cys Trp Glu Asp Ser Trp
        115                 120                 125

Gly Gly Glu Val Cys Trp Leu Phe Gly Thr
```

130 135

<210> SEQ ID NO 179
<211> LENGTH: 54
<212> TYPE: PRT
<213> ORGANISM: Artificial Sequence
<220> FEATURE:
<223> OTHER INFORMATION: AET-VEGFR_D2-GS16
<220> FEATURE:
<221> NAME/KEY: DISULFID
<222> LOCATION: (9)..(16)
<223> OTHER INFORMATION: Disulfid bridge between Cys-9 and Cys-16
<220> FEATURE:
<221> NAME/KEY: DISULFID
<222> LOCATION: (39)..(49)
<223> OTHER INFORMATION: Disulfid bridge between Cys-39 and Cys-49

<400> SEQUENCE: 179

Ala Glu Thr Ala Gly Pro Thr Trp Cys Glu Asp Asp Trp Tyr Tyr Cys
1 5 10 15

Trp Leu Phe Gly Thr Gly Gly Gly Gly Ser Gly Gly Gly Gly Ser Gly
20 25 30

Gly Gly Gly Ser Gly Val Cys Trp Glu Asp Ser Trp Gly Gly Glu Val
35 40 45

Cys Trp Leu Phe Gly Thr
50

<210> SEQ ID NO 180
<211> LENGTH: 354
<212> TYPE: DNA
<213> ORGANISM: Artificial Sequence
<220> FEATURE:
<223> OTHER INFORMATION: CspBss-VEGFR_D2-PAS49

<400> SEQUENCE: 180
atgtttaaca accgtatccg cactgcagct ctcgctggtg caatcgcaat ctccaccgca 60
gcttccggcg tagctatccc agcattcgct gcagagaccg ctggccctac ctggtgtgag 120
gacgattggt actactgttg gctctttggc accgccgccc ctgctgctcc cgccccccgcc 180 gcccctgccg caccagctcc agcagcccca gctgcaccag caccagccgc tccagcagct 240
ccagcaccag ctgctccagc agcaccagcc ccagcagctc cagccgcacc agctcctgcg 300
gtttgctggg aggattcttg gggcggcgaa gtttgctggc tctttggcac ctaa 354

<210> SEQ ID NO 181
<211> LENGTH: 117
<212> TYPE: PRT
<213> ORGANISM: Artificial Sequence
<220> FEATURE:
<223> OTHER INFORMATION: CspBss-VEGFR_D2-PAS49
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (102)..(112)
<223> OTHER INFORMATION: Disulfid bridge between Cys-102 and Cys-112

<400> SEQUENCE: 181

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Ala Gly Pro Thr Trp Cys Glu Asp Asp Trp Tyr Tyr Cys Trp Leu

```
        35                  40                  45

Phe Gly Thr Ala Ala Pro Ala Ala Pro Ala Pro Ala Ala Pro Ala Ala
    50                  55                  60

Pro Ala Pro Ala Ala Pro Ala Ala Pro Ala Pro Ala Ala Pro Ala Ala
65                  70                  75                  80

Pro Ala Pro Ala Ala Pro Ala Ala Pro Ala Pro Ala Ala Pro Ala Ala
                85                  90                  95

Pro Ala Pro Ala Val Cys Trp Glu Asp Ser Trp Gly Gly Glu Val Cys
            100                 105                 110

Trp Leu Phe Gly Thr
        115


<210> SEQ ID NO 182
<211> LENGTH: 354
<212> TYPE: DNA
<213> ORGANISM: Artificial Sequence
<220> FEATURE:
<223> OTHER INFORMATION: CspBss-VEGFR_D2-PAS49-b

<400> SEQUENCE: 182

atgtttaaca accgtatccg cactgcagct ctcgctggtg caatcgcaat ctccaccgca      60

gcttccggcg tagctatccc agcattcgct gcagagaccg caggacccac ttggtgcgaa     120

gatgactggt actattgctg gctctttggc acctcagcac ccagcccatc ctccgctcca     180

gcgtctgcga gcgctcctgc atccccagcc tctgcctccg catcggcatc accggcttcc     240

agcccagcgt cggcatcgtc agcctctccg gctgcctcct ccgcttctcc tgcgtcctcc     300

gtgtgttggg aggattcctg ggtggtgaa gtctgctggc tgttcggcac ctaa            354


<210> SEQ ID NO 183
<211> LENGTH: 117
<212> TYPE: PRT
<213> ORGANISM: Artificial Sequence
<220> FEATURE:
<223> OTHER INFORMATION: CspBss-VEGFR_D2-PAS49-b
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (102)..(112)
<223> OTHER INFORMATION: Disulfid bridge between Cys-102 and Cys-112

<400> SEQUENCE: 183

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Ala Gly Pro Thr Trp Cys Glu Asp Asp Trp Tyr Tyr Cys Trp Leu
        35                  40                  45

Phe Gly Thr Ser Ala Pro Ser Pro Ser Ser Ala Pro Ala Ser Ala Ser
    50                  55                  60

Ala Pro Ala Ser Pro Ala Ser Ala Ser Ala Ser Ala Ser Pro Ala Ser
65                  70                  75                  80

Ser Pro Ala Ser Ala Ser Ser Ala Ser Pro Ala Ala Ser Ser Ala Ser
                85                  90                  95

Pro Ala Ser Ser Val Cys Trp Glu Asp Ser Trp Gly Gly Glu Val Cys
            100                 105                 110

Trp Leu Phe Gly Thr
```

115

<210> SEQ ID NO 184
<211> LENGTH: 507
<212> TYPE: DNA
<213> ORGANISM: Artificial Sequence
<220> FEATURE:
<223> OTHER INFORMATION: CspBss-VEGFR_D2-PAS100

<400> SEQUENCE: 184
atgtttaaca accgtatccg cactgcagct ctcgctggtg caatcgcaat ctccaccgca 60
gcttccggcg tagctatccc agcattcgct gcagagaccg ccggtccaac ctggtgtgag 120
gatgactggt actactgctg gctctttggc accgctgctc ccgctgctcc cgcccctgct 180
gctccagctg ccccagcccc agctgcccca gctgctccag caccagccgc tccagctgcc 240
ccagcaccag ctgcaccagc agcaccagca ccagcagctc cagccgctcc agccccagcc 300
gctccagcag caccagcccc agcagctcca gctgcaccag ctccagccgc cccagcagca 360
ccagctccag cagccccagc agctccagct ccagccgcac cagctgctcc agccccagcc 420
gcaccagcag ccccagctcc agctgctcct gctgtctgtt gggaggactc ttggggcggc 480
gaagtttgtt ggttgtttgg cacctaa 507

<210> SEQ ID NO 185
<211> LENGTH: 168
<212> TYPE: PRT
<213> ORGANISM: Artificial Sequence
<220> FEATURE:
<223> OTHER INFORMATION: CspBss-VEGFR_D2-PAS100
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (153)..(163)
<223> OTHER INFORMATION: Disulfid bridge between Cys-153 and Cys-163

<400> SEQUENCE: 185

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Ala Gly Pro Thr Trp Cys Glu Asp Asp Trp Tyr Tyr Cys Trp Leu
        35                  40                  45

Phe Gly Thr Ala Ala Pro Ala Ala Pro Ala Pro Ala Ala Pro Ala Ala
    50                  55                  60

Pro Ala Pro Ala Ala Pro Ala Ala Pro Ala Pro Ala Ala Pro Ala Ala
65                  70                  75                  80

Pro Ala Pro Ala Ala Pro Ala Ala Pro Ala Pro Ala Ala Pro Ala Ala
                85                  90                  95

Pro Ala Pro Ala Ala Pro Ala Ala Pro Ala Pro Ala Ala Pro Ala Ala
            100                 105                 110

Pro Ala Pro Ala Ala Pro Ala Ala Pro Ala Pro Ala Ala Pro Ala Ala
        115                 120                 125

Pro Ala Pro Ala Ala Pro Ala Ala Pro Ala Pro Ala Ala Pro Ala Ala
    130                 135                 140

Pro Ala Pro Ala Ala Pro Ala Val Cys Trp Glu Asp Ser Trp Gly Gly
145                 150                 155                 160

Glu Val Cys Trp Leu Phe Gly Thr

165

<210> SEQ ID NO 186
<211> LENGTH: 507
<212> TYPE: DNA
<213> ORGANISM: Artificial Sequence
<220> FEATURE:
<223> OTHER INFORMATION: CspBss-VEGFR_D2-PAS100-b

<400> SEQUENCE: 186
atgtttaaca accgtatccg cactgcagct ctcgctggtg caatcgcaat ctccaccgca 60
gcttccggcg tagctatccc agcattcgct gcagagaccg ccggacctac ctggtgtgag 120
gatgactggt actattgctg gctcttcggc acttccgccc cttccccttc cagcgcacca 180
gcgagcgctt cggctccggc ctccccagcg tccgcatctg cgtctgcatc ccctgcgtcg 240
tcacccgctt cagcctcctc agcctcccct gcggcttcat ccgcctcgcc cgcatccagc 300
tccgcatcac cctctgcgcc agcagctcca tccgcttctg ctgccccatc ggcctctccg 360
gcttccagct ctcccgcacc ggcatccgct ccgagcccag cagcagctgc atcctcccca 420
tctccggcac catcctcggc ctctagcgcg gctgtgtgct gggaagattc ctggggtggt 480
gaagtctgct ggctgtttgg cacctaa 507

<210> SEQ ID NO 187
<211> LENGTH: 168
<212> TYPE: PRT
<213> ORGANISM: Artificial Sequence
<220> FEATURE:
<223> OTHER INFORMATION: CspBss-VEGFR_D2-PAS100-b
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (153)..(163)
<223> OTHER INFORMATION: Disulfid bridge between Cys-153 and Cys-163

<400> SEQUENCE: 187

Met Phe Asn Asn Arg Ile Arg Thr Ala Ala Leu Ala Gly Ala Ile Ala
1 5 10 15

Ile Ser Thr Ala Ala Ser Gly Val Ala Ile Pro Ala Phe Ala Ala Glu
20 25 30

Thr Ala Gly Pro Thr Trp Cys Glu Asp Asp Trp Tyr Tyr Cys Trp Leu
35 40 45

Phe Gly Thr Ser Ala Pro Ser Pro Ser Ser Ala Pro Ala Ser Ala Ser
50 55 60

Ala Pro Ala Ser Pro Ala Ser Ala Ser Ala Ser Ala Ser Pro Ala Ser
65 70 75 80

Ser Pro Ala Ser Ala Ser Ser Ala Ser Pro Ala Ala Ser Ser Ala Ser
85 90 95

Pro Ala Ser Ser Ser Ala Ser Pro Ser Ala Pro Ala Ala Pro Ser Ala
100 105 110

Ser Ala Ala Pro Ser Ala Ser Pro Ala Ser Ser Ser Pro Ala Pro Ala
115 120 125

Ser Ala Pro Ser Pro Ala Ala Ala Ala Ser Ser Pro Ser Pro Ala Pro
130 135 140

Ser Ser Ala Ser Ser Ala Ala Val Cys Trp Glu Asp Ser Trp Gly Gly
145 150 155 160

Glu Val Cys Trp Leu Phe Gly Thr

165

<210> SEQ ID NO 188
<211> LENGTH: 255
<212> TYPE: DNA
<213> ORGANISM: Artificial Sequence
<220> FEATURE:
<223> OTHER INFORMATION: CspBss-VEGFR_D2-GS16

<400> SEQUENCE: 188
atgtttaaca accgtatccg cactgcagct ctcgctggtg caatcgcaat ctccaccgca 60
gcttccggcg tagctatccc agcattcgct gcagagaccg cgggtccgac ctggtgtgag 120
gatgactggt actactgttg gttgttcggc accggcggcg gcggctccgg cggcggcggc 180
tctggcggcg gcggctctgg cgtttgttgg gaggactctt ggggcggcga agtttgctgg 240
ctgtttggca cctaa 255

<210> SEQ ID NO 189
<211> LENGTH: 84
<212> TYPE: PRT
<213> ORGANISM: Artificial Sequence
<220> FEATURE:
<223> OTHER INFORMATION: CspBss-VEGFR_D2-GS16
<220> FEATURE:
<221> NAME/KEY: DISULFID
<222> LOCATION: (39)..(46)
<223> OTHER INFORMATION: Disulfid bridge between Cys-39 and Cys-46
<220> FEATURE:
<221> NAME/KEY: DISULFID
<222> LOCATION: (69)..(79)
<223> OTHER INFORMATION: Disulfid bridge between Cys-69 and Cys-79

<400> SEQUENCE: 189

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Ala Glu
            20                  25                  30

Thr Ala Gly Pro Thr Trp Cys Glu Asp Asp Trp Tyr Tyr Cys Trp Leu
        35                  40                  45

Phe Gly Thr Gly Gly Gly Gly Ser Gly Gly Gly Gly Ser Gly Gly Gly
    50                  55                  60

Gly Ser Gly Val Cys Trp Glu Asp Ser Trp Gly Gly Glu Val Cys Trp
65                  70                  75                  80

Leu Phe Gly Thr

<210> SEQ ID NO 190
<211> LENGTH: 85
<212> TYPE: PRT
<213> ORGANISM: Artificial Sequence
<220> FEATURE:
<223> OTHER INFORMATION: TPO2-PAS49
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (70)..(83)
<223> OTHER INFORMATION: Disulfid bridge between Cys-70 and Cys-83

<400> SEQUENCE: 190

Gly Gly Cys Ala Asp Gly Pro Thr Leu Arg Glu Trp Ile Ser Phe Cys
1               5                   10                  15

Gly Gly Ala Ala Pro Ala Ala Pro Ala Pro Ala Ala Pro Ala Ala Pro

```
            20                  25                  30

Ala Pro Ala Ala Pro Ala Ala Pro Ala Pro Ala Ala Pro Ala Ala Pro
        35                  40                  45

Ala Pro Ala Ala Pro Ala Ala Pro Ala Pro Ala Ala Pro Ala Ala Pro
    50                  55                  60

Ala Pro Ala Gly Gly Cys Ala Asp Gly Pro Thr Leu Arg Glu Trp Ile
65                  70                  75                  80

Ser Phe Cys Gly Gly
                85


<210> SEQ ID NO 191
<211> LENGTH: 85
<212> TYPE: PRT
<213> ORGANISM: Artificial Sequence
<220> FEATURE:
<223> OTHER INFORMATION: TPO2-PAS49-b
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (70)..(83)
<223> OTHER INFORMATION: Disulfid bridge between Cys-70 and Cys-83

<400> SEQUENCE: 191

Gly Gly Cys Ala Asp Gly Pro Thr Leu Arg Glu Trp Ile Ser Phe Cys
1               5                   10                  15

Gly Gly Ser Ala Pro Ser Pro Ser Ser Ala Pro Ala Ser Ala Ser Ala
            20                  25                  30

Pro Ala Ser Pro Ala Ser Ala Ser Ala Ser Ala Ser Pro Ala Ser Ser
        35                  40                  45

Pro Ala Ser Ala Ser Ser Ala Ser Pro Ala Ala Ser Ser Ala Ser Pro
    50                  55                  60

Ala Ser Ser Gly Gly Cys Ala Asp Gly Pro Thr Leu Arg Glu Trp Ile
65                  70                  75                  80

Ser Phe Cys Gly Gly
                85


<210> SEQ ID NO 192
<211> LENGTH: 136
<212> TYPE: PRT
<213> ORGANISM: Artificial Sequence
<220> FEATURE:
<223> OTHER INFORMATION: TPO2-PAS100
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (121)..(134)
<223> OTHER INFORMATION: Disulfid bridge between Cys-121 and Cys-134

<400> SEQUENCE: 192

Gly Gly Cys Ala Asp Gly Pro Thr Leu Arg Glu Trp Ile Ser Phe Cys
1               5                   10                  15

Gly Gly Ala Ala Pro Ala Ala Pro Ala Pro Ala Ala Pro Ala Ala Pro
            20                  25                  30

Ala Pro Ala Ala Pro Ala Ala Pro Ala Pro Ala Ala Pro Ala Ala Pro
        35                  40                  45

Ala Pro Ala Ala Pro Ala Ala Pro Ala Pro Ala Ala Pro Ala Ala Pro
    50                  55                  60
```

Ala Pro Ala Ala Pro Ala Ala Pro Ala Pro Ala Ala Pro Ala Ala Pro
65 70 75 80

Ala Pro Ala Ala Pro Ala Ala Pro Ala Pro Ala Ala Pro Ala Ala Pro
85 90 95

Ala Pro Ala Ala Pro Ala Ala Pro Ala Pro Ala Ala Pro Ala Ala Pro
100 105 110

Ala Pro Ala Ala Pro Ala Gly Gly Cys Ala Asp Gly Pro Thr Leu Arg
115 120 125

Glu Trp Ile Ser Phe Cys Gly Gly
130 135

<210> SEQ ID NO 193
<211> LENGTH: 136
<212> TYPE: PRT
<213> ORGANISM: Artificial Sequence
<220> FEATURE:
<223> OTHER INFORMATION: TPO2-PAS100-b
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (121)..(134)
<223> OTHER INFORMATION: Disulfid bridge between Cys-121 and Cys-134

<400> SEQUENCE: 193

Gly Gly Cys Ala Asp Gly Pro Thr Leu Arg Glu Trp Ile Ser Phe Cys
1 5 10 15

Gly Gly Ser Ala Pro Ser Pro Ser Ser Ala Pro Ala Ser Ala Ser Ala
20 25 30

Pro Ala Ser Pro Ala Ser Ala Ser Ala Ser Ala Ser Pro Ala Ser Ser
35 40 45

Pro Ala Ser Ala Ser Ser Ala Ser Pro Ala Ala Ser Ser Ala Ser Pro
50 55 60

Ala Ser Ser Ser Ala Ser Pro Ser Ala Pro Ala Ala Pro Ser Ala Ser
65 70 75 80

Ala Ala Pro Ser Ala Ser Pro Ala Ser Ser Ser Pro Ala Pro Ala Ser
85 90 95

Ala Pro Ser Pro Ala Ala Ala Ala Ser Ser Pro Ser Pro Ala Pro Ser
100 105 110

Ser Ala Ser Ser Ala Ala Gly Gly Cys Ala Asp Gly Pro Thr Leu Arg
115 120 125

Glu Trp Ile Ser Phe Cys Gly Gly
130 135

<210> SEQ ID NO 194
<211> LENGTH: 44
<212> TYPE: PRT
<213> ORGANISM: Artificial Sequence
<220> FEATURE:
<223> OTHER INFORMATION: TPO2-GS8
<220> FEATURE:
<221> NAME/KEY: DISULFID
<222> LOCATION: (3)..(16)
<223> OTHER INFORMATION: Disulfid bridge between Cys-3 and Cys-16
<220> FEATURE:
<221> NAME/KEY: DISULFID
<222> LOCATION: (29)..(42)
<223> OTHER INFORMATION: Disulfid bridge between Cys-29 and Cys-42

<400> SEQUENCE: 194

```
Gly Gly Cys Ala Asp Gly Pro Thr Leu Arg Glu Trp Ile Ser Phe Cys
1               5                   10                  15

Gly Gly Gly Gly Gly Gly Ser Gly Gly Gly Gly Gly Cys Ala Asp Gly
            20                  25                  30

Pro Thr Leu Arg Glu Trp Ile Ser Phe Cys Gly Gly
        35                  40


<210> SEQ ID NO 195
<211> LENGTH: 333
<212> TYPE: DNA
<213> ORGANISM: Artificial Sequence
<220> FEATURE:
<223> OTHER INFORMATION: CspAss-TPO2-PAS49

<400> SEQUENCE: 195

atgaaacgca tgaaatcgct ggctgcggcg ctcaccgtcg ctggggccat gctggccgca      60

cctgtggcaa cggcaggtgg ctgtgctgac ggtcctaccc ttcgtgagtg gatttctttt     120

tgcggcggtg ctgctcctgc tgcccctgct cctgctgctc ctgcagcacc agccccagca     180

gctccagccg ccccagctcc agccgcacca gctgccccag caccagccgc tccagcagca     240

ccagctccag cagccccagc tgcaccagcc ccagcgggcg gttgtgctga cggtcctacc     300

cttcgtgagt ggatttcctt ctgtggtggc taa                                  333


<210> SEQ ID NO 196
<211> LENGTH: 110
<212> TYPE: PRT
<213> ORGANISM: Artificial Sequence
<220> FEATURE:
<223> OTHER INFORMATION: CspAss-TPO2-PAS49
<220> FEATURE:
<221> NAME/KEY: DISULFID
<222> LOCATION: (28)..(41)
<223> OTHER INFORMATION: Disulfid bridge between Cys-28 and Cys-41
<220> FEATURE:
<221> NAME/KEY: DISULFID
<222> LOCATION: (95)..(108)
<223> OTHER INFORMATION: Disulfid bridge between Cys-95 and Cys-108

<400> SEQUENCE: 196

Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Ala Ala Pro Ala Ala
        35                  40                  45

Pro Ala Pro Ala Ala Pro Ala Ala Pro Ala Pro Ala Ala Pro Ala Ala
    50                  55                  60

Pro Ala Pro Ala Ala Pro Ala Ala Pro Ala Pro Ala Ala Pro Ala Ala
65                  70                  75                  80

Pro Ala Pro Ala Ala Pro Ala Ala Pro Ala Pro Ala Gly Gly Cys Ala
                85                  90                  95

Asp Gly Pro Thr Leu Arg Glu Trp Ile Ser Phe Cys Gly Gly
            100                 105                 110


<210> SEQ ID NO 197
<211> LENGTH: 333
<212> TYPE: DNA
<213> ORGANISM: Artificial Sequence
<220> FEATURE:
<223> OTHER INFORMATION: CspAss-TPO2-PAS49-b

<400> SEQUENCE: 197
```

```
atgaaacgca tgaaatcgct ggctgcggcg ctcaccgtcg ctggggccat gctggccgca     60

cctgtggcaa cggcaggcgg gtgtgcagac ggacccactc tgcgcgaatg gatctccttt    120

tgcggcggtt ccgctccgtc gccatcctct gctccggcat ccgcgtctgc gccagcatcc    180

ccagccagcg cttcagcctc agcgtcccct gcctcctctc cagcatccgc cagcagcgca    240

tctcctgcgg ctagctcggc atcacccgct tcgtccggag gttgcgctga tggccctacc    300

ctccgtgagt ggatttcctt ctgcggtggc taa                                 333


<210> SEQ ID NO 198
<211> LENGTH: 110
<212> TYPE: PRT
<213> ORGANISM: Artificial Sequence
<220> FEATURE:
<223> OTHER INFORMATION: CspAss-TPO2-PAS49-b
<220> FEATURE:
<221> NAME/KEY: DISULFID
<222> LOCATION: (28)..(41)
<223> OTHER INFORMATION: Disulfid bridge between Cys-28 and Cys-41
<220> FEATURE:
<221> NAME/KEY: DISULFID
<222> LOCATION: (95)..(108)
<223> OTHER INFORMATION: Disulfid bridge between Cys-95 and Cys-108

<400> SEQUENCE: 198

Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Ser Ala Pro Ser Pro
        35                  40                  45

Ser Ser Ala Pro Ala Ser Ala Ser Ala Pro Ala Ser Pro Ala Ser Ala
    50                  55                  60

Ser Ala Ser Ala Ser Pro Ala Ser Ser Pro Ala Ser Ala Ser Ser Ala
65                  70                  75                  80

Ser Pro Ala Ala Ser Ser Ala Ser Pro Ala Ser Ser Gly Gly Cys Ala
                85                  90                  95

Asp Gly Pro Thr Leu Arg Glu Trp Ile Ser Phe Cys Gly Gly
            100                 105                 110


<210> SEQ ID NO 199
<211> LENGTH: 486
<212> TYPE: DNA
<213> ORGANISM: Artificial Sequence
<220> FEATURE:
<223> OTHER INFORMATION: CspAss-TPO2-PAS100

<400> SEQUENCE: 199

atgaaacgca tgaaatcgct ggctgcggcg ctcaccgtcg ctggggccat gctggccgca     60

cctgtggcaa cggcaggcgg ttgtgctgac ggtcctacct tgcgtgaatg gatttctttc    120

tgtggtggtg cggctccggc tgctccggct cctgcggctc cggctgcacc agcaccagcc    180

gcaccagctg caccagcccc agctgcacca gccgctccag caccagctgc cccagctgca    240

ccagctccag ccgcaccagc agccccagct ccagcagccc cagcagctcc agcaccagcc    300

gctccagctg ccccagcacc agctgctcca gcagctccag caccagcagc tccagctgct    360

ccagccccag ccgccccagc cgctccagcc ccagcagcac cagccgcccc agctccagcc    420

gccccagcag gtggctgtgc tgatggtcct acccttcgtg aatggatttc cttttgtggc    480

ggttag                                                               486
```

<210> SEQ ID NO 200
<211> LENGTH: 161
<212> TYPE: PRT
<213> ORGANISM: Artificial Sequence
<220> FEATURE:
<223> OTHER INFORMATION: CspAss-TPO2-PAS100
<220> FEATURE:
<221> NAME/KEY: DISULFID
<222> LOCATION: (28)..(41)
<223> OTHER INFORMATION: Disulfid bridge between Cys-28 and Cys-41
<220> FEATURE:
<221> NAME/KEY: DISULFID
<222> LOCATION: (146)..(159)
<223> OTHER INFORMATION: Disulfid bridge between Cys-146 and Cys-159

<400> SEQUENCE: 200

```
Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Ala Ala Pro Ala Ala
        35                  40                  45

Pro Ala Pro Ala Ala Pro Ala Ala Pro Ala Pro Ala Ala Pro Ala Ala
    50                  55                  60

Pro Ala Pro Ala Ala Pro Ala Ala Pro Ala Pro Ala Ala Pro Ala Ala
65                  70                  75                  80

Pro Ala Pro Ala Ala Pro Ala Ala Pro Ala Pro Ala Ala Pro Ala Ala
                85                  90                  95

Pro Ala Pro Ala Ala Pro Ala Ala Pro Ala Pro Ala Ala Pro Ala Ala
            100                 105                 110

Pro Ala Pro Ala Ala Pro Ala Ala Pro Ala Pro Ala Ala Pro Ala Ala
        115                 120                 125

Pro Ala Pro Ala Ala Pro Ala Ala Pro Ala Pro Ala Ala Pro Ala Gly
    130                 135                 140

Gly Cys Ala Asp Gly Pro Thr Leu Arg Glu Trp Ile Ser Phe Cys Gly
145                 150                 155                 160

Gly
```

<210> SEQ ID NO 201
<211> LENGTH: 486
<212> TYPE: DNA
<213> ORGANISM: Artificial Sequence
<220> FEATURE:
<223> OTHER INFORMATION: CspAss-TPO2-PAS100-b

<400> SEQUENCE: 201

```
atgaaacgca tgaaatcgct ggctgcggcg ctcaccgtcg ctggggccat gctggccgca     60

cctgtggcaa cggcaggcgg gtgtgcagac ggtcccactc tccgcgaatg gatctccttt    120

tgcggcggaa gcgcgccctc cccgtcatct gcccctgcat ctgcgtccgc accagcatcc    180

ccagcctctg cgtctgcttc tgcatcaccg gcctcgtccc cagcaagcgc atcgtccgcg    240

tcaccagctg cgtcctcagc ctcccctgct tcctcgtccg cttcgccttc ggctcctgcc    300

gctccctctg catccgctgc cccatccgcc tcaccagcca gctcctctcc ggcaccagcg    360

tccgctcctt cccctgcagc tgcggcgagc tctccaagcc cggctccctc ctccgcatcc    420

agcgctgccg gtggatgcgc agatggcccg accctgcgtg agtggattag cttctgcggc    480

ggttaa                                                               486
```

<210> SEQ ID NO 202
<211> LENGTH: 161
<212> TYPE: PRT
<213> ORGANISM: Artificial Sequence
<220> FEATURE:
<223> OTHER INFORMATION: CspAss-TPO2-PAS100-b
<220> FEATURE:
<221> NAME/KEY: DISULFID
<222> LOCATION: (28)..(41)
<223> OTHER INFORMATION: Disulfid bridge between Cys-28 and Cys-41
<220> FEATURE:
<221> NAME/KEY: DISULFID
<222> LOCATION: (146)..(159)
<223> OTHER INFORMATION: Disulfid bridge between Cys-146 and Cys-159

<400> SEQUENCE: 202

```
Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Ser Ala Pro Ser Pro
        35                  40                  45

Ser Ser Ala Pro Ala Ser Ala Ser Ala Pro Ala Ser Pro Ala Ser Ala
    50                  55                  60

Ser Ala Ser Ala Ser Pro Ala Ser Ser Pro Ala Ser Ala Ser Ser Ala
65                  70                  75                  80

Ser Pro Ala Ala Ser Ser Ala Ser Pro Ala Ser Ser Ser Ala Ser Pro
                85                  90                  95

Ser Ala Pro Ala Ala Pro Ser Ala Ser Ala Ala Pro Ser Ala Ser Pro
            100                 105                 110

Ala Ser Ser Ser Pro Ala Pro Ala Ser Ala Pro Ser Pro Ala Ala Ala
        115                 120                 125

Ala Ser Ser Pro Ser Pro Ala Pro Ser Ser Ala Ser Ser Ala Ala Gly
    130                 135                 140

Gly Cys Ala Asp Gly Pro Thr Leu Arg Glu Trp Ile Ser Phe Cys Gly
145                 150                 155                 160

Gly
```

<210> SEQ ID NO 203
<211> LENGTH: 210
<212> TYPE: DNA
<213> ORGANISM: Artificial Sequence
<220> FEATURE:
<223> OTHER INFORMATION: CspAss-TPO2-GS8

<400> SEQUENCE: 203

```
atgaaacgca tgaaatcgct ggctgcggcg ctcaccgtcg ctggggccat gctggccgca      60

cctgtggcaa cggcaggtgg ctgtgcggat ggtcctacct tgcgtgagtg gatttctttc     120

tgtggcggtg gtggtggtgg ttctggtggt ggtggtggtt gcgcagatgg cccaaccctg     180

cgcgaatgga tctccttctg cggcggctaa                                      210
```

<210> SEQ ID NO 204
<211> LENGTH: 69
<212> TYPE: PRT
<213> ORGANISM: Artificial Sequence
<220> FEATURE:
<223> OTHER INFORMATION: CspAss-TPO2-GS8
<220> FEATURE:
<221> NAME/KEY: DISULFID
<222> LOCATION: (28)..(41)
<223> OTHER INFORMATION: Disulfid bridge between Cys-28 and Cys-41

-continued

```
<220> FEATURE:
<221> NAME/KEY: DISULFID
<222> LOCATION: (54)..(67)
<223> OTHER INFORMATION: Disulfid bridge between Cys-54 and Cys-67

<400> SEQUENCE: 204

Met Lys Arg Met Lys Ser Leu Ala Ala Ala Leu Thr Val Ala Gly Ala
1               5                   10                  15

Met Leu Ala Ala Pro Val Ala Thr Ala Gly Gly Cys Ala Asp Gly Pro
            20                  25                  30

Thr Leu Arg Glu Trp Ile Ser Phe Cys Gly Gly Gly Gly Gly Gly Ser
        35                  40                  45

Gly Gly Gly Gly Gly Gly Cys Ala Asp Gly Pro Thr Leu Arg Glu Trp Ile
    50                  55                  60

Ser Phe Cys Gly Gly
65
```